US010774388B2

(12) United States Patent
Bedoya et al.

(10) Patent No.: US 10,774,388 B2
(45) Date of Patent: Sep. 15, 2020

(54) BIOMARKERS PREDICTIVE OF THERAPEUTIC RESPONSIVENESS TO CHIMERIC ANTIGEN RECEPTOR THERAPY AND USES THEREOF

(71) Applicants: Novartis AG, Basel (CH); The Trustees of the University of Pennsylvania, Philadelphia, PA (US)

(72) Inventors: Felipe Bedoya, Melrose, MA (US); Hans Bitter, Lincoln, MA (US); Jennifer Brogdon, Cambridge, MA (US); Corin Dorfmeier, Hayfield, PA (US); Abhishek Garg, Cambridge, MA (US); David Jonathan Glass, Cambridge, MA (US); Joan Mannick, Cambridge, MA (US); Jan J. Melenhorst, Cherry Hill, NJ (US); Michael Milone, Cherry Hill, NJ (US); Leon Murphy, Cambridge, MA (US); Elena Orlando, Somerville, MA (US); Nicholas Wilcox, Southlake, TX (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 141 days.

(21) Appl. No.: 15/517,597

(22) PCT Filed: Oct. 7, 2015

(86) PCT No.: PCT/US2015/054542
§ 371 (c)(1),
(2) Date: Apr. 7, 2017

(87) PCT Pub. No.: WO2016/057705
PCT Pub. Date: Apr. 14, 2016

(65) Prior Publication Data
US 2017/0306416 A1 Oct. 26, 2017

Related U.S. Application Data

(60) Provisional application No. 62/144,682, filed on Apr. 8, 2015, provisional application No. 62/061,553, filed on Oct. 8, 2014.

(51) Int. Cl.
C12Q 1/6886 (2018.01)
G01N 33/574 (2006.01)
C12N 5/0783 (2010.01)
A61K 39/00 (2006.01)

(52) U.S. Cl.
CPC ........ C12Q 1/6886 (2013.01); A61K 39/0011 (2013.01); C12N 5/0636 (2013.01); G01N 33/574 (2013.01); G01N 33/57426 (2013.01); A61K 2039/5158 (2013.01); C12Q 2600/118 (2013.01); C12Q 2600/158 (2013.01); G01N 2800/52 (2013.01)

(58) Field of Classification Search
CPC .................................................... C12Q 1/6886
USPC ........................................................ 424/133.1
See application file for complete search history.

(56) References Cited

U.S. PATENT DOCUMENTS

| | | |
|---|---|---|
| 5,359,046 A | 10/1994 | Capon et al. |
| 5,686,281 A | 11/1997 | Roberts |
| 5,712,149 A | 1/1998 | Roberts |
| 5,874,240 A | 2/1999 | Ni et al. |
| 5,906,936 A | 5/1999 | Eshhar et al. |
| 6,103,521 A | 8/2000 | Capon et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang |
| 8,211,422 B2 | 7/2012 | Eshhar et al. |
| 8,252,914 B2 | 8/2012 | Zhang et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |

(Continued)

FOREIGN PATENT DOCUMENTS

| | | |
|---|---|---|
| CA | 2878928 A1 | 1/2014 |
| EP | 0871495 A1 | 10/1998 |

(Continued)

OTHER PUBLICATIONS

Ye et al (World J Gastrenterol, 2008, 14(28): 4551-4557).*

(Continued)

*Primary Examiner* — Sean E Aeder

(74) *Attorney, Agent, or Firm* — Lando & Anastasi, LLP

(57) ABSTRACT

Cancer biomarkers and methods of using them are disclosed.

31 Claims, 29 Drawing Sheets
Specification includes a Sequence Listing.

(56) References Cited

U.S. PATENT DOCUMENTS

| | | |
|---|---|---|
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0257994 A1 | 10/2009 | Jensen |
| 2011/0052554 A1 | 3/2011 | Zakrzewski et al. |
| 2012/0148552 A1 | 6/2012 | Jensen |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370045 A1 | 12/2014 | June et al. |
| 2015/0017141 A1 | 1/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |

FOREIGN PATENT DOCUMENTS

| | | |
|---|---|---|
| EP | 1226244 A2 | 7/2002 |
| WO | 1992015322 A1 | 9/1992 |
| WO | 0574512 A1 | 12/1993 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |
| WO | 9818809 A1 | 5/1998 |
| WO | 9900494 A2 | 1/1999 |
| WO | 9957268 A1 | 11/1999 |
| WO | 0014257 A1 | 3/2000 |
| WO | 2002033101 A1 | 4/2002 |
| WO | 02077029 A2 | 10/2002 |
| WO | 02088334 A1 | 11/2002 |
| WO | 2003057171 A2 | 7/2003 |
| WO | 2005019429 A2 | 3/2005 |
| WO | 2005044996 A2 | 5/2005 |
| WO | 2005/118788 A2 | 12/2005 |
| WO | 2006060878 A1 | 6/2006 |
| WO | 2008045437 A2 | 4/2008 |
| WO | 2009091826 A2 | 7/2009 |
| WO | 2010085660 A2 | 7/2010 |
| WO | 2011059836 A2 | 5/2011 |
| WO | 2011097477 A1 | 8/2011 |
| WO | 2012058460 A2 | 5/2012 |
| WO | 2012079000 A1 | 6/2012 |
| WO | 2012082841 A2 | 6/2012 |
| WO | 2012/099973 A2 | 7/2012 |
| WO | 2012127464 A2 | 9/2012 |
| WO | 2012129514 A1 | 9/2012 |
| WO | 2012135854 A2 | 10/2012 |
| WO | 2012138858 A1 | 10/2012 |
| WO | 2013019615 A2 | 2/2013 |
| WO | 2013033626 A2 | 3/2013 |
| WO | 2013040371 A2 | 3/2013 |
| WO | 2013040557 A2 | 3/2013 |
| WO | 2013059593 A1 | 4/2013 |
| WO | 2013/126712 A1 | 8/2013 |
| WO | 2013126729 A1 | 8/2013 |
| WO | 2013126733 A1 | 8/2013 |
| WO | 2014/011984 A1 | 1/2014 |
| WO | 2014/011987 A1 | 1/2014 |
| WO | 2014/011993 A2 | 1/2014 |
| WO | 2014/012001 A2 | 1/2014 |
| WO | 2014011988 A2 | 1/2014 |
| WO | 2014011996 A1 | 1/2014 |
| WO | 2014031687 A1 | 2/2014 |
| WO | 2014039044 A1 | 3/2014 |
| WO | 2014039513 A2 | 3/2014 |
| WO | 2014/055442 A2 | 4/2014 |
| WO | 2014055657 A1 | 4/2014 |
| WO | 2014130635 A1 | 8/2014 |

(56) References Cited

FOREIGN PATENT DOCUMENTS

| | | | |
|---|---|---|---|
| WO | 2014/145252 A2 | 9/2014 | |
| WO | 2014153270 A1 | 9/2014 | |
| WO | 2015090229 A1 | 6/2015 | |
| WO | 2015090230 A1 | 6/2015 | |
| WO | 2015112626 A1 | 7/2015 | |
| WO | 2015/142661 A1 | 9/2015 | |
| WO | 2015142675 A2 | 9/2015 | |
| WO | 2015157252 A1 | 10/2015 | |
| WO | 2015193740 A2 | 12/2015 | |
| WO | 2016014501 A1 | 1/2016 | |
| WO | 2016014530 A1 | 1/2016 | |
| WO | 2016014535 A1 | 1/2016 | |
| WO | 2016014553 A1 | 1/2016 | |
| WO | 2016014565 A2 | 1/2016 | |
| WO | 2016014576 A1 | 1/2016 | |
| WO | 2016019300 A1 | 2/2016 | |
| WO | 2016025880 A1 | 2/2016 | |
| WO | 2016028896 A1 | 2/2016 | |
| WO | 2016044605 A1 | 3/2016 | |
| WO | 2016/057705 A1 | 4/2016 | |
| WO | 2016090034 A2 | 6/2016 | |
| WO | 2017040930 A2 | 3/2017 | |
| WO | 2017096331 A1 | 6/2017 | |

OTHER PUBLICATIONS

Tockman et al (Cancer Res., 1992, 52:2711s-2718s).*
International Search Report and Written Opinion for International Application No. PCT/US2017/042129 dated Jan. 3, 2018.
Clark et al. "Discovery and Development of Janus Kinase (JAK) Inhibitors for Inflammatory Diseases" Jounal of Medicinal Chemistry (2014) vol. 57, pp. 5023-5038.
Partial International Search Report and Invitation to Pay Additional Fees for International Application No. PCT/US2017/042129 dated Nov. 3, 2017.
Ye et al. "Programmed death-1 expression is associated with the disease status in hepatitis B virus infection" World Journal of Gastroenterology (2008) vol. 14, No. 28, pp. 4551-4557.
Singapore Search Report for SG Application No. 11201702895S dated May 9, 2018.
Kershaw et al., "A Phase I Study on Adoptive Immunotherapy Using Gene-Modified T cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH), Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Macallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
Maude et al. "Managing Cytokine Release Syndrome Associated with Novel T Cell-Engaging Therapies" Cancer J. (2014) vol. 20, No. 2, pp. 119-122.
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.

(56) References Cited

OTHER PUBLICATIONS

Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Teachey et al. "Identification of Predictive Biomarkers for Cytokine Release Syndrome after Chimeric Antigen Receptor T-cell Therapy for Acute Lymphoblastic Leukemia" Cancer Discovery (2016) vol. 6, No. 6, pp. 664-679.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Van Der Stegen et al. "Preclinical In Vivo Modeling of Cytokine Release Syndrome Induced by ErbB-Retargeted Human T Cells: Identifying a Window of Therapeutic Opportunity?" Journal of Immunology (2013) vol. 191, pp. 4589-4598.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Xu et al. "Closely related T-memory stem cells correlate with in vivo expansion of CAR.CD19-T cells and are preserved by IL-7 and IL-15" Blood (2014) vol. 123, No. 24, pp. 3750-3759.
Baeksgaard & Sorensen, "Acute tumor lysis syndrome in solid tumors—a case report and review of the literature" Cancer Chemotherapy Pharmacology (2003) vol. 51 pp. 187-192.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-1428.
Brocker and Karjalainen, "Signals through T Cell Receptor-Chain alone are Insufficient to Prime Resting T Lymphocytes" J. Exp. Met (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Mad Sci USA (2009) vol. 106 pp. 3360-3365.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Epstein et al. "Temporal stability of serum concentrations of cytokines and soluble receptors measured across two years in low-risk HIVseronegative men" Cancer Epidemiol Biomarkers Prev. (2013) vol. 22, No. 11, pp. 1-12.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Mol-

(56) References Cited

OTHER PUBLICATIONS ecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
He et al. "Expression Pattern of Serum Cytokines in Hepatitis B Virus Infected Patients with Persistently Normal Alanine Aminotransferase Levels" Journal of Clinical Immunology (2013) vol. 33, pp. 1240-1249.
Hekele et al., "Growth Retardation of Tumors by Adoptive Transfer of Cytotoxic T Lymphocytes Reprogrammed by CD44V6-Specific SCFV:~-CHIMERA" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Preliminary Report on Patentability for International Application No. PCT/US2015054542 dated Apr. 11, 2017.
International Search Report and Written Opinion for International Application No. PCT/US2015/054542 dated Mar. 14, 2016.
International Search Report and Written Opinion for International Application No. PCT/US2016/050112 dated Feb. 27, 2017.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "Adoptive T Cell Transfer for Cancer Immunotherapy in the Era of Synthetic Biology" Immunity (2013) vol. 39, pp. 49-60.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.

\* cited by examiner

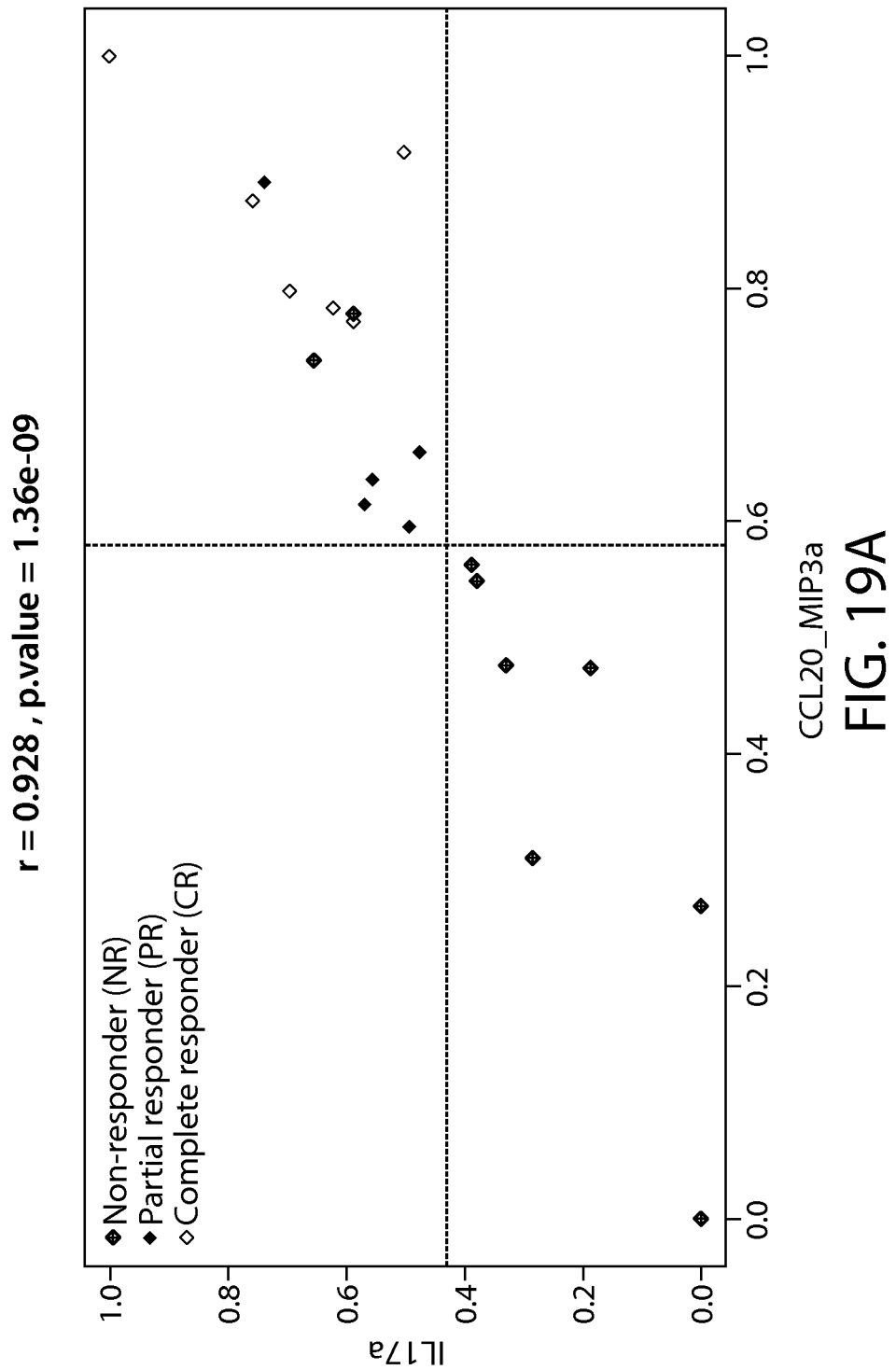

BIOMARKERS PREDICTIVE OF THERAPEUTIC RESPONSIVENESS TO CHIMERIC ANTIGEN RECEPTOR THERAPY AND USES THEREOF

This application is a U.S. national phase application under 35 U.S.C. § 371 of International Application No. PCT/US2015/054542, filed Oct. 7, 2015, which claims priority to U.S. Ser. No. 62/061,553 filed Oct. 8, 2014 and U.S. Ser. No. 62/144,682 filed Apr. 8, 2015, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Oct. 7, 2015, is named N2067-7057WO_SL.txt and is 219,221 bytes in size.

FIELD OF THE INVENTION

The invention relates to cancer biomarkers and uses thereof.

BACKGROUND OF THE INVENTION

Many patients with B cell malignancies are incurable with standard therapy. In addition, traditional treatment options often have serious side effects. Attempts have been made in cancer immunotherapy, however, several obstacles render the goal of clinical effectiveness difficult to achieve. Although hundreds of so-called tumor antigens have been identified, these are generally derived from self and thus are poorly immunogenic. Furthermore, tumors use several mechanisms to render themselves hostile to the initiation and propagation of immune attack.

Recent developments using chimeric antigen receptor (CAR) modified autologous T cell (CART) therapy, which relies on redirecting T cells to a suitable cell-surface molecule on cancer cells such as B cell malignancies, show promising results in harnessing the power of the immune system to treat B cell malignancies and other cancers (see, e.g., Sadelain et al., CANCER DISCOVERY 3:388-398 (2013)). For example, the clinical results of a CART that binds to CD19 (i.e., "CTL019") have shown promise in establishing complete remissions in patients suffering with chronic lymphocytic leukemia (CLL), as well as in childhood acute lymphocytic leukemia (ALL) (see, e.g., Kalos et al., SCI TRANSL MED 3:95ra73 (2011), Porter et al., NEJM 365:725-733 (2011), Grupp et al., NEJM 368:1509-1518 (2013)).

Besides the ability for the chimeric antigen receptor on the genetically modified T cells to recognize and destroy the targeted cells, a successful therapeutic T cell therapy needs to have the ability to proliferate, to persist over time, and to further monitor for leukemic cell escapees. The variable phenotypic state of T cells, whether it is in a state of anergy, suppression or exhaustion, will have effects on CAR-transformed T cells' efficacy. To be effective, CAR transformed patient T cells need to persist and maintain the ability to proliferate in response to the CAR's antigen.

A need, therefore, exists for a method of using biomarkers for use in connection with the differential diagnosis and treatment of cancer with CAR-expressing cell (e.g., T cell, NK cell) therapy. In particular, there is an unmet need for effective predictors of therapeutic response in subjects having a hematological cancer, such as CLL and ALL, to a CAR-expressing cell therapy, e.g., with CTL019 or other CD19 CAR-expressing cells.

SUMMARY OF THE INVENTION

The present disclosure relates to the identification and use of analytes, analyte profiles, or markers (e.g., gene expression, flow cytometry and/or protein expression profiles) with clinical relevance to cancer (e.g., a hematological cancer such as chronic lymphocytic leukemia (CLL) and acute lymphocytic leukemia (ALL)). In some embodiments, the disclosure provides the identity of genes, whose expression, at the transcriptional and protein levels, are correlated with CLL and ALL progression, e.g., as a way of predicting a response to a Chimeric Antigen Receptor (CAR)-expressing cell therapy (e.g., a therapy comprising a cell (e.g., an immune effector cell or population of cells) that expresses a CAR that binds to CD19 (also referred to herein as a "CAR19" or "CD19 CAR"-expressing cell). In certain embodiments, one or more of a CD19 CAR-expressing cell gene set signature, a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and combinations thereof) are evaluated. These gene expression profiles may be applied to the diagnosis and/or prognosis of a cancer, e.g., a hematological cancer such as CLL and ALL, and are particularly useful in predicting whether a subject will respond favorably to a CAR therapy (e.g., a CD19 CAR therapy as described here, e.g., a CTL019 therapy) in a subject diagnosed with a cancer, e.g., a hematological cancer such as CLL or ALL. Compared to clinical parameters or biochemical markers used in existing prognosis methods, the expression profiles of the genes disclosed herein constitute a more robust signature of hematological cancer progression (e.g., CLL and ALL progression) and provide a more reliable, non-subjective basis for the selection of appropriate therapeutic regimens.

Amongst other things, the present disclosure provides novel gene signatures, e.g., at the transcriptional and protein levels, and methods of use thereof, that predict subject response to a cell expressing a CAR, e.g., a CD19 CAR (e.g., a CD19 CAR-expressing cell, e.g., T cell, NK cell, described herein such as, e.g., CTL019) therapy in a cancer, e.g., a hematological cancer such as CLL and ALL.

The present disclosure demonstrates, at least in part, that expression profiles and gene signatures, e.g., at the transcriptional and protein levels, are useful to distinguish among a responder, a partial responder, a non-responder, a relapser or a non-relapser to a therapy comprising a CAR-expressing cell (e.g., a CAR-expressing immune effector cell, e.g., a T cell, or an NK cell), (also referred to herein as a "CAR-expressing cell therapy"), in a cancer (e.g., a hematological cancer such as CLL and ALL). In one embodiment, the CAR-expressing cell is a CD19 CAR-expressing cell. In one embodiment, the therapy is a CTL019 therapy. In embodiments, the expression profiles and gene signatures disclosed herein distinguish among a CAR (or CD19 CAR)-expressing cell responder, a CAR (or CD19 CAR)-expressing cell partial responder, or a CAR (or CD19 CAR)-expressing cell non-responder (e.g., a CTL019-responder, a CTL019-partial responder, and a CTL019-non-responder); or a CAR (or CD19 CAR)-expressing cell relapser, or a CAR (or CD19 CAR)-expressing cell non-relapser (e.g., a CTL019-relapser, or a CTL019-relapser), in a cancer (e.g., a hematological cancer such as CLL and ALL). The present disclosure encompasses the identification of novel gene signatures predictive of subject response to a CAR-expressing cell therapy, e.g., a CD19 CAR-expressing cell therapy such as CTL019.

Thus, disclosed herein are methods, systems, compositions, and kits for the identification, assessment and/or treatment of a subject having cancer. Exemplary cancers include, but are not limited to, B-cell acute lymphocytic leukemia (B-ALL), T-cell acute lymphocytic leukemia (T-ALL), acute lymphocytic leukemia (ALL), chronic myelogenous leukemia (CML), chronic lymphocytic leukemia (CLL), B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma (HL), plasmablastic lymphoma, plasmacytoid dendritic cell neoplasm, and Waldenstrom macroglobulinemia. In one embodiment, the cancer is ALL. In another embodiment, the cancer is CLL. In an embodiment, the cancer is associated with CD19 expression.

Accordingly, in one aspect, the invention features a method of evaluating a subject having a cancer, e.g., a hematological cancer. The method includes acquiring a value of responder or relapser status (e.g., a value of responder or relapser status as described herein) to a therapy comprising a CAR-expressing cell (e.g., a plurality (e.g., a population) of CAR (e.g., CAR19–)-expressing cells) for the subject, wherein said value is indicative of the subject's responsiveness or relapsing status to the CAR-expressing cell therapy.

In a related aspect, the invention features a method of evaluating or monitoring the effectiveness of a CAR-expressing cell therapy in a subject having a cancer, e.g., a hematological cancer. The method includes acquiring a value of responder or relapser status (e.g., a value of responder or relapser status as described herein) to a therapy comprising a CAR-expressing cell (e.g., a plurality (e.g., a population) of CAR (e.g., CAR19–)-expressing cells) for the subject, wherein said value is indicative of the effectiveness of the CAR-expressing cell therapy, thereby evaluating the effectiveness of the CAR-expressing cell therapy in the subject.

In another aspect, the invention features a method for treating a subject having a cancer, e.g., a hematological cancer. The method includes administering to the subject a therapeutically effective dose of a CAR-expressing cell therapy, if the subject is identified as being responsive (e.g., identified as a complete responder, partial responder or a non-relapser) to a therapy comprising a CAR-expressing cell (e.g., a plurality (e.g., a population) of CAR (e.g., CAR19–)-expressing cells), wherein said identifying comprises a value of responder or relapser status (e.g., a value of responder or relapser status as described herein).

In a related aspect, the invention features a method of treating a cancer, e.g., a hematological cancer, in a subject. The method includes acquiring a value of responder or relapser status (e.g., a value of responder or relapser status as described herein) to a therapy comprising a CAR-expressing cell (e.g., a plurality (e.g., a population) of CAR (e.g., CAR19–)-expressing cells) for the subject; and responsive to said value, treating the cancer.

In embodiments of any of the methods and compositions for use described herein, the value of responder or relapser status comprises a measure of one, two, three, four, five, six, seven or more (all) of the following:

(i) the level or activity of CD27 and/or CD45RO– (e.g., CD27+ CD45RO–) immune effector cells, e.g., in a CD4+ or a CD8+ T cell population, in a subject, e.g., a sample from the subject (e.g., an apheresis sample or a CAR-expressing cell product sample);

(ii) the level or activity of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, in a subject, e.g., a sample from the subject (e.g., an apheresis sample or a CAR-expressing cell product sample);

(iii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in a subject, e.g., a sample from the subject (e.g., an apheresis sample or a manufactured CAR-expressing cell product sample);

(iv) the level or activity of an immune cell exhaustion marker, e.g., one, two or more immune checkpoint inhibitors (e.g., PD-1, TIM-3 and/or LAG-3) in a subject, e.g., a sample from the subject (e.g., an apheresis sample or a manufactured CAR-expressing cell product sample);

(v) the level or activity of one, two, three, four, five, ten, twenty or more of the biomarkers listed in Table 1A, Table 1B, Table 7A, Table 7B, Table 8, Table 9, Table 10, Table 14 (e.g., CCL20, IL-17a and/or IL-6), Table 16, Table 17, Table 18, Table 20, FIG. 2B, PD-1, LAG-3, TIM-3, CD57, CD27, CD122, CD62L, KLRG1, or a CD19 CAR-expressing cell gene set signature;

(vi) a cytokine level or activity (e.g., quality of cytokine reportoire) in a CAR-expressing cell product sample, e.g., CAR19-expressing cell product sample (e.g., CTL019), wherein the cytokine is chosen from one, two, three, four, five or more (or all) of the cytokines listed in Table 16;

(vii) a transduction efficiency of a CAR-expressing cell in a CAR-expressing cell product sample; or (viii) a quantity of CD27+ PD-1– cells in a subject, e.g., a sample from the subject (e.g., an apheresis sample or a CAR-expressing cell product sample, e.g., CAR19-expressing cell product sample (e.g., CTL019)), e.g., a quantity greater than or equal to $1 \times 10^7$ cells.

In an aspect, the invention provides a CAR expressing cell therapy (e.g., CD19 CART cell, e.g., CTL019 cell) for use in the treatment of a subject, wherein the CAR expressing cell has been assayed according to a method herein, e.g., before or after transduction or transfection with a CAR nucleic acid. In a related aspect, the invention provides a CAR expressing cell therapy (e.g., CD19 CART cell, e.g., CTL019 cell), for use in the treatment of a subject that has been identified as being responsive (e.g., identified as a complete responder, partial responder or a non-relapser) to a therapy comprising a CAR-expressing cell population (e.g., a CAR19-expressing cell population). The composition for use can comprise a measure of one, two, three, four, five, six, seven, or more (all) of (i)-(viii) described herein.

Alternatively, or in combination with the methods and compositions for use disclosed herein, responsive to said value, performing one, two, three, four, five, six, seven, or more (e.g., all) of:

identifying the subject as a complete responder, partial responder or non-responder, or a relapser or a non-relapser;

administering e.g., to a responder or a non-relapser, a CAR-expressing cell therapy;

administering an altered dosing of a CAR-expressing cell therapy;

altering the schedule or time course of a CAR-expressing cell therapy;

administering, e.g., to a non-responder or a partial responder, an additional agent in combination with a CAR-expressing cell therapy, e.g., a checkpoint inhibitor, e.g., a checkpoint inhibitor described herein;

administering to a non-responder or partial responder a therapy that increases the number of younger T cells in the subject prior to treatment with a CAR-expressing cell therapy;

modifying a process, e.g., a manufacturing process, of a CAR-expressing cell therapy, e.g., enriching for younger T cells prior to introducing a nucleic acid encoding a CAR, or increasing the transduction efficiency, e.g., for a subject identified as a non-responder or a partial responder;

administering an alternative therapy, e.g., for a non-responder or partial responder or relapser, e.g., a standard of care for a particular cancer type; or if the subject is, or is identified as, a non-responder or a relapser, decreasing the $T_{REG}$ cell population and/or $T_{REG}$ gene signature, e.g., by one or more of CD25 depletion, or administration of cyclophosphamide, anti-GITR antibody, an mTOR inhibitor, or a combination thereof.

In certain embodiments, the subject is pre-treated with an anti-GITR antibody. In certain embodiment, the subject is treated with an anti-GITR antibody prior to infusion or re-infusion. In some embodiments, the subject is a patient with CLL.

In another aspect, the invention features a method of, or assay for, identifying a subject having a cancer as having an increased or decreased likelihood to respond to a treatment that comprises a CAR-expressing cell (e.g., a plurality (e.g., a population) of CAR (e.g., CAR19−)-expressing cells). The method includes:

(1) providing, e.g., acquiring, a sample from the subject;

(2) determining a level or activity of one or more biomarkers listed in Table 1A, Table 1B, Table 7A, Table 7B, Table 8, Table 9, Table 10, Table 14 (e.g., CCL20, IL-17a and/or IL-6), Table 17, Table 18, Table 20, PD-1, LAG-3, TIM-3, CD57, CD27, CD122, CD62L, KLRG1 in the sample;

wherein a difference, e.g., a statistically significant difference, between the determined level compared to a reference level is predictive of the subject's responsiveness to the CAR-expressing cell therapy; and (3) (optionally) identifying the subject as a complete responder, partial responder, non-responder, a relapser or a non-relapser, to the CAR-expressing cell therapy.

In yet another aspect, the invention features a method for treating a subject having a cancer comprising:

determining if the subject has an increased likelihood to respond, or a decreased likelihood to relapse, to a CAR-expressing cell therapy (e.g., a CAR19-expressing therapy, e.g., CTL019) by determining the level or activity of one or more biomarkers in Table 1A, Table 1B, Table 7A, Table 7B, Table 8, Table 9, Table 10, Table 14 (e.g., CCL20, IL-17a and/or IL-6), FIG. 2B, Table 17, Table 18, Table 20, PD-1, LAG-3, TIM-3, CD57, CD27, CD122, CD62L, KLRG1, or a CD19 CAR-expressing cell gene set signature in a sample from the subject, e.g., relative to a reference level; and administering to the subject a therapeutically effective dose of a CAR-expressing cell therapy.

In yet another aspect, the invention features a method for treating a subject having cancer comprising:

(1) determining if the subject has an increased likelihood to relapse to a CAR-expressing cell therapy by acquiring a value for the level or activity of one or more markers in a Table herein, e.g., Table 17 in a sample from the subject (e.g., an apheresis sample or a manufactured CAR-expressing product sample), wherein a difference, e.g., a statistically significant difference, in the level or activity of one or more biomarker genes relative to the reference level is indicative of an increased likelihood of relapse to a CAR-expressing cell therapy; and (2) for a subject with an increased likelihood of relapse, decreasing the $T_{REG}$ cell population and/or decreasing $T_{REG}$ gene signature; and (3) administering to the subject a therapeutically effective dose of a CAR-expressing cell therapy.

Additional features and embodiments of the present invention include one or more of the following:

In some embodiments of any of the methods and compositions for use disclosed herein, an immune cell has an exhausted phenotype, e.g., co-expresses at least two exhaustion markers, e.g., co-expresses PD-1 and TIM-3. In other embodiments, an immune cell has an exhausted phenotype, e.g., co-expresses at least two exhaustion markers, e.g., co-expresses PD-1 and LAG-3.

In some embodiments of any of the methods, systems, compositions for use, and kits disclosed herein, the CAR-expressing cell therapy comprises a plurality (e.g., a population) of CAR-expressing immune effector cells, e.g., a plurality (e.g., a population) of T cells or NK cells, or a combination thereof. In one embodiment, the CAR-expressing cell therapy is a CAR19 therapy (e.g., CTL019 therapy). In an embodiment, the CAR-expressing cell therapy comprises or consists of CTL019. In an embodiment, the CAR-expressing cell is a CTL019 product. In an embodiment, the CAR-expressing cell is a T cell. In an embodiment, the CAR-expressing cell is a NK cell.

In some embodiments of any of the methods and compositions for use disclosed herein, the measure of one or more of (i)-(viii) is obtained from an apheresis sample acquired from the subject. The apheresis sample can be evaluated prior to infusion or re-infusion.

In some embodiments of any of the methods and compositions for use disclosed herein, the measure of one or more of (i)-(viii) is obtained from a manufactured CAR-expressing cell product sample, e.g., CAR19-expressing cell product sample (e.g., CTL019). The manufactured CAR-expressing cell product can be evaluated prior to infusion or re-infusion.

In some embodiments of any of the methods and compositions for use disclosed herein, the subject is evaluated prior to receiving, during, or after receiving, the CAR-expressing cell therapy.

In some embodiments of any of the methods and compositions for use disclosed herein, the hematological cancer is an ALL or a CLL. The subject can be a human patient.

In some embodiments of any of the methods and compositions for use disclosed herein, the cell, e.g., the population of immune effector cells (e.g., cells expressing a CAR molecule described herein) is administered in combination with an inhibitor of an immune checkpoint molecule chosen from one or more of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, TGFR (e.g., TGFR beta), or a combination thereof.

In some embodiments of any of the methods and compositions for use disclosed herein, the subject receives concurrent treatment with an agent, e.g., an mTOR inhibitor, and/or a checkpoint inhibitor. In some embodiments, the subject receives treatment with an agent, e.g., an mTOR inhibitor, and/or a checkpoint inhibitor, post-CAR-expressing cell therapy. In some embodiments, the subject receives a pre-treatment of with an agent, e.g., an mTOR inhibitor, and/or a checkpoint inhibitor, prior to the initiation of a CAR-expressing cell therapy.

In some embodiments of any of the methods and compositions for use disclosed herein, $T_{REG}$ cell population and/or $T_{REG}$ gene signature is decreased prior to collection of cells for manufacturing. In some embodiments, the $T_{REG}$ cell population and/or $T_{REG}$ gene signature is decreased prior to CAR-expressing cell (e.g., T cell, NK cell) therapy. In some embodiments, the $T_{REG}$ cell population and/or $T_{REG}$ gene signature is decreased by administration of cyclophosphamide, anti-GITR antibody, an mTOR inhibitor, or a combination thereof.

In some embodiments of any of the methods and compositions for use disclosed herein the value of responder or relapser status comprises a measure of a combination of a gene signature and a biomarker. In some embodiments, the value of the responder or relapser status comprises a measure of a CD19 CAR-expressing cell gene set signature and a combination of one or more of: a biomarker listed in Table 1A, Table 1B, Table 7A, Table 7B, Table 8, Table 9, Table 10, Table 14 (e.g., CCL20, IL-17a and/or IL-6), Table 17, Table 18, Table 20, PD-1, LAG-3, TIM-3, CD57, CD27, CD122, CD62L, or KLRG1.

In some embodiments of any of the methods and compositions for use disclosed herein, the method further comprises identifying the subject as a responder (e.g., a complete or partial responder), a non-responder, a relapser or a non-relapser, based on a measure of one or more of (i)-(viii).

In some embodiments of any of the methods and compositions for use disclosed herein, the measure of one or more of (i)-(viii) evaluates a profile for one or more of gene expression, flow cytometry or protein expression.

In some embodiments of any of the methods and compositions for use disclosed herein, the expression profile includes one or more gene signatures based on mRNA expression levels of selected genes obtained from the apheresis sample or a manufactured CD19 CAR-expressing cell product (e.g., CTL019). In one embodiment, the expression profile includes one, two, three, four, five, ten, twenty or more of a biomarker listed in Table 1A, Table 1B, Table 7A, Table 7B, Table 8, Table 9, Table 10, Table 14 (e.g., CCL20, IL-17a and/or IL-6), Table 16, Table 17, Table 18, Table 20, FIG. 2B, PD-1, LAG-3, TIM-3, CD57, CD27, CD122, CD62L, KLRG1, or a CD19 CAR-expressing cell gene set signature.

In some embodiments of any of the methods and compositions for use disclosed herein, the level or activity of a CD8+ T cell is evaluated using a profile or signature indicative of the percentage of CD8+ T cell in the sample.

In some embodiments of any of the methods and compositions for use disclosed herein, the level or activity of CD27+ CD45RO− immune effector cells is evaluated using a profile or signature indicative of the percentage of CD27+ CD45RO− immune effector cells in the sample.

In some embodiments of any of the methods and compositions for use disclosed herein, the level or activity, e.g., in (i), (ii), or (v), is evaluated using a profile or gene signature according to one, two, three, four, five, ten, twenty, fifty, sixty, seventy, one hundred or more of a biomarker or gene set listed in Tables 1A, 1B, 3, 4, 5, 6, or FIG. 2B.

In some embodiments of any of the methods and compositions for use disclosed herein, the level or activity one, two or more immune checkpoint inhibitors is evaluated, e.g., using flow cytometry, as an indicator of the percentage of PD-1+/LAG-3+ cells in the CAR-expressing cell population (e.g., a CAR19+ cell population).

In some embodiments of any of the methods and compositions for use disclosed herein, the level or activity one, two or more immune checkpoint inhibitors is evaluated, e.g., using flow cytometry, as an indicator of the percentage of PD-1+/TIM-3+ cells in the CAR-expressing cell population (e.g., a CAR19+ cell population).

In some embodiments of any of the methods and compositions for use disclosed herein, the level or activity of one, two, three, four, five, ten, twenty, fifty, sixty, seventy, one hundred or more of a biomarker or gene set listed in Table 7A, Table 7B, Table 8 and FIG. 2B predicts a subject's response to a CAR19+ cell product (e.g., CTL019).

In some embodiments of any of the methods and compositions for use disclosed herein, the value of responder or relapser status comprises a measure of the level or activity of one, two, three, four, five, ten, twenty or more (e.g., all) of the biomarkers having a given FDR p-value, listed herein, e.g., in a Table herein. In some embodiments, the FDR p-value is below 0.2, 0.1, 0.05, 0.02, 0.01, 0.005, 0.002, or 0.001. In some embodiments, the FDR p-value is below 0.1 or 0.01. In some embodiments, the biomarkers are biomarkers listed in Table 1A, Table 1B, Table 16, Table 17, Table 18, or Table 20, or a combination thereof. In some embodiments, the measure comprises a measure of all of the biomarkers in Table 1A that have a p-value below a threshold of 0.2, 0.1, 0.05, 0.02, 0.01, 0.005, 0.002, or 0.001. In some embodiments, the measure comprises a measure of all of the biomarkers in Table 1B that have a p-value below a threshold of 0.2, 0.1, 0.05, 0.02, 0.01, 0.005, 0.002, or 0.001. In some embodiments, the measure comprises a measure of all of the biomarkers in Table 16 that have a p-value below a threshold of 0.2, 0.1, 0.05, 0.02, 0.01, 0.005, 0.002, or 0.001. In some embodiments, the measure comprises a measure of all of the biomarkers in Table 17 that have a p-value below a threshold of 0.2, 0.1, 0.05, 0.02, 0.01, 0.005, 0.002, or 0.001. In some embodiments, the measure comprises a measure of all of the biomarkers in Table 18 that have a p-value below a threshold of 0.2, 0.1, 0.05, 0.02, 0.01, 0.005, 0.002, or 0.001. In some embodiments, the measure comprises a measure of all of the biomarkers in Table 20 that have a p-value below a threshold of 0.2, 0.1, 0.05, 0.02, 0.01, 0.005, 0.002, or 0.001. In some embodiments, the measure comprises a measure of all of the biomarkers having a p-value below the threshold. In some embodiments, the measure comprises a measure of one, two, three, four, five, ten, twenty, fifty, or one hundred biomarkers having a p-value below the threshold. In some embodiments, the measure comprises a measure of at least one, two, three, four, five, ten, twenty, fifty, or one hundred biomarkers having a p-value below the threshold. In some embodiments, the measure comprises a measure of 1-5, 5-10, 10-20, 20-50, or 50-100 biomarkers having a p-value below the threshold.

In some embodiments, biomarkers of Table 7B that are designated "CR" in the table are upregulated in complete responders compared to non-responders. In some embodiments, biomarkers of Table 7B that are designated "NR" in the table are upregulated in non-responders compared to complete responders.

In some embodiments of any of the methods and compositions for use disclosed herein, the biomarker is a secreted or a cell surface biomarker listed in Table 8. For example the biomarker can be measured by flow cytometry.

In some embodiments of any of the methods and compositions for use disclosed herein, a responder (e.g., a complete responder) has, or is identified as having, a greater level or activity of one, two, or more (all) of GZMK, PPF1BP2, or naïve T cells as compared to a non-responder.

In some embodiments of any of the methods and compositions for use disclosed herein, a non-responder has, or is identified as having, a greater level or activity of one, two, three, four, five, six, seven, or more (e.g., all) of IL22, IL-2RA, IL-21, IRF8, IL8, CCL17, CCL22, effector T cells, or regulatory T cells, as compared to a responder.

In an embodiment of any of the methods and compositions for use disclosed herein, a relapser is a patient having, or who is identified as having, an increased level of expression of one or more of (e.g., 2, 3, 4, or all of) the following genes, compared to non relapsers: MIR199A1, MIR1203, uc021ovp, ITM2C, and HLA-DQB1 and/or a decreased levels of expression of one or more of (e.g., 2, 3, 4, 5, 6, 7, 8, 9, 10, 11, or all of) the following genes, compared to non relapsers: PPIAL4D, TTTY10, TXLNG2P, MIR4650-1, KDM5D, USP9Y, PRKY, RPS4Y2, RPS4Y1, NCRNA00185, SULT1E1, and EIF1AY.

In some embodiments of any of the methods and compositions for use disclosed herein, a complete responder has, or is identified as having, a greater, e.g., a statistically significant greater, percentage of CD8+ T cells compared to a reference value, e.g., a non-responder percentage of CD8+ T cells.

In some embodiments of any of the methods and compositions for use disclosed herein, a complete responder has, or is identified as having, a greater percentage (e.g., 5%, 6%, 7%, 10%, 15%, 20%, 25%, 27%, 30%, 35%, or 40% or greater number) of CD27+ CD45RO− immune effector cells, e.g., in the CD8+ population, compared to a reference value, e.g., a non-responder number of CD27+ CD45RO− immune effector cells.

In some embodiments of any of the methods and compositions for use disclosed herein, a complete responder or a partial responder has, or is identified as having, a greater, e.g., a statistically significant greater, percentage of CD4+ T cells compared to a reference value, e.g., a non-responder percentage of CD4+ T cells.

In some embodiments of any of the methods and compositions for use disclosed herein, a complete responder has, or is identified as having, a greater percentage of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, compared to a reference value, e.g., a non-responder number of resting $T_{EFF}$ cells, resting $T_{REG}$ cells, younger T cells (e.g., younger CD4 or CD8 cells), or early memory T cells.

In some embodiments of any of the methods and compositions for use disclosed herein, a non-responder has, or is identified as having, a greater percentage of one, two, three, or more (e.g., all) of activated $T_{EFF}$ cells, activated $T_{REG}$ cells, older T cells (e.g., older CD4 or CD8 cells), or late memory T cells, or a combination thereof, compared to a reference value, e.g., a responder number of activated $T_{EFF}$ cells, activated $T_{REG}$ cells, older T cells (e.g., older CD4 or CD8 cells), or late memory T cells.

In some embodiments of any of the methods and compositions for use disclosed herein, a non-responder has, or is identified as having, a greater percentage of an immune cell exhaustion marker, e.g., one, two or more immune checkpoint inhibitors (e.g., PD-1, TIM-3 and/or LAG-3). In one embodiment, a non-responder has, or is identified as having, a greater percentage of PD-1 or LAG-3 expressing immune effector cells (e.g., CD4+ T cells and/or CD8+ T cells) (e.g., CAR-expressing CD4+ cells and/or CD8+ T cells) compared to the percentage of PD-1 or LAG-3 expressing immune effector cells from a responder.

In some embodiments of any of the methods and compositions for use disclosed herein, a non-responder has, or is identified as having, a greater percentage of immune cells having an exhausted phenotype, e.g., immune cells that co-express at least two exhaustion markers, e.g., co-expresses PD-1 and TIM-3. In other embodiments, a non-responder has, or is identified as having, a greater percentage of immune cells having an exhausted phenotype, e.g., immune cells that co-express at least two exhaustion markers, e.g., co-expresses PD-1 and LAG-3.

In some embodiments of any of the methods and compositions for use disclosed herein, a non-responder has, or is identified as having, a greater percentage of PD-1+/LAG-3+ cells in the CAR-expressing cell population (e.g., a CAR19+ cell population) compared to a responder (e.g., a complete responder) to the CAR-expressing cell therapy.

In some embodiments of any of the methods and compositions for use disclosed herein, a partial responder has, or is identified as having, a higher percentages of PD-1+/LAG-3+ cells, than a responder, in the CAR-expressing cell population (e.g., a CAR19+ cell population).

In some embodiments of any of the methods and compositions for use disclosed herein, a non-responder has, or is identified as having, an exhausted phenotype of PD1+ CAR+ and co-expression of LAG3 in the CAR-expressing cell population (e.g., a CAR19+ cell population).

In some embodiments of any of the methods and compositions for use disclosed herein, a non-responder has, or is identified as having, a greater percentage of PD-1+/TIM-3+ cells in the CAR-expressing cell population (e.g., a CAR19+ cell population) compared to the responder (e.g., a complete responder).

In some embodiments of any of the methods and compositions for use disclosed herein, a partial responders has, or is identified as having, a higher percentage of PD-1+/TIM-3+ cells, than responders, in the CAR-expressing cell population (e.g., a CAR19+ cell population).

In some embodiments of any of the methods and compositions for use disclosed herein, the presence of CD8+ CD27+ CD45RO− T cells in an apheresis sample is a positive predictor of the subject response to a CAR-expressing cell therapy (e.g., a CAR19 therapy (e.g., CTL019 therapy)).

In some embodiments of any of the methods and compositions for use disclosed herein, a high percentage of PD1+ CAR+ and LAG3+ or TIM3+ T cells in an apheresis sample is a poor prognostic predictor of the subject response to a CAR-expressing cell therapy (e.g., a CAR19 therapy (e.g., CTL019 therapy)).

In some embodiments of any of the methods and compositions for use disclosed herein, a responder (e.g., a complete responder) to a CAR19 therapy has, or is identified as having, the biomarker profile of Table 9.

In some embodiments of any of the methods and compositions for use disclosed herein, a non-responder to a CAR19 therapy has, or is identified as having, the biomarker comprising one or more of PD-1+ immune effector cells, TIM-3+ immune effector cells, LAG-3+ immune effector cells, KLRG1+ immune effector cells, CD27-immune effector cells, activated $T_{EFF}$ cells, activated $T_{REG}$ cells, activated TH1, activated TH2 cells, stimulated memory cells, or late T memory cells, or a combination thereof, In some embodiments of any of the methods and compositions for use disclosed herein, a non-responder to a CAR19 therapy has, or is identified as having, the biomarker profile of Table 10.

In some embodiments of any of the methods and compositions for use disclosed herein, expression of one, two, three, four or more (all) of KLRG1, CD57, CD27, CD122, or CD62L is predictive of patient response to CTL019 therapy.

In some embodiments of any of the methods and compositions for use disclosed herein, a non-relapser is a patient with B-ALL, and has, or is identified as having, one or more expression profiles (e.g., protein or gene expression profiles) or gene signatures characteristic of resting $T_{EFF}$ cells or resting $T_{REG}$ cells.

In some embodiments of any of the methods and compositions for use disclosed herein, a relapser is a patient with B-ALL, and has, or is identified as having, one or more expression profiles (e.g., protein or gene expression profiles) or gene signatures characteristic of activated $T_{EFF}$ cells or activated $T_{REG}$ cells.

In some embodiments of any of the aforesaid methods and compositions for use, a $T_{REG}$ cell (e.g., an activated $T_{REG}$ cell) has upregulated expression of one or more (e.g., at least 10, 20, 30, 40, 50, 60, 70, or all) of the following biomarkers: AIM2, ALAS1, BATF, C5orf32, CCL17, CD40LG, CHAC2, CSF1, CTSL1, EBNA1BP2, EDARADD, EMP1, EPAS1, FABP5, FAM40B, FKBP4, FOSL1, GCLM, GK, GPR56, HMOX1, HSPD1, HSPE1, IKBIP, IL10, IL13, IL15RA, IL1RN, IL2RA, IL3, IL4, IL5, IL9, KCNK5, LTA, MANF, MIR1182, MIR155, MIR155HG, MYOF, NDUFAF1, NLN, NME1, NME1-NME2, PANX2, PDIA6, PGAM4, PPIL1, PPPDE2, PRDX4, PRKAR1B, PSMD1, PSMD11, PUS7, RBBP8, SLC27A2, SLC39A14, SLC43A3, SRXN1, STIP1, STT3A, TBX21, TNFRSF11A, TNFRSF1B, TNFRSF8, TNFRSF9, TXN, UCK2, VDR, VTRNA1-3, WDR12, YWHAG, ZDHHC16, or ZNF282. The upregulated expression may be, e.g., measured 16 hours after stimulation. The upregulated expression may be determined, e.g., by measuring RNA levels for the indicated genes.

In some embodiments of any of the aforesaid methods and compositions for use, a $T_{EFF}$ cell (e.g., an activated $T_{EFF}$ cell) has upregulated expression of one or more (e.g., at least 10, 20, 30, 40, 50, 60, 70, or all) of the following biomarkers: AIM2, ALAS1, B4GALT5, BATF, C3orf26, C4orf43, CCL3, CCL4, CCT3, CCT7, CD40LG, CHAC2, CSF2, CTNNA1, EBNA1BP2, EDARADD, EEF1E1, EIF2B3, EIF2S1, FABP5, FAM40B, FKBP4, FOSL1, GFOD1, GLRX2, HSPD1, HSPE1, IFNG, IL15RA, IL21, IL2RA, IL3, KCNK5, KIAA0020, LARP4, LRP8, LTA, MANF, MIR1182, MIR155, MIR155HG, MTCH2, MYOF, NDUFAF1, NLN, NME1, NME1-NME2, OTUD7B, PAM, PDIA6, PEA15, PFKM, PGAM1, PGAM4, PPIL1, PRDX4, PRSS23, PSMD1, PSMD11, PSMD14, PTRH2, PUS7, RBBP8, RPF2, RPP25, SFXN1, SLC27A2, SLC39A14, SLC43A3, SORD, SPR, SRXN1, STIP1, STT3A, TBX21, TMCC2, TMEM165, TNFRSF9, TXN, TXNDC5, UCK2, VDR, WDR12, YWHAG, or ZDHHC16. The upregulated expression may be, e.g., measured 16 hours after stimulation. The upregulated expression may be determined, e.g., by measuring RNA levels for the indicated genes.

In some embodiments of any of the methods and compositions for use disclosed herein, a relapser is a patient with B-ALL and has, or is identified as having, one or more protein or gene expression profiles comprising one, two, three, four, five, ten or more genes according to Table 7A, Table 7B or FIG. 2B or a combination thereof.

In some embodiments of any of the methods and compositions for use disclosed herein, a relapser has, or is identified as having, an elevated level of one or more $T_{REG}$ cell biomarkers, or a combination thereof. In some embodiments, the relapser has, or is identified as having, upregulated expression of one or more (e.g., at least 10, 20, 30, 40, 50, 60, 70, or all) of the following genes: AIM2, ALAS1, BATF, C5orf32, CCL17, CD40LG, CHAC2, CSF1, CTSL1, EBNA1BP2, EDARADD, EMP1, EPAS1, FABP5, FAM40B, FKBP4, FOSL1, GCLM, GK, GPR56, HMOX1, HSPD1, HSPE1, IKBIP, IL10, IL13, IL15RA, IL1RN, IL2RA, IL3, IL4, IL5, IL9, KCNK5, LTA, MANF, MIR1182, MIR155, MIR155HG, MYOF, NDUFAF1, NLN, NME1, NME1-NME2, PANX2, PDIA6, PGAM4, PPIL1, PPPDE2, PRDX4, PRKAR1B, PSMD1, PSMD11, PUS7, RBBP8, SLC27A2, SLC39A14, SLC43A3, SRXN1, STIP1, STT3A, TBX21, TNFRSF11A, TNFRSF1B, TNFRSF8, TNFRSF9, TXN, UCK2, VDR, VTRNA1-3, WDR12, YWHAG, ZDHHC16, or ZNF282. In certain embodiment, the relapser has, or is identified as having, upregulated expression of one or more (e.g., at least 10, 20, 25, or all) of the following genes: C5orf32, CCL17, CSF1, CTSL1, EMP1, EPAS1, GCLM, GK, GPR56, HMOX1, IKBIP, IL10, IL13, IL1RN, IL4, IL5, IL9, MIR155, PANX2, PGAM4, PRKAR1B, TNFRSF11A, TNFRSF1B, TNFRSF8, VTRNA1-3, or ZNF282. The upregulated expression may be, e.g., measured 16 hours after stimulation. The upregulated expression may be determined, e.g., by measuring RNA levels for the indicated genes.

In some embodiments of any of the methods and compositions for use disclosed herein, a subject has, or is identified as having, an elevated level of one or more $T_{EFF}$ cell biomarkers, or a combination thereof. In some embodiments, the subject has, or is identified as having, upregulated expression of one or more (e.g., at least 10, 20, 30, 40, 50, 60, 70, or all) of the following genes: AIM2, ALAS1, B4GALT5, BATF, C3orf26, C4orf43, CCL3, CCL4, CCT3, CCT7, CD40LG, CHAC2, CSF2, CTNNA1, EBNA1BP2, EDARADD, EEF1E1, EIF2B3, EIF2S1, FABP5, FAM40B, FKBP4, FOSL1, GFOD1, GLRX2, HSPD1, HSPE1, IFNG, IL15RA, IL21, IL2RA, IL3, KCNK5, KIAA0020, LARP4, LRP8, LTA, MANF, MIR1182, MIR155, MIR155HG, MTCH2, MYOF, NDUFAF1, NLN, NME1, NME1-NME2, OTUD7B, PAM, PDIA6, PEA15, PFKM, PGAM1, PGAM4, PPIL1, PRDX4, PRSS23, PSMD1, PSMD11, PSMD14, PTRH2, PUS7, RBBP8, RPF2, RPP25, SFXN1, SLC27A2, SLC39A14, SLC43A3, SORD, SPR, SRXN1, STIP1, STT3A, TBX21, TMCC2, TMEM165, TNFRSF9, TXN, TXNDC5, UCK2, VDR, WDR12, YWHAG, or ZDHHC16. In certain embodiment, the subject has, or is identified as having, upregulated expression of one or more (e.g., at least 10, 20, 25, or all) of the following genes: B4GALT5, C3orf26, C4orf43, CCL3, CCL4, CCT3, CCT7, CSF2, CTNNA1, EEF1E1, EIF2B3, EIF2S1, GFOD1, GLRX2, IL21, IL2RA, IL3, KIAA0020, LARP4, LRP8, OTUD7B, PAM, PEA15, PFKM, PGAM1, PGAM4, PRSS23, PSMD1, PSMD11, PSMD14, PTRH2, RPF2, SORD, SPR, TMCC2, TMEM165, or TXNDC5. The upregulated expression may be, e.g., measured 16 hours after stimulation. The upregulated expression may be determined, e.g., by measuring RNA levels for the indicated genes.

In some embodiments of any of the methods and compositions for use disclosed herein, the responder (e.g., the complete or partial responder) has one, two, three or more (or all) of the following profile:

(i) has a greater number of CD27+ immune effector cells compared to a reference value, e.g., a non-responder number of CD27+ immune effector cells;

(ii) has a greater number of CD8+ T cells compared to a reference value, e.g., a non-responder number of CD8+ T cells;

(iii) has a lower number of immune cells expressing one or more checkpoint inhibitors, e.g., a checkpoint inhibitor chosen from PD-1, LAG-3, TIM-3, or KLRG-1, or a combination, compared to a reference value, e.g., a non-responder number of cells expressing one or more checkpoint inhibitors; or (iv) has a greater number of one, two, three, four or more (all) of resting $T_{EFF}$ cells, resting $T_{REG}$ cells, younger cells, naïve CD4 cells, unstimulated memory cells or early memory T cells, or a combination thereof, compared to a reference value, e.g., a non-responder number of resting $T_{EFF}$ cells, resting $T_{REG}$ cells, naïve CD4 cells, unstimulated memory cells or early memory T cells.

In some embodiments of any of the methods and compositions for use disclosed herein, the cytokine level or activity, e.g., of (vi), is chosen from one, two, three, four, five, six, seven, eight, or more (or all) of cytokine CCL20/MIP3a, IL17A, IL6, GM-CSF, IFNγ, IL10, IL13, IL2, IL21, IL4, IL5, IL9 or TNFα, or a combination thereof. The cytokine can be chosen from one, two, three, four or more (all) of IL-17a, CCL20, IL2, IL6, or TNFα. In one embodiment, an increased level or activity of a cytokine is chosen from one or both of IL-17a and CCL20, is indicative of increased responsiveness or decreased relapse. In some embodiments, the cytokine level is measured after T cell activation.

In some embodiments of any of the methods and compositions for use disclosed herein, a transduction efficiency of 15% or higher, e.g., in (vii), is indicative of increased responsiveness or decreased relapse.

In some embodiments of any of the methods and compositions for use disclosed herein, a transduction efficiency of less than 15%, e.g., in (vii), is indicative of decreased responsiveness or increased relapse.

In another aspect, the invention features a method to identify a likely responder (e.g., a complete responder or a partial responder, a non-relapser) to a therapy comprising a CAR-expressing cell (e.g., a T cell, an NK cell) (e.g., a CD19 CAR-expressing cell therapy, e.g., described herein, e.g., a CTL019 therapy). In an embodiment, a responder status (e.g. a complete responder, a partial responder, a non-responder, a relapser or a non-relapser to a therapy comprising a CAR-expressing cell (e.g., a T cell, an NK cell)) is determined by measuring one or more of a CD19 CAR-expressing cell gene set signature, a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and combinations thereof. In one embodiment, a complete responder (CR) has, e.g., two, three, four or more (e.g., all) of CD27+, CD45RO−, PD-1−, LAG-3−, and TIM-3−, as described in Table 9. In one embodiment, a non-responder (NR) has, e.g., two, three, or more of (e.g., all) of CD27− CD45RO+, PD-1+, LAG-3+, and TIM-3+, as described in Table 10.

In an embodiment, the responder or relapser status (e.g. complete responder, partial responder, non-responder, relapser or non-relapser to a CAR-expressing cell therapy) is determined by evaluating, e.g., measuring, two, three, four, five, six, seven, eight, nine, ten, fifteen or more of a CD19 CAR-expressing cell gene set signature, a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1.

In an embodiment, any of the methods and compositions for use disclosed herein can be used prior to administration of a CAR-expressing cell therapy. In some embodiments, provided methods can be used before, at the same time, or during course of a CAR-expressing cell therapy.

In an embodiment, any of the methods and compositions for use disclosed herein can be used to identify a subject having cancer, e.g., a hematological cancer such as, e.g., CLL or ALL, as having an increased or a decreased likelihood to respond to a treatment that comprises a CAR-expressing cell (e.g., T cell, NK cell) therapy, e.g., a CD19 CAR-expressing cell therapy. The method comprises: (1) acquiring a sample from the subject (e.g., an apheresis sample obtained from the blood of the subject; and/or e.g., a manufactured product sample, e.g., genetically engineered T cells); (2) determining a level (e.g., amount or activity) of one or more biomarkers (e.g., 2, 3, 4, 5, 10, 15 or more) listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 in the sample; and (3) (optionally) comparing the determined level of the one or more markers to a reference level; and (4) identifying the subject as a complete responder, partial responder, non-responder, a relapser or non-relapser to the CAR-expressing cell therapy. In embodiments, a difference, e.g., a statistically significant difference, between the determined level compared to a reference level is predictive of the subjects responsiveness to the CAR-expressing cell therapy.

In an aspect, provided methods comprise (1) acquiring a sample (e.g., an apheresis sample obtained from the subject; and/or e.g., a manufactured product sample, e.g., genetically engineered T cells, e.g., a manufactured CD19 CAR-expressing cell product); (2) acquiring, e.g., determining a gene signature of the sample; and (3) (optionally) comparing the gene signature to a reference gene signature; wherein a difference, e.g., a statistically significant difference, in expression level of one or more of the biomarkers in the determined gene signature is predictive of the subjects responsiveness to the CAR-expressing cell therapy. In an embodiment, the gene signature comprises one or more markers selected from Table 1A, Table 1B, Table 2, Table 3, Table 4, Table 5, Table 6, Table 7A, Table 7B, Table 8, Table 9, Table 10, Table 14 (e.g., CCL20, IL-17a and/or IL-6), Table 17, Table 18, Table 20, PD-1, LAG-3, TIM-3, CD57, CD27, CD122, CD62L, KLRG1, and combinations thereof. In one embodiment, the sample is a biological sample selected from a blood, plasma, or a serum sample. In a particular embodiment, a biological sample is a blood sample. In an embodiment, the sample is an apheresis sample, e.g., immune effector cells (e.g., T cells) obtained from the blood of the subject. In an embodiment, the sample is a manufactured product sample, e.g. genetically engineered T cells, e.g., a manufactured CD19 CAR-expressing cell product.

In an aspect, methods are provided for determining the responsiveness of a subject having cancer, e.g., a hematological cancer such as, e.g., CLL or ALL, to a treatment comprising a CAR-expressing cell (e.g., a T cell, an NK cell) therapy, e.g., a CD19 CAR-expressing cell therapy, e.g., described herein. The method includes: determining a level or activity of one or more biomarkers (e.g., 2, 3, 4, 5, 10, 15 or more) listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 in a sample obtained prior to treatment; wherein a difference, e.g., a statistically significant difference, in a level (e.g., amount or activity) of one or more markers in the sample relative to a predetermined value is indicative of increased responsiveness to the CAR-expressing cell. In one embodiment, the sample is a biological sample selected from a blood, plasma, or a serum sample. In a particular embodiment, a biological sample is a blood sample. In one embodiment, the sample is an apheresis sample, e.g., T cells obtained from the blood of the subject. In an embodiment, the sample is a manufactured product sample, e.g. genetically engineered T cells, e.g., obtained from the blood of the subject, e.g., a manufactured CAR-expressing cell product, e.g., a manufactured CD19 CAR-expressing cell product.

In an embodiment, methods are provided for evaluating a subject having cancer, e.g., a hematological cancer such as, e.g., CLL or ALL, comprising acquiring a value of responder or relapser status for the subject that comprises a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4+ biomarker, a CD8+ biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and a CD19 CAR-expressing cell (e.g., T cell, NK cell) gene set signature, thereby evaluating the subject. In an embodiment, methods comprise a measure of one or more of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, and a CD19 CAR-expressing cell gene set signature. In one embodiment, methods comprise a measure of one or more of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, and a CD19 CAR-expressing cell gene set signature, for evaluating a subject having CLL. In another embodiment, methods comprise a measure of one or more of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, and a CD19 CAR-expressing cell gene set signature, for evaluating a subject having ALL. In one embodiment, the method comprises a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, or a CD19 CAR-expressing cell gene set signature in a biological sample selected from a blood, plasma, or a serum sample. In a particular embodiment, a biological sample is a blood sample. In an embodiment, the sample is an apheresis sample, e.g., T cells obtained from the blood of the subject. In an embodiment, the sample is a manufactured product sample, e.g. genetically engineered T cells, e.g., obtained from the blood of the subject, e.g., a manufactured CAR-expressing cell product, e.g., a manufactured CD19 CAR-expressing cell product.

In an embodiment, methods are provided for evaluating or monitoring the effectiveness of a CAR-expressing cell (e.g., T cell, NK cell) therapy, e.g., a CD19 CAR-expressing cell therapy, in a subject having cancer comprising acquiring a value of responder or relapser status for the subject that comprises a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and a CD19 CAR-expressing cell gene set signature, thereby evaluating or monitoring the effectiveness of the CAR-expressing cell therapy in the subject. In an embodiment, methods comprise a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, or a CD19 CAR-expressing cell gene set signature. In an embodiment, methods comprise a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, or a CD19 CAR-expressing cell gene set signature, for evaluating or monitoring the effectiveness of a CAR-expressing cell therapy in a subject having CLL. In another embodiment, methods comprise a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, or a CD19 CAR-expressing cell gene set signature, for evaluating or monitoring the effectiveness of a CAR-expressing cell therapy in a subject having ALL. In one embodiment, the method comprises a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, or a CD19 CAR-expressing cell gene set signature in a biological sample selected from a blood, plasma, or a serum sample. In one embodiment, a biological sample is a blood sample. In an embodiment, the sample is an apheresis sample, e.g., T cells obtained from the blood of the subject. In an embodiment, the sample is a manufactured product sample, e.g. genetically engineered T cells, e.g., obtained from the blood of the subject.

In an embodiment, methods are provided for providing a prediction for success rate of a CAR-expressing cell therapy, e.g., a CD19 CAR-expressing cell therapy, e.g., described herein, in a subject having cancer, said method comprising steps of providing a biological sample from the subject; determining the levels of expression of one or more (e.g., 2, 3, 4, 5, 10, 15 or more) genes listed in Table 1A, Table 1B, Table 7A, Table 7B, Table 8, Table 9, Table 10, Table 14, Table 15, Table 16 (e.g., CCL20, IL-17a and/or IL-6), and Table 17 to obtain a gene expression pattern for the sample; and based on the gene expression pattern obtained, providing a prognosis to the subject. In an embodiment, a biological sample includes, but is not limited to a blood, plasma, or a serum sample. In a particular embodiment, a biological sample is a blood sample. In one embodiment, the sample is an apheresis sample, e.g., T cells obtained from the blood of the subject. In an embodiment, the subject has CLL. In an embodiment, the subject has ALL.

In another aspect, methods for treating a subject having cancer, e.g., a hematological cancer, are provided. In an embodiment, methods are provided for treating a subject having cancer determining if a subject has a difference, e.g., a statistically significant difference, in expression level of one or more (e.g., 2, 3, 4, 5, 10, 15 or more) markers listed in Table 1A, Table 1B, Table 7A, Table 7B, Table 8, Table 9, Table 10, Table 14, Table 15, Table 16 (e.g., CCL20, IL-17a and/or IL-6) and Table 17 relative to a reference level, and if there is a difference, e.g., a statistically significant difference, between the determined level and reference level, administering to the subject a therapeutically effective dose of a CAR-expressing cell (e.g., T cell, NK cell), thereby treating the subject. In an embodiment, wherein there is a difference, e.g., a statistically significant difference, between the determined level and reference level, the method comprises modifying the CAR-expressing cell product prior to infusion into the subject. In an embodiment, wherein there is a difference, e.g., a statistically significant difference, between the determined level and the reference level, the method comprises modifying the manufacture of a CAR-expressing cell product prior to infusion into the subject. In an embodiment, if there is a difference, e.g., a statistically significant difference, between the determined level and reference level, the method comprises adjusting the CAR-expressing cell infusion dose to achieve an anti-cancer effect.

In an embodiment, the methods of treatment described herein comprise determining if a subject has an increased likelihood to respond to a CAR-expressing cell (e.g., T cell, NK cell) therapy, e.g., a CD19 CAR-expressing cell therapy, e.g., a CD19 CAR-expressing cell therapy described herein, by comparing the level of one or more (e.g., 2, 3, 4, 5, 10, 15 or more) markers in Table 1A, Table 1B, Table 7A, Table 7B, Table 8, Table 9, Table 10, Table 14, Table 15 and Table 16 (e.g., CCL20, IL-17a and/or IL-6) in a sample from the subject relative to a reference level, wherein a difference, e.g., a statistically significant difference, in expression level of one or more maker genes relative to the reference level is indicative of an increased likelihood of response; and administering to the subject a therapeutically effective dose of a CAR-expressing cell, thereby treating the subject. In one embodiment, the sample is selected from a blood, plasma or a serum sample. In one embodiment, the sample is an apheresis sample, e.g., T cells obtained from the blood of the subject.

In an embodiment, the methods of treatment described herein further comprise obtaining a sample from a subject; determining a level of one or more (e.g., 2, 3, 4, 5, 10, 15 or more) markers in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1, in the sample; comparing the determined level of one or more markers in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1, to a reference level; and administering a therapeutically effective dose of a CAR-expressing cell (e.g., T cell, NK cell), if the subject is identified as having a difference, e.g., a statistically significant difference, in the determined level of one or more markers in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1, to a reference level in the sample.

In an embodiment, the methods of treatment described herein comprise, or further comprise, acquiring a value of responder or relapser status for the subject that comprises a measure of one or more (e.g., 2, 3, 4, 5, 10, 15 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and a CD19 CAR-expressing cell gene set signature, and responsive to a determination of responder or relapser status, performing one, two, three four or more of: identifying the subject as a complete responder, partial responder or non-responder; administering a CAR-expressing cell therapy; selecting or altering a dosing of a CAR-expressing cell therapy; selecting or altering the schedule or time course of a CAR-expressing cell therapy; administering, e.g., to a non-responder or a partial responder, an additional agent in combination with a CAR-expressing cell therapy, e.g., a checkpoint inhibitor, e.g., a checkpoint inhibitor described herein, or a kinase inhibitor, e.g., a kinase inhibitor described herein; administering to a non-responder or partial responder a therapy that increases the number of naïve T cells in the subject prior to treatment with a CAR-expressing cell therapy; modifying a manufacturing process of a CAR-expressing cell therapy, e.g., enrich for naïve T cells prior to introducing a nucleic acid encoding a CAR, e.g., for a subject identified as a non-responder or a partial responder; or selecting an alternative therapy, e.g., a standard of care for a particular cancer (e.g., as described herein), e.g., for a non-responder, partial responder or relapser; thereby treating cancer in the subject.

Systems

In still another aspect, the present disclosure provides kits for predicting subject response to CAR-expressing cell (e.g., T cell, NK cell) therapy, e.g., a CD19 CAR-expressing cell therapy, e.g., a CD19 CAR-expressing cell therapy described herein. The kits comprise at least one reagent that specifically detects the level or activity of a set of genes (e.g., 2, 3, 4, 5, 10, 15 or more of the genes) selected from Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and/or KLRG1; and instructions for using the kits, e.g., for predicting a subject's response to a CAR-expressing cell therapy. In some embodiments, said instructions for use provide that if one or more of the detected expression levels is different from, e.g., greater than a reference level, the subject is more likely to respond positively to a CAR-expressing cell therapy. In some embodiments, said instructions for use provide that if one or more of the detected expression levels is less than a reference level, the subject is more likely to respond positively to a CAR-expressing cell therapy. In some embodiments, if the level or activity of PD-1, LAG-3, or TIM-3, or any combination thereof, is less than a reference value, the subject is more likely to respond positively to the therapy.

In certain embodiments, at least one reagent that specifically detects expression levels of the set of genes comprises a nucleic acid probe complementary to mRNA expressed from the genes, for example a cDNA or an oligonucleotide. The nucleic acid probe may be immobilized on a substrate surface or may be in solution. The set of reagents may detect the expression of polypeptides, e.g., surface polypeptides, encoded by said set of genes. In one embodiment, the nucleic acid probe comprises a nucleic acid of about 10, 15, 20, 25, 30, 35, 40, 45, 50 or 100 nucleic acid residues complementary the nucleic acid sequence of a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and/or KLRG1. The kits may further comprise one or more of: extraction buffer/reagents and protocol, amplification buffer/reagents and protocol, hybridization buffer/reagents and protocol, and labeling buffer/reagents and protocol.

In certain embodiments, the kits further comprise at least one CD19 CAR-expressing cell (e.g., T cell, NK cell) gene set signature. In one embodiment, the kit further comprises a reference standard.

In an embodiment, the subject has CLL.
In an embodiment, the subject has ALL.
In an embodiment, the subject has B-cell ALL.

In an aspect, the disclosure features a reaction mixture comprising at least one reagent that specifically detects expression levels of a set of genes (e.g., 2, 3, 4, 5, 10, 15 or more of the genes) selected from Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and/or KLRG1; and a biological sample. In one embodiment, the sample is selected from a blood, plasma or a serum sample. In one embodiment, the sample is an apheresis sample, e.g., T cells obtained from the blood of the subject. In one embodiment, the sample comprises CAR-expressing cells, e.g., CART-expressing cells, e.g., CART19 cells.

In certain embodiments, at least one reagent that specifically detects expression levels of the set of genes comprises a nucleic acid probe complementary to mRNA expressed from the genes, for example a cDNA or an oligonucleotide. The nucleic acid probe may be immobilized on a substrate surface or may be in solution. The set of reagents may detect the expression of polypeptides, e.g., surface polypeptides, encoded by said set of genes. In one embodiment, the nucleic acid probe comprises a nucleic acid of about 10, 15, 20, 25, 30, 35, 40, 45, 50 or 100 nucleic acid residues complementary the nucleic acid sequence of a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and/or KLRG1. The reaction mixture may further comprise one or more of: extraction buffer/reagents, amplification buffer/reagents, hybridization buffer/reagents, and labeling buffer/reagents.

In another aspect, the present disclosure features a system for evaluating cancer in a subject. The system comprises at least one processor operatively connected to a memory, the at least one processor when executing is configured to perform any one or more of the steps described herein.

In still another aspect, the present disclosure features a system for evaluating cancer in a subject. The system includes at least one processor operatively connected to a memory, the at least one processor when executing is configured to:

acquire a value of responder or relapser status that comprises a measure of one, two, three, four, five, six, seven or more (all) of the following:

(i) the level or activity of CD27 and/or CD45RO− (e.g., CD27+ CD45RO−) immune effector cells, e.g., in a CD4+ or a CD8+ T cell population in a sample (e.g., an apheresis sample or a manufactured CAR-expressing cell product sample);

(ii) the level or activity of one, two, three, or more (e.g., all) of resting $T_{EFF}$ cells, resting $T_{REG}$ cells, younger T cells (e.g., younger CD4 or CD8 cells, or gamma/delta T cells), early memory T cells, or a combination thereof, in a sample (e.g., an apheresis sample or a manufactured CAR-expressing cell product sample);

(iii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in a sample (e.g., an apheresis sample or a manufactured CAR-expressing cell product sample);

(iv) the level or activity of an immune cell exhaustion marker, e.g., one, two or more immune checkpoint inhibitors (e.g., PD-1, TIM-3 and/or LAG-3) in a sample (e.g., an apheresis sample or a manufactured CAR-expressing cell product sample);

(v) the level or activity of one, two, three, four, five, ten, twenty or more of the biomarkers listed in Table 1A, Table 1B, Table 7A, Table 7B, Table 8, Table 9, Table 10, Table 14 (e.g., CCL20, IL-17a and/or IL-6), Table 16, Table 17, Table 18, Table 20, FIG. 2B, PD-1, LAG-3, TIM-3, CD57, CD27, CD122, CD62L, KLRG1, or a CD19 CAR-expressing cell gene set signature;

(vi) a cytokine level or activity (e.g., quality of cytokine repertoire) in a CAR-expressing cell product sample, e.g., CAR19-expressing cell product sample (e.g., CTL019), wherein the cytokine is chosen from one, two, three, four, five or more (or all) of the cytokines listed in Table 16;

(vii) a transduction efficiency of a CAR-expressing cell in a manufactured CAR-expressing cell product sample; or (viii) a quantity of CD27+ PD-1− cells in a subject, e.g., a sample from the subject (e.g., an apheresis sample or a CAR-expressing cell product sample, e.g., CAR19-expressing cell product sample (e.g., CTL019)), e.g., a quantity greater than or equal to $1\times10^7$ cells.

responsive to a determination of the value of responder status, perform one, two, three, four, five, six, seven, or more (e.g., all) of:

identify the subject as a complete responder, partial responder, non-responder, relapser or non-relapser;

recommend administering a CAR-expressing cell therapy;

recommend a selection or alteration of a dosing of a CAR-expressing cell therapy;

recommend a selection or alteration of a schedule or time course of a CAR-expressing cell therapy;

recommend administering, e.g., to a non-responder or a partial responder, an additional agent in combination with a CAR-expressing cell therapy, e.g., a checkpoint inhibitor, e.g., a checkpoint inhibitor described herein;

recommend administering to a non-responder or partial responder a therapy that increases the number of naïve T cells in the subject prior to treatment with a CAR-expressing cell therapy;

recommend modifying a manufacturing process of a CAR-expressing cell therapy, e.g., enrich for naïve T cells prior to introducing a nucleic acid encoding a CAR, e.g., for a subject identified as a non-responder or a partial responder;

recommend modifying the CAR-expressing cell product prior to infusion into the patient;

recommend adjusting the CAR-expressing cell infusion dose to achieve clinical efficacy;

recommend administering an alternative therapy, e.g., for a non-responder or partial responder or relapser;

recommend a selection of an alternative therapy, e.g., for a non-responder or partial responder, e.g., a standard of care for a particular cancer type, or if the subject is, or is identified as, a non-responder or a relapser, recommend decreasing the $T_{REG}$ cell population and/or $T_{REG}$ gene signature, e.g., by CD25 depletion, administration of cyclophosphamide, anti-GITR antibody, mTOR inhibitor, or a combination thereof.

In one embodiment, the value includes a measure of a CD19 CAR-expressing cell gene set signature and a combination of one or more (e.g., 2, 3, 4, 5, 10, 15 or more) of: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, and a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature; and responsive to a determination of the value of responder status, perform one, two, three, four or more of: identify the subject as a complete responder, partial responder, or non-responder; recommend a CAR-expressing cell therapy; recommend a selection or alteration of a dosing of a CAR-expressing cell therapy; recommend an alternative therapy, recommend a combination therapy, e.g., a combination with a CAR-expressing cell therapy, recommend or alter a manufacturing process of a CAR-expressing cell therapy.

In one embodiment, the at least one processor when executing is configured to: acquire a value of responder status that comprises a measure of a CD19 CAR-expressing cell gene set signature and a combination of one or more (e.g., 2, 3, 4, 5, 10, 15 or more) of: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1; and responsive to a determination of the value of responder status, perform one, two, three, four or more of: identify the subject as a complete responder, partial responder, or non-responder; recommend a CAR-expressing cell therapy; recommend a selection or alteration of a dosing of a CAR-expressing cell therapy; recommend an alternative therapy, e.g., a standard of care for a particular cancer (e.g., as described herein); recommend a combination therapy, e.g., a combination with a CAR-expressing cell therapy, recommend or alter a manufacturing process of a CAR-expressing cell therapy, e.g., as described herein.

Manufacturing Methods

In another aspect, the invention features a method of evaluating the potency of a CAR-expressing cell product, e.g., CAR19-expressing cell product sample (e.g., CTL019). The method includes acquiring a value for one, two, three, four, five, six, seven, eight, or more (e.g., all) of:

(i) the level or activity of CD27 and/or CD45RO− (e.g., CD27+ CD45RO−) immune effector cells, e.g., in a CD4+ or a CD8+ T cell population, in the CAR-expressing cell product;

(ii) the level or activity of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, in the CAR-expressing cell product;

(iii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in the CAR-expressing cell product;

(iv) the level or activity of an immune cell exhaustion marker, e.g., one, two or more immune checkpoint inhibitors (e.g., PD-1, TIM-3 and/or LAG-3) in the CAR-expressing cell product;

(v) the level or activity of one, two, three, four, five, ten, twenty or more of the biomarkers listed in Table 1A, Table 1B, Table 7A, Table 7B, Table 8, Table 9, Table 10, Table 14 (e.g., CCL20, IL-17a and/or IL-6), Table 16, Table 17, Table 18, Table 20, FIG. 2B, PD-1, LAG-3, TIM-3, CD57, CD27, CD122, CD62L, KLRG1, or a CD19 CAR-expressing cell gene set signature;

(vi) a cytokine level or activity in a CAR-expressing cell product sample, e.g., CAR19-expressing cell product sample (e.g., CTL019), wherein the cytokine is chosen from one, two, three, four, five or more (or all) of the cytokines listed in Table 16;

(vii) a transduction efficiency of CAR-expressing cells in the product;

(viii) a quantity of CD27+ PD-1− cells in a subject, e.g., a sample from the subject (e.g., an apheresis sample or a CAR-expressing cell product sample, e.g., CAR19-expressing cell product sample (e.g., CTL019)), e.g., a quantity greater than or equal to $1 \times 10^7$ cells; or (ix) the level or activity of a $T_{REG}$ cell or cell population, wherein an increase in (i), (ii), (vi), (vii), (viii), or any combination thereof, is indicative of increased potency of the CAR-expressing cell product, and wherein an increase in (iii), (iv), (ix), or any combination thereof is indicative of decreased potency of the CAR-expressing cell product.

In a related aspect, the invention features a method for optimizing manufacturing of a CAR-expressing cell product, e.g., CAR19-expressing cell product sample (e.g., CTL019). The method includes:

(1) acquiring a sample comprising CAR-expressing cell (e.g., a population of CAR-expressing immune effector cells);

(2) activating the CAR-expressing cell in vitro;

(3) evaluating the potency of the potency of the activated CAR-expressing cell by determining one, two, three, four, five, six, seven, eight, or more (e.g., all) of:

(i) the level or activity of CD27 and/or CD45RO− (e.g., CD27+ CD45RO−) immune effector cells, e.g., in a CD4+ or a CD8+ T cell population, in the CAR-expressing cell product;

(ii) the level or activity of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, in the CAR-expressing cell product;

(iii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in the CAR-expressing cell product;

(iv) the level or activity of an immune cell exhaustion marker, e.g., one, two or more immune checkpoint inhibitors (e.g., PD-1, TIM-3 and/or LAG-3) in the CAR-expressing cell product;

(v) the level or activity of one, two, three, four, five, ten, twenty or more of the biomarkers listed in Table 1A, Table 1B, Table 7A, Table 7B, Table 8, Table 9, Table 10, Table 14 (e.g., CCL20, IL-17a and/or IL-6), Table 16, Table 17, Table 18, Table 20, FIG. 2B, PD-1, LAG-3, TIM-3, CD57, CD27, CD122, CD62L, KLRG1, or a CD19 CAR-expressing cell gene set signature;

(vi) a cytokine level or activity in a CAR-expressing cell product sample, e.g., CAR19-expressing cell product sample (e.g., CTL019), wherein the cytokine is chosen from one, two, three, four, five or more (or all) of the cytokines listed in Table 16;

(vii) a transduction efficiency of CAR-expressing cells in the product;

(viii) a quantity of CD27+ PD-1− cells in a subject, e.g., a sample from the subject (e.g., an apheresis sample or a CAR-expressing cell product sample, e.g., CAR19-expressing cell product sample (e.g., CTL019)), e.g., a quantity greater than or equal to $1 \times 10^7$ cells; or (ix) the level or activity of a $T_{REG}$ cell or cell population, wherein an increase in (i), (ii), (vi), (vii), (viii), or any combination thereof is indicative of increased potency of the CAR-expressing cell product, and wherein an increase in (iii), (iv), (ix), or any combination thereof, is indicative of decreased potency of the CAR-expressing cell product.

In a related aspect, disclosed herein is a manufacturing process of a CAR-expressing cell (e.g., T cell, NK cell) product (e.g., a CD19 CAR-expressing cell, e.g., a CD19 CAR-expressing cell described herein, e.g., CTL019) to determine the potency or efficacy of the product. In an embodiment, provided methods comprise steps of providing a biological sample from a subject, e.g., a blood, serum or plasma sample; determining the levels of expression of one or more (e.g., 2, 3, 4, 5, 10, 15 or more) genes listed in Table 1A, 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1, to obtain a gene expression pattern for the sample; (optionally) comparing the obtained gene expression pattern to a predetermined value; and determining a difference between the obtained and the predetermined value. In an embodiment, the determined difference is recorded in a quality control record.

In some embodiments, any of the methods disclosed herein further comprise a step of enriching for, e.g., isolating, cells having an increase in any of (i), (ii), (vi), (vii), (viii), or any combination thereof, or a decrease in any of (iii), (iv), (ix), or any combination thereof.

In another aspect, the invention features a method for manufacturing of a product sample, e.g., genetically engineered T cells, e.g., obtained from the blood of a subject, e.g., a manufactured CAR-expressing cell (e.g., T cell, NK cell) product, e.g., a CD 19 CAR-expressing cell product, e.g., a CD19 CAR-expressing cell product described herein, e.g., CTL019). In an embodiment, the method comprises:

providing a manufactured product sample, e.g., genetically engineered T cells, e.g., obtained from the blood of a subject, e.g., a manufactured CAR-expressing cell product, e.g., a CD 19 CAR-expressing cell product, e.g., a CD19 CAR-expressing cell product described herein, e.g., CTL019);

(i) acquiring a cytokine expression profile (e.g., of Table 14, Table 15 or Table 16 (e.g., CCL20, IL-6 and/or IL-17a) secreted from the CAR-expressing cell product; and/or (ii) acquiring measure of a transduction efficiency of CAR-expressing cells in the product;

identifying the CAR-expressing cell product as suitable for administration based on the determined cytokine level or transduction efficiency (or both); and optionally, selecting the CAR-expressing cell product for administration to a subject, thereby manufacturing a CAR-expressing cell product.

In certain embodiments of the aforesaid manufacturing methods, the cytokine is chosen from one, two, three, four, five, six, seven, eight, or more (or all) of CCL20/MIP3a, IL17A, IL6, GM-CSF, IFNγ, IL10, IL13, IL2, IL21, IL4, IL5, IL9 or TNFα, or a combination thereof. In one embodiment, the cytokine is chosen from one, two, three, four or more (all) of IL-17a, CCL20, IL2, IL6, or TNFa. For example, the cytokine can be chosen from: one or both of IL-17a and CCL20; one or both of CCL20/MIP3a and IL17A; or one, two, or all of CCL20/MIP3a, IL17A and IL6. In one embodiment, the cytokine is CCL20/MIP3a. In another embodiment, the cytokine is IL17A. In yet another embodiment, the cytokine is IL6.

In certain embodiments of the aforesaid manufacturing methods, a transduction efficiency of 15% or higher is indicative of increased potency. In other embodiments, a transduction efficiency of less than 15% is indicative of decreased potency.

In certain embodiments, any of the aforesaid manufacturing methods further comprise reducing the number (e.g., depleting) $T_{REG}$ cells, e.g., via CD25-depletion, GITR depletion, or mTOR inhibition. Alternatively, or in combination, the manufacturing methods further comprise contacting the sample, e.g., the apheresis sample, with an anti-GITR antibody.

In certain embodiments, any of the aforesaid manufacturing methods each of (i), (ii) or (iii), (iv), (v), (vi), (vii), (viii), (ix), or any combination thereof (e.g., all) are evaluated following activation in vitro.

In an embodiment, the cytokine profile includes one or more (e.g., one, two, three, four, five, six or more) of CCL20 (also referred to as MIP3a), IL-17a, IL-6, GM-CSF, IFNγ, IL-10, IL-13, IL-2, IL-21, IL-4, IL-5, IL-9 and TNFα. In an embodiment, the cytokine profile includes CCL20. In an embodiment, the cytokine profile includes IL-17a. In an embodiment, the cytokine profile includes IL-6. In one embodiment, the cytokine profile includes two or more (e.g., all three) of CCL20, IL-17a and IL-6.

In one embodiment, the method further includes determining an expression level of one or more cytokines of Table 14, Table 15 or Table 16 (e.g., CCL20, IL-17a and/or IL-6) secreted by the CAR-expressing cell (e.g., T cell, NK cell) product. In an embodiment, secretion of one or more cytokines of Table 14, Table 15 or Table 16 (e.g., CCL20, IL-17a and/or IL-6) is in response to CAR-expressing cell product stimulation with one or more target tumor antigen(s).

In an embodiment, the cytokine signature or level described herein is indicative of the potency of a CAR-expressing cell product. In an embodiment, cytokine signatures described herein are markers of response to a CAR-expressing cell product in a hematological cancer (e.g., CLL and ALL).

In an embodiment, the cytokine signature or level described herein predict subject response to a CAR-expressing cell product.

In an embodiment, the cytokine signature or level described in Table 16 predict subject response to a CAR-expressing cell product.

In an embodiment, the IL-17a and CCL-20 expression level predict subject response to a CAR-expressing cell product.

In an embodiment, the method further includes one or more of (e.g., one, two, three or all of): obtaining a blood sample, e.g., a population of T cells obtained from the blood of a subject; activating the population of T cells, e.g., by a method described herein; genetically engineering a cell from the population of T cells, e.g., transducing a cell from the population of T cells, with a vector comprising a nucleic acid encoding a CAR, e.g., a CAR described herein, e.g., a CD19 CAR described herein, e.g., CTL019; expanding a population of T cells that comprises a genetically engineered T cell, e.g., a cell transduced with a nucleic acid encoding a CAR, e.g., a CAR described herein, e.g., a CD19 CAR described herein, e.g., by a method described herein.

In an embodiment, the CAR transduction efficiency described herein is indicative of subject's response to a CAR-expressing cell therapy in a hematological cancer (e.g., CLL and ALL).

In an embodiment, a CAR transduction efficiency described herein is predictive of subject response to CAR-expressing cell therapy in a hematological disease (e.g., CLL and ALL).

In an embodiment, a cytokine signature or level described herein is used to improve and/or modify CAR-expressing cell product (e.g., a CD19 CAR-expressing cell product such as, e.g., CTL019) prior to infusion in patients.

In an embodiment, a cytokine signature or level described herein is used to assess manufactured CAR-expressing cell (e.g., T cell, NK cell) products. In an embodiment, the cytokine signature or level described herein provide an end point in manufacturing process optimization.

In an embodiment, any of the aforesaid manufacturing methods comprise a step of recording the result of the comparison in a quality control record for the CAR-expressing cell (e.g., T cell, NK cell) preparation (e.g., a CD19 CAR-expressing cell preparation as described herein such as, e.g., CTL019). In an embodiment, the method further comprises obtaining a preparation of T cells from a subject identified as a partial responder or non-responder and increasing the number of naïve T cells in the preparation. In one embodiment, the method further comprises introducing a nucleic acid encoding a CAR into the T cell preparation.

In an embodiment, the method further comprises obtaining a preparation of immune effector cells (e.g., T cells) from a subject identified as a partial responder or non-responder and who has been subsequently treated with an agent that increases the number of naïve T cells in the subject, e.g., the subject has been treated with a kinase inhibitor, e.g., an mTOR inhibitor, e.g., as described herein, and/or a checkpoint inhibitor, e.g., as described herein. In one embodiment, the method further comprises introducing a nucleic acid encoding a CAR into a plurality of the immune effector cells (e.g., T cells) of the preparation.

In an embodiment, the CAR-expressing cell (e.g., T cell, NK cell) product is a CD19 CAR-expressing cell, e.g., a CD19 CAR-expressing cell described herein, e.g., CTL019.

In still another aspect, the present disclosure provides one or more gene signatures or expression profiles that discriminate relapsers to CAR-expressing cell (e.g., T cell, NK cell) therapy from non-relapsers to CAR-expressing cell therapy in a cancer, e.g., a hematological cancer (e.g., ALL and CLL).

In an embodiment, the one or more gene signatures or expression profiles described herein enable manufactured product improvements, thereby reducing the likelihood of patient relapse. In an embodiment, gene signatures described herein are used to modify therapeutic application of manufactured product, thereby reducing the likelihood of patient relapse.

In an embodiment, the one or more gene signatures or expression profiles described herein are identified in a subject prior to CAR-expressing cell treatment (e.g., a CD19 CAR-expressing cell treatment, e.g., CTL019 therapy) that predict relapse to CAR-expressing cell treatment. In an embodiment, the one or more gene signatures or expression profiles described herein are identified in an apheresis sample. In an embodiment, the one or more gene signatures or expression profiles described herein are identified in a bone marrow sample. In an embodiment, the one or more gene signatures or expression profiles described herein are identified in a manufactured CAR-expressing cell product (e.g., a CD19 CAR-expressing cell product, e.g., CTL019) prior to infusion.

In an embodiment, decreasing the $T_{REG}$ level or gene signature in a subject prior to apheresis or during manufacturing of a CAR-expressing cell product significantly reduces the risk of subject relapse.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment (e.g., CTL019 treatment). In an embodiment, methods of decreasing $T_{REG}$ cells include, but are not limited to, administration to the subject of one or more of cyclophosphamide, anti-GITR antibody, CD25-depletion, mTOR inhibitor, or a combination thereof. Administration of one or more of cyclophosphamide, anti-GITR antibody, CD25-depletion, mTOR inhibitor, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment (e.g., CTL019 treatment).

In an embodiment, a subject is pre-treated with an anti-GITR antibody prior to collection of cells for CAR-expressing cell product manufacturing, thereby reducing the risk of subject relapse to CAR-expressing cell treatment (e.g., CTL019 treatment).

In an embodiment, a CAR-expressing cell manufacturing process is modified to deplete $T_{REG}$ cells prior to manufacturing of the CAR-expressing cell product (e.g., a CTL019 product). In an embodiment, CD25-depletion is used to deplete $T_{REG}$ cells prior to manufacturing of the CAR-expressing cell product (e.g., a CTL019 product). Accordingly, in some embodiments, the method further comprises:

a. providing a population of immune effector cells (e.g., T cells or NK cells); and b. removing T regulatory cells from the population, thereby providing a population of T regulatory-depleted cells;

wherein steps a) and b) are performed prior to introducing the nucleic acid encoding the CAR to the population.

In embodiments of the methods, the T regulatory cells comprise CD25+ T cells, and are removed from the cell population using an anti-CD25 antibody, or fragment thereof. The anti-CD25 antibody, or fragment thereof, can be conjugated to a substrate, e.g., a bead.

In other embodiments, the population of T regulatory-depleted cells provided from step (b) contains less than 30%, 25%, 20%, 15%, 10%, 5%, 4%, 3%, 2%, 1% of CD25+ cells.

In yet other embodiments, the method further comprises removing cells from the population which express a tumor antigen that does not comprise CD25 to provide a population of T regulatory-depleted and tumor antigen depleted cells prior to introducing the nucleic acid encoding a CAR to the population. The tumor antigen can be selected from CD19, CD30, CD38, CD123, CD20, CD14 or CD11b, or a combination thereof.

In other embodiments, the method further comprises removing cells from the population which express a checkpoint inhibitor, to provide a population of T regulatory-depleted and inhibitory molecule depleted cells prior to introducing the nucleic acid encoding a CAR to the population. An inhibitory molecule, e.g., a checkpoint inhibitor, can be chosen from PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta), e.g., as described herein.

Further embodiments disclosed herein encompass providing a population of immune effector cells. The population of immune effector cells provided can be selected based upon the expression of one or more of CD3, CD28, CD4, CD8, CD45RA, and/or CD45RO. In certain embodiments, the population of immune effector cells provided are CD3+ and/or CD28+.

In certain embodiments of the method, the method further comprises expanding the population of cells after the nucleic acid molecule encoding a CAR has been introduced.

In embodiments, the population of cells is expanded for a period of 8 days or less.

In certain embodiments, the population of cells is expanded in culture for 5 days, and the resulting cells are more potent than the same cells expanded in culture for 9 days under the same culture conditions.

In other embodiments, the population of cells is expanded in culture for 5 days, and shows at least a one, two, three or four fold increase in cell doublings upon antigen stimulation as compared to the same cells expanded in culture for 9 days under the same culture conditions.

In yet other embodiments, the population of cells is expanded in culture for 5 days, and the resulting cells exhibit higher proinflammatory IFN-γ and/or GM-CSF levels, as compared to the same cells expanded in culture for 9 days under the same culture conditions.

In other embodiments, the population of cells is expanded by culturing the cells in the presence of an agent that stimulates a CD3/TCR complex associated signal and/or a ligand that stimulates a costimulatory molecule on the surface of the cells. The agent can be a bead conjugated with anti-CD3 antibody, or a fragment thereof, and/or anti-CD28 antibody, or a fragment thereof.

In other embodiments, the population of cells is expanded in an appropriate media that includes one or more interleukin that result in at least a 200-fold, 250-fold, 300-fold, or 350-fold increase in cells over a 14 day expansion period, as measured by flow cytometry.

In other embodiments, the population of cells is expanded in the presence IL-15 and/or IL-7.

In certain embodiments, the method further includes cryopreserving the population of the cells after the appropriate expansion period.

In yet other embodiments, the method of making disclosed herein further comprises contacting the population of immune effector cells with a nucleic acid encoding a telomerase subunit, e.g., hTERT. The nucleic acid encoding the telomerase subunit can be DNA.

In yet other embodiments, the method of making disclosed herein further comprises culturing the population of immune effector cells in serum comprising 2% hAB serum.

In any of the methods, systems and kits described herein, the CD19 CAR can comprise an anti-CD19 binding domain described in Table 12, or CDRs, e.g., one or more (e.g., all) of HC CDR1, HC CDR2, HC CDR3, LC CDR1, LC CDR2, and LC CDR3 of an anti-CD19 binding domain described in Table 12. In an embodiment, the CAR can comprise one of more of: a leader sequence, e.g., a leader sequence described herein, e.g., in Table 11; an anti-CD19 binding domain, e.g., an anti-CD19 binding domain described herein, e.g., in Table 12; a hinge region, e.g., a hinge region described herein, e.g., a hinge region described in Table 11; a transmembrane domain, e.g., a transmembrane domain described herein, e.g., in Table 11; and an intracellular signaling domain (e.g., a costimulatory domain and/or a primary signaling domain, e.g., a costimulatory domain described herein, e.g., in Table 11 and/or a primary signaling domain described herein, e.g., in Table 11). In an embodiment, the CD19 CAR-expressing cell (e.g., T cell, NK cell) is CTL019 or a CD19 CAR described in Table 13.

Although methods and materials similar or equivalent to those described herein can be used in the practice or testing of the present invention, suitable methods and materials are described below. All publications, patent applications, patents, and other references (e.g., sequence database reference numbers) mentioned herein are incorporated by reference in their entirety. For example, all GenBank, Unigene, and Entrez sequences referred to herein, e.g., in any Table herein, e.g., in any of Table 1A, Table 1B, Table 7A, Table 7B, Table 8, Table 14, Table 17, Table 18, and Table 20, are incorporated by reference. Unless otherwise specified, the sequence accession numbers specified herein, including in any Table herein, e.g., in any of Table 1A, Table 1B, Table 7A, Table 7B, Table 8, Table 14, Table 17, Table 18, and Table 20, refer to the database entries current as of Oct. 8, 2014. When one gene or protein references a plurality of sequence accession numbers, all of the sequence variants are encompassed.

In addition, the materials, methods, and examples are illustrative only and not intended to be limiting. Headings, sub-headings or numbered or lettered elements, e.g., (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIG. 7A depicts an exemplary result illustrating percent CD4+ cells and patient response. FIG. 7B depicts an exemplary result illustrating percent CD8+ cells and patient response.

FIG. 8A and FIG. 8B are representative flow cytometry profiles demonstrating the distribution of PD-1 and CAR19 expression on CD4+ T cells from subjects that are complete responders (CR) or non-responders (NR) to CAR-expressing cell therapy. FIG. 8C is a graph showing the percent of PD1 cells in the CD4+ T cell population from groups of subjects with different responses to CAR-expressing cell therapy. FIG. 8D is a graph showing the percent of PD1 cells in the CD8+ T cell population from groups of subjects with different responses to CAR-expressing cell therapy.

FIG. 19A depicts an exemplary scatter plot showing log-normalized correlation of IL17A (y-axis) and CCL20 (x-axis) expression. Dashed lines represent the classification boundary for separating NRs from CRs/PRs. Each dot represents a CLL patient, and the cross-hatch (NR), black (PR) and white (CR) represent the clinical response. The correlation coefficient is represented by "r" (e.g., a correlation coefficient of 0.928) and corresponding p-value for correlation using "p.value" (e.g., corresponding p-value of 1.36e-09).

DEFINITIONS

Figure 1:
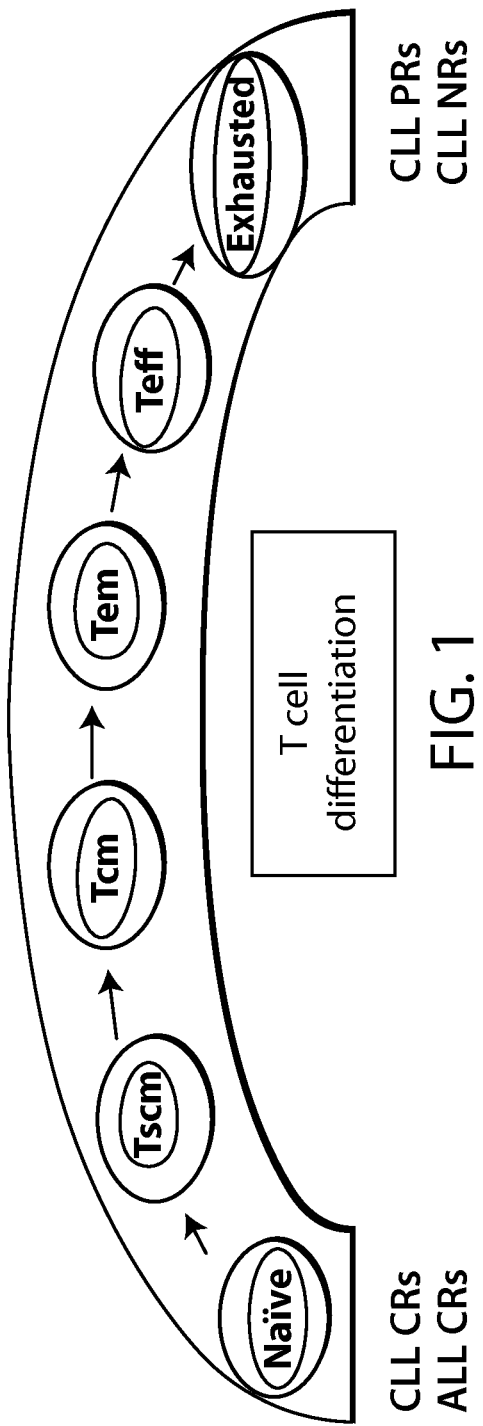
FIG. 1 depicts an exemplary model illustrating findings from a whole genome CTL019 RNAseq analysis performed on T cells at apheresis and after CTL019 manufacturing for 21 CLL and 7 ALL samples. This model demonstrates that expression patterns of complete responders (CRs) have a younger T cell phenotype than non-responders (NRs). Memory T cell subsets are differentially enriched between CRs versus NRs with CRs showing similarity to T memory stem cells.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

"Acquire" or "acquiring" as the terms are used herein, refer to obtaining possession of a physical entity (e.g., a sample, a polypeptide, a nucleic acid, or a sequence), or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "altered level of expression" of a biomarker as described herein (e.g., a biomarker listed in Table 1A, Table 1B, Table 7A, Table 7B, Table 8, Table 9, Table 10, Table 14, Table 15, Table 16, Table 18, Table 20, PD-1, LAG-3, TIM-3, CD57, CD27, CD122, CD62L, KLRG1, and a CD19 CAR-expressing cell (e.g., T cell, NK cell) gene signature) refers to an increase (or decrease) in the expression level of a marker in a test sample, such as a sample derived from a patient suffering from cancer (e.g., a hematological cancer such as ALL and CLL) that is greater or less than the standard error of the assay employed to assess expression. In embodiments, the alteration can be at least twice, at least twice three, at least twice four, at least twice five, or at least twice ten or more times greater than or less than the expression level of the biomarkers in a control sample (e.g., a sample from a healthy subject not having the associated disease), or the average expression level in several control samples. An "altered level of expression" can be determined at the protein or nucleic acid (e.g., mRNA) level.

The term "antibody fragment" refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies). The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "apheresis" as used herein refers to an extracorporeal process by which the blood of a donor or patient is removed from the donor or patient and passed through an apparatus that separates out selected particular constituent(s) and returns the remainder to the circulation of the donor or patient, e.g., by retransfusion, Thus, in the context of "an apheresis sample" refers to a sample obtained using apheresis.

The term "autologous" refers to any material derived from the same individual to whom it is later to be re-introduced into the individual.

A "biomarker" or "marker" is a gene, mRNA, or protein that undergoes alterations in expression that are associated with progression of cancer (e.g., a hematological cancer such as ALL and CLL) or responsiveness to treatment. The alteration can be in amount and/or activity in a biological sample (e.g., a blood, plasma, or a serum sample) obtained from a subject having cancer, as compared to its amount and/or activity, in a sample obtained from a baseline or prior value for the subject, the subject at a different time interval, an average or median value for a cancer patient population, a healthy control, or a healthy subject population (e.g., a control); such alterations in expression and/or activity are associated with of the responsiveness of a subject having a cancer disease state (e.g., a hematological cancer such as ALL and CLL) to a CAR-expressing cell (e.g., a CAR-expressing immune effector cell (e.g., a CAR-expressing T cell, NK cell) therapy, e.g., a CD19 CAR-expressing cell therapy. For example, a marker of the invention which is predictive of responsiveness to therapeutics can have an altered expression level, protein level, or protein activity, in a biological sample obtained from a subject having, or suspected of having, cancer as compared to a biological sample obtained from a control subject.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. Cancers include, but are not limited to, B-cell acute lymphocytic leukemia (B-ALL), T-cell acute lymphocytic leukemia (T-ALL), acute lymphocytic leukemia (ALL), chronic myelogenous leukemia (CML), chronic lymphocytic leukemia (CLL), B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, and Waldenstrom macroglobulinemia. In an embodiment, the cancer is associated with CD19 expression. The terms "tumor" and "cancer" are used interchangeably herein, e.g., both terms encompass solid and liquid tumors. As used herein, the term "cancer" or "tumor" includes premalignant, as well as malignant cancers and tumors.

The terms "cancer associated antigen" or "tumor antigen" interchangeably refers to a molecule (typically protein, carbohydrate or lipid) that is preferentially expressed on the surface of a cancer cell, either entirely or as a fragment (e.g., MHC/peptide), in comparison to a normal cell, and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a cancer-associated antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

As used herein, the term "CD19" refers to the Cluster of Differentiation 19 protein, which is an antigenic determinant detectable on leukemia precursor cells. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleotide sequence encoding of the human CD19 can be found at Accession No. NM_001178098. As used herein, "CD19" includes proteins comprising mutations, e.g., point mutations, fragments, insertions, deletions and splice variants of full length wild-type CD19. CD19 is expressed on most B lineage cancers, including, e.g., acute lymphoblastic leukemia, chronic lymphocyte leukemia and non-Hodgkin lymphoma. Other cells which express CD19 are provided below in the definition of "disease associated with expression of CD19." It is also an early marker of B cell progenitors. See, e.g., Nicholson et al., MOL. IMMUN. 34 (16-17): 1157-1165 (1997). In one aspect the antigen-binding portion of the CAR-expressing cell (e.g., T cell, NK cell) recognizes and binds an antigen within the extracellular domain of the CD19 protein. In one aspect, the CD19 protein is expressed on a cancer cell. In one embodiment, the CD19 has a wild-type sequence, e.g., a wild-type human sequence. In another embodiment, the CD19 has a mutant sequence, e.g., a mutant human sequence.

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below.

In some embodiments, the set of polypeptides are in the same polypeptide chain (e.g., comprise a chimeric fusion protein). In some embodiments, the set of polypeptides are not contiguous with each other, e.g., are in different polypeptide chains. In some aspects, the set of polypeptides include a dimerization switch that, upon the presence of a dimerization molecule, can couple the polypeptides to one another, e.g., can couple an antigen binding domain to an intracellular signaling domain. In one aspect, the stimulatory molecule of the CAR is the zeta chain associated with the T cell receptor complex. In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27, ICOS, and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., a scFv) during cellular processing and localization of the CAR to the cellular membrane. In an embodiment, the CAR is CTL019.

The portion of the CAR composition comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: USING ANTIBODIES: A LABORATORY MANUAL, COLD SPRING HARBOR LABORATORY PRESS, NY; Harlow et al., 1989, In: ANTIBODIES: A LABORATORY MANUAL, Cold Spring Harbor, N.Y.; Houston et al., 1988, PROC. NATL. ACAD. SCI. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The phrase "disease associated with expression of CD19" includes, but is not limited to, a disease associated with expression of CD19 (e.g., wild type or mutant CD19) or condition associated with cells which express, or at any time expressed, CD19 including, e.g., proliferative diseases such as a cancer or malignancy or a precancerous condition such as a myelodysplasia, a myelodysplastic syndrome or a preleukemia; or a noncancer related indication associated with cells which express CD19. For the avoidance of doubt, a disease associated with expression of CD19 may include a condition associated with cells which do not presently express CD19, e.g., because CD19 expression has been downregulated, e.g., due to treatment with a molecule targeting CD19, e.g., a CD19 CAR, but which at one time expressed CD19. In one aspect, a cancer associated with expression of CD19 is a hematological cancer. In one aspect, the hematological cancer is a leukemia or a lymphoma. In one aspect, a cancer associated with expression of CD19 includes cancers and malignancies including, but not limited to, e.g., one or more acute leukemias including but not limited to, e.g., acute myeloid leukemia (AML), B-cell acute lymphocytic leukemia ("B-ALL"), T-cell acute lymphocytic leukemia ("T-ALL"), acute lymphocytic leukemia (ALL); one or more chronic leukemias including but not limited to, e.g., chronic myelogenous leukemia (CML), chronic lymphocytic leukemia (CLL). Additional cancers or hematologic conditions associated with expression of CD19 comprise, but are not limited to, e.g., B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, myeloproliferative neoplasm; a histiocytic disorder (e.g., a mast cell disorder or a blastic plasmacytoid dendritic cell neoplasm); a mast cell disorder, e.g., systemic mastocytosis or mast cell leukemia; B-cell prolymphocytic leukemia, plasma cell myeloma, and "preleukemia" which are a diverse collection of hematological conditions united by ineffective production (or dysplasia) of myeloid blood cells, and the like. Further diseases associated with expression of CD19 expression include, but not limited to, e.g., atypical and/or non-classical cancers, malignancies, precancerous conditions or proliferative diseases associated with expression of CD19. Non-cancer related indications associated with expression of CD19 include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein. In other embodiments, the disease is a CD19-negative cancer, e.g., a CD19-negative relapsed cancer. In some embodiments, the tumor antigen (e.g., CD19)-expressing cell expresses, or at any time expressed, mRNA encoding the tumor antigen. In an embodiment, the tumor antigen (e.g., CD19)-expressing cell produces the tumor antigen protein (e.g., wild-type or mutant), and the tumor antigen protein may be present at normal levels or reduced levels. In an embodiment, the tumor antigen (e.g., CD19)-expressing cell produced detectable levels of a tumor antigen protein at one point, and subsequently produced substantially no detectable tumor antigen protein.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to MHC class I molecule, TNF receptor proteins, Immunoglobulin-like proteins, cytokine receptors, integrins, signalling lymphocytic activation molecules (SLAM proteins), activating NK cell receptors, BTLA, a Toll ligand receptor, OX40, CD2, CD7, CD27, CD28, CD30, CD40, CD5, ICAM-1, LFA-1 (CD11a/CD18), 4-1BB (CD137), B7-H3, CD5, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain refers to an intracellular portion of a costimulatory molecule. The intracellular signaling domain can comprise the entire intracellular portion, or the entire native intracellular signaling domain, of the molecule from which it is derived, or a functional fragment thereof.

As used herein, a "value of responder or relapser status" includes a measure (e.g., level) predictive of responsiveness or relapse of a subject to a treatment (e.g., a treatment that comprises, or consists of, a CAR-expressing cell therapy as described herein). In some embodiments, the measure is qualitative or quantitative. In some embodiments, the value of responder or relapser status is complete responder, partial responder, non-responder, relapser or non-relapser. In some embodiments, the value of responder or relapser status is a probability of being a complete responder, a partial responder, a non-responder, a relapser or a non-relapser. In some embodiments, the value of responder or relapser status can be determined based on the measure of any of (i)-(viii) as described herein.

With respect to responsiveness, a subject responds to treatment if a parameter of a cancer (e.g., a hematological cancer, e.g., cancer cell growth, proliferation and/or survival) in the subject is retarded or reduced by a detectable amount, e.g., about 5%, 10%, 20%, 30%, 40%, 50%, 60%, 70%, 80%, 90% or more as determined by any appropriate measure, e.g., by mass, cell count or volume. In one example, a subject responds to treatment if the subject experiences a life expectancy extended by about 5%, 10%, 20%, 30%, 40%, 50% or more beyond the life expectancy predicted if no treatment is administered. In another example, a subject responds to treatment, if the subject has an increased disease-free survival, overall survival or increased time to progression.

Several methods can be used to determine if a patient responds to a treatment including, for example, criteria provided by NCCN Clinical Practice Guidelines in Oncology (NCCN Guidelines®). For example, in the context of B-ALL, a complete response or complete responder, may involve one or more of: <5% BM blast, >1000 neutrophil/ANC (/μL). >100,000 platelets (/μL) with no circulating blasts or extramedullary disease (No lymphadenopathy, splenomegaly, skin/gum infiltration/testicular mass/CNS involvement), Trilineage hematopoiesis, and no recurrence for 4 weeks. A partial responder may involve one or more of ≥50% reduction in BM blast, >1000 neutrophil/ANC (/μL). >100,000 platelets (/μL). A non-responder can show disease progression, e.g., >25% in BM blasts.

A "complete responder" as used herein refers to a subject having a disease, e.g., a cancer, who exhibits a complete response, e.g., a complete remission, to a treatment. A complete response may be identified, e.g., using the NCCN Guidelines®, or Cheson et al, J Clin Oncol 17:1244 (1999) and Cheson et al., "Revised Response Criteria for Malignant Lymphoma", J Clin Oncol 25:579-586 (2007) (both of which are incorporated by reference herein in their entireties), as described herein.

A "partial responder" as used herein refers to a subject having a disease, e.g., a cancer, who exhibits a partial response, e.g., a partial remission, to a treatment. A partial response may be identified, e.g., using the NCCN Guidelines®, or Cheson criteria as described herein.

A "non-responder" as used herein refers to a subject having a disease, e.g., a cancer, who does not exhibit a response to a treatment, e.g., the patient has stable disease or progressive disease. A non-responder may be identified, e.g., using the NCCN Guidelines®, or Cheson criteria as described herein.

The term "relapse" as used herein refers to reappearance of a disease (e.g., cancer) after an initial period of responsiveness, e.g., after prior treatment with a therapy, e.g., cancer therapy (e.g., complete response or partial response). The initial period of responsiveness may involve the level of cancer cells falling below a certain threshold, e.g., below 20%, 15%, 10%, 5%, 4%, 3%, 2%, or 1%. The reappearance may involve the level of cancer cells rising above a certain threshold, e.g., above 20%, 15%, 10%, 5%, 4%, 3%, 2%, or 1%. For example, e.g., in the context of B-ALL, the reappearance may involve, e.g., a reappearance of blasts in the blood, bone marrow (>5%), or any extramedullary site, after a complete response. A complete response, in this context, may involve <5% BM blast. More generally, in an embodiment, a response (e.g., complete response or partial response) can involve the absence of detectable MRD (minimal residual disease). In an embodiment, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

In some embodiments, a therapy that includes a CD19 inhibitor, e.g., a CD19 CAR therapy, may relapse or be refractory to treatment. The relapse or resistance can be caused by CD19 loss (e.g., an antigen loss mutation) or other CD19 alteration that reduces the level of CD19 (e.g., caused by clonal selection of CD19-negative clones). A cancer that harbors such CD19 loss or alteration is referred to herein as a "CD19-negative cancer" or a "CD19-negative relapsed cancer"). It shall be understood that a CD19-negative cancer need not have 100% loss of CD19, but a sufficient reduction to reduce the effectiveness of a CD19 therapy such that the cancer relapses or becomes refractory. In some embodiments, a CD19-negative cancer results from a CD19 CAR therapy. In some embodiments, a CD19-negative multiple myeloma can be treated with a CD19 CAR-expressing therapy, e.g., as described in PCT/US2015/024671, filed Apr. 7, 2015 (e.g., paragraphs 9 and 90, and Example 6 therein), which is incorporated by reference in its entirety. In some embodiments, a CD19-negative cancer can be treated with a CAR-expressing therapy, e.g., a CD123 CAR-expressing therapy, e.g., as described in PCT/US2015/045898 filed Aug. 19, 2015 (e.g., p. 26, p. 30, and Example 7 therein) which is incorporated by reference in its entirety.

The term "endogenous" refers to any material from or produced inside an organism, cell, tissue or system.

The term "effective amount" or "therapeutically effective amount" are used interchangeably herein, and refer to an amount of a compound, formulation, material, or composition, as described herein effective to achieve a particular biological result.

The term "exogenous" refers to any material introduced from or produced outside an organism, cell, tissue or system.

The term "expression" refers to the transcription and/or translation of a particular nucleotide sequence driven by a promoter.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$, where n is a positive integer equal to or greater than 1. For example, n=1, n=2, n=3, n=4, n=5, n=6, n=7, n=8, n=9 and n=10 (SEQ ID NO:28). In one embodiment, the flexible polypeptide linkers include, but are not limited to, (Gly$_4$Ser)$_4$ (SEQ ID NO:29) or (Gly$_4$Ser)$_3$ (SEQ ID NO:30). In another embodiment, the linkers include multiple repeats of (Gly$_2$Ser), (GlySer) or (Gly$_3$Ser) (SEQ ID NO:31). Also included within the scope of the invention are linkers described in WO2012/138475, incorporated herein by reference.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantial homology," as used herein, refers to homology of at least 50%, at least 60%, at least 65%, at least 70%, at least 75%, at least 80%, at least 85%, at least 90%, at least 95% or more.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., NATURE, 321: 522-525, 1986; Reichmann et al., NATURE, 332: 323-329, 1988; Presta, CURR. OP. STRUCT. BIOL., 2: 593-596, 1992.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NK-T) cells, mast cells, and myeloid-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc No. AAA62478.2, or the equivalent residues from a non-human species, e.g., mouse, rodent, monkey, ape and the like. In one aspect, the "4-1BB costimulatory domain" is the sequence provided as SEQ ID NO:14 or the equivalent residues from a non-human species, e.g., mouse, rodent, monkey, ape and the like.

An "intracellular signaling domain," as the term is used herein, refers to an intracellular portion of a molecule. The intracellular signaling domain can generate a signal that promotes an immune effector function of the CAR containing cell, e.g., a CAR-expressing cell, e.g., a T cell or an NK cell. Examples of immune effector function, e.g., in a CAR-expressing cell include, cytolytic activity and helper activity, including the secretion of cytokines. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CAR-expressing cell (e.g., a T cell, an NK cell), a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 ("ICOS"), FcεRI, CD66d, CD32, DAP10, and DAP12.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., MOL. THER. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term 'low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive immune effector cells, e.g., T cells or NK cells and/or an increase in the number of PD-1 negative immune effector cells, e.g., T cells or NK cells, or an increase in the ratio of PD-1 negative immune effector cells, e.g., T cells or NK cells/PD-1 positive immune effector cells, e.g., T cells or NK cells.

In general, the term "naïve T cell" refers to immune cells that comprise antigen-inexperienced cells, e.g., immune cells that are precursors of memory cells. In some embodiments, naïve T cells may be differentiated, but have not yet encountered their cognate antigen, and therefore are not activated T cells or memory T cells. In some embodiments, naïve T cells may be characterized by expression of CD62L, CD27, CCR7, CD45RA, CD28, and CD127, and the absence of CD95, or CD45RO isoform. In certain embodiments, a naïve T cells is a type of younger T cell as described herein.

The term "less exhausted" or "less exhausted phenotype" refers to immune effector cells that have reduced (e.g., lack) expression of immune cell exhaustion markers, e.g. PD1, TIM3, and LAG3. In some embodiments, a less exhausted cell may be a younger T cell as described herein.

The term "nucleic acid" or "polynucleotide" refers to deoxyribonucleic acid (DNA) or ribonucleic acid (RNA), or a combination of a DNA or RNA thereof, and polymers thereof in either single- or double-stranded form. The term "nucleic acid" includes a gene, cDNA or an mRNA. In one embodiment, the nucleic acid molecule is synthetic (e.g., chemically synthesized) or recombinant. Unless specifically limited, the term encompasses nucleic acids containing analogues or derivatives of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., NUCLEIC ACID RES. 19:5081 (1991); Ohtsuka et al., J. BIOL. CHEM. 260:2605-2608 (1985); and Rossolini et al., MOL. CELL. Probes 8:91-98 (1994)). In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "nucleic acid" "marker" or "biomarker" is a nucleic acid (e.g., DNA, mRNA, cDNA) encoded by or corresponding to a marker as described herein. For example, such marker nucleic acid molecules include DNA (e.g., genomic DNA and cDNA) comprising the entire or a partial sequence of any of the nucleic acid sequences set forth, or the complement or hybridizing fragment of such a sequence. The marker nucleic acid molecules also include RNA comprising the entire or a partial sequence of any of the nucleic acid sequences set forth herein, or the complement of such a sequence, wherein all thymidine residues are replaced with uridine residues. A "marker protein" is a protein encoded by or corresponding to a marker of the invention. A marker protein comprises the entire or a partial sequence of a protein encoded by any of the sequences set forth herein, or a fragment thereof. The terms "protein" and "polypeptide" are used interchangeably herein.

An "overexpression" or "significantly higher level of expression" of the gene products refers to an expression level or copy number in a test sample that is greater than the standard error of the assay employed to assess the level of expression. In embodiments, the overexpression can be at least two, at least three, at least four, at least five, or at least ten or more times the expression level of the gene in a control sample or the average expression level of gene products in several control samples.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

As used herein, a "poly(A)" is a series of adenosines attached by polyadenylation to the mRNA. In some embodiments of a construct for transient expression, the polyA is between 50 and 5000 (SEQ ID NO: 34) (e.g., 2000; SEQ ID NO: 32), e.g., 64 (SEQ ID NO: 37), e.g., greater than 100 (e.g., 150, SEQ ID NO: 33), e.g., greater than 400 (SEQ ID NO: 38). poly(A) sequences can be modified chemically or enzymatically to modulate mRNA functionality such as localization, stability or efficiency of translation.

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes can be specifically designed to be labeled, as described herein. Examples of molecules that can be utilized as probes include, but are not limited to, RNA, DNA, proteins, antibodies, and organic monomers.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "prophylaxis" as used herein means the prevention of or protective treatment for a disease or disease state.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

In embodiments, a reference or control level or activity is the level and/or activity in a subject, e.g., a sample obtained from one or more of: a baseline or prior value for the subject (e.g., prior to treatment with a CAR-expressing cell); the subject at a different time interval; an average or median value for a cancer patient population; a healthy control; or a healthy subject population (e.g., a control).

"Sample," "tissue sample," "patient sample," "patient cell or tissue sample" or "specimen" each refers to a biological sample obtained from a tissue or bodily fluid of a subject or patient. The source of the tissue sample can be solid tissue as from a fresh, frozen and/or preserved organ, tissue sample, biopsy, or aspirate; blood or any blood constituents (e.g., serum, plasma); bodily fluids such as urine, cerebral spinal fluid, whole blood, plasma and serum. The sample can include a non-cellular fraction (e.g., urine, plasma, serum, or other non-cellular body fluid). In one embodiment, the sample is a urine sample. In other embodiments, the body fluid from which the sample is obtained from an individual comprises blood (e.g., whole blood). In an embodiment, the sample is a whole blood sample obtained from the subject. In certain embodiments, the blood can be further processed to obtain plasma or serum. In an embodiment, the sample is an apheresis sample obtained from the blood of the subject. In an embodiment, the sample is a manufactured product sample, e.g., genetically engineered T cells obtained from the blood of the subject, e.g., a manufactured CAR-expressing cell (e.g., T cell, NK cell) product, e.g., a manufactured CD19 CAR-expressing cell product. In another embodiment, the sample contains a tissue, cells (e.g., peripheral blood mononuclear cells (PBMC)). For example, the sample can be a fine needle biopsy sample, an archival sample (e.g., an archived sample with a known diagnosis and/or treatment history), a histological section (e.g., a frozen or formalin-fixed section, e.g., after long term storage), among others. The term sample includes any material obtained and/or derived from a biological sample, including a polypeptide, and nucleic acid (e.g., genomic DNA, cDNA, RNA) purified or processed from the sample. Purification and/or processing of the sample can involve one or more of extraction, concentration, antibody isolation, sorting, concentration, fixation, addition of reagents and the like. The sample can contain compounds that are not naturally intermixed with the tissue in nature such as preservatives, anticoagulants, buffers, fixatives, nutrients, antibiotics or the like.

The term "product" or "manufactured product" as used herein, refers to a manufactured composition comprising a genetically engineered cell (e.g., an immune effector cell), e.g., a population of cells in which a plurality of cells are engineered to express a CAR, e.g., a CAR described herein. A manufactured product can be any genetically engineered immune effector cell (e.g., T cell, NK cell), e.g., genetically engineered immune effector cells obtained from the blood of the subject, e.g., a manufactured CAR-expressing cell product, e.g., a manufactured CD19 CAR-expressing cell product. In an embodiment, a cell (e.g., an immune effector cell) engineered to express a CAR may be obtained from an activated cryopreserved expanded cell population (e.g., an expanded immune effector cell population).

The term "signaling domain" refers to the functional portion of a protein which acts by transmitting information within the cell to regulate cellular activity via defined signaling pathways by generating second messengers or functioning as effectors by responding to such messengers.

The amount of a biomarker, e.g., expression of gene products (e.g., one or more the biomarkers described herein), in a subject is "significantly" higher or lower than the normal amount of a marker, if the amount of the marker is greater or less, respectively, than the normal level by an amount greater than the standard error of the assay employed to assess amount, or at least two, three, four, five, ten or more times that amount. Alternatively, the amount of the marker in the subject can be considered "significantly" higher or lower than the normal amount if the amount is at least about 1.5, two, at least about three, at least about four, or at least about five times, higher or lower, respectively, than the normal amount of the marker.

The term "specifically binds," refers to an antibody, or a ligand, which recognizes and binds with a cognate binding partner protein present in a sample, but which antibody or ligand does not substantially recognize or bind other molecules in the sample.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as down regulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:18 (mutant CD3 zeta), or the equivalent residues from a non-human species, e.g., mouse, rodent, monkey, ape and the like. In a specific CAR of the invention, the primary signaling sequence of CD3-zeta is the sequence as provided in SEQ ID NO:20 (wild-type human CD3 zeta), or the equivalent residues from a non-human species, e.g., mouse, rodent, monkey, ape and the like.

The term "subject" is intended to include living organisms in which an immune response can be elicited (e.g., mammals, human). In an embodiment, a subject is a mammal. In an embodiment, a subject is a human. In an embodiment, a subject is a patient.

The term "therapeutic" as used herein means a treatment. A therapeutic effect is obtained by reduction, suppression, remission, or eradication of a disease state.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "transmembrane domain," refers to a polypeptide that spans the plasma membrane. In an embodiment, it links an extracellular sequence, e.g., a switch domain, an extracellular recognition element, e.g., an antigen binding domain, an inhibitory counter ligand binding domain, or costimulatory ECD domain, to an intracellular sequence, e.g., to a switch domain or an intracellular signaling domain. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). Examples of transmembrane domains are disclosed herein.

The terms "treat", "treatment" and "treating" refer to the reduction or amelioration of the progression, severity and/or duration of a proliferative disorder, or the amelioration of one or more symptoms (e.g., one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"- refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

An "underexpression" or "significantly lower level of expression" of products (e.g., the markers set forth herein) refers to an expression level in a test sample that is greater than the standard error of the assay employed to assess expression, for example, at least 1.5, twice, at least three, at least four, at least five, or at least ten or more times less than the expression level of the gene in a control sample, or the average expression level of gene products in several control samples.

The term "xenogeneic" refers to a graft derived from an animal of a different species.

As used herein, the term "young T cell" or "younger T cell", refers to an immune effector cell that comprises a less differentiated phenotype, e.g., a younger cell, e.g., a young T cell. In some embodiments, a younger T cell may be a naïve T cell ($T_N$). In some embodiments, a young T cell may be characterized by expression of CD62L, and the absence of CD25, CD44, or CD45RO isoform. In some embodiments, a younger T cell may be a memory stem cell ($T_{SCM}$). In some embodiments, a younger T cells may be a central memory T cell ($T_{CM}$). Phenotypic markers associated with $T_N$, $T_{SCM}$ and $T_{CM}$ are disclosed in, e.g., Maus, M. et al. (2014) Annu. Rev. Immunol. 32:189-225 (see for example, FIG. 3), incorporated by reference herein. Exemplary phenotypes of $T_N$ include one or more (or all) of the following: CD45RA+, CD45RO−, CD62L$^{high}$, CCR7$^{high}$, CD95−, CD122−, CD27$^{high}$, CD28+, CD57−, KLRG-1−, or long telomere length (or any combination of two, three, four, five, six, seven, eight, nine, or all of the aforesaid $T_N$ markers). Exemplary phenotypes of $T_{SCM}$ include one or more (or all) of the following: CD45RA+, CD45RO−, CD62L$^{high}$, CCR7$^{high}$, CD95+, CD122+, CD27$^{high}$, CD28$^{high}$, CD57−, KLRG-1−, or long telomere length (or any combination of two, three, four, five, six, seven, eight, nine, or all of the aforesaid $T_{SCM}$ markers). Exemplary phenotypes of $T_{CM}$ include one or more (or all) of the following: CD45RA−, CD45RO$^{high}$, CD62L$^{high}$, CCR7+, CD95+, CD122$^{high}$ CD27+, CD28$^{high}$ CD57−, KLRG-1−/+, or long/intermediate telomere length (or any combination of two, three, four, five, six, seven, eight, nine, or all of the aforesaid $T_{CM}$ markers).

As used herein, the term "older T cell" refers to an immune effector cell that comprises a more exhausted phenotype. In some embodiments, an older T cell may be an effector memory T cell ($T_{EM}$). In other embodiments, an older T cell may be an effector T cell ($T_{EFF}$). In other embodiments, an older T cell has an exhausted phenotype. Phenotypic markers associated with $T_{EM}$, $T_{EFF}$ and exhausted T cells are disclosed in, e.g., Maus, M. et al. (2014) Annu. Rev. Immunol. 32:189-225 (see for example, FIG. 3), incorporated by reference herein. Exemplary phenotypes of $T_{EM}$ include one or more (or all) of the following: CD45RA−/+, CD45RO$^{high}$, CD62L−, CCR7−, CD95−, CD122$^{high}$, CD27−/+, CD28−/+, CD57$^{low}$, KLRG-1+, or intermediate telomere length (or any combination of two, three, four, five, six, seven, eight, nine, or all of the aforesaid $T_{EM}$ markers). Exemplary phenotypes of $T_{EFF}$ include one or more (or all) of the following: CD45RA−/+, CD45RO+, CD62L−, CCR7−, CD95$^{high}$ CD122−/+, CD27−, CD28−, CD57+, KLRG-1$^{high}$ or short/intermediate telomere length (or any combination of two, three, four, five, six, seven, eight, nine, or all of the aforesaid $T_{EFF}$ markers). Exemplary phenotypes of an exhausted T cell phenotype include one or more (or all) of the following: CD45RA−/+, CD45RO+, CD62L−, CCR7−, CD95$^{high}$, CD122$^{low}$, CD27−, CD28−, CD57$^{high}$, KLRG-1$^{high}$, or short telomere length (or any combination of two, three, four, five, six, seven, eight, nine, or all of the aforesaid markers).

The term "zeta" or alternatively "zeta chain", "CD3-zeta" or "TCR-zeta" is defined as the protein provided as GenBank Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:18. In one aspect, the "zeta stimulatory domain" or a "CD3-zeta stimulatory domain" is the sequence provided as SEQ ID NO:20.

Various aspects of the invention are described in further detail below. Additional definitions are set out throughout the specification.

DETAILED DESCRIPTION OF CERTAIN EMBODIMENTS

Biomarkers predicting response to a therapy in subjects having cancer (e.g., a hematological cancer such as chronic lymphocytic leukemia (CLL) and acute lymphoblastic leukemia (ALL)) are provided herein.

In one aspect, biomarkers predicting response to a cell expressing a CAR, e.g., a CD19 CAR-expressing cell (e.g., T cell, NK cell) (e.g., a CD19 CAR-expressing cell described herein such as, e.g., CTL019) in subjects having CLL and ALL are provided herein.

Methods are provided for the diagnosis and monitoring of treatment of cancer (e.g., a hematological cancer such as ALL and CLL) based on detection of certain biomarkers in samples from patients who have, or are suspected of having, cancer. Further, expression of one or more such biomarkers can be used to distinguish subjects that respond favorably to a CAR-expressing cell (e.g., T cell, NK cell) therapy (e.g., "complete responders" or "CR") from subjects that don't respond to a CAR-expressing cell therapy (e.g., "non-responders" or "NR") and from subjects that have a partial response to a CAR-expressing cell therapy (e.g., "partial responders" or "PR").

Use of Biomarkers to Evaluate Disease Progression and Predict Subject Response to CAR-Expressing Cell Therapy In an embodiment, 1, 2, 3, 4, 5, 6, 7, 8, 9, 10, 15, 20 or more genes in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1 and/or a CD19 CAR-expressing cell (e.g., T cell, NK cell) gene signature can be used with methods of the present disclosure to acquire a disease progression value. The disease progression value can be used for, e.g., in evaluating the effectiveness of therapies in treating cancer (e.g., a hematological cancer such as ALL and CLL). In an embodiment, 1, 2, 3, 4, 5, 6, 7, 8, 9, 10, 15, 20 or more genes in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and/or KLRG1 and/or a CD19 CAR-expressing cell gene signature are used to classify a subject as a complete responder, partial responder, or non-responder to CAR-expressing cell therapy (e.g., a CD19 CAR-expressing cell therapy described herein such as, e.g., CTL019). In an embodiment, 1, 2, 3, 4, 5, 6, 7, 8, 9, 10, 15, 20 or more genes in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and/or KLRG1, and/or a CD19 CAR-expressing cell gene signature are used to predict a subject's responsiveness to a CAR-expressing cell therapy (e.g., a CD19 CAR-expressing cell therapy described herein such as, e.g., CTL019).

Subjects

For any of the methods and kits disclosed herein, the subject treated, or the subject from which the value is obtained, is a subject having, or at risk of having, cancer at any stage of treatment. Exemplary cancers include, but are not limited to, B-cell acute lymphocytic leukemia (B-ALL), T-cell acute lymphocytic leukemia (T-ALL), acute lymphocytic leukemia (ALL), chronic myelogenous leukemia (CML), chronic lymphocytic leukemia (CLL), B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, and Waldenstrom macroglobulinemia. In an embodiment, the cancer is a hematological cancer. In an embodiment, the cancer is ALL. In another embodiment, the cancer is CLL. In an embodiment, the cancer is associated with CD19 expression.

In an embodiment, the subject has received a pretreatment of an additional therapy, e.g., a subject that has been identified as a partial responder or non-responder and subsequently has been pretreated with an additional therapy. In an embodiment, the subject receives pretreatment with an mTOR inhibitor. In an embodiment, the mTOR inhibitor is administered at a dose or dosing schedule described herein. In one embodiment, a low, immune enhancing dose of an mTOR inhibitor is given to the subject prior to treatment with a CAR-expressing cell (e.g., a T cell, an NK cell). In an embodiment, administration of a low, immune enhancing, dose of an mTOR inhibitor, e.g., an allosteric inhibitor, e.g., RAD001, or a catalytic inhibitor, is initiated prior to administration of a CAR expressing cell described herein, e.g., T cells. In an embodiment, the CAR cells are administered after a sufficient time, or sufficient dosing, of an mTOR inhibitor, such that the level of PD1 negative immune effector cells, e.g., T cells, or the ratio of PD1 negative immune effector cells, e.g., T cells/PD1 positive immune effector cells, e.g., T cells, has been, at least transiently, increased. In an embodiment, the cell, e.g., T cell, to be engineered to express a CAR, is harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In one embodiment, the subject has received a pretreatment with a checkpoint inhibitor, e.g., a checkpoint inhibitor described herein. Examples of inhibitory molecules, e.g., checkpoint molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta). In embodiments, an inhibitory nucleic acid, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In one embodiment, the inhibitor of checkpoint molecule can be, e.g., an antibody or antibody fragment that binds to a checkpoint molecule. For example, the agent can be an antibody or antibody fragment that binds to PD1, PD-L1, PD-L2 (e.g., as described herein) or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206)). In an embodiment, the agent is an antibody or antibody fragment that binds to TIM3, e.g., as described herein. In an embodiment, the agent is an antibody or antibody fragment that binds to LAG3, e.g., as described herein. In an embodiment, the agent is an antibody or antibody fragment that binds to CEACAM, e.g., as described herein.

In an embodiment, the subject receives an additional therapy in combination with CAR-expressing cell (e.g., a T cell, an NK cell) therapy (e.g., a CD19 CAR-expressing cell therapy described herein such as, e.g., CTL019). In an embodiment, the subject receives an mTOR inhibitor, e.g., an mTOR inhibitor described herein, in combination with CAR-expressing cell therapy. In one embodiment, the mTOR inhibitor is administered at a dose and/or dosing schedule described herein. In one embodiment, the subject receives a checkpoint inhibitor, e.g., a checkpoint inhibitor described herein, in combination with CAR-expressing cell therapy. In one embodiment, the checkpoint inhibitor is administered at a dose and/or dosing schedule described herein. In an embodiment, the subject receives a kinase inhibitor, e.g., a kinase inhibitor described herein. In one embodiment, the kinase inhibitor is administered at a dose and/or dosing schedule described herein.

In an embodiment, the subject has been identified as a non-responder and the subject receives a therapy other than a CAR-expressing cell therapy, e.g., a standard of care therapy for the particular cancer type. In one embodiment, the subject receives one or more of an anti-CD20 antibody, or functional fragment thereof (e.g., ofatumumab, rituximab, obinutuzumab), an anti-CD52 antibody or functional fragment thereof (e.g., alemtuzumab), an alkylating agent (e.g., a nitrogen mustard alkylating agent such as, e.g., bendamustine HCl, chlorambucel, cyclophosphamide), a kinase inhibitor (e.g., a kinase inhibitor described herein such as, e.g., a BTK inhibitor described herein or a phosphonositide-3 kinase inhibitor described herein). In one embodiment, the subject receives a stem cell transplant.

Biomarkers Assessment
Analysis of CTL019 Biomarkers

Analysis of levels of expression and/or activity of gene products correlated with a subject's response to CAR-expressing cell (e.g., T cell, NK cell) therapy (e.g., a CD19 CAR-expressing cell therapy described herein such as, e.g., CTL019) and cancer disease progression (e.g., a hematological cancer such as CLL and ALL) has led to the identification of novel CD19 CAR-expressing cell gene signatures. For example, the present invention provides methods for evaluation of expression level of one, two, three, four, five, six, seven, eight, nine, ten, fifteen, twenty, twenty-five, thirty, thirty-five, forty, forty-five, fifty, one hundred, or more genes from Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 that comprise a CD19 CAR-expressing cell gene signature.

Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and/or KLRG1 lists genes (e.g., protein biomarkers) that are differentially expressed by complete responders compared to partial responders and non-responders.

In some embodiments, methods of the present disclosure can be used to determine the responsiveness of a subject to treatment with a CAR-expressing cell therapy (e.g., a CD19 CAR-expressing cell (e.g., T cell, NK cell) therapy described herein such as, e.g., CTL019), wherein a statistically significant difference in the amount, e.g., expression, and/or activity of a marker disclosed herein relative to a reference, e.g., a median value for a cancer patient population (e.g., a hematological cancer such as CLL and ALL), a median value for a population of healthy, cancer-free subjects, a median value for a population of non-responders or partial responders, in a subjects sample, then the more likely the disease is to respond to CAR-expressing cell therapy.

In an embodiment, the disclosure provides a method of, or assay for, identifying a subject having cancer (e.g., a hematological cancer such as CLL and ALL) as having an increased or decreased likelihood to respond to a treatment that comprises a CAR-expressing cell therapy (e.g., a CD19 CAR-expressing cell therapy described herein such as, e.g., CTL019), the method comprising:

(1) acquiring a sample from the subject;
(2) determining a level of one or more (e.g., 2, 3, 4, 5, 6, 7, 8, 9, 10, 15 or more) markers listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 in the sample; and
(3) comparing the determined level of one or more markers to a reference level; wherein a difference, e.g., statistically significant difference in the determined level to the reference level is predictive of the subjects responsiveness to the CAR-expressing cell therapy; and
(4) identifying the subject as a complete responder, partial responder or non-responder to the CAR-expressing cell therapy.

In one embodiment, the sample is a blood, plasma or a serum sample. In one embodiment, the sample is an apheresis sample, e.g., T cells obtained from the blood of the subject. In an embodiment, the sample is a manufactured product sample, e.g., genetically engineered T cells obtained from the blood of the subject, e.g., a manufactured CAR-expressing cell product, e.g., a manufactured CD19 CAR-expressing cell product.

In an embodiment, the disclosure provides a method of, or assay for, identifying a subject having a cancer including, but not limited to, B-cell acute lymphocytic leukemia (B-ALL), T-cell acute lymphocytic leukemia (T-ALL), acute lymphocytic leukemia (ALL), chronic myelogenous leukemia (CML), chronic lymphocytic leukemia (CLL), B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, and Waldenstrom macroglobulinemia. In an embodiment, the cancer is a hematological cancer. In an embodiment, the cancer is ALL. In another embodiment, the cancer is CLL. In an embodiment, the cancer is associated with CD19 expression.

In an embodiment, a CAR-expressing cell therapy comprises a CAR-expressing cell therapy described herein, e.g., CTL019.

In an embodiment, a CAR-expressing cell therapy consists of a CAR-expressing cell therapy described herein, e.g., CTL019.

In an embodiment, the disclosure provides a method of, or assay for, identifying a subject having cancer (e.g., a hematological cancer such as CLL and ALL) as having an increased or decreased likelihood to respond to a treatment that comprises a CAR-expressing cell therapy (e.g., a CD19 CAR-expressing cell therapy described herein such as, e.g., CTL019), the method comprising:
 (1) acquiring a sample from the subject;
 (2) determining a gene signature of the sample; and
 (3) comparing the determined gene signature to a reference gene signature;
wherein a difference, e.g., statistically significant difference in expression level of one or more of the markers in the determined gene signature, e.g., as compared to a predetermined value, is predictive of the subjects responsiveness to the CAR-expressing cell therapy.

In an embodiment, the disclosure provides a method of, or assay for, determining the responsiveness of a subject having cancer (e.g., a hematological cancer such as CLL and ALL) to a treatment comprising a cell expressing a CAR (e.g., a cell expressing a CD19 CAR, e.g., a CD19 CAR-expressing cell (e.g., T cell, NK cell) described herein such as, e.g., CTL019), the method comprising:
 determining a level of one or more markers listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 in a sample obtained prior to treatment;
 wherein a statistically significant difference in expression level of one or more markers in the sample relative to a predetermined value is indicative of increased responsiveness to the CAR-expressing cell.

The methods provided herein are particularly useful for identifying subjects that are likely to respond to CAR-expressing cell (e.g., T cell, NK cell) therapy (e.g., a CD19 CAR-expressing cell therapy described herein such as, e.g., CTL019) prior to initiation of such treatment (e.g., pre-therapy) or early in the therapeutic regimen. In some embodiments, expression or activity of biomarkers is measured in a subject at least 2 weeks, at least 1 month, at least 3 months, at least 6 months, or at least 1 year prior to initiation of therapy. In some embodiments, expression or activity of biomarkers is measured less than 6 months prior to the initiation of therapy. Thus, in some embodiments, expression or activity of biomarkers is measured within 6 months, 5 months, 4 months, 3 months, 2 months, 1 month, 2 weeks, 1 week, 6 days, 5 days, 4 days, 3 days, 2 days, or 1 day prior to the initiation of therapy. In other embodiments, the expression or activity of biomarkers is determined after initiation of therapy (e.g., 1 month, 2 months, 3 months, 3.5 months, 4 months, 4.5 months, 5 months, 5.5 months, 6 months).

In an embodiment, the invention provides a method of evaluating a subject having cancer (e.g., a hematological cancer such as CLL and ALL) comprising:
 acquiring a value of responder status for the subject that comprises a measure of one or more of the following:
 one or more (e.g., 2, 3, 4, 5, 6, 7, 8, 9, 10, 15, 20, 25, 30, 35, 40, 45, 50 or more) biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and a CD19 CAR-expressing cell gene set signature, thereby evaluating the subject.

In an embodiment, the disclosure provides a method of evaluating a subject having cancer (e.g., a hematological cancer such as CLL and ALL) comprising acquiring a value of responder status for the subject that comprises a measure of one or more (e.g., 2, 3, 4, 5, 6, 7, 8, 9, 10, 15, 20, 25, 30, 35, 40, 45, 50 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, and a CD19 CAR-expressing cell gene set signature, thereby evaluating the subject.

In an embodiment, the disclosure provides a method of evaluating or monitoring the effectiveness of a CAR-expressing cell therapy in a subject having cancer comprising:
 acquiring a value of responder status for the subject that comprises a measure of one or more of the following:
 a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and a CD19 CAR-expressing cell gene set signature,
thereby evaluating or monitoring the effectiveness of the CAR therapy in the subject.

In an embodiment, the disclosure provides a method of evaluating or monitoring the effectiveness of a CAR-expressing cell (e.g., T cell, NK cell) therapy (e.g., a CD19 CAR-expressing cell therapy described herein such as, e.g., CTL019) in a subject having cancer (e.g., a hematological cancer such as CLL and ALL) comprising: acquiring a value of responder status for the subject that comprises a measure of one or more (e.g., 2, 3, 4, 5, 6, 7, 8, 9, 10, 15, 20, 25, 30, 35, 40, 45, 50 or more) of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, and a CD19 CAR-expressing cell (e.g., T cell, NK cell) gene set signature, thereby evaluating or monitoring the effectiveness of the CAR-expressing cell (e.g., T cell, NK cell) therapy in the subject.

In an embodiment, the value of responder status comprises a measure of a combination of a gene signature and a biomarker.

In an embodiment, the value of the responder status comprises a measure of a CD19 CAR-expressing cell gene set signature and a combination of one or more of: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, and a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature.

In an embodiment, the value of the responder status comprises a measure of a CD19 CAR-expressing cell gene set signature and a combination of one or more of: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1.

In an embodiment, the value of the responder status comprises a measure of one or more biomarkers listed in Table 1A, Table 1B, Table 7A, Table 7B and a combination of one or more of: a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and a CD19 CAR-expressing cell gene set signature.

In an embodiment, the value of the responder status comprises a measure of one or more biomarkers listed in Table 1A, Table 1B, Table 7A, Table 7B and a combination of one or more of: CD57, CD27, CD122, CD62L, and KLRG1.

In an embodiment, the CD19 CAR-expressing cell gene signature comprises a value for expression of at least 5, 6, 7, 8, 9 or 10 genes comprising a CD19 CAR-expressing cell gene signature.

In an embodiment, the value for expression of the gene comprises a value for a transcriptional parameter, e.g., the level of an mRNA encoded by the gene.

In an embodiment, the value for expression of the protein comprises a value for a translational parameter, e.g., the level of a protein.

In an embodiment, provided methods further comprise obtaining a sample from the subject, wherein the sample comprises a cellular or tissue fraction. In an embodiment, the cellular fraction comprises blood.

In an embodiment, the measure of biomarker and/or gene signature is acquired before, at the same time, or during course of a CAR-expressing cell therapy (e.g., a CD19 CAR-expressing cell therapy described herein such as, e.g., CTL019).

In an embodiment, the measure of biomarker and/or gene signature is acquired less than 6 months, 5 months, 4 months, 3 months, 2 months, 1 month, 2 weeks, 1 week, 6 days, 5 days, 4 days, 3 days, 2 days prior to the initiation of a CAR-expressing cell therapy (e.g., a CD19 CAR-expressing cell therapy described herein such as, e.g., CTL019).

The methods described herein can also be used to monitor a positive response of a subject to CAR-expressing cell (e.g., T cell, NK cell) treatment (e.g., a CD19 CAR-expressing cell treatment described herein such as, e.g., CTL019). Such methods are useful for early detection of tolerance to therapy or to predict whether disease in a subject will progress. In such embodiments, the expression or activity of biomarkers is determined e.g., at least every week, at least every 2 weeks, at least every month, at least every 2 months, at least every 3 months, at least every 4 months, at least every 5 months, at least every 6 months, at least every 7 months, at least every 8 months, at least every 9 months, at least every 10 months, at least every 11 months, at least every year, at least every 18 months, at least every 2 years, at least every 3 years, at least every 5 years or more. It is also contemplated that expression or activity of the biomarkers is at irregular intervals e.g., biomarkers can be detected in a subject at 3 months of treatment, at 6 months of treatment, and at 7 months of treatment. Thus, in some embodiments, the expression or activity of the biomarkers is determined when deemed necessary by the skilled physician monitoring treatment of the subject.

The methods described herein can be used in treating any subject having cancer (e.g., a hematological cancer such as CLL and ALL). In one aspect, the invention pertains to methods of treating cancer (e.g., a hematological cancer such as CLL and ALL) in a subject.

In an embodiment, the disclosure provides methods for treating cancer including, but not limited to, B-cell acute lymphocytic leukemia (B-ALL), T-cell acute lymphocytic leukemia (T-ALL), acute lymphocytic leukemia (ALL), chronic myelogenous leukemia (CML), chronic lymphocytic leukemia (CLL), B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, and Waldenstrom macroglobulinemia. In an embodiment, the invention provides methods for treating ALL. In another embodiment, the invention provides methods for treating CLL. In an embodiment, the invention provides methods for treating cancer that is associated with CD19 expression.

In an embodiment, provided methods comprise administering to the subject a cell expressing a CAR, e.g. a CAR T cell, e.g. a CD19 CAR T cell, e.g., a CTL019 product, if the subject is identified as having a difference, e.g., statistically significant difference in expression level of one or more markers listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 relative to a reference level, such that the cancer (e.g., a hematological cancer such as ALL and CLL) is treated in the subject.

As discussed above, an example of a cancer that is treatable by disclosed methods is a cancer associated with expression of CD19. In one aspect, the cancer associated with expression of CD19 is a hematological cancer. In one aspect, the hematological cancer is a leukemia or a lymphoma. In one aspect, a cancer associated with expression of CD19 includes cancers and malignancies including, but not limited to, e.g., one or more acute leukemias including but not limited to, e.g., B-cell acute lymphoid leukemia ("B-ALL"), T-cell acute lymphoid leukemia ("T-ALL"), acute lymphoid leukemia (ALL); one or more chronic leukemias including but not limited to, e.g., chronic myelogenous leukemia (CML), chronic lymphocytic leukemia (CLL). Additional cancers or hematologic conditions associated with expression of CD19 include, but are not limited to, e.g., B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further, a disease associated with CD19 expression include, but not limited to, e.g., atypical and/or non-classical cancers, malignancies, precancerous conditions or proliferative diseases associated with expression of CD19.

In an embodiment, the disclosure provides a method for treating a subject having cancer (e.g., a hematological cancer such as ALL and CLL) comprising:

determining if the subject has an increased likelihood to respond to a CAR-expressing cell (e.g., T cell, NK cell) therapy (e.g., a CD19 CAR-expressing cell therapy described herein such as, e.g., CTL019) by comparing the level of one or more (e.g., 2, 3, 4, 5, 6, 7, 8, 9, 10, 15, 20, 25, 30, 35, 40, 45, 50 or more) markers in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 in a sample from the subject relative to a reference level, wherein a statistically significant difference in expression level of one or more maker genes relative to the reference level is indicative of an increased likelihood of response; and administering to the subject a therapeutically effective dose of a CAR-expressing cell therapy.

In an embodiment, the disclosure provides a method for treating a subject having cancer (e.g., a hematological cancer such as ALL and CLL), comprising:

obtaining a sample from the subject;

determining a level of one or more markers in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 in the sample;

comparing the determined level of one or more markers in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 to a reference level; and administering a therapeutically effective dose of a CAR-expressing cell (e.g., T cell, NK cell) therapy (e.g., a CD19 CAR-expressing cell therapy described herein such as, e.g., CTL019), if the subject is identified as having a statistically significant difference in the determined level of one or more markers in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 to a reference level, in the sample.

In an embodiment, the disclosure provides a method of treating cancer (e.g., a hematological cancer such as ALL and CLL) in a subject, comprising:

acquiring a value of responder status for the subject that comprises a measure of one or more of the following:

a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature, and a CD19 CAR-expressing cell gene set signature, and responsive to a determination of responder status, performing one, two, three, four or more of:

identifying the subject as a complete responder, partial responder or non-responder;

administering a CAR-expressing cell therapy (e.g., a CD19 CAR-expressing cell therapy described herein such as, e.g., CTL019);

selecting or altering a dosing of a CAR-expressing cell therapy;

selecting or altering the schedule or time course of a CAR-expressing cell therapy;

administering, e.g., to a non-responder or a partial responder, an additional agent in combination with a CAR-expressing cell therapy, e.g., a checkpoint inhibitor, e.g., a checkpoint inhibitor described herein;

administering to a non-responder or partial responder a therapy that increases the number of naïve T cells in the subject prior to treatment with a CAR-expressing cell therapy;

modifying a manufacturing process of a CAR-expressing cell therapy, e.g., enrich for naïve T cells prior to introducing a nucleic acid encoding a CAR, e.g., for a subject identified as a non-responder or a partial responder; or selecting an alternative therapy, e.g., for a non-responder or partial responder; or selecting an alternative therapy, e.g., an alternative therapy described herein, e.g., a standard of care therapy for the cancer; thereby treating cancer in a subject.

In an embodiment, the disclosure provides a method of treating cancer (e.g., a hematological cancer such as ALL and CLL) in a subject, comprising: acquiring a value of responder status for the subject that comprises a measure of one or more of the following: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, KLRG1, and a CD19 CAR-expressing cell gene set signature, and responsive to a determination of responder status, performing one, two, three four or more of: identifying the subject as a complete responder, partial responder or non-responder; administering a CAR-expressing cell therapy (e.g., a CD19 CAR-expressing cell therapy described herein such as, e.g., CTL019); selecting or altering a dosing of a CAR-expressing cell therapy; selecting or altering the schedule or time course of a CAR-expressing cell therapy; administering, e.g., to a non-responder or a partial responder, an additional agent in combination with a CAR-expressing cell therapy, e.g., a checkpoint inhibitor, e.g., a checkpoint inhibitor described herein; administering to a non-responder or partial responder a therapy that increases the number of naïve T cells in the subject prior to treatment with a CAR-expressing cell therapy; modifying a manufacturing process of a CAR-expressing cell therapy, e.g., enrich for naïve T cells prior to introducing a nucleic acid encoding a CAR into the T cells, e.g., for a subject identified as a non-responder or a partial responder; selecting an alternative therapy, e.g., a standard of care for the cancer, e.g., for a non-responder or partial responder; or selecting an alternative CAR-expressing cell therapy; thereby treating cancer in a subject.

In some embodiments, the amount of the biomarker determined in a sample from a subject is quantified as an absolute measurement (e.g., ng/mL). Absolute measurements can easily be compared to a reference value or cut-off value. For example, a cut-off value can be determined that represents a disease progressing status; any absolute values falling either above (i.e., for biomarkers that increase expression with progression of a cancer, e.g., a hematological cancer such as ALL and CLL) or falling below (i.e., for biomarkers with decreased expression with progression of a cancer, e.g., a hematological cancer such as ALL and CLL) the cut-off value are likely to be disease progressing.

Alternatively, the relative amount of a biomarker is determined. In one embodiment, the relative amount is determined by comparing the expression and/or activity of one or more biomarkers in a subject with cancer to the expression of the biomarkers in a reference parameter. In some embodiments, a reference parameter is obtained from one or more of: a baseline or prior value for the subject, the subject at a different time interval, an average or median value for a cancer subject (e.g., patient) population, a healthy control, or a healthy subject population.

The present disclosure also pertains to the field of predictive medicine in which diagnostic assays, pharmacogenomics, and monitoring clinical trials are used for predictive purposes to thereby treat an individual prophylactically. Accordingly, one aspect of the present disclosure relates to assays for determining the amount, structure, and/or activity of polypeptides or nucleic acids corresponding to one or more markers described herein, in order to determine whether an individual having cancer (e.g., a hematological cancer such as CLL and ALL) or at risk of developing cancer (e.g., a hematological cancer such as CLL and ALL) will be more likely to respond to CAR-expressing cell therapy (e.g., a CD19 CAR-expressing cell therapy described herein such as, e.g., CTL019).

Accordingly, in one aspect, the disclosure provides a method for determining whether a subject with cancer (e.g., a hematological cancer such as CLL and ALL) is likely to respond to a cell expressing a CAR, e.g., a CD19 CAR-expressing cell described herein, such as CTL019. In another aspect, the disclosure is drawn to a method for predicting a time course of disease. In still another aspect, the method is drawn to a method for predicting a probability of a significant event in the time course of the disease (e.g., reoccurrence or remission). In certain embodiments, the method comprises detecting a combination of biomarkers associated with responsiveness to treatment as described herein and determining whether the subject is likely to respond to treatment.

In an aspect, the disclosure provides a method for providing a prognosis for success rate of a CAR-expressing cell therapy (e.g., a CD19 CAR-expressing cell therapy described herein such as, e.g., CTL019) in a subject having cancer (e.g., a hematological cancer such as ALL and CLL), said method comprising steps of:

providing a biological sample from the subject;

determining the levels of expression of one or more (e.g., 2, 3, 4, 5, 6, 7, 8, 9, 10, 15, 20 or more) genes listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 to obtain a gene expression pattern for the sample; and based on the gene expression pattern obtained, providing a prognosis to the subject.

In an embodiment, the step of determining the levels of expression of the set of genes further comprises detecting the expression of mRNA expressed from said genes. In an embodiment, provided methods further comprise a step wherein determining the expression of mRNA comprises exposing said mRNA to a nucleic acid probe complementary to said mRNA.

In an embodiment, the step of determining the levels of expression of the set of genes further comprises detecting the expression of a polypeptide encoded by said genes.

In an embodiment, provided methods comprise selecting a CAR-expressing cell (e.g., T cell, NK cell) therapy (e.g., a CD19 CAR-expressing cell therapy described herein such as, e.g., CTL019) for the subject, based on the prognosis provided.

In some embodiments, the methods involve evaluation of a biological sample, e.g., a sample from a subject, e.g., a patient who has been diagnosed with or is suspected of having cancer (e.g., a hematological cancer such as CLL or ALL, e.g., presents with symptoms of CLL or ALL) to detect changes in expression and/or activity of 1, 2, 3, 4, 5, 6, 7, 8, 9, 10, 15 or more genes in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 and a CD19 CAR-expressing cell (e.g., T cell, NK cell) gene signature.

The results of the screening method and the interpretation thereof are predictive of the patient's disease progression (e.g., progression of a cancer, e.g., a hematological cancer such as ALL or CLL). According to the present invention, alterations in expression or activity of 1, 2, 3, 4, 5, 6, 7, 8, 9, 10, 15 or more genes in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 and a CD19 CAR-expressing cell (e.g., T cell, NK cell) gene signature is indicative of cancer progression (e.g., a hematological cancer such as ALL and CLL) relative to an average or median value for a cancer patient population or to an average median for a population of healthy, cancer free subjects.

In yet another embodiment, the one or more alterations, e.g., alterations in biomarker expression are assessed at pre-determined intervals, e.g., a first point in time and at least at a subsequent point in time. In one embodiment, a time course is measured by determining the time between significant events in the course of a subject's disease, wherein the measurement is predictive of whether a subject has a long time course. In another embodiment, the significant event is the progression from diagnosis to death. In another embodiment, the significant event is the progression from diagnosis to worsening disease.

Methods for Detection of Gene Expression

Biomarker expression level can also be assayed. Expression of a marker described herein can be assessed by any of a wide variety of known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the gene transcript (mRNA or cDNA made therefrom) using nucleic acid hybridization techniques are known to those of skill in the art (see e.g., Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the target cDNA.

A general principle of such diagnostic and prognostic assays involves preparing a sample or reaction mixture that can contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

In order to conduct assays with the above-mentioned approaches, the non-immobilized component is added to the solid phase upon which the second component is anchored. After the reaction is complete, uncomplexed components can be removed (e.g., by washing) under conditions such that any complexes formed will remain immobilized upon the solid phase. The detection of marker/probe complexes anchored to the solid phase can be accomplished in a number of methods outlined herein.

In another embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, ANAL. CHEM. 63:2338-2345 and Szabo et al., 1995, CURR. OPIN. STRUCT. BIOL. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes can be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques can also be utilized to separate complexed molecules from uncomplexed ones. For example, gel filtration chromatography separates molecules based on size, and through the utilization of an appropriate gel filtration resin in a column format, for example, the relatively larger complex can be separated from the relatively smaller uncomplexed components. Similarly, the relatively different charge properties of the marker/probe complex as compared to the uncomplexed components can be exploited to differentiate the complex from uncomplexed components, for example, through the utilization of ion-exchange chromatography resins. Such resins and chromatographic techniques are well known to one skilled in the art (see, e.g., Heegaard, N. H., 1998, J. MOL. RECOGNIT. Winter 11(1-6):141-8; Hage, D. S., and Tweed, S. A. J CHROMATOGR B BIOMED SCI APPL 1997 Oct. 10; 699(1-2): 499-525). Gel electrophoresis can also be employed to separate complexed assay components from unbound components (see, e.g., Ausubel et al., ed., CURRENT PROTOCOLS IN MOLECULAR BIOLOGY, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typical. Appropriate conditions to the particular assay and components thereof will be well known to one skilled in the art.

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., CURRENT PROTOCOLS IN MOLECULAR BIOLOGY, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated nucleic acid can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers described herein.

The probes can be full length or less than the full length of the nucleic acid sequence encoding the protein. Shorter probes are empirically tested for specificity. Exemplary nucleic acid probes are 20 bases or longer in length (See, e.g., Sambrook et al. for methods of selecting nucleic acid probe sequences for use in nucleic acid hybridization). Visualization of the hybridized portions allows the qualitative determination of the presence or absence of cDNA.

An alternative method for determining the level of a transcript corresponding to a marker of the present invention in a sample involves the process of nucleic acid amplification, e.g., by rtPCR (the experimental embodiment set forth in Mullis, 1987, U.S. Pat. No. 4,683,202), ligase chain reaction (Barany, 1991, Proc. Natl. Acad. Sci. USA, 88:189-193), self-sustained sequence replication (Guatelli et al., 1990, PROC. NATL. ACAD. SCI. USA 87:1874-1878), transcriptional amplification system (Kwoh et al., 1989, PROC. NATL. ACAD. SCI. USA 86:1173-1177), Q-Beta Replicase (Lizardi et al., 1988, BIO/TECHNOLOGY 6:1197), rolling circle replication (Lizardi et al., U.S. Pat. No. 5,854,033) or any other nucleic acid amplification method, followed by the detection of the amplified molecules using techniques well known to those of skill in the art. Fluorogenic rtPCR can also be used in the methods of the invention. In fluorogenic rtPCR, quantitation is based on amount of fluorescence signals, e.g., TaqMan and sybr green. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations can be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a healthy subject, or between samples from different sources.

Alternatively, the expression level can be provided as a relative expression level. To determine a relative expression level of a marker, the level of expression of the marker can be determined for 10 or more samples of normal versus cancer isolates, or even 50 or more samples, prior to the determination of the expression level for the sample in question. The mean expression level of each of the genes assayed in the larger number of samples can be determined and this can be used as a baseline expression level for the marker. The expression level of the marker determined for the test sample (absolute level of expression) then can be divided by the mean expression value obtained for that marker. This provides a relative expression level.

In certain embodiments, the samples used in the baseline determination will be from samples derived from a subject having cancer (e.g., a hematological cancer such as ALL and CLL) versus samples from a healthy subject of the same tissue type. The choice of the cell source is dependent on the use of the relative expression level. Using expression found in normal tissues as a mean expression score aids in validating whether the marker assayed is specific to the tissue from which the cell was derived (versus normal cells). In addition, as more data is accumulated, the mean expression value can be revised, providing improved relative expression values based on accumulated data. Expression data from normal cells provides a means for grading the severity of the cancer disease state.

In another embodiment, expression of a marker is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the marker, and fragments thereof. cDNA can, optionally, be amplified using any of a variety of polymerase chain reaction methods prior to hybridization with the reference polynucleotide. Expression of one or more markers can likewise be detected using quantitative PCR (QPCR) to assess the level of expression of the marker(s). Alternatively, any of the many known methods of detecting mutations or variants (e.g., single nucleotide polymorphisms, deletions, etc.) of a marker of the invention can be used to detect occurrence of a mutated marker in a subject.

In a related embodiment, a mixture of transcribed polynucleotides obtained from the sample is contacted with a substrate having fixed thereto a polynucleotide complementary to or homologous with at least a portion (e.g., at least 7, at least 10, at least 15, at least 20, at least 25, at least 30, at least 40, at least 50, at least 100, at least 500, or more nucleotide residues) of a marker described herein. If polynucleotides complementary to, or homologous with, a marker described herein are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, the hybridization can be performed under stringent hybridization conditions.

In another embodiment, a combination of methods to assess the expression of a marker is utilized.

Because the compositions, kits, and methods rely on detection of a difference in expression levels of one or more markers described herein, in certain embodiments the level of expression of the marker is significantly greater than the minimum detection limit of the method used to assess expression in at least one of a biological sample from a subject with cancer (e.g., a hematological cancer such as ALL and CLL) or a reference (e.g., a biological sample from a healthy subject, e.g., a subject without cancer).

Nucleic Acid Molecules and Probes

One aspect of the disclosure pertains to isolated nucleic acid molecules that correspond to one or markers described herein, including nucleic acids which encode a polypeptide corresponding to one or more markers described herein or a portion of such a polypeptide. The nucleic acid molecules include those nucleic acid molecules which reside in genomic regions identified herein. Isolated nucleic acid molecules also include nucleic acid molecules sufficient for use as hybridization probes to identify nucleic acid molecules that correspond to a marker described herein, including nucleic acid molecules which encode a polypeptide corresponding to a marker described herein, and fragments of such nucleic acid molecules, e.g., those suitable for use as PCR primers for the amplification or mutation of nucleic acid molecules. Nucleic acid molecules can be DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

If so desired, a nucleic acid molecule, e.g., the marker gene products identified herein, can be isolated using standard molecular biology techniques and the sequence information in the database records described herein. Using all or a portion of such nucleic acid sequences, nucleic acid molecules can be isolated using standard hybridization and cloning techniques (e.g., as described in Sambrook et al., ed., MOLECULAR CLONING: A LABORATORY MANUAL, 2nd ed., Cold Spring Harbor Laboratory Press, Cold Spring Harbor, N.Y., 1989).

A nucleic acid molecule can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Probes based on the sequence of a nucleic acid molecule of the invention can be used to detect transcripts (e.g., mRNA) or genomic sequences corresponding to one or more markers described herein. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

Polypeptide Detection

Methods to measure biomarkers described herein, include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF) mass spectrometry, microcytometry, microarray, microscopy, fluorescence activated cell sorting (FACS), magnetic activated cell sorting (MACS), flow cytometry, laser scanning cytometry, hematology analyzer and assays based on a property of the protein including but not limited to DNA binding, ligand binding, or interaction with other protein partners.

The activity or level of a marker protein can also be detected and/or quantified by detecting or quantifying the expressed polypeptide. The polypeptide can be detected and quantified by any of a number of means well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry and the like. A skilled artisan can readily adapt known protein/antibody detection methods for use in determining the expression level of one or more biomarkers in a serum sample.

Another agent for detecting a polypeptide is an antibody capable of binding to a polypeptide corresponding to a marker described herein, e.g., an antibody with a detectable label. Antibodies can be polyclonal or monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair (e.g., biotin-streptavidin)), or an antibody fragment (e.g., a single-chain antibody, an isolated antibody hypervariable domain, etc.) which binds specifically with a protein corresponding to the marker, such as the protein encoded by the open reading frame corresponding to the marker or such a protein which has undergone all or a portion of its normal post-translational modification, is used.

Proteins from cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

In one format, antibodies, or antibody fragments, can be used in methods such as Western blots or immunofluorescence techniques to detect the expressed proteins. In such uses, one can immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The polypeptide is detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition.

In another embodiment, the polypeptide is detected and/or quantified using Luminex® assay technology. The Luminex® assay separates tiny color-coded beads into e.g., distinct sets that are each coated with a reagent for a particular bioassay, allowing the capture and detection of specific analytes from a sample in a multiplex manner. The Luminex® assay technology can be compared to a multiplex ELISA assay using bead-based fluorescence cytometry to detect analytes such as biomarkers.

The disclosure also encompasses kits for detecting the presence of a polypeptide or nucleic acid corresponding to a marker described herein in a biological sample, e.g., a sample containing tissue, whole blood, serum, plasma, buccal scrape, saliva, cerebrospinal fluid, urine, stool, and bone marrow. Such kits can be used to determine if a subject is suffering from or is at increased risk of developing cancer (e.g., a hematological cancer such as CLL and ALL). For example, the kit can comprise a labeled compound or agent capable of detecting a polypeptide or an mRNA encoding a polypeptide corresponding to a marker described herein in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

The disclosure thus includes a kit for assessing the disease progression of a subject having cancer (e.g., a hematological cancer such as CLL and ALL).

In an embodiment, a kit can be used to assess the disease progression of a cancer including, but not limited to, B-cell acute lymphocytic leukemia (B-ALL), T-cell acute lymphocytic leukemia (T-ALL), acute lymphocytic leukemia (ALL), chronic myelogenous leukemia (CML), chronic lymphocytic leukemia (CLL), B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, and Waldenstrom macroglobulinemia. In an embodiment, the disclosure provides a kit for assessing the disease progression of a subject having a hematological cancer. In an embodiment, the disclosure provides a kit for assessing the disease progression of a subject having ALL.

In another embodiment, the disclosure provides a kit for assessing the disease progression of a subject having CLL. In an embodiment, the disclosure provides a kit for assessing the disease progression of a subject having cancer that is associated with CD19 expression.

In an embodiment, the disclosure provides a kit for assessing and characterizing responder status (e.g., compete responder, partial responder or non-responder) of a subject having a hematological cancer to a CAR-expressing cell (e.g., T cell, NK cell) therapy (e.g., a CD19 CAR-expressing cell therapy as described herein, such as e.g., CTL019). In an embodiment, the disclosure provides a kit for assessing and characterizing responder status (e.g., compete responder, partial responder or non-responder) of a subject having ALL to a CAR-expressing cell therapy (e.g., a CD19 CAR-expressing cell therapy as described herein, such as e.g., CTL019). In an embodiment, the disclosure provides a kit for assessing and characterizing responder status (e.g., compete responder, partial responder or non-responder) of a subject having CLL to a CAR-expressing cell therapy (e.g., a CD19 CAR-expressing cell therapy as described herein, such as e.g., CTL019).

Suitable reagents for binding with a polypeptide corresponding to a marker described herein include antibodies, antibody derivatives, antibody fragments, and the like. Suitable reagents for binding with a nucleic acid (e.g., a genomic DNA, an mRNA, a spliced mRNA, a cDNA, or the like) include complementary nucleic acids. For example, the nucleic acid reagents can include oligonucleotides (labeled or non-labeled) fixed to a substrate, labeled oligonucleotides not bound with a substrate, pairs of PCR primers, molecular beacon probes, and the like.

The kit can optionally comprise additional components useful for performing the methods described herein. By way of example, the kit can comprise fluids (e.g., SSC buffer) suitable for annealing complementary nucleic acids or for binding an antibody with a protein with which it specifically binds, one or more sample compartments, an instructional material which describes performance of a method of the invention, a reference sample for comparison of expression levels of the biomarkers described herein, and the like.

A kit of the invention can comprise a reagent useful for determining protein level or protein activity of a marker.

In an embodiment, a kit is provided for providing a prognosis for success rate of a CAR-expressing cell (e.g., T cell, NK cell) therapy (e.g., a CD19 CAR-expressing cell therapy as described herein, such as e.g., CTL019) in a subject having cancer (e.g., a hematological cancer such as CLL and ALL), said kit comprising:

a set of reagents that specifically detects expression levels of one or more (e.g., 2, 3, 4, 5, 6, 7, 8, 9, 10, 15, 20, 25, 30, 35, 40, 50 or more) genes listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 and a CD19 CAR-expressing cell gene set signature; and instructions for using said kit;
wherein said instructions for use provide that if one or more of the detected expression levels is greater than a reference level, the subject is more likely to respond positively to a CAR-expressing cell therapy.

In an embodiment, the set of reagents detects the expression of mRNA expressed from said set of genes.

In an embodiment, the set of reagents comprises nucleic acid probes complementary to mRNA expressed from said set of genes.

In an embodiment, the nucleic acid probes complementary to mRNA are cDNA or oligonucleotides.

In an embodiment, the nucleic acid probes complementary to mRNA are immobilized on a substrate surface.

In an embodiment, the set of reagents detects the expression of polypeptides encoded by said set of genes.

Therapeutic Agents, Compositions and Administration

The methods described herein can be used to assess a responder status to a cell expressing a CAR. In one embodiment, the cell expresses a CAR molecule comprising an antigen binding domain (e.g., an antibody or antibody fragment that specifically binds to a tumor antigen), a transmembrane domain, and an intracellular signaling domain (e.g., an intracellular signaling domain comprising a costimulatory domain and/or a primary signaling domain). In an embodiment, the antigen binding domain comprises any antibody, or a fragment thereof, e.g., an scFv, known in the art that targets or specifically binds to any of the tumor antigens described herein. For example, the tumor antigen is BCMA (also known as TNFRSF17, Tumor Necrosis Factor Receptor Superfamily, Member 17, or B Cell Maturation Antigen), CD33, CLL-1 (also known as C-type Lectin-Like domain family 1, or CLECL1) or claudin-6 (CLDN6). The antibody, or fragment thereof, can be a murine, humanized, or fully human antibody or fragment thereof, e.g., an scFv.

In one embodiment, the CAR comprises an antibody or antibody fragment which includes an anti-CD19 binding domain described herein (e.g., a murine or humanized antibody or antibody fragment that specifically binds to CD19 as described herein), a transmembrane domain described herein, and an intracellular signaling domain described herein (e.g., an intracellular signaling domain comprising a costimulatory domain and/or a primary signaling domain described herein).

Antigen Binding Domain

In one aspect, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the portion of the CAR comprising the antigen binding domain comprises an antigen binding domain that targets a tumor antigen, e.g., a tumor antigen described herein.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

Any known CD19 CAR, e.g., the CD19 antigen binding domain of any known CD19 CAR, in the art can be used in accordance with the instant invention. For example, LG-740; CD19 CAR described in the U.S. Pat. Nos. 8,399,645; 7,446,190; Xu et al., Leuk Lymphoma. 2013 54(2): 255-260 (2012); Cruz et al., Blood 122(17):2965-2973 (2013); Brentjens et al., Blood, 118(18):4817-4828 (2011); Kochenderfer et al., Blood 116(20):4099-102 (2010); Kochenderfer et al., Blood 122 (25):4129-39 (2013); and 16th Annu Meet Am Soc Gen Cell Ther (ASGCT) (May 15-18, Salt Lake City) 2013, Abst 10.

Exemplary target antigens that can be targeted using the CAR-expressing cells, include, but are not limited to, CD19, CD123, EGFRvIII, mesothelin, among others, as described in, for example, WO 2014/130635, WO 2014/130657, and WO 2015/090230, each of which is herein incorporated by reference in its entirety.

In one embodiment, the CAR T cell that specifically binds to CD19 has the USAN designation TISAGENLECLEUCEL-T. CTL019 is made by a gene modification of T cells is mediated by stable insertion via transduction with a self-inactivating, replication deficient Lentiviral (LV) vector containing the CTL019 transgene under the control of the EF-1 alpha promoter. CTL019 can be a mixture of transgene positive and negative T cells that are delivered to the subject on the basis of percent transgene positive T cells.

In other embodiments, the CAR-expressing cells can specifically bind to human CD19, e.g., can include a CAR molecule, or an antigen binding domain (e.g., a humanized antigen binding domain) according to Table 3 of WO2014/153270, incorporated herein by reference.

In other embodiments, the CAR-expressing cells can specifically bind to CD123, e.g., can include a CAR molecule (e.g., any of the CAR1-CAR8), or an antigen binding domain according to Tables 1-2 of WO 2014/130635, incorporated herein by reference.

In other embodiments, the CAR-expressing cells can specifically bind to EGFRvIII, e.g., can include a CAR molecule, or an antigen binding domain according to Table 2 or SEQ ID NO:11 of WO 2014/130657, incorporated herein by reference.

In other embodiments, the CAR-expressing cells can specifically bind to mesothelin, e.g., can include a CAR molecule, or an antigen binding domain according to Tables 2-3 of WO 2015/090230, incorporated herein by reference.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed or described above.

In some embodiments, the tumor antigen is a tumor antigen described in International Application WO2015/142675, filed Mar. 13, 2015, which is herein incorporated by reference in its entirety. In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

CD19 CAR Constructs

Murine CD19 CAR constructs are described in PCT publication WO 2012/079000, incorporated herein by reference, and the amino acid sequence of the murine CD19 CAR and scFv constructs are shown in Table 2 below.

TABLE 2

| Murine CD19 CAR Constructs | | |
|---|---|---|
| CTL019 Full-aa | SEQ ID NO: 81 | MALPVTALLLPLALLLHAARPdigmtqttsslsaslgdrvtiscrasqdiskylnw yqqkpdgtvklliyhtsrlhsgvpsrfsgsgsgtdysltisnlegediatyfcqqg ntlpytfgggtkleitgggsggggsggggsevklgesgpglvapsgslsvtctvs gvslpdygvswirqpprkglewlgviwgsettyynsalksrltiikdnsksqvflk mnslqtddtaiyycakhyyyggsyamdywgqgtsvtvsstttpaprpptpaptias qplslrpeacrpaaggavhtrgldfacdiyiwaplagtcgvillslvitlyckrgr kkllyifkgpfmrpvqttgeedgcscrfpeeeeggcelrvkfsrsadapaykqgqn glynelnlgrreeydvldkrrgrdpemggkprrknpqeglynelqkdkmaeaysei gmkgerrrgkghdglycolstatkdtydalhmgalppr |
| CTL019scF1/domain | SEQ ID NO: 52 | Digmtqttsslsaslgdrvtiscrasqdiskylnwyqqkpdgtvklliyhtsrlhs gvpsrfsgsgsgtdysltisnlegediatyfcqqgntlpytfgggtkleitgggs ggggsggggsevklgesgpglvapsgslsvtctvsgvslpdygvswirqpprkgle wlgviwgsettyynsalksrltiikdnsksqvflkmnslqtddtaiyycakhyyyg gsyamdywgqgtsvtvss |
| mCAR1 scFv | SEQ ID NO: 84 | QVQLLESGAELVRPGSSVKISCKASGYAFSSYWMNWVKQRPGQGLEWIGQIYPGDG DTNYNGKFKGQATLTADKSSSTAYMQLSGLTSEDSAVYSCARKTISSVVDFYFDYW GQGTTVTGGGSGGGSGGGSGGGSELVLTQSPKFMSTSVGDRVSVTCKASQNVGTNV AWYQQKPGQSPKPLIYSATYRNSGVPDRFTGSGSGTDFTLTITNVQSKDLADYFCQ YNRYPYTSFFFTKLEIKRRS |
| mCAR1 Full-aa | SEQ ID NO: 85 | QVQLLESGAELVRPGSSVKISCKASGYAFSSYWMNWVKQRPGQGLEWIGQIYPGDG DTNYNGKFKGQATLTADKSSSTAYMQLSGLTSEDSAVYSCARKTISSVVDFYFDYW GQGTTVTGGGSGGGSGGGSGGGSELVLTQSPKFMSTSVGDRVSVTCKASQNVGTNV AWYQQKPGQSPKPLIYSATYRNSGVPDRFTGSGSGTDFTLTITNVQSKDLADYFCQ YNRYPYTSFFFTKLEIKRRSKIEVMYPPPYLDNEKSNGTIIHVKGKHLCPSPLFPG PSKPFWVLVVVGGVLACYSLLVTVAFIIFWVRSKRSRLLHSDYMNMTPRRPGPTRK HYQPYAPPRDFAAYRSRVKFSRSADAPAYQQGQNQLYNELNLGRREEYDVLDKRRG RDPEMGGKPRRKNPQEGLYNELQKDKMAEAYSEIGMKGERRRGKHDGLYQGLSTA TKDTYDALHMQALPPR |
| mCAR2 scFv | SEQ ID NO: 86 | DIQMTQTTSSLSASLGDRVTISCRASQDISKYLNWYQQKPDGTVKLLIYHTSRLHS GVPSRFSGSGSGTDYSLTISNLEQEDIATYFCQQGNTLPYTFGGGTKLEITGSTSG SGKPGSGEGSTKGEVKLQESGPGLVAPSQSLSVTCTVSGVSLPDYGVSWIRQPPRK GLEWLGVINGSETTYYNSALKSRLTIIKDNSKSQVFLKMNSLQTDDTAIYYCAKHY YYGGSYAMDYWGQGTSVTVSSE |
| rrAAUCAR-aa | SEQ ID NO: 87 | DIQMTQTTSSLSASLGDRVTISCRASQDISKYLNWYQQKPDGTVKLLIYHTSRLHS GVPSRFSGSGSGTDYSLTISNLEQEDIATYFCQQGNTLPYTFGGGTKLEITGSTSG SGKPGSGEGSTKGEVKLQESGPGLVAPSQSLSVTCTVSGVSLPDYGVSWIRQPPRK GLEWLGVINGSETTYYNSALKSRLTIIKDNSKSQVFLKMNSLQTDDTAIY YCAKHYYYGGSYAMDYWGQGTSVTVSSESKYGPPCPPCPMFWVLVVVGGVLACYSL LVTVAFIIFWVKRGRKKLLYIFKQPFMRPVQTTQEEDGCSCRFEEEEGGCELRVKF SRSADAPAYQQGQNQLYNELNLGRREEYDVLDKRRGRDPEMGGKPRRKNPQEGLYN ELQKDKMAEAYSEIGMKGERRRGKHDGLYQGLSTATKDTYDALHMQALPPRL |
| mCAR2 Full-aa | SEQ ID NO:88 | DIQMTQTT SSLSASLGDR VTISCRASQD ISKYLNWYQQ KPDGTVKLLI YHTSRLHSGV PSRFSGSGSG TDYSLTISNL EQEDIATYFC QQGNTLPYTF GGGTKLEITG STSGSGKPGS GEGSTKGEVK LQESGPGLVA PSQSLSVTCT VSGVSLPDYG VSWIRQPPRK GLEWLGVIWG SETTYYNSAL KSRLTIIKDN SKSQVFLKMN SLQTDDTAIY YCAKHYYGG SYAMDYWGQG TSVTVSSESK YGPPCPPCPM FWVLVVVGGV LACYSLLVTV AFIIFWVKRG RKKLLYIFKQ PFMRPVQTTQ EEDGCSCRFE EEGGCELRV KFSRSADAPA YQQGQNQLYN ELNLGRREEY DVLDKRRGRD PEMGGKPRRK NPQEGLYNEL QKDKMAEAYS EIGMKGERRR GKGHDGLYQG LSTATKDTYD ALHMQALPPR LEGGGEGRGS LLTCGDVEEN PGPRMLLLVT SLLLCELPHP AFLLIPRKVC NGIGIGEFKD SLSINATNIK HFKNCTSISG DLHILPVAFR GDSFTHTPPL DPQELDILKT VKEITGFLLI QAWPENRTDL HAFENLEIIR |

TABLE 2-continued

Murine CD19 CAR Constructs

| | | |
|---|---|---|
| | | GRTKQHGQFS LAVVSLNITS LGLRSLKEIS DGDVIISGNK NLCYANTINW KKLFGTSGQK TKIISNRGEN SCKATGQVCH ALCSPEGCWG PEPRDCVSCR NVSRGRECVD KCNLLEGEPR EFVENSECIQ CHPECLPQAM NITCTGRGPD NCIQCAHYID GPHCVKTCPA GVMGENNTLV WKYADAGHVC HLCHPNCTYG CTGPGLEGCP TNGPKIPSIA TGMVGALLLL LVVALGIGLF M |
| mCAR3 scFv | SEQ ID NO: 89 | DIQMTQTTSSLSASLGDRVTISCRASQDISKYLNWYQQKPDGTVKLLIYHTSRLHS GVPSRFSGSGSGTDYSLTISNLEQEDIATYFCQQGNTLPYTFGGGTKLEITGSTSG SGKPGSGEGSTKGEVKLQESGPGLVAPSQSLSVTCTVSGVSLPDYGVSWIRQPPRK GLEWLGVIWGSETTYYNSALKSRLTIIKDNSKSQVFLKMNSLQTDDTAIYYCAKHY YYGGSYAMDYWGQGTSVTVSS |
| mCAR3 Full-aa | SEQ ID NO: 90 | DIQMTQTTSSLSASLGDRVTISCRASQDISKYLNWYQQKPDGTVKLLIYHTSRLHS GVPSRFSGSGSGTDYSLTISNLEQEDIATYFCQQGNTLPYTFGGGTKLEITGSTSG SGKPGSGEGSTKGEVKLQESGPGLVAPSQSLSVTCTVSGVSLPDYGVSWIRQPPRK GLEWLGVIWGSETTYYNSALKSRLTIIKDNSKSQVFLKMNSLQTDDTAIYYCAKHY YYGGSYAMDYWGQGTSVTVSSAAAIEVMYPPPYLDNEKSNGTIIHVKGKHLCPSPL FPGPSKPFWVLVVVGGVLACYSLLVTVAFIIFWVRSKRSRLLHSDYMNMTPRRPGP TRKHYQPYAPPRDFAAYRSRVKFSRSADAPAYQQGQNQLYNELNLGRREEYDVLDK RRGRDPEMGGKPRRKNPQEGLYNELQKDKMAEAYSEIGMKGERRRGKGHDGLYQGL STATKDTYDALHMQALPPR |

CD19 CAR constructs containing humanized anti-CD19 scFv domains are described in PCT publication WO 2014/153270, incorporated herein by reference.

In an embodiment, the antigen binding domain comprises an anti-CD19 antibody, or fragment thereof, e.g., an scFv. For example, the antigen binding domain comprises a variable heavy chain and a variable light chain listed in Table 12. The linker sequence joining the variable heavy and variable light chains can be, e.g., any of the linker sequences described herein, or alternatively, can be GSTSGSGKPGS-GEGSTKG (SEQ ID NO:45).

TABLE 12

Anti-CD 19 antibody binding domains

| CD19 | huscFv1 | EIVMTQSPATLSLSPGERATLSCRASQDISKYLNWYQQKPGQAPRLLIYHTSRL HSGIPARFSGSGSGTDYTLTISSLQPEDFAVYFCQQGNTLPYTFGQGTKLEIK<u>G GGGSGGGGSGGGGS</u>QVQLQESGPGLVKPSETLSLTCTVSGVSLPDYGVSWIRQP PGKGLEWIGVIWGSETTYYSSSLKSRVTISKDNSKNQVSLKLSSVTAADTAVYY CAKHYYYGGSYAMDYWGQGTLVTVSS (SEQ ID NO: 24) |
|---|---|---|
| CD19 | huscFv2 | Eivmtqspatlslspgeratlscrasqdiskylnwyqqkpgqaprllyhtsrlhsgip arfsgsgsgtdytltisslqpedfavyfcqqgntlpytfgqgtkleik<u>ggggsggggsq gggs</u>qvqlqesgpglvkpsetlsltctvsgvslpdygvswirqppgkglewigviwgse ttyyqsslksrvtiskdnsknqvslklssvtaadtavyycakhyyyggsyamdywgqgt lvtvss (SEQ ID NO: 25) |
| CD19 | huscFv3 | Qvqlqesgpglvkpsetlsltctvsgvslpdygvswirqppgkglewigviwgsettyy ssslksrvtiskdnsknqvslklssvtaadtavyycakhyyyggsyamdywgqgtivtv ss<u>ggggsggggsggggs</u>elvmtqspatlslspgeratlscrasqdiskylnwyqqkpgq aprlliyhtsrlhsgiparfsgsgsgtdytltisslqpedfavyfcqqgntlpytfgqg tkleik (SEQ ID NO: 26) |
| CD19 | huscFv4 | Qvqlqesgpglvkpsetlsltctvsgvslpdygvswirqppgkglewigviwgsettyy qsslksrvtiskdnsknqvslklssvtaadtavyycakhyyyggsyamdywgqgtivtv ss<u>ggggsggggsggggs</u>elvmtqspatlslspgeratlscrasqdiskylnwyqqkpgq aprlliyhtsrlhsgiparfsgsgsgtdytltisslqpedfavyfcqqgntlpytfgqg tkleik (SEQ ID NO: 27) |
| CD19 | huscFv5 | Eivmtqspatlslspgeratlscrasqdiskylnwyqqkpgqaprllyhtsrlhsgip arfsgsgsgtdytltisslqpedfavyfcqqgntlpytfgqgtkleik<u>ggggsggggsq gggsggggs</u>qvqlqesgpglvkpsetlsltctvsgvslpdygvswirqppgkglewigv iwgsettyyssslksrvtiskdnsknqvslklssvtaadtavyycakhyyyggsyamdy wgqgtivtvss (SEQ ID NO: 39) |
| CD19 | huscFv6 | Eivmtqspatlslspgeratlscrasqdiskylnwyqqkpgqaprllyhtsrlhsgip arfsgsgsgtdytltisslqpedfavyfcqqgntlpytfgqgtkleik<u>ggggsggggsq gggsggggs</u>qvglqesgpglvkpsetlsltctvsgvslpdygvswirqppgkglewigv iwgsettyygsslksrvtiskdnsknqvslklssvtaadtavyycakhyyyggsyamdy wgqgtivtvss (SEQ ID NO: 43) |
| CD19 | huscFv7 | Qvqlgesgpglvkpsetlsltctvsgvslpdygvswirqppgkglewigviwgsettyy ssslksrvtiskdnsknqvslklssvtaadtavyycakhyyyggsyamdywgqgtivtv ss<u>ggggsggggsggggsggggs</u>elvmtqspatlslspgeratlscrasqdiskylnwyq qkpgqaprlliyhtsrlhsgiparfsgsgsgtdytltisslqpedfavyfcqqgntlpy tfgqgtkleik (SEQ ID NO: 46) |

TABLE 12-continued

Anti-CD 19 antibody binding domains

| | | |
|---|---|---|
| CD19 | huscFv8 | Qvqlgesgpglvkpsetlsltctvsgvslpdygvswirqppgkglewigviwgsettyy<br>qsslksrvtiskdnsknqvslklssvtaadtavyycakhyyyggsyamdywgqgtivtv<br>ssgggqsggggsggggsggggselvmtgspatlslspgeratlscrasqdiskylnwyq<br>qkpgqaprlliyhtsrlhsgiparfsgsgsgtdytltisslqpedfavyfcqqgntlpy<br>tfgqgtkleik (SEQ ID NO: 47) |
| CD19 | huscFv9 | Eivmtgspatlslspgeratlscrasqdiskylnwyqqkpgqaprillyhtsrlhsgip<br>arfsgsgsgtdytltisslqpedfavyfcqqgntlpytfgqgtkleikggggsggggsg<br>gggsggggsqvglgesgpglvkpsetlsltctvsgvslpdygvswirqppgkglewigv<br>iwgsettyynsslksrvtiskdnsknqvslklssvtaadtavyycakhyyyggsyamdy<br>wgqgtivtvss (SEQ ID NO: 48) |
| CD19 | Hu scFv10 | Qvglgesgpglvkpsetlsltctvsgvslpdygvswirqppgkglewigviwgsettyy<br>nsslksrvtiskdnsknqvslklssvtaadtavyycakhyyyggsyamdywgqgtivtv<br>ssgggqsggggsggggsggggselvmtgspatlslspgeratlscrasqdiskylnwyq<br>qkpgqaprlliyhtsrlhsgiparfsgsgsgtdytltisslqpedfavyfcqqgntlpy<br>tfgqgtkleik (SEQ ID NO: 49) |
| CD19 | Hu scFv11 | Eivmtgspatlslspgeratlscrasqdiskylnwyqqkpgqaprillyhtsrlhsgip<br>arfsgsgsgtdytltisslqpedfavyfcqqgntlpytfgqgtkleikggggsggggsg<br>gggsqvglgesgpglvkpsetlsltctvsgvslpdygvswirqppgkglewigviwgse<br>ttyynsslksrvtiskdnsknqvslklssvtaadtavyycakhyyyggsyamdywgqgt<br>lvtvss (SEQ ID NO: 50) |
| CD19 | Hu scFv12 | Qvglgesgpglvkpsetlsltctvsgvslpdygvswirqppgkglewigviwgsettyy<br>nsslksrvtiskdnsknqvslklssvtaadtavyycakhyyyggsyamdywgqgtivtv<br>ssgggqsggggsggggselvmtgspatlslspgeratlscrasqdiskylnwyqqkpgq<br>aprlliyhtsrlhsgiparfsgsgsgtdytltisslqpedfavyfcqqgntlpytfgqg<br>tkleik (SEQ ID NO: 51) |
| CD19 | muCTL019 | Digmtqttsslsaslgdrvtiscrasqdiskylnwyqqkpdgtvklliyhtsrlhsgvp<br>srfsgsgsgtdysltisnleqediatyfcqqgntlpytfgggtkleitggggsggggsg<br>gggsevklgesgpglvapsgslsvtctvsgvslpdygvswirqpprkglewlgviwgse<br>ttyynsalksrltilkdnsksqvflkmnslqtddtalyycakhyyyggsyamdywgqgt<br>svtvss (SEQ ID NO: 52) |
| CD19 | SSJ25-C1 VH sequence | QVQLLESGAELVRPGSSVKISCKASGYAFSSYWMNWVKQRPGQGLEWIGQIYPGDGDTN<br>YNGKFKGQATLTADKSSSTAYMQLSGLTSEDSAVYSCARKTISSVVDFYFDYWGQGTTV<br>T (SEQ ID NO: 53) |
| CD19 | SSJ25-C1 VL sequence | ELVLTQSPKFMSTSVGDRVSVTCKASQNVGTNVAWYQQKPGQSPKPLIYSATYRNSGVP<br>DRFTGSGSGTDFTLTITNVQSKDLADYFYFCQYNRYPYTSGGGTKLEIKRRS (SEQ ID NO: 54) |

Any known CD19 CAR, e.g., the CD19 antigen binding domain of any known CD19 CAR, in the art can be used in accordance with the present disclosure. For example, LG-740; CD19 CAR described in the U.S. Pat. Nos. 8,399,645; 7,446,190; Xu et al., LEUK LYMPHOMA. 2013 54(2):255-260 (2012); Cruz et al., BLOOD 122(17):2965-2973 (2013); Brentjens et al., BLOOD, 118(18):4817-4828 (2011); Kochenderfer et al., BLOOD 116(20):4099-102 (2010); Kochenderfer et al., BLOOD 122 (25):4129-39 (2013); and 16th Annu Meet Am Soc Gen Cell Ther (ASGCT) (May 15-18, Salt Lake City) 2013, Abst 10.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed or described above.

In an embodiment, an antigen binding domain against CD22 is an antigen binding portion, e.g., CDRs, of an antibody described in, e.g., Haso et al., BLOOD, 121(7): 1165-1174 (2013); Wayne et al., CLIN CANCER RES 16(6): 1894-1903 (2010); Kato et al., LEUK RES 37(1):83-88 (2013); Creative BioMart (creativebiomart.net): MOM-18047-S(P).

In an embodiment, an antigen binding domain against CD20 is an antigen binding portion, e.g., CDRs, of the anitbody Rituximab, Ofatumumab, Ocrelizumab, Veltuzumab, or GA101.

In an embodiment, an antigen binding domain against ROR1 is an antigen binding portion, e.g., CDRs, of an antibody described in, e.g., Hudecek et al., CLIN CANCER RES 19(12):3153-3164 (2013); WO 2011159847; and US20130101607.

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multi-specific (e.g., a bispecific or a trispecific) antibody molecule. Protocols for generating bispecific or heterodimeric antibody molecules, and various configurations for bispecific antibody molecules, are described in, e.g., paragraphs 455-458 of WO2015/142675, filed Mar. 13, 2015, which is incorporated by reference in its entirety.

In one aspect, the bispecific antibody molecule is characterized by a first immunoglobulin variable domain sequence, e.g., a scFv, which has binding specificity for CD19, e.g., comprises a scFv as described herein, or comprises the light chain CDRs and/or heavy chain CDRs from a scFv described herein, and a second immunoglobulin variable domain sequence that has binding specificity for a second epitope on a different antigen.

Chimeric TCR

In one aspect, the antibodies and antibody fragments of the present invention (e.g., CD19 antibodies and fragments) can be grafted to one or more constant domain of a T cell receptor ("TCR") chain, for example, a TCR alpha or TCR beta chain, to create a chimeric TCR. Without being bound by theory, it is believed that chimeric TCRs will signal through the TCR complex upon antigen binding. For example, an scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, an antibody fragment, for example a VL domain as described herein, can be grafted to the constant domain of a TCR alpha chain, and an antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of an antibody or antibody fragment may be grafted into a TCR alpha and/or beta chain to create a chimeric TCR. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced, e.g., by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Non-Antibody Scaffolds

In embodiments, the antigen binding domain comprises a non-antibody scaffold, e.g., a fibronectin, ankyrin, domain antibody, lipocalin, small modular immuno-pharmaceutical, maxybody, Protein A, or affilin. The non-antibody scaffold has the ability to bind to target antigen on a cell. In embodiments, the antigen binding domain is a polypeptide or fragment thereof of a naturally occurring protein expressed on a cell. In some embodiments, the antigen binding domain comprises a non-antibody scaffold. A wide variety of non-antibody scaffolds can be employed so long as the resulting polypeptide includes at least one binding region which specifically binds to the target antigen on a target cell.

Non-antibody scaffolds include: fibronectin (Novartis, MA), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

In an embodiment the antigen binding domain comprises the extracellular domain, or a counter-ligand binding fragment thereof, of molecule that binds a counterligand on the surface of a target cell.

Transmembrane Domain

In embodiments, a CAR described herein comprises a transmembrane domain that is fused to an extracellular sequence, e.g., an extracellular recognition element, which can comprise an antigen binding domain. In an embodiment, the transmembrane domain is one that naturally is associated with one of the domains in the CAR. In an embodiment, the transmembrane domain is one that is not naturally associated with one of the domains in the CAR.

A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region).

In embodiments, the transmembrane domain is one which minimizes interactions with other elements, e.g., other transmembrane domains. In some instances, the transmembrane domain minimizes binding of such domains to the transmembrane domains of the same or different surface membrane proteins, e.g., to minimize interactions with other members of the receptor complex. Suitable examples can be derived by selection or modification of amino acid substitution of a known transmembrane domain. In an embodiment, the transmembrane domain is capable of promoting homodimerization with another CAR on the cell surface.

The transmembrane domain may comprise a naturally occurring, or a non-naturally occurring synthetic sequence. Where naturally occurring, the transmembrane domain may be derived from any membrane-bound or transmembrane protein.

Transmembrane regions suitable for use in molecules described herein may be derived from any one or more of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM (e.g., CEACAM-1, CEACAM-3 and/or CEACAM-5), CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C, or CD19. In an embodiment the transmembrane domain is derived from CD8. In an embodiment the transmembrane domain is derived from CD28. In one aspect, the transmembrane domain is a transmembrane domain from the sequence provided as SEQ ID NO: 12 or SEQ ID NO: 42.

In an embodiment, a sequence, e.g., a hinge or spacer sequence, can be disposed between a transmembrane domain and another sequence or domain to which it is fused. In embodiments, a variety of human hinges (aka "spacers") can be employed as well, e.g., including but not limited to the human Ig (immunoglobulin) hinge. Optionally, a short oligo- or polypeptide linker, between 2 and 10 amino acids in length may form the linkage between the transmembrane domain and another domain, e.g., an intracellular signaling domain or costimulatory domain, of a CAR. A glycine-serine doublet provides a particularly suitable linker. In one aspect, the hinge or spacer is the amino acid sequence provided as SEQ ID NO: 4, SEQ ID NO: 6, or SEQ ID NO: 8. In one aspect, the hinge or spacer comprises a KIR2DS2 hinge.

In an embodiment, the transmembrane domain may be a non-naturally occurring sequence, in which case can comprise predominantly hydrophobic residues such as leucine and valine. In an embodiment, a triplet of phenylalanine, tryptophan and valine will be found at each end of a transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO:10). In some embodiments, the linker is encoded by a nucleotide sequence of GGTGGCGGAGGTTCTGGAGGTGGAGGTTCC (SEQ ID NO:11).

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

Primary Signaling Domain

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In one embodiment, a CAR of the invention comprises an intracellular signaling domain, e.g., a primary signaling domain of CD3-zeta, e.g., a CD3-zeta sequence described herein.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs. Further examples of molecules containing a primary intracellular signaling domain that are of particular use in the invention include those of DAP10, DAP12, and CD32.

A primary intracellular signaling domain comprises a functional fragment, or analog, of a primary stimulatory molecule (e.g., CD3 zeta-GenBank Acc. No. BAG36664.1). The primary intracellular signaling domain can comprise the entire intracellular region or a fragment of the intracellular region which is sufficient for generation of an intracellular signal when an antigen binding domain to which it is fused binds cognate antigen. In embodiments the primary intracellular signaling domain has at least 70, 75, 80, 85, 90, 95, 98, or 99% sequence identity with the entire intracellular region, or a fragment of the intracellular region which is sufficient for generation of an intracellular signal, of a naturally occurring primary stimulatory molecule, e.g., a human (GenBank Acc No. BAG36664.1), or other mammalian, e.g., a nonhuman species, e.g., rodent, monkey, ape or murine intracellular primary stimulatory molecule. In embodiments the primary intracellular signaling domain has at least 70, 75, 80, 85, 90, 95, 98, or 99% sequence identity with SEQ ID NO: 18 or SEQ ID NO: 20.

In embodiments, the primary intracellular signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of the entire intracellular region, or a fragment of the intracellular region which is sufficient for generation of an intracellular signal, of a naturally occurring human primary stimulatory molecule, e.g., a naturally occurring human primary stimulatory molecule disclosed herein.

Costimulatory Signaling Domain

The intracellular signalling domain of the CAR can comprise the CD3-zeta signalling domain by itself or it can be combined with any other desired intracellular signalling domain(s) useful in the context of a CAR of the invention. For example, the intracellular signalling domain of the CAR can comprise a CD3 zeta chain portion and a costimulatory signaling domain. The costimulatory signaling domain refers to a portion of the CAR comprising the intracellular domain of a costimulatory molecule. In one embodiment, the intracellular domain is designed to comprise the signaling domain of CD3-zeta and the signaling domain of CD28. In one aspect, the intracellular domain is designed to comprise the signaling domain of CD3-zeta and the signaling domain of ICOS.

A costimulatory molecule is a cell surface molecule other than an antigen receptor or its ligands that is required for an efficient response of lymphocytes to an antigen. Examples of such molecules include MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CD5, ICAM-1, LFA-1 (CD11a/CD18), 4-1BB (CD137), B7-H3, CD5, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, and the like. For example, CD27 costimulation has been demonstrated to enhance expansion, effector function, and survival of human CAR-expressing cell (e.g., T cell, NK cell) cells in vitro and augments human T cell persistence and antitumor activity in vivo (Song et al. BLOOD. 2012; 119(3):696-706). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKG2D and NKG2C.

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

A costimulatory domain comprises a functional fragment, or analog, of a costimulatory molecule (e.g., ICOS, CD28, or 4-1BB). It can comprise the entire intracellular region or a fragment of the intracellular region which is sufficient for generation of an intracellular signal, e.g., when an antigen binding domain to which it is fused binds cognate antigen. In embodiments the costimulatory domain has at least 70%, 75%, 80%, 85%, 90%, 95%, 98%, or 99% sequence identity with the entire intracellular region, or a fragment of the intracellular region which is sufficient for generation of an intracellular signal, of a naturally occurring costimulatory molecule as described herein, e.g., a human, or other mammalian, e.g., a nonhuman species, e.g., rodent, monkey, ape or murine intracellular costimulatory molecule. In embodiments the costimulatory domain has at least 70%, 75%, 80%, 85%, 90%, 95%, 98%, or 99% sequence identity with SEQ ID NO: 14, SEQ ID NO: 16, SEQ ID NO: 40, or SEQ ID NO: 44.

In embodiments the costimulatory signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of the entire intracellular region, or a fragment of the intracellular region which is sufficient for generation of an intracellular signal, of, a naturally occurring human costimulatory molecule, e.g., a naturally occurring human costimulatory molecule disclosed herein.

Any of the CARs described herein can include one or more of the components listed in Table 11.

TABLE 11

Sequences of various components of CAR (aa-amino acids, na-nucleic acids that encodes the corresponding protein)

| SEQ ID NO | description | Sequence |
| --- | --- | --- |
| 1 | EF-1 promoter | CGTGAGGCTCCGGTGCCCGTCAGTGGGCAGAGCGCACATCGCCCACAGTCC<br>CCGAGAAGTTGGGGGGAGGGGTCGGCAATTGAACCGGTGCCTAGAGAAGG<br>TGGCGCGGGGTAAACTGGGAAAGTGATGTCGTGTACTGGCTCCGCCTTTTTC<br>CCGAGGGTGGGGAGAACCGTATATAAGTGCAGTAGTCGCCGTGAACGTTC<br>TTTTTCGCAACGGGTTTGCCGCCAGAACACAGGTAAGTGCCGTGTGTGGTTC<br>CCGCGGGCCTGGCCTCTTTACGGGTTATGGCCCTTGCGTGCCTTGAATTACTT<br>CCACCTGGCTGCAGTACGTGATTCTTGATCCCGAGCTTCGGGTTGGAAGTGG<br>GTGGGAGAGTTCGAGGCCTTGCGCTTAAGGAGCCCCTTCGCCTCGTGCTTGA<br>GTTGAGGCCTGGCCTGGGCGCTGGGGCCGCCGCGTGCGAATCTGGTGGCAC |

TABLE 11-continued

Sequences of various components of CAR (aa-amino acids, na-nucleic acids that encodes the corresponding protein)

| SEQ ID NO | description | Sequence |
|---|---|---|
| | | CTTCGCGCCTGTCTCGCTGCTTTCGATAAGTCTCTAGCCATTTAAAATTTTTGA<br>TGACCTGCTGCGACGCTTTTTTTCTGGCAAGATAGTCTTGTAAATGCGGGCC<br>AAGATCTGCACACTGGTATTTCGGTTTTTGGGGCCGCGGGCGGCGACGGGG<br>CCCGTGCGTCCCAGCGCACATGTTCGGCGAGGCGGGGCCTGCGAGCGCGGC<br>CACCGAGAATCGGACGGGGGTAGTCTCAAGCTGGCCGGCCTGCTCTGGTGC<br>CTGGCCTCGCGCCGCCGTGTATCGCCCCGCCCTGGGCGGCAAGGCTGGCCC<br>GGTCGGCACCAGTTGCGTGAGCGGAAAGATGGCCGCTTCCCGGCCCTGCTG<br>CAGGGAGCTCAAAATGGAGGACGCGGCGCTCGGGAGAGCGGGCGGGTGA<br>GTCACCCACACAAAGGAAAAGGGCCTTTCCGTCCTCAGCCGTCGCTTCATGT<br>GACTCCACGGAGTACCGGGCGCCGTCCAGGCACCTCGATTAGTTCTCGAGCT<br>TTTGGAGTACGTCGTCTTTAGGTTGGGGGGAGGGGTTTTATGCGATGGAGT<br>TTCCCCACACTGAGTGGGTGGAGACTGAAGTTAGGCCAGCTTGGCACTTGAT<br>GTAATTCTCCTTGGAATTTGCCCTTTTTGAGTTTGGATCTTGGTTCATTCTCAA<br>GCCTCAGACAGTGGTTCAAAGTTTTTTTCTTCCATTTCAGGTGTCGTGA |
| 2 | Leader (aa) | MALPVTALLLPLALLLHAARP |
| 3 | Leader (na) | ATGGCCCTGCCTGTGACAGCCCTGCTGCTGCCTCTGGCTCTGCTGCTGCATGC<br>CGCTAGACCC |
| 4 | CD 8 hinge (aa) | TTTPAPRPPTPAPTIASQPLSLRPEACRPAAGGAVHTRGLDFACD |
| 5 | CD8 hinge (na) | ACCACGACGCCAGCGCCGCGACCACCAACACCGGCGCCCACCATCGCGTCG<br>CAGCCCCTGTCCCTGCGCCCAGAGGCGTGCCGGCCAGCGGCGGGGGGCGCA<br>GTGCACACGAGGGGGCTGGACTTCGCCTGTGAT |
| 6 | Ig4 hinge (aa) | ESKYGPPCPPCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKCKVSN<br>KGLPSSIEKTISKAKGQPREPQVYTLPPSQEEMTKNQVSLTCLVKGFYPSDIAVE<br>WESNGQPENNYKTTPPVLDSDGSFFLYSRLTVDKSRWQEGNVFSCSVMHEALH<br>NHYTQKSLSLSLGKM |
| 7 | Ig4 hinge (na) | GAGAGCAAGTACGGCCCTCCCTGCCCCCCTTGCCCTGCCCCCGAGTTCCTGG<br>GCGGACCCAGCGTGTTCCTGTTCCCCCCCAAGCCCAAGGACACCCTGATGAT<br>CAGCCGGACCCCCGAGGTGACCTGTGTGGTGGTGGACGTGTCCCAGGAGGA<br>CCCCGAGGTCCAGTTCAACTGGTACGTGGACGGCGTGGAGGTGCACAACGC<br>CAAGACCAAGCCCCGGGAGGAGCAGTTCAATAGCACCTACCGGGTGGTGTC<br>CGTGCTGACCGTGCTGCACCAGGACTGGCTGAACGGCAAGGAATACAAGTG<br>TAAGGTGTCCAACAAGGGCCTGCCCAGCAGCATCGAGAAAACCATCAGCAA<br>GGCCAAGGGCCAGCCTCGGGAGCCCCAGGTGTACACCCTGCCCCCTAGCCA<br>AGAGGAGATGACCAAGAACCAGGTGTCCCTGACCTGCCTGGTGAAGGGCTT<br>CTACCCCAGCGACATCGCCGTGGAGTGGGAGAGCAACGGCCAGCCCGAGAA<br>CAACTACAAGACCACCCCCCCTGTGCTGGACAGCGACGGCAGCTTCTTCCTG<br>TACAGCCGGCTGACCGTGGACAAGAGCCGGTGGCAGGAGGGCAACGTCTTT<br>AGCTGCTCCGTGATGCACGAGGCCCTGCACAACCACTACACCCAGAAGAGCC<br>TGAGCCTGTCCCTGGGCAAGATG |
| 8 | IgD hinge (aa) | RWPESPKAQASSVPTAQPQAEGSLAKATTAPATTRNTGRGGEEKKKEKEKEEQ<br>EERETKTPECPSHTQPLGVYLLTPAVQDLWLRDKATFTCFVVGSDLKDAHLTWE<br>VAGKVPTGGVEEGLLERHSNGSQSQHSRLTLPRSLWNAGTSVTCTLNHPSLPPQ<br>RLMALREPAAQAPVKLSLNLLASSDPPEAASWLLCEVSGFSPPNILLMWLEDQR<br>EVNTSGFAPARPPPQPGSTTFWAWSVLRVPAPPSPQPATYTCVVSHEDSRTLL<br>NASRSLEVSYVTDH |
| 9 | IgD hinge (na) | AGGTGGCCCGAAAGTCCCAAGGCCCAGGCATCTAGTGTTCCTACTGCACAGC<br>CCCAGGCAGAAGGCAGCCTAGCCAAAGCTACTACTGCACCTGCCACTACGCG<br>CAATACTGGCCGTGGCGGGAGGAGAAGAAAAAGGAGAAAGAGAAAGAA<br>GAACAGGAAGAGAGGGAGACCAAGACCCCTGAATGTCCATCCCATACCCAG<br>CCGCTGGGCGTCTATCTCTTGACTCCCGCAGTACAGGACTTGTGGCTTAGAG<br>ATAAGGCCACCTTTACATGTTTCGTCGTGGGCTCTGACCTGAAGGATGCCCA<br>TTTGACTTGGGAGGTTGCCGGAAAGGTACCCACAGGGGGGGTTGAGGAAG<br>GGTTGCTGGAGCGCCATTCCAATGGCTCTCAGAGCCAGCACTCAAGACTCAC<br>CCTTCCGAGATCCCTGTGGAACGCCGGGACCTCTGTCACATGTACTCTAAATC<br>ATCCTAGCCTGCCCCCACAGCGTCTGATGGCCCTTAGAGAGCCAGCCGCCCA<br>GGCACCAGTTAAGCTTAGCCTGAATCTGCTCGCCAGTAGTGATCCCCCAGAG<br>GCCGCCAGCTGGCTCTTATGCGAAGTGTCCGGCTTTAGCCCGCCCAACATCT<br>TGCTCATGTGGCTGGAGGACCAGCGAGAAGTGAACACCAGCGGCTTCGCTC<br>CAGCCCGGCCCCCACCCCAGCCGGGTTCTACCACATTCTGGGCCTGGAGTGT<br>CTTAAGGGTCCCAGCACCACCTAGCCCCCAGCCAGCCACATACACCTGTGTT<br>GTGTCCCATGAAGATAGCAGGACCCTGCTAAATGCTTCTAGGAGTCTGGAG<br>GTTTCCTACGTGACTGACCATT |

TABLE 11-continued

Sequences of various components of CAR (aa-amino acids, na-nucleic acids that encodes the corresponding protein)

| SEQ ID NO | description | Sequence |
|---|---|---|
| 10 | GS hinge/linker (aa) | GGGGSGGGGS |
| 11 | GS hinge/linker (na) | GGTGGCGGAGGTTCTGGAGGTGGAGGTTCC |
| 12 | CD8 TM (aa) | IYIWAPLAGTCGVLLLSLVITLYC |
| 13 | CD8 TM (na) | ATCTACATCTGGGCGCCCTTGGCCGGGACTTGTGGGGTCCTTCTCCTGTCACTGGTTATCACCCTTTACTGC |
| 14 | 4-1BB intracellular domain (aa) | KRGRKKLLYIFKQPFMRPVQTTQEEDGCSCRFPEEEEGGCEL |
| 15 | 4-1BB intracellular domain (na) | AAACGGGGCAGAAAGAAACTCCTGTATATATTCAAACAACCATTTATGAGACCAGTACAAACTACTCAAGAGGAAGATGGCTGTAGCTGCCGATTTCCAGAAGAAGAAGAAGGAGGATGTGAACTG |
| 16 | CD27 (aa) | QRRKYRSNKGESPVEPAEPCRYSCPREEEGSTIPIQEDYRKPEPACSP |
| 17 | CD27 (na) | AGGAGTAAGAGGAGCAGGCTCCTGCACAGTGACTACATGAACATGACTCCCCGCCGCCCCGGGCCCACCCGCAAGCATTACCAGCCCTATGCCCCACCACGCGACTTCGCAGCCTATCGCTCC |
| 18 | CD3-zeta (aa) | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 19 | CD3-zeta (na) | AGAGTGAAGTTCAGCAGGAGCGCAGACGCCCCCGCGTACAAGCAGGGCCAGAACCAGCTCTATAACGAGCTCAATCTAGGACGAAGAGAGGAGTACGATGTTTTGGACAAGAGACGTGGCCGGGACCCTGAGATGGGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCAGGGTCTCAGTACAGCCACCAAGGACACCTACGACGCCCTTCACATGCAGGCCCTGCCCCCTCGC |
| 20 | CD3-zeta (aa) | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 21 | CD3-zeta (na) | AGAGTGAAGTTCAGCAGGAGCGCAGACGCCCCCGCGTACCAGCAGGGCCAGAACCAGCTCTATAACGAGCTCAATCTAGGACGAAGAGAGGAGTACGATGTTTTGGACAAGAGACGTGGCCGGGACCCTGAGATGGGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCAGGGTCTCAGTACAGCCACCAAGGACACCTACGACGCCCTTCACATGCAGGCCCTGCCCCCTCGC |
| 22 | linker | GGGGS |
| 23 | linker | GGTGGCGGAGGTTCTGGAGGTGGAGGTTCC |
| 28 | linker | (Gly-Gly-Gly-Ser)$_n$, where n = 1-10 |
| 29 | linker | (Gly4 Ser)4 |
| 30 | linker | (Gly4 Ser)3 |
| 31 | linker | (Gly3Ser) |
| 32 | polyA | $A_{2000}$ |
| 33 | polyA | $A_{150}$ |
| 34 | polyA | $A_{5000}$ |
| 35 | polyT | $T_{100}$ |
| 36 | polyT | $T_{5000}$ |

TABLE 11-continued

Sequences of various components of CAR (aa-amino acids, na-nucleic acids that encodes the corresponding protein)

| SEQ ID NO | description | Sequence |
|---|---|---|
| 37 | polyA | $A_{64}$ |
| 38 | polyA | $A_{400}$ |

Combination of CARs

In one aspect, the CAR-expressing cell described herein can further comprise a second CAR, e.g., a second CAR that includes a different antigen binding domain, e.g., to the same target or a different target (e.g., a target other than a cancer associated antigen described herein or a different cancer associated antigen described herein, e.g., CD19, CD33, CLL-1, CD34, FLT3, or folate receptor beta). In one embodiment, the second CAR includes an antigen binding domain to a target expressed the same cancer cell type as the cancer associated antigen. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, ICOS, CD27 or OX-40, onto the first CAR, and the primary signaling domain, e.g., CD3 zeta, on the second CAR can limit the CAR activity to cells where both targets are expressed. In one embodiment, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In one embodiment, the CAR-expressing cell comprises a CAR described herein (e.g., a CD19 CAR) and an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta).

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first CAR said second CAR, associate with one another less than if both were scFv antigen binding domains. In some embodiments, the antigen binding domains of the first CAR and the second CAR, associate with one another 85%, 90%, 95%, 96%, 97%, 98% or 99% less than if both were scFv antigen binding domains.

CAR-Expressing Cells

The CARs described herein are expressed on cells, e.g., immune effector cells, e.g., T cells. For example, a nucleic acid construct of a CAR described herein is transduced to a T cell. In embodiments, the cells expressing the CARs described herein are an in vitro transcribed RNA CAR T cell.

Sources of Cells, e.g., T cells

Prior to expansion and genetic modification or other modification, a source of cells, e.g., immune effector cells, e.g., T cells or NK cells, can be obtained from a subject. Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, the cells obtained as described in this section are subjected to an assay described herein, e.g., one or more biomarkers are assayed.

In certain aspects of the present disclosure, immune effector cells, e.g., T cells or NK cells, can be obtained from a unit of blood collected from a subject using any number of techniques known to the skilled artisan, such as Ficoll™ separation. In one aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. In embodiments, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, e.g., IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. In an embodiment, a patient is pre-treated with one or more therapies that reduce $T_{REG}$ cells prior to collection of cells for CAR-expressing cell (e.g., T cell, NK cell) product manufacturing, thereby reducing the risk of patient relapse to CAR-expressing cell (e.g., T cell, NK cell) treatment (e.g., CTL019 treatment). Methods of depleting $T_{REG}$ cells are known in the art. Methods of decreasing $T_{REG}$ cells include, but are not limited to, cyclophosphamide, anti-GITR antibody, CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a patient is pre-treated with cyclophosphamide prior to collection of cells for CAR-expressing cell (e.g., T cell, NK cell) product manufacturing, thereby reducing the risk of patient relapse to CAR-expressing cell treatment (e.g., CTL019 treatment). In an embodiment, a patient is pre-treated with an anti-GITR antibody prior to collection of cells for CAR-expressing cell (e.g., T cell, NK cell) product manufacturing, thereby reducing the risk of patient relapse to CAR-expressing cell treatment (e.g., CTL019 treatment).

In an embodiment, the CAR-expressing cell (e.g., T cell, NK cell) manufacturing process is modified to deplete $T_{REG}$ cells prior to manufacturing of the CAR-expressing cell (e.g., T cell, NK cell) product (e.g., a CTL019 product). In an embodiment, CD25-depletion is used to deplete $T_{REG}$ cells prior to manufacturing of the CAR-expressing cell (e.g., T cell, NK cell) product (e.g., a CTL019 product).

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B&-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, IL-5, IL-6, IL-9, IL-21, CCL20, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712. In an embodiment, the T cell population expresses cytokine CCL20, IL-17a, IL-6, and combinations thereof.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diacylglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

Allogeneic CAR

In embodiments described herein, the immune effector cell can be an allogeneic immune effector cell, e.g., T cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some embodiments, downregulation of HLA may be accomplished by reducing or eliminating expression of beta-2 microglobulin (B2M).

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta). Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

Expression systems for siRNA and shRNAs, and exemplary shRNAs, are described, e.g., in paragraphs 649 and 650 of International Application WO2015/142675, filed Mar. 13, 2015, which is incorporated by reference in its entirety.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

The CRISPR/Cas system, and uses thereof, are described, e.g., in paragraphs 651-658 of International Application WO2015/142675, filed Mar. 13, 2015, which is incorporated by reference in its entirety.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

TALENs, and uses thereof, are described, e.g., in paragraphs 659-665 of International Application WO2015/142675, filed Mar. 13, 2015, which is incorporated by reference in its entirety.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

ZFNs, and uses thereof, are described, e.g., in paragraphs 666-671 of International Application WO2015/142675, filed Mar. 13, 2015, which is incorporated by reference in its entirety.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as set out in SEQ ID NO: 82 herein.

In an embodiment, the hTERT has a sequence at least 80%, 85%, 90%, 95%, 96^, 97%, 98%, or 99% identical to the sequence of SEQ ID NO: 82. In an embodiment, the hTERT has a sequence of SEQ ID NO: 82. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as set out in SEQ ID NO: 83 herein.

In an embodiment, the hTERT is encoded by a nucleic acid having a sequence at least 80%, 85%, 90%, 95%, 96, 97%, 98%, or 99% identical to the sequence of SEQ ID NO: 83. In an embodiment, the hTERT is encoded by a nucleic acid of SEQ ID NO: 83.

Activation and Expansion of Immune Effector Cells (e.g., T Cells)

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. In some embodiments, immune effector cells are subjected to an assay as described herein (e.g., one or more biomarkers are assayed) before, during, or after activation, or before, during, or after expansion.

Generally, a population of immune effector cells may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain suitable values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one suitable ratio being at least 1:1 particles per T cell. In one aspect, a ratio of particles to cells of 1:1 or less is used. In one particular aspect, a suitable particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CD19 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, tenfold or more increase in pg/ml of proinflammatory cytokine production, e.g., IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

In one embodiment, the cells are cultured (e.g., expanded, simulated, and/or transduced) in media comprising serum. The serum may be, e.g., human AB serum (hAB). In some embodiments, the hAB serum is present at about 2%, about 5%, about 2-3%, about 3-4%, about 4-5%, or about 2-5%. As shown in Example 15 herein, 2% and 5% serum are each suitable levels that allow for many fold expansion of T cells. Furthermore, as shown in Smith et al., "Ex vivo expansion of human T cells for adoptive immunotherapy using the novel Xeno-free CTS Immune Cell Serum Replacement" Clinical & Translational Immunology (2015) 4, e31; doi: 10.1038/cti.2014.31, medium containing 2% human AB serum is suitable for ex vivo expansion of T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some embodiments, cells transduced with a nucleic acid encoding a CAR, e.g., a CAR described herein, can be selected for administration based upon, e.g., protein expression levels of one or more of CCL20, GM-CSF, IFNγ, IL-10, IL-13, IL-17a, IL-2, IL-21, IL-4, IL-5, IL-6, IL-9, TNFα and/or combinations thereof. In some embodiments, cells transduced with a nucleic acid encoding a CAR, e.g., a CAR described herein, can be selected for administration based upon, e.g., protein expression levels of CCL20, IL-17a, IL-6 and combinations thereof.

Once a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CAR are described in further detail below.

Western blot analysis of CAR expression in primary T cells can be used to detect the presence of monomers and dimers, e.g., as described in paragraph 695 of International Application WO2015/142675, filed Mar. 13, 2015, which is herein incorporated by reference in its entirety.

In vitro expansion of CAR$^+$ T cells following antigen stimulation can be measured by flow cytometry. For example, a mixture of CD4$^+$ and CD8$^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4$^+$ and/or CD8$^+$ T cell subsets by flow cytometry. See, e.g., Milone ET AL., MOLECULAR THERAPY 17(8): 1453-1464 (2009). Alternatively, a mixture of CD4$^+$ and CD8$^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associate antigen as described herein$^+$ K562 cells (K562—a cancer associate antigen as described herein), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. GFP$^+$ T cells are enumerated by flow cytometry using bead-based counting. See, e.g., Milone et al., MOLECULAR THERAPY 17(8): 1453-1464 (2009).

Sustained CAR$^+$ T cell expansion in the absence of re-stimulation can also be measured. See, e.g., Milone et al., MOLECULAR THERAPY 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CAR-expressing cell (e.g., T cell, NK cell) activity, e.g., as described in paragraph 698 of International Application WO2015/142675, filed Mar. 13, 2015, which is herein incorporated by reference in its entirety.

Dose dependent CAR treatment response can be evaluated, e.g., as described in paragraph 699 of International Application WO2015/142675, filed Mar. 13, 2015, which is herein incorporated by reference in its entirety.

Assessment of cell proliferation and cytokine production has been previously described, e.g., as described in paragraph 700 of International Application WO2015/142675, filed Mar. 13, 2015, which is herein incorporated by reference in its entirety.

In another embodiment, potency of a cell (e.g., T cell, NK cell) population (e.g. a CAR-expressing cell) product, e.g., a CD19 CAR-expressing cell (e.g., T cell, NK cell) cell product, e.g., CTL019 cells) is assessed using a Luminex® panel of cytokines to determine cytokine expression levels. Cell (e.g., T cell, NK cell) populations (e.g, a manufactured CAR-expressing cell) cell product, e.g., a CD19 CAR-expressing cell product, e.g., CTL019 cells) are activated in vitro by CD19-expressing K562 (K562-19) cells, which mimic CD19-expressing B cells in CLL. Following cell (e.g., T cell, NK cell) activation, cytokine expression profiles are measured in the co-cultured cell media and potency of activated cells (e.g., a CAR-expressing cell product, e.g., a CD19 CAR-expressing cell product, e.g., CTL019 cells) is correlated with expression of different cytokines including, but not limited to CCL-20/MIP-3a, GM-CSF, IFNγ, IL-10, IL-13, IL-17a, IL-2, IL-21, IL-4, IL-5, IL-6, IL-9, TNFα and/or combinations thereof.

In an embodiment, cytokine expression levels are informative with regards to the potency of a cell (e.g., T cell, NK cell) population (e.g., to kill tumor cells). In an embodiment, cytokine expression levels described herein are used to improve a cell (e.g., T cell, NK cell) population (e.g., a CAR-expressing cell product, e.g., a CD 19 CAR-expressing cell product, e.g., CTL019 cells) prior to infusion in patients. In an embodiment, cytokine expression levels described herein provide an endpoint during optimization of the manufacturing process.

Cytotoxicity can be assessed by a standard 51Cr-release assay, e.g., as described in paragraph 701 of International Application WO2015/142675, filed Mar. 13, 2015, which is herein incorporated by reference in its entirety.

Imaging technologies can be used to evaluate specific trafficking and proliferation of CARs in tumor-bearing animal models, e.g., as described in paragraph 702 of International Application WO2015/142675, filed Mar. 13, 2015, which is herein incorporated by reference in its entirety.

Other assays, including those described in the Example section herein as well as those that are known in the art can also be used to evaluate the CARs described herein.

Alternatively, or in combination to the methods disclosed herein, methods and compositions for one or more of: detection and/or quantification of CAR-expressing cells (e.g., in vitro or in vivo (e.g., clinical monitoring)); immune cell expansion and/or activation; and/or CAR-specific selection, that involve the use of a CAR ligand, are disclosed. In one exemplary embodiment, the CAR ligand is an antibody that binds to the CAR molecule, e.g., binds to the extracellular antigen binding domain of CAR (e.g., an antibody that binds to the antigen binding domain, e.g., an anti-idiotypic antibody; or an antibody that binds to a constant region of the extracellular binding domain). In other embodiments, the CAR ligand is a CAR antigen molecule (e.g., a CAR antigen molecule as described herein).

In one aspect, a method for detecting and/or quantifying CAR-expressing cells is disclosed. For example, the CAR ligand can be used to detect and/or quantify CAR-expressing cells in vitro or in vivo (e.g., clinical monitoring of CAR-expressing cells in a patient, or dosing a patient). The method includes:

providing the CAR ligand (optionally, a labelled CAR ligand, e.g., a CAR ligand that includes a tag, a bead, a radioactive or fluorescent label);

acquiring the CAR-expressing cell (e.g., acquiring a sample containing CAR-expressing cells, such as a manufacturing sample or a clinical sample);

contacting the CAR-expressing cell with the CAR ligand under conditions where binding occurs, thereby detecting the level (e.g., amount) of the CAR-expressing cells present.

Binding of the CAR-expressing cell with the CAR ligand can be detected using standard techniques such as FACS, ELISA and the like.

In another aspect, a method of expanding and/or activating cells (e.g., immune effector cells) is disclosed. The method includes:

providing a CAR-expressing cell (e.g., a first CAR-expressing cell or a transiently expressing CAR cell);

contacting said CAR-expressing cell with a CAR ligand, e.g., a CAR ligand as described herein), under conditions where immune cell expansion and/or proliferation occurs, thereby producing the activated and/or expanded cell population.

In certain embodiments, the CAR ligand is present on (e.g., is immobilized or attached to a substrate, e.g., a non-naturally occurring substrate). In some embodiments, the substrate is a non-cellular substrate. The non-cellular substrate can be a solid support chosen from, e.g., a plate (e.g., a microtiter plate), a membrane (e.g., a nitrocellulose membrane), a matrix, a chip or a bead. In embodiments, the CAR ligand is present in the substrate (e.g., on the substrate surface). The CAR ligand can be immobilized, attached, or associated covalently or non-covalently (e.g., cross-linked) to the substrate. In one embodiment, the CAR ligand is attached (e.g., covalently attached) to a bead. In the aforesaid embodiments, the immune cell population can be expanded in vitro or ex vivo. The method can further include culturing the population of immune cells in the presence of the ligand of the CAR molecule, e.g., using any of the methods described herein.

In other embodiments, the method of expanding and/or activating the cells further comprises addition of a second stimulatory molecule, e.g., CD28. For example, the CAR ligand and the second stimulatory molecule can be immobilized to a substrate, e.g., one or more beads, thereby providing increased cell expansion and/or activation.

In yet another aspect, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In one embodiment, the CAR ligand is coupled to a toxic agent (e.g., a toxin or a cell ablative drug). In another embodiment, the anti-idiotypic antibody can cause effector cell activity, e.g., ADCC or ADC activities.

Exemplary anti-CAR antibodies that can be used in the methods disclosed herein are described, e.g., in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference.

In some aspects and embodiments, the compositions and methods herein are optimized for a specific subset of T cells, e.g., as described in US Serial No. PCT/US2015/043219 filed Jul. 31, 2015, the contents of which are incorporated herein by reference in their entirety. In some embodiments, the optimized subsets of T cells display an enhanced persistence compared to a control T cell, e.g., a T cell of a different type (e.g., $CD8^+$ or $CD4^+$) expressing the same construct.

In some embodiments, a CD4⁺ T cell comprises a CAR described herein, which CAR comprises an intracellular signaling domain suitable for (e.g., optimized for, e.g., leading to enhanced persistence in) a CD4⁺ T cell, e.g., an ICOS domain. In some embodiments, a CD8⁺ T cell comprises a CAR described herein, which CAR comprises an intracellular signaling domain suitable for (e.g., optimized for, e.g., leading to enhanced persistence of) a CD8⁺ T cell, e.g., a 4-1BB domain, a CD28 domain, or another costimulatory domain other than an ICOS domain. In some embodiments, the CAR described herein comprises an antigen binding domain described herein, e.g., a CAR comprising an antigen binding domain.

In an aspect, described herein is a method of treating a subject, e.g., a subject having cancer. The method includes administering to said subject, an effective amount of:

1) a CD4⁺ T cell comprising a CAR (the CAR$^{CD4+}$) comprising:
  an antigen binding domain, e.g., an antigen binding domain described herein;
  a transmembrane domain; and
  an intracellular signaling domain, e.g., a first costimulatory domain, e.g., an ICOS domain; and
2) a CD8⁺ T cell comprising a CAR (the CAR$^{CD8+}$) comprising:
  an antigen binding domain, e.g., an antigen binding domain described herein;
  a transmembrane domain; and
  an intracellular signaling domain, e.g., a second co stimulatory domain, e.g., a 4-1BB domain, a CD28 domain, or another costimulatory domain other than an ICOS domain;
  wherein the CAR$^{CD4+}$ and the CAR$^{CD8+}$ differ from one another.

Optionally, the method further includes administering:
3) a second CD8+ T cell comprising a CAR (the second CAR$^{CD8+}$) comprising:
  an antigen binding domain, e.g., an antigen binding domain described herein;
  a transmembrane domain; and
  an intracellular signaling domain, wherein the second CAR$^{CD8+}$ comprises an intracellular signaling domain, e.g., a costimulatory signaling domain, not present on the CAR$^{CD8+}$, and, optionally, does not comprise an ICOS signaling domain.

RNA Transfection

Disclosed herein are methods for producing an in vitro transcribed RNA CAR. RNA CAR and methods of using the same are described, e.g., in paragraphs 553-570 of in International Application WO2015/142675, filed Mar. 13, 2015, which is herein incorporated by reference in its entirety.

In one embodiment, the in vitro transcribed RNA CAR can be introduced to a cell as a form of transient transfection. The RNA may have a 3' UTR, a 5' UTR, or both. The 5' UTR may contain a Kozak sequence. The RNA may comprise an IRES. The RNA may comprise a 5' cap. The RNA may comprise a polyA sequence. RNA can be produced using a DNA template that comprises a promoter, e.g., a T7, T7, or SP6 promoter. RNA can be introduced into target cells using any of a number of different methods, for instance, commercially available methods which include, but are not limited to, electroporation, the Gene Pulser II, Multiporator, cationic liposome mediated transfection using lipofection, polymer encapsulation, peptide mediated transfection, or biolistic particle delivery systems such as "gene guns".

Non-Viral Delivery Methods

In some aspects, non-viral methods can be used to deliver a nucleic acid encoding a CAR described herein into a cell or tissue or a subject. Suitable non-viral delivery methods include transposons (e.g., Sleeping Beauty, piggyBac, and pT2-based transposons). Exemplary non-viral delivery methods and methods of using the same are described, e.g., in paragraphs 571-579 of International Application WO2015/142675, filed Mar. 13, 2015, which is herein incorporated by reference in its entirety.

Methods of Manufacture/Production

In one aspect, methods of manufacturing a CAR-expressing cell according to the invention are disclosed herein (e.g., in "Source of Cells" and "Activation and Expansion of Cells").

In an embodiment, a method of manufacturing a CAR-expressing cell is provided. The method comprises:
  providing a preparation of a CAR-expressing cell (e.g., a plurality of CAR-expressing immune effector cells, such as a T cells, or an NK cells) (e.g., a CD19 CAR-expressing cell as described herein, such as, e.g., CTL019);
  acquiring a value for the level of (e.g., determining the level of expression of) one or more genes listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 to obtain a gene expression pattern for the sample;
  (optionally) comparing the obtained gene expression pattern to that of a historical record of gene expression;
  determining a difference between the obtained and historical gene expression; and
  recording the determined difference in a quality control record.

In an embodiment, provided methods comprise steps of providing a CAR-expressing cell (e.g., T cell, NK cell) preparation (e.g., a CD19 CAR-expressing cell (e.g., T cell, NK cell) as described herein, such as, e.g., CTL019);
  determining the levels of expression of one or more genes listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1 to obtain a gene expression pattern (e.g., a gene signature) for the sample;
  correlating the gene signature with patient response to a CAR-expressing cell (e.g., T cell, NK cell) therapy (e.g. a CD19 CAR-expressing cell (e.g., T cell, NK cell) as described herein, such as, e.g., CTL019);
  and optimizing the CAR-expressing cell (e.g., T cell, NK cell) preparation based on the correlation of the gene signature and patient response prior to infusion into patients.

In an embodiment, provided methods comprise acquiring a value for the level (e.g., determining the expression level) of a cytokine, e.g., one or more cytokines listed in Table 14, Table 15, Table 16 (e.g., CCL20, IL-17a and/or IL-6), and Table 17, Table 18, Table 20, secreted by CAR-expressing cells (e.g., T cell, NK cell) in response to antigen recognition. In an embodiment, provided methods comprise determining the expression levels of one or more cytokines CCL20/MIP3a, IL-17a, IL-6 and/or combinations thereof, secreted by CAR-expressing cells (e.g., T cell, NK cell) in response to antigen recognition. In an embodiment, provided methods further comprise integration of cytokines secreted by CAR-expressing cells (e.g., T cells, NK cells), e.g., one or more cytokines listed in Table 14, Table 15 and Table 16, in a potency assay. In an embodiment, provided methods further comprise integration of cytokines CCL20/MIP3a, IL-17a, IL-6 and/or combinations thereof, in a potency assay.

In an embodiment, provided methods comprise integration of cytokines secreted by CAR-expressing cells (e.g., T cells, NK cells), e.g., one or more cytokines listed in Table 14, Table 15, Table 16 (e.g., CCL20, IL-17a and/or IL-6), and Table 17 in a potency assay, and determining whether a CAR-expressing cell (e.g., T cell, NK cell) preparation (e.g., a CD19 CAR-expressing cell (e.g., T cell, NK cell) as described herein, such as, e.g., CTL019) may have a clinical effect. In an embodiment, CCL20/MIP3a, IL-17a, IL-6 and/or combinations thereof are used in a potency assay to determine whether a CAR-expressing cell (e.g., T cell, NK cell) preparation (e.g., a CD19 CAR-expressing cell (e.g., T cell, NK cell) as described herein, such as, e.g., CTL019) may have a clinical effect. In an embodiment, provided methods further comprise adjusting the CAR-expressing cell (e.g., T cell, NK cell) infusion dose to achieve clinical efficacy.

In an embodiment, provided methods comprise a step of providing a blood sample, e.g., a T cell sample, from a subject having cancer.

In an embodiment, provided methods further comprise a step of comparing the obtained gene expression pattern difference with that of a reference sample.

In an embodiment, a reference sample is a CAR-expressing cell (e.g., T cell, NK cell) preparation (e.g., a CD19 CAR-expressing cell as described herein, such as, e.g., CTL019) from a different batch of cells producing the therapeutic CAR-expressing cell preparation.

In an embodiment, a reference sample is a healthy donor sample with a manufactured CAR-expressing cell (e.g., T cell, NK cell) product (e.g., a CD19 CAR-expressing cell as described herein, such as, e.g., CTL019). In an embodiment, a reference sample is a healthy donor sample with a manufactured CD19 CAR-expressing cell product, such as, e.g., CTL019 product.

In an embodiment, provided methods further comprise a step of recording the result of the comparing in a quality control record for the therapeutic CAR-expressing cell (e.g., T cell, NK cell) preparation.

In an embodiment, the determined difference is compared with a historical record of the reference sample.

In an embodiment, the CAR-expressing cell (e.g., T cell, NK cell) preparation is a CD19 CAR-expressing cell (e.g., CTL019) preparation.

In an embodiment, the CAR-expressing cell (e.g., T cell, NK cell) preparation comprises a CD19 CAR-expressing cell (e.g., CTL019) preparation.

In an embodiment, the CAR-expressing cell (e.g., T cell, NK cell) preparation consists of a CD19 CAR-expressing cell (e.g., CTL019) preparation.

In an aspect, a method is provided, comprising:
providing a blood sample, e.g., a T cell sample, from a subject having cancer;
determining the levels of expression of one or more genes listed in Table 1A, Table 1B, Table 7A, Table 7B, Table 8, Table 9, Table 10, Table 14 (e.g., CCL20, IL-17a and/or IL-6), Table 17, Table 18, Table 20, PD-1, LAG-3, TIM-3, CD57, CD27, CD122, CD62L, or KLRG1 to obtain a gene expression pattern for the sample;
comparing the obtained gene expression pattern to that of a reference value, e.g., a historical record of gene expression;

determining a difference between the obtained and the reference value; and
recording the determined difference in a quality control record.

The method can comprise a step of comparing the obtained gene expression pattern difference with that of a reference sample.

In some embodiments, the methods disclosed herein further include administering a T cell depleting agent after treatment with the cell (e.g., an immune effector cell as described herein), thereby reducing (e.g., depleting) the CAR-expressing cells (e.g., the CD19CAR-expressing cells). Such T cell depleting agents can be used to effectively deplete CAR-expressing cells (e.g., CD19CAR-expressing cells) to mitigate toxicity. In some embodiments, the CAR-expressing cells were manufactured according to a method herein, e.g., assayed (e.g., before or after transfection or transduction) according to a method herein.

In some embodiments, the T cell depleting agent is administered one, two, three, four, or five weeks after administration of the cell, e.g., the population of immune effector cells, described herein.

In one embodiment, the T cell depleting agent is an agent that depletes CAR-expressing cells, e.g., by inducing antibody dependent cell-mediated cytotoxicity (ADCC) and/or complement-induced cell death. For example, CAR-expressing cells described herein may also express an antigen (e.g., a target antigen) that is recognized by molecules capable of inducing cell death, e.g., ADCC or complement-induced cell death. For example, CAR expressing cells described herein may also express a target protein (e.g., a receptor) capable of being targeted by an antibody or antibody fragment. Examples of such target proteins include, but are not limited to, EpCAM, VEGFR, integrins (e.g., integrins αvβ3, α4, αI3/4β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain).

In some embodiments, the CAR expressing cell co-expresses the CAR and the target protein, e.g., naturally expresses the target protein or is engineered to express the target protein. For example, the cell, e.g., the population of immune effector cells, can include a nucleic acid (e.g., vector) comprising the CAR nucleic acid (e.g., a CAR nucleic acid as described herein) and a nucleic acid encoding the target protein.

In one embodiment, the T cell depleting agent is a CD52 inhibitor, e.g., an anti-CD52 antibody molecule, e.g., alemtuzumab.

In other embodiments, the cell, e.g., the population of immune effector cells, expresses a CAR molecule as described herein (e.g., CD19CAR) and the target protein recognized by the T cell depleting agent. In one embodiment, the target protein is CD20. In embodiments where the target protein is CD20, the T cell depleting agent is an anti-CD20 antibody, e.g., rituximab.

In further embodiments of any of the aforesaid methods, the methods further include transplanting a cell, e.g., a hematopoietic stem cell, or a bone marrow, into the mammal.

In another aspect, the invention features a method of conditioning a mammal prior to cell transplantation. The method includes administering to the mammal an effective amount of the cell comprising a CAR nucleic acid or polypeptide, e.g., a CD19 CAR nucleic acid or polypeptide. In some embodiments, the cell transplantation is a stem cell transplantation, e.g., a hematopoietic stem cell transplantation, or a bone marrow transplantation. In other embodiments, conditioning a subject prior to cell transplantation includes reducing the number of target-expressing cells in a subject, e.g., CD19-expressing normal cells or CD19-expressing cancer cells.

Nucleic Acid Constructs Encoding a CAR

Nucleic acid molecules encoding one or more CAR constructs can be introduced into an immune effector cell (e.g., a T cell) as described herein. In one aspect, the nucleic acid molecule is provided as a messenger RNA transcript. In one aspect, the nucleic acid molecule is provided as a DNA construct.

In some embodiments, a nucleic acid described herein is introduced into a cell that has been assayed by a method described herein, e.g., one or more biomarkers has been assayed. In some embodiments, a cell comprising a nucleic acid described herein is assayed by a method described herein, e.g., one or more biomarkers has been assayed.

The nucleic acid molecules described herein can be a DNA molecule, an RNA molecule, or a combination thereof. In one embodiment, the nucleic acid molecule is an mRNA encoding a CAR polypeptide as described herein. In other embodiments, the nucleic acid molecule is a vector that includes any of the aforesaid nucleic acid molecules.

Nucleic acid molecules can encode, e.g., a CAR molecule described herein, and can comprise, e.g., a nucleic acid sequence described herein, e.g., in Table 11, Table 12 or Table 13.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Also described are vectors in which a nucleic acid of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, CRISPR, CAS9, and zinc finger nucleases. See below June et al. 2009 NATURE REVIEWS IMMUNOLOGY 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., MOL. THER. 17(8): 1453-1464 (2009). In one aspect, the EF1a promoter comprises the sequence provided as SEQ ID NO:11.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. Reporter genes are described, e.g., in paragraph 599 of International Application WO2015/142675, filed Mar. 13, 2015, which is herein incorporated by reference in its entirety.

In embodiments, the vector may comprise two or more nucleic acid sequences encoding a CAR, e.g., a CAR described herein, e.g., a CD19 CAR, and a second CAR, e.g., an inhibitory CAR or a CAR that specifically binds to an antigen other than CD19. In such embodiments, the two or more nucleic acid sequences encoding the CAR are encoded by a single nucleic molecule in the same frame and as a single polypeptide chain. In this aspect, the two or more CARs, can, e.g., be separated by one or more peptide cleavage sites. (e.g., an auto-cleavage site or a substrate for an intracellular protease). Examples of peptide cleavage sites include T2A, P2A, E2A, or F2A sites.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means, e.g., those described in paragraphs 601-603 of International Application WO2015/142675, filed Mar. 13, 2015, which is herein incorporated by reference in its entirety.

In the case where a non-viral delivery system is utilized, an exemplary delivery vehicle is a liposome. The use of lipid formulations is contemplated for the introduction of the nucleic acids into a host cell (in vitro, ex vivo or in vivo), and is described, e.g., in paragraphs 604-605 of International Application WO2015/142675, filed Mar. 13, 2015, which is herein incorporated by reference in its entirety.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Therapeutic Methods

In one aspect, the disclosure provides methods for treating a disease associated with expression of a tumor antigen described herein. In some embodiments, immune effector cells are assayed by a method described herein, e.g., one or more biomarkers is assayed, and the cells are administered to a subject as part of a treatment described herein. For example, the immune effector cells can be administered as part of a combination therapy described herein.

In one aspect, the present disclosure provides methods of treating cancer (e.g., a hematological cancer such as ALL and CLL) by providing to the subject in need thereof immune effector cells (e.g., T cells, NK cells) that are engineered to express a CAR. In one embodiment, the cancer to be treated is a B cell malignancy. In one embodiment, the cancer to be treated is ALL (acute lymphoblastic leukemia), CLL (chronic lymphocytic leukemia), DLBCL (diffuse large B-cell lymphoma), MCL (Mantle cell lymphoma, or MM (multiple myeloma).

In one aspect, the disclosure provides methods of treating cancer (e.g., a hematological cancer such as ALL and CLL) by providing to the subject in need thereof immune effector cells (e.g., T cells, NK cells) that are engineered to express a CD19 CAR, wherein the cancer cells express CD19. In one embodiment, the cancer to be treated is a B cell malignancy. In one embodiment, the cancer to be treated is ALL (acute lymphoblastic leukemia), CLL (chronic lymphocytic leukemia), DLBCL (diffuse large B-cell lymphoma), MCL (Mantle cell lymphoma), Hodgkin lymphoma, or MM (multiple myeloma).

In one aspect, the present invention provides methods of treating cancer (e.g., a hematological cancer such as ALL and CLL) by providing to the subject in need thereof immune effector cells (e.g., T cells, NK cells) that are engineered to express a CD22 CAR, wherein the cancer cells express CD22. In one embodiment, the cancer to be treated is a B cell malignancy. In one embodiment, the cancer to be treated is ALL (acute lymphoblastic leukemia), CLL (chronic lymphocytic leukemia), DLBCL (diffuse large B-cell lymphoma), MCL (Mantle cell lymphoma), Hodgkin lymphoma, or MM (multiple myeloma).

In one aspect, the present invention provides methods of treating cancer (e.g., a hematological cancer such as ALL and CLL) by providing to the subject in need thereof immune effector cells (e.g., T cells, NK cells) that are engineered to express a CD20 CAR, wherein the cancer cells express CD20. In one embodiment, the cancer to be treated is a B cell malignancy. In one embodiment, the cancer to be treated is ALL (acute lymphoblastic leukemia), CLL (chronic lymphocytic leukemia), DLBCL (diffuse large B-cell lymphoma), MCL (Mantle cell lymphoma), Hodgkin lymphoma, or MM (multiple myeloma).

In one aspect, the present invention provides methods of treating cancer (e.g., a hematological cancer such as ALL and CLL) by providing to the subject in need thereof immune effector cells (e.g., T cells, NK cells) that are engineered to express a ROR1 CAR, wherein the cancer cells express ROR1. In one embodiment, the cancer to be treated is a B cell malignancy. In one embodiment, the cancer to be treated is ALL (acute lymphoblastic leukemia), CLL (chronic lymphocytic leukemia), DLBCL (diffuse large B-cell lymphoma), MCL (Mantle cell lymphoma), Hodgkin lymphoma, or MM (multiple myeloma).

The disclosure includes a type of cellular therapy where immune effector cells (e.g., T cells, NK cells) are genetically modified (e.g., via transduction of a lentiviral vector) to express a CAR and the CAR-expressing cell is infused to a recipient in need thereof. The infused cell is able to kill tumor cells in the recipient. Unlike antibody therapies, CAR-modified immune effector cells (e.g., T cells, NK cells) are able to replicate in vivo resulting in long-term persistence that can lead to sustained tumor control. CAR-expressing cells (e.g., T cells or NK cells) generated using lentiviral vectors will have stable CAR expression. In various aspects, the immune effector cells (e.g., T cells, NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

The invention also includes a type of cellular therapy where immune effector cells (e.g., T cells, NK cells) are modified, e.g., by in vitro transcribed RNA, to transiently express a CAR and the CAR-expressing cell is infused to a recipient in need thereof. CAR-expressing cells (e.g., T cells, NK cells) generated through transduction of CAR RNA (e.g., by transfection or electroporation) transiently express RNA CARs for 4, 5, 6, 7, 8, 9, 10, 11, 12, 13, 14, 15 days after transduction. The infused cell is able to kill tumor cells in the recipient. Thus, in various aspects, the immune effector cells (e.g., T cells, NK cells) administered to the patient, is present for less than one month, e.g., three weeks, two weeks, one week, after administration of the T cell to the patient.

In one aspect, the present disclosure provides methods of treating cancer (e.g., a hematological cancer such as ALL and CLL) by providing to the subject in need thereof immune effector cells (e.g., T cells, NK cells) that are engineered to express a CAR, e.g., a CAR described herein.

In one embodiment, the present disclosure provides methods of treating cancer (e.g., a hematological cancer such as ALL and CLL) by providing to the subject in need thereof immune effector cells (e.g., T cells, NK cells) that are engineered to express a CAR that specifically targets or binds to a tumor antigen (or cancer associated antigen) described herein, wherein the subject has been identified as a responder or partial responder. In other embodiments, the methods provide treating a cancer (e.g., a hematological cancer such as ALL and CLL) as a partial responder or non-responder by providing to the subject a cancer therapy other than a CAR therapy, e.g., providing the subject a treatment that is the standard of care for that particular type of cancer. In yet another embodiment, the method of treatment includes altering the manufacturing of a CAR-expressing cell to enrich for naïve T cells, e.g., as described herein, for a subject identified as a partial responder or non-responder prior to administering a CAR-expressing cell, e.g., a CAR-expressing cell described herein.

In one embodiment, the immune effector cells (e.g., T cells, NK cells) are engineered to express CD19 CAR, for treating a subject having cancer (e.g., a hematological cancer such as ALL and CLL), wherein the cancer cells express CD19. In one embodiment, the cancer to be treated is ALL or CLL. The CD19 CAR molecules to be expressed in an immune effector cell can comprise any anti-CD19 antigen binding domain in the art (e.g., those provided in Table 12) in combination with any of the CAR domains described herein to generate a full CAR construct. For example, the full CAR construct is a CAR listed in Table 13. Table 13 provides the exemplary full CD19 CAR constructs generated using the various CAR domains (e.g., transmembrane and intracellular signaling domains) listed in Table 12, and the anti-CD19 antigen binding domains listed in Table 12. Amino acid sequences are designated (aa) and nucleic acid sequences are designated (nt).

TABLE 13

CD19 CAR Constructs

| Name | Sequence |
|---|---|
| | CAR 1 |
| 104875 | atggccctccctgtcaccgccctgctgcttccgctggctcttctgctccacgccgctcggcccga |

TABLE 13-continued

CD19 CAR Constructs

| Name | Sequence |
|---|---|
| CAR 1-<br>Full-nt | aattgtgatgacccagtcacccgccactcttagcctttcacccggtgagcgcgcaaccctgtctt<br>gcagagcctcccaagacatctcaaaatacctttaattggtatcaacagaagcccggacaggctcct<br>cgccttctgatctaccacaccagccggctccattctggaatccctgccaggttcagcggtagcgg<br>atctgggaccgactacaccctcactatcagctcactgcagccagaggacttcgctgtctatttct<br>gtcagcaagggaacaccctgccctacacctttggacagggcaccaagctcgagattaaaggtgga<br>ggtggcagcggaggaggtgggtccggcggtggaggaagccaggtccaactccaagaaagcggacc<br>gggtcttgtgaagccatcagaaactctttcactgacttgtactgtgagcggagtgtctctccccg<br>attacggggtgtcttggatcagacagccaccggggaagggtctggaatggattggagtgatttgg<br>ggctctgagactacttactactcttcatccctcaagtcacgcgtcaccatctcaaaggacaactc<br>taagaatcaggtgtcactgaaactgtcatctgtgaccgcagccgacaccgccgtgtactattgcg<br>ctaagcattactattatggcggggagctacgcaatggattactggggacagggtactctggtcacc<br>gtgtccagcaccactaccccagcaccgaggccacccaccccggctcctaccatcgcctcccagcc<br>tctgtccctcgctccggaggcatgtagacccgcagctggtggggccgtgcatacccggggtcttg<br>acttcgcctgcgatatctacatttgggcccctctggctggtacttgcgggtcctgctgctttca<br>ctcgtgatcactctttactgtaagcgcggtcggaagaagctgctgtacatctttaagcaacccttt<br>catgaggcctgtgcagactactcaagaggaggacggctgttcatgccggttcccagaggaggagg<br>aaggcggctgcgaactgcgcgtgaaattcagccgcagcgcagatgctccagcctacaagcagggg<br>cagaaccagctctacaacgaactcaatcttggtcggagagaggagtacgacgtgctggacaagcg<br>gagaggacgggacccagaaatgggcgggaagccgcgcagaaagaatcccaagagggcctgtaca<br>acgagctccaaaaggataagatggcagaagcctatagcgagattggtatgaaaggggaacgcaga<br>agaggcaaaggccacgacggactgtaccagggactcagcaccgccaccaaggacacctatgacgc<br>tcttcacatgcaggccctgccgcctcgg (SEQ ID NO: 55) |
| 104875<br>CAR 1-<br>Full-aa | MALPVTALLLPLALLLHAARPeivmtgspatlslspgeratlscrasqdiskylnwyqqkpgqap<br>rlliyhtsrlhsgiparfsgsgsgtdytltisslqpedfavyfcqqgntlpytfgqgtkleikgg<br>ggsgggggsggggsqvqlqesgpglvkpsetsltctvsgvslpdygvswirqppgkglewigviw<br>gsettyyssslksrvtiskdnsknqvslklssvtaadtavyycakhyyyggsyamdy**wgqgtivt<br>vssttpaprppptpaptiasqplslrpeacrpaaggavhtrgldfacdiyiwaplagtcgvills<br>lvitlyckrgrkkllyifkqpfmrpvqttqeedgcscrfpeeeeggcelrykfsrsadapaykqg<br>qnqlynelnlgrreeydvldkrrgrdpemggkprrknpqeglynelqkdkmaeayseigmkgerr<br>rgkghdglyqglstatkdtydalhmqalppr (SEQ ID NO: 56) |

CAR 2

| 104876<br>CAR 2-<br>Full-nt | atggccctccctgtcaccgccctgctgcttccgctggctcttctgctccacgccgctcggcccga<br>aattgtgatgacccagtcacccgccactcttagcctttcacccggtgagcgcgcaaccctgtctt<br>gcagagcctcccaagacatctcaaaatacctttaattggtatcaacagaagcccggacaggctcct<br>cgccttctgatctaccacaccagccggctccattctggaatccctgccaggttcagcggtagcgg<br>atctgggaccgactacaccctcactatcagctcactgcagccagaggacttcgctgtctatttct<br>gtcagcaagggaacaccctgccctacacctttggacagggcaccaagctcgagattaaaggtgga<br>ggtggcagcggaggaggtgggtccggcggtggaggaagccaggtccaactccaagaaagcggacc<br>gggtcttgtgaagccatcagaaactctttcactgacttgtactgtgagcggagtgtctctccccg<br>attacggggtgtcttggatcagacagccaccggggaagggtctggaatggattggagtgatttgg<br>ggctctgagactacttactaccaatcatccctcaagtcacgcgtcaccatctcaaaggacaactc<br>taagaatcaggtgtcactgaaactgtcatctgtgaccgcagccgacaccgccgtgtactattgcg<br>ctaagcattactattatgcggggagctacgcaatggattctggggacagggtactctggtcacc<br>gtgtccagcaccactaccccagcaccgaggccacccaccccggctcctaccatcgcctcccagcc<br>tctgtccctcgctccggaggcatgtagacccgcagctggtggggccgtgcatacccggggtcttg<br>acttcgcctgcgatatctacatttgggcccctctggctggtacttgcgggtcctgctgctttca<br>ctcgtgatcactctttactgtaagcgcggtcggaagaagctgctgtacatctttaagcaacccttt<br>catgaggcctgtgcagactactcaagaggaggacggctgttcatgccggttcccagaggaggagg<br>aaggcggctgcgaactgcgcgtgaaattcagccgcagcgcagatgctccagcctacaagcagggg<br>cagaaccagctctacaacgaactcaatcttggtcggagagaggagtacgacgtgctggacaagcg<br>gagaggacgggacccagaaatgggcgggaagccgcgcagaaagaatcccaagagggcctgtaca<br>acgagctccaaaaggataagatggcagaagcctatagcgagattggtatgaaaggggaacgcaga<br>agaggcaaaggccacgacggactgtaccagggactcagcaccgccaccaaggacacctatgacgc<br>tcttcacatgcaggccctgccgcctcgg (SEQ ID NO: 57) |
|---|---|
| 104876<br>CAR 2-<br>Full-aa | MALPVTALLLPLALLLHAARPeivmtgspatlslspgeratlscrasqdiskylnwyqqkpgqap<br>rlliyhtsrlhsgiparfsgsgsgtdytltisslqpedfavyfcqqgntlpytfgqgtkleikgg<br>ggsgggggsggggsqvqlqesgpglvkpsetsltctvsgvslpdygvswirqppgkglewigviw<br>gsettyygsslksrvtiskdnsknqvslklssvtaadtavyycakhyyyggsyamdy**wgqgtivt<br>vssttpaprppptpaptiasqplslrpeacrpaaggavhtrgldfacdiyiwaplagtcgvills<br>lvitlyckrgrkkllyifkqpfmrpvqttqeedgcscrfpeeeeggcelrykfsrsadapaykqg<br>qnqlynelnlgrreeydvldkrrgrdpemggkprrknpqeglynelqkdkmaeayseigmkgerr<br>rgkghdglyqglstatkdtydalhmqalppr (SEQ ID NO: 58) |

CAR 3

| 104877<br>CAR 3-<br>Full-nt | atggctctgcccgtgaccgcactcctcctgccactggctctgctgcttcacgccgctcgcccaca<br>agtccagcttcaagaatcagggcctggtctggtgaagccatctgagactctgtccctcaacttgca<br>ccgtgagcggagtgtccctcccagactacgagtgagctggattagacagcctcccgggaaaggca<br>ctggagtggatcggagtgatttgggtagcgaaaccacttactattcatcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactac<br>tggggccagggaactctggtcactgtgtcatctggtggaggaggtagcggaggaggcgggagcgg |

TABLE 13-continued

CD19 CAR Constructs

| Name | Sequence |
|---|---|
| | tggaggtggctccgaaatcgtgatgacccagagccctgcaaccctgtccttctcccggggaac<br>gggctaccctttcttgtcgggcatcacaagatatctcaaaatacctcaattggtatcaacagaag<br>ccgggacaggcccctaggcttcttatctaccacacctctcgcctgcatagcgggattcccgcacg<br>ctttagcgggtctggaagcgggaccgactacactctgaccatctcatctccagcccgaggact<br>tcgccgtctacttctgccagcagggtaacaccctgccgtacacccttcggcagggcaccaagctt<br>gagatcaaaaccactactcccgctccaaggccacccacccctgccccgaccatcgcctctcagcc<br>gctttccctgcgtccggaggcatgtagacccgcagctggtggggccgtgcatacccggggtcttg<br>acttcgcctgcgatatctacatttgggcccctctggctggtacttgcgggtcctgctgctttca<br>ctcgtgatcactctttactgtaagcgcggtcggaagaagctgctgtacatctttaagcaacccttt<br>catgaggcctgtgcagactactcaagaggaggacggctgttcatgccggttcccagaggaggagg<br>aaggcggctgcgaactgcgcgtgaaattcagccgcagcgcagatgctccagcctacaagcagggg<br>cagaaccagctctacaacgaactcaatcttggtcggagagaggagtacgacgtgctggacaagcg<br>gagaggacgggacccagaaatgggcgggaagccgcgcagaaagaatcccaagagggcctgtaca<br>acgagctccaaaaggataagatggcagaagcctatagcgagattggtatgaaaggggaacgcaga<br>agaggcaaaggccacgacggactgtaccagggactcagcaccgccaccaaggacacctatgacgc<br>tcttcacatgcaggccctgccgcctcgg (SEQ ID NO: 59) |
| 104877<br>CAR 3-<br>Full-aa | MALPVTALLLPLALLLHAARPqvqlqesgpglvkpsetlsltctvsgvslpdygvswirqppkg<br>lewigviwgsettyyssslksrvtiskdnsknqvslklssvtaadtavyycakhyyyggsyamdy<br>wgqgtivtvssggggsggggsggggseivmtqspatlslspgeratlscrasqdiskylnwyqqk<br>pgqaprlliyhtsrlhsgiparfsgsgsgtdytltisslqpedfavyfcqqgntlpytfgqgtkl<br>eiktttpaprpptpaptiasqplslrpeacrpaaggavhtrgldfacdiyiwaplagtcgvills<br>lvitlyckrgrkkllyifkqpfmrpvqttqeedgcscrfpeeeeggcelvykfsrsadapaykqg<br>qnqlynelnlgrreeydvldkrrgrdpemggkprrknpqeglynelqkdkmaeayseigmkgerr<br>rgkghdglyqglstatkdtydalhmqalppr (SEQ ID NO: 60) |

CAR 4

| 104878<br>CAR 4-<br>Full-nt | atggctctgccgtgaccgcactcctcctgccactggctctgctgcttcacgccgctcgcccaca<br>agtccagcttcaagaatcagggcctggtctggtgaagccatctgaagctctgagactctgtccctcacttgca<br>ccgtgagcggagtgtccctcccagactacgagtgagctggattagacagcctcccggaaaggga<br>ctggagtggatcggagtgatttgggtagcgaaaccacttactatcaatcttccctgaagtcacg<br>gtcaccatttcaaaggataactcaaagaatcaagtgagcctcaagctctcatcagtcaccgccg<br>ctgacaccgccgtgtattactgtgccaagcattactactatggaggtcctacgccatggactac<br>tggggccaggggaactctggtcactgtgtcatctggtggaggaggtagcggaggaggcgggagcgg<br>tggaggtggctccgaaatcgtgatgacccagagccctgcaaccctgtcctttctcccggggaac<br>gggctaccctttcttgtcgggcatcacaagatatctcaaaatacctcaattggtatcaacagaag<br>ccgggacaggcccctaggcttcttatctaccacacctctcgcctgcatagcgggattcccgcacg<br>ctttagcgggtctggaagcgggaccgactacactctgaccatctcatctccagcccgaggact<br>tcgccgtctacttctgccagcagggtaacaccctgccgtacacccttcggcagggcaccaagctt<br>gagatcaaaaccactactcccgctccaaggccacccacccctgccccgaccatcgcctctcagcc<br>gctttccctgcgtccggaggcatgtagacccgcagctggtggggccgtgcatacccggggtcttg<br>acttcgcctgcgatatctacatttgggcccctctggctggtacttgcgggtcctgctgctttca<br>ctcgtgatcactctttactgtaagcgcggtcggaagaagctgctgtacatctttaagcaacccttt<br>catgaggcctgtgcagactactcaagaggaggacggctgttcatgccggttcccagaggaggagg<br>aaggcggctgcgaactgcgcgtgaaattcagccgcagcgcagatgctccagcctacaagcagggg<br>cagaaccagctctacaacgaactcaatcttggtcggagagaggagtacgacgtgctggacaagcg<br>gagaggacgggacccagaaatgggcgggaagccgcgcagaaagaatcccaagagggcctgtaca<br>acgagctccaaaaggataagatggcagaagcctatagcgagattggtatgaaaggggaacgcaga<br>agaggcaaaggccacgacggactgtaccagggactcagcaccgccaccaaggacacctatgacgc<br>tcttcacatgcaggccctgccgcctcgg (SEQ ID NO: 61) |
|---|---|
| 104878<br>CAR 4-<br>Full-aa | MALPVTALLLPLALLLHAARPqvqlqesgpglvkpsetlsltctvsgvslpdygvswirqppkg<br>lewigviwgsettyygsslksrvtiskdnsknqvslklssvtaadtavyycakhyyyggsyamdy<br>wgqgtivtvssggggsggggsggggseivmtqspatlslspgeratlscrasqdiskylnwyqqk<br>pgqaprlliyhtsrlhsgiparfsgsgsgtdytltisslqpedfavyfcqqgntlpytfgqgtkl<br>eiktttpaprpptpaptiasqplslrpeacrpaaggavhtrgldfacdiyiwaplagtcgvills<br>lvitlyckrgrkkllyifkqpfmrpvqttqeedgcscrfpeeeeggcelrvkfsrsadapaykqg<br>qnqlynelnlgrreeydvldkrrgrdpemggkprrknpqeglynelqkdkmaeayseigmkgerr<br>rgkghdglyqglstatkdtydalhmqalppr (SEQ ID NO: 62) |

CAR 5

| CAR5 scFv<br>domain | eivmtqspatlslspgeratlscrasqdiskylnwyqqkpgqaprlliyhtsrlhsgiparfsgs<br>gsgtdytltisslqpedfavyfcqqgntlpytfgqgtkleikggggsggggsggggsqvg<br>lqesgpglvkpsetlsltctvsgvslpdygvswirqppkglewigviwgsettyysssksrvt<br>iskdnsknqvslklssvtaadtavyycakhyyyggsyamdywgqgtivtvss (SEQ ID NO:<br>63) |
|---|---|
| 104879<br>CAR 5-<br>Full-nt | atggccctccctgtcaccgccctgctgcttccgctggctcttctgctccacgccgctcggcccga<br>aattgtgatgacccagtcacccgccactcttagccttcacccggtgagcgcgcaaccctgtctt<br>gcagagcctcccaagacatctcaaaatacctcaattggtatcaacagaagcccggacaggctcct<br>cgccttctgatctaccaaccagccggctccattctggaatcccctgccaggttcagcggtagcgg<br>atctgggaccgactacacccctcactatcagctcactgcagccagaggacttcgctgtctatttct<br>gtcagcaagggaacacctgccctacacctttggacagggcaccaagctcgagattaaaggtgga<br>ggtggcagcggaggaggtgggtccggcggtggaggaagcggcggaggcgggagccaggtccaact |

TABLE 13-continued

CD19 CAR Constructs

| Name | Sequence |
|---|---|
| | ccaagaaagcggaccgggtcttgtgaagccatcagaaactctttcactgacttgtactgtgagcg<br>gagtgtctctccccgattacggggtgtcttggatcagacagccaccggggaagggtctggaatgg<br>attggagtgatttggggctctgagactacttactactcttcatccctcaagtcacgcgtcaccat<br>ctcaaaggacaactctaagaatcaggtgtcactgaaactgtcatctgtgaccgcagccgacaccg<br>ccgtgtactattgcgctaagcattactattatggcgggagctacgcaatggattactggggacag<br>ggtactctggtcaccgtgtccagcaccactaccccagcaccgaggccacccacccccggctcctac<br>catcgcctccagctctgtccctgcgtccggaggcatgtagaccccgcagctggtggggccgtgc<br>atacccggggtcttgacttcgcctgcgatatctacatttgggcccctctggctggtacttgcggg<br>gtcctgctgctttcactcgtgatcactctttactgtaagcgcggtcggaagaagctgctgtacat<br>cttaagcaaccttcatgaggcctgtgcagactactcaagaggaggacggctgttcatgccggt<br>tcccagaggaggaggaaggcggctgcgaactgcgcgtgaaattcagccgcagcgcagatgctcca<br>gcctacaagcaggggcagaaccagctctacaacgaactcaatcttggtcggagagaggagtacga<br>cgtgctggacaagcggagaggacgggacccagaaatgggcgggaagccgcgcagaaagaatcccc<br>aagagggcctgtacaacgagctccaaaaggataagatggcagaagcctatagcgagattggtatg<br>aaaggggaacgcagaagaggcaaaggccacgacggactgtaccagggactcagcaccgccaccaa<br>ggacacctatgacgctcttcacatgcaggccctgccgcctcgg (SEQ ID NO: 64) |
| 104879<br>CAR 5-<br>Full-aa | MALPVTALLLPLALLLHAARPeivmtgspatlslspgeratlscrasqdiskylnwyqqkpgqap<br>rlliyhtsrlhsgiparfsgsgsgtdytltisslqpedfavyfcqqgntlpytfgqgtkleikgg<br>ggsggggsggggsggggsqvqlqesgpglvkpsetlsltctvsgvslpdygvswirqppgkglew<br>igviwgsettyyssslksrvtiskdnsknqvslklssvtaadtavyycakhyyyggsyamdywgq<br>gtivtvssttttpaprpptpaptiasqplslrpeacrpaaggavhtrgldfacdiyiwaplagtcg<br>vlllslvitlyckrgrkkllyifkqpfmrpvqttqeedgcscrfpeeeeggcelrvkfsrsadap<br>aykqgqnqlynelnlgrreeydvldkrrgrdpemggkprrknpqeglynelqkdkmaeayseigm<br>kgerrrgkghdglyqglstatkdtydalhmqalppr (SEQ ID NO: 65) |

CAR 6

| 104880<br>CAR6-<br>Full-nt | atggccctccctgtcaccgccctgctgcttccgctggctcttctgctccacgccgctcggcccga<br>aattgtgatgacccagtcacccgccactcttagcctttcacccggtgagcgcgcaaccctgtctt<br>gcagagcctcccaagacatctcaaaatacccttaattggtatcaacagaagcccggacaggctcct<br>cgccttctgatctaccaccagccggctccattctgaatccctgccaggttcagcggtagcgg<br>atctgggaccgactacaccctcactatcagctcactgcagccagaggacttcgctgtctatttct<br>gtcagcaaggaaccctgccctacacctttggacagggcaccaagctcgagattaaaggtgga<br>ggtggcagcggaggaggtgggtccggcggtggaggaagcggaggcggagggagccaggtccaact<br>ccaagaaagcggaccgggtcttgtgaagccatcagaaactctttcactgacttgtactgtgagcg<br>gagtgtctctccccgattacggggtgtcttggatcagacagccaccggggaagggtctggaatgg<br>attggagtgatttggggctctgagactacttactaccaatcatccctcaagtcacgcgtcaccat<br>ctcaaaggacaactctaagaatcaggtgtcactgaaactgtcatctgtgaccgcagccgacaccg<br>ccgtgtactattgcgctaagcattactattatggcgggagctacgcaatggattactggggacag<br>ggtactctggtcaccgtgtccagcaccactaccccagcaccgaggccacccacccccggctcctac<br>catcgcctccagctctgtccctgcgtccggaggcatgtagaccccgcagctggtggggccgtgc<br>atacccggggtcttgacttcgcctgcgatatctacatttgggcccctctggctggtacttgcggg<br>gtcctgctgctttcactcgtgatcactctttactgtaagcgcggtcggaagaagctgctgtacat<br>cttaagcaaccttcatgaggcctgtgcagactactcaagaggaggacggctgttcatgccggt<br>tcccagaggaggaggaaggcggctgcgaactgcgcgtgaaattcagccgcagcgcagatgctcca<br>gcctacaagcaggggcagaaccagctctacaacgaactcaatcttggtcggagagaggagtacga<br>cgtgctggacaagcggagaggacgggacccagaaatgggcgggaagccgcgcagaaagaatcccc<br>aagagggcctgtacaacgagctccaaaaggataagatggcagaagcctatagcgagattggtatg<br>aaaggggaacgcagaagaggcaaaggccacgacggactgtaccagggactcagcaccgccaccaa<br>ggacacctatgacgctcttcacatgcaggccctgccgcctcgg (SEQ ID NO: 66) |
|---|---|
| 104880<br>CAR6-<br>Full-aa | MALPVTALLLPLALLLHAARPeivmtgspatlslspgeratlscrasqdiskylnwyqqkpgqap<br>rlliyhtsrlhsgiparfsgsgsgtdytltisslqpedfavyfcqqgntlpytfgqgtkleikgg<br>ggsggggsggggsggggsqvqlqesgpglvkpsetlsltctvsgvslpdygvswirqppgklew<br>igviwgsettyygsslksrvtiskdnsknqvslklssvtaadtavyycakhyyyggsyamdywgq<br>gtivtvssttttpaprpptpaptiasqplslrpeacrpaaggavhtrgldfacdiyiwaplagtcg<br>vlllslvitlyckrgrkkllyifkomfmrpvqttqeedgcscrfpeeeeggcelrvkfsrsadap<br>aykqgqnqlynelnlgrreeydvldkrrgrdpemggkprrknpqeglynelqkdkmaeayseigm<br>kgerrrgkghdglyqglstatkdtydalhmqalppr (SEQ ID NO: 67) |

CAR 7

| 104881<br>CAR 7<br>Full-nt | atggctctgcccgtgaccgcactcctcctgccactggctctgctgcttcacgccgctcgcccaca<br>agtccagcttcaagaatcagggcctggtctggtgaagccatctgagactctgtccctcacttgca<br>ccgtgagcggagtgtccctcccagactacggagtgagctggattagacagcctcccggaaaggga<br>ctggagtggatcggagtgatttggggtagcgaaaccacttactattcatcctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactac<br>tggggccagggaactctggtcactgtgtcatctggtggaggaggtagcggaggaggcgggagcgg<br>tggaggtggctccggaggtggcggaagcgaaatctgatgacccagagaccctgcaaccctgtcc<br>tttctcccgggaacgggctacccttcttgtcgggcatcacaagatatctcaaaatacctcaat<br>tggtatcaacagaagcccggacaggcccctaggcttcttatctaccacacctctcgcctgcatag<br>cggattcccgcacgctttagcgggtctggaagcgggaccgactacactctgaccatctcatctc<br>tccagcccgaggacttcgccgtctacttctgccagcagggtaacaccctgccgtacacccttggc<br>cagggcaccaagcttgagatcaaaaccactactcccgctccaaggccacccacccctgccccgac |

TABLE 13-continued

CD19 CAR Constructs

| Name | Sequence |
|---|---|
| | catcgcctctcagccgctttccctgcgtccggaggcatgtagacccgcagctggtggggccgtgc<br>ataccggggtcttgacttcgcctgcgatatctacatttgggcccctctggctggtacttgcggg<br>gtcctgctgctttcactcgtgatcactctttactgtaagcgcggtcggaagaagctgctgtacat<br>ctttaagcaaccccttcatgaggcctgtgcagactactcaagaggaggacggctgttcatgccggt<br>tcccagaggaggaggaaggcggctgcgaactgcgcgtgaaattcagccgcagcgcagatgctcca<br>gcctacaagcaggggcagaaccagctctacaacgaactcaatcttggtcggagagaggagtacga<br>cgtgctggacaagggagaggacgggacccagaaatgggcgggaagccgcgcagaaagaatcccc<br>aagagggcctgtacaacgagctccaaaaggataagatggcagaagcctatagcgagattggtatg<br>aaaggggaacgcagaagaggcaaaggccacgacggactgtaccagggactcagcaccgccaccaa<br>ggacacctatgacgctcttcacatgcaggccctgccgcctcgg (SEQ ID NO: 68) |
| 104881<br>CAR 7<br>Full-aa | MALPVTALLLPLALLLHAARPqvqlqesgpglvkpsetlsltctvsgvslpdygvswirqppgkg<br>lewigviwgsettyyssslksrvtiskdnsknqvslklssvtaadtavyycakhyyyggsyamdy<br>wgqgtivtvssggggsggggsggggsggggseivmtqspatlslspgeratlscrasqdiskyln<br>wyqqkpgqaprlliyhtsrlhsgiparfsgsgsgtdytltisslqpedfavyfcqqgntlpytfg<br>qgtkleiktttpaprppptpaptiasqplslrpeacrpaaggavhtrgldfacdiyiwaplagtcg<br>vllslvitlyckrgrkkllyifkomfmrpvqttqeedgcscrfpeeeeggcelrvkfsrsadap<br>aykqgqnqlynelnlgrreeydvldkrrgrdpemggkprrknpqeglynelqkdkmaeayseigm<br>kgerrrgkghdglyqglstatkdtydalhmqalppr (SEQ ID NO: 69) |

CAR 8

| | |
|---|---|
| 104882<br>CAR 8-<br>Full-nt | atggctctgccgtgaccgcactcctcctgccactggctctgctgcttcacgccgctcgcccaca<br>agtccagcttcaagaatcagggcctggtctggtgaagccatctgagactctgtccctcacttgca<br>ccgtcgcggagtgtccctcccagactacggagtgagctggattagacagcctcccggaaaggga<br>ctggagtggatcggagtgatttgggtagcgaaaccacttactatcaatcttccctgaagtcacg<br>ggtcaccatttcaaaggataactcaaagaatcaagtgagcctcaagctctcatcagtcaccgcg<br>ctgacaccgccgtgtattactgtgccaagcattactactatggagggtcctacgccatggactac<br>tgggggcaggaactctggtcactgtgtcatctggtggaggaggtagcggaggaggcgggagcgg<br>tggaggtggctccggaggcggtgggtcagaaatcgtgatgacccagagccctgcaaccctgtccc<br>tttctcccggggaacgggctacccttcttgtcgggcatcacaagatatctcaaaatacctcaat<br>tggtatcaacagaagcgggacaggcccctaggcttcttatctaccacacctctcgcctgcatag<br>cgggattcccgcacgctttagcgggtctggaagcgggaccgactacactctgaccatctcatct<br>tccagcccgaggacttcgccgtctacttctgccagcagggtaacccctgccgtacaccttcggc<br>cagggcaccaagcttgagatcaaaaccactactcccgctccaaggccacccacccctgccccgac<br>catcgcctctcagccgctttccctgcgtccggaggcatgtagacccgcagctggtggggccgtgc<br>ataccggggtcttgacttcgcctgcgatatctacatttgggcccctctggctggtacttgcggg<br>gtcctgctgctttcactcgtgatcactctttactgtaagcgcggtcggaagaagctgctgtacat<br>ctttaagcaaccccttcatgaggcctgtgcagactactcaagaggaggacggctgttcatgccggt<br>tcccagaggaggaggaaggcggctgcgaactgcgcgtgaaattcagccgcagcgcagatgctcca<br>gcctacaagcaggggcagaaccagctctacaacgaactcaatcttggtcggagagaggagtacga<br>cgtgctggacaagggagaggacgggacccagaaatgggcgggaagccgcgcagaaagaatcccc<br>aagagggcctgtacaacgagctccaaaaggataagatggcagaagcctatagcgagattggtatg<br>aaaggggaacgcagaagaggcaaaggccacgacggactgtaccagggactcagcaccgccaccaa<br>ggacacctatgacgctcttcacatgcaggccctgccgcctcgg (SEQ ID NO: 70) |
| 104882<br>CAR 8-<br>Full-aa | MALPVTALLLPLALLLHAARPqvqlqesgpglvkpsetlsltctvsgvslpdygvswirqppgkg<br>lewigviwgsettyygsslksrvtiskdnsknqvslklssvtaadtavyycakhyyyggsyamdy<br>wgqgtivtvssggggsggggsggggsggggseivmtqspatlslspgeratlscrasqdiskyln<br>wyqqkpgqaprlliyhtsrlhsgiparfsgsgsgtdytltisslqpedfavyfcqqgntlpytfg<br>qgtkleiktttpaprppptpaptiasqplslrpeacrpaaggavhtrgldfacdiyiwaplagtcg<br>vlllslvitlyckrgrkkllyifkomfmrpvqttqeedgcscrfpeeeeggcelrvkfsrsadap<br>aykqgqnqlynelnlgrreeydvldkrrgrdpemggkprrknpqeglynelqkdkmaeayseigm<br>kgerrrgkghdglyqglstatkdtydalhmqalppr (SEQ ID NO: 71) |

CAR9

| | |
|---|---|
| 105974<br>CAR 9-<br>Full-nt | atggccctccctgtcaccgccctgctgcttccgctggctcttctgctccacgccgctcggcccga<br>aattgtgatgacccagtcacccgccactcttagccttcaccccggtgagcgtgcgcaaccctgtctt<br>gcagagcctcccaagacatctcaaaataccttaattggtatcaacagaagcccggacaggctcct<br>cgccttctgatctaccaacagccggctccattctggaatcctgccaggttcagcggtagcgg<br>atctgggaccgactacaccctcactatcagctcactgcagccagaggacttcgctgtctatttct<br>gtcagcaagggaacacccctgccctacacctttggacagggcaccaagctcgagattaaaggtgga<br>ggtggcagcggaggaggtgggtccggcggtggaggaagcggaggcggtgggagccaggtccaact<br>ccaagaaagcggaccgggtcttgtgaagccatcagaaactctttcactgacttgtactgtgagcg<br>gagtgtctctcccgattacggggtgtcttggatcagacagccaccggggaagggtctggaatgg<br>attggagtgatttgggctctgagactacttactacaactcatccctcaagtcacgcgtcaccat<br>ctcaaaggacaactctaagaatcaggtgtcactgaaactgtcatctgtgaccgcagccgacaccg<br>ccgtgtactattgcgctaagcattactattatggcgggagctacgcaatggattactggggacag<br>ggtactctggtcaccgtgtccagcaccactaccccagcaccgaggccacccaccccggctcctac<br>catcgcctcccagcctctgtcctgcgtccggaggcatgtagacccgcagctggtggggccgtgc<br>ataccggggtcttgacttcgcctgcgatatctacatttgggcccctctggctggtacttgcggg<br>gtcctgctgctttcactcgtgatcactctttactgtaagcgcggtcggaagaagctgctgtacat<br>ctttaagcaaccccttcatgaggcctgtgcagactactcaagaggaggacggctgttcatgccggt<br>tcccagaggaggaggaaggcggctgcgaactgcgcgtgaaattcagccgcagcgcagatgctcca<br>gcctacaagcaggggcagaaccagctctacaacgaactcaatcttggtcggagagaggagtacga |

TABLE 13-continued

CD19 CAR Constructs

| Name | Sequence |
|---|---|
| | cgtgctggacaagcggagaggacgggacccagaaatgggcggaagccgcgcagaaagaatcccc<br>aagagggcctgtacaacgagctccaaaaggataagatggcagaagcctatagcgagattggtatg<br>aaaggggaacgcagaagaggcaaaggccacgacggactgtaccagggactcagcaccgccaccaa<br>ggacacctatgacgctcttcacatgcaggccctgccgcctcgg (SEQ ID NO: 72) |
| 105974<br>CAR 9-<br>Full-aa | MALPVTALLLPLALLLHAARPeivmtgspatlslspgeratlscrasqdiskylnwyqqkpgqap<br>rlliyhtsrlhsgiparfsgsgsgtdytltisslqpedfavyfcqqgntlpytfgqgtkleikgg<br>ggsggggsggggsggggsqvqlqesgpglvkpsetlsltctvsgvslpdygvswirqppgkglew<br>igviwgsettyynsslksrvtiskdnsknqvslklssvtaadtavyycakhyyyggsyamdywgq<br>gtivtvsstttpaprpptpaptiasqplslrpeacrpaaggavhtrgldfacdiyiwaplagtcg<br>vlllslvitlyckrgrkkllyifkqpfmrpvqttqeedgcscrfpeeeeggcelrvkfsrsadap<br>aykqgqnqlynelnlgrreeydvldkrrgrdpemggkprrknpqeglynelqkdkmaeayseigm<br>kgerrrgkghdglyaglstatkdtydalhmaalppr (SEQ ID NO: 73) |

CAR10

| 105975<br>CAR 10<br>Full-nt | atggcctccctgtcaccgccctgctgcttccgctggctcttctgctccacgccgctcggcccga<br>aattgtgatgacccagtcacccgccactcttagcctttcaccggtgagcgcgcaaccctgtctt<br>gcagagcctccaagacatctcaaaataccttaattggtatcaacagaagcccggacaggctcct<br>cgccttctgatctaccacaccagccggctccattctgaatccctgccaggttcagcggtagcgg<br>atctgggaccgactacacctcactatcagctcactgcagccagaggacttcgctgtctatttct<br>gtcagcaagggaacaccctgccctacacctttggacagggcaccaagctcgagattaaaggtgga<br>ggtggcagcggaggaggtgggtccggcggtggaggaagcggaggcggtgggagccaggtccaact<br>ccaagaaagcggaccgggtcttgtgaagccatcagaaactctttcactgacttgtactgtgagcg<br>gagtgtctctccccgattacggggtgtcttggatcagacagccaccggggaagggtctggaatgg<br>attggagtgatttgggggctctgagactacttactacaactcatccctcaagtcacgcgtcaccat<br>ctcaaaggacaactctaagaatcaggtgtcactgaaactgtcatctgtgaccgcagccgacaccg<br>ccgtgtactattgcgctaagcattactattatggcgggagctacgcaatggattactggggacag<br>ggtactctggtcaccgtgtccagcaccactaccccagcaccgaggccacccacccccgctcctac<br>catcgcctcccagcctctgtccctgcgtccggaggcatgtagacccgcagctggtggggccgtgc<br>atacccgggtcttgacttcgcctgcgatatctacatttgggcccctctggctggtacttgcggg<br>gtcctgctgctttcactcgtgatcactctttactgtaagcgcggtcggaagaagctgctgtacat<br>cttaagcaacccttcatgaggcctgtgcagactactcaagaggaggacggctgttcatgccggt<br>tcccagagaggaggaggaaggcggctgcgaactgcgcgtgaaattcagccgcagcgcagatgctcca<br>gcctacaagcaggggcagaaccagctctacaacgaactcaatcttggtcggagagaggagtacga<br>cgtgctggacaagcggagaggacgggacccagaaatgggcggaagccgcgcagaaagaatcccc<br>aagagggcctgtacaacgagctccaaaaggataagatggcagaagcctatagcgagattggtatg<br>aaaggggaacgcagaagaggcaaaggccacgacggactgtaccagggactcagcaccgccaccaa<br>ggacacctatgacgctcttcacatgcaggccctgccgcctcgg (SEQ ID NO: 74) |
| 105975<br>CAR 10<br>Full-aa | MALPVTALLLPLALLLHAARPEIVMTQSPATLSLSPGERATLSCRASQDISKYLNWYQQKPGQAP<br>RLLIYHTSRLHSGIPARFSGSGSGTDYTLTISSLQPEDFAVYFCQQGNTLPYTFGQGTKLEIKGG<br>GGSGGGGSGGGGSGGGGSQVQLQESGPGLVKPSETLSLTCTVSGVSLPDYGVSWIRQPPGKGLEW<br>IGVIWGSETTYYNSSLKSRVTISKDNSKNQVSLKLSSVTAADTAVYYCAKHYYYGGSYAMDYWGQ<br>GTLVTVSSTTTPAPRPPTPAPTIASQPLSLRPEACRPAAGGAVHTRGLDFACDIYIWAPLAGTCG<br>VLLLSLVITLYCKRGRKKLLYIFKQPFMRPVQTTQEEDGCSCRFPEEEEGGCELRVKFSRSADAP<br>AYKQGQNQLYNELNLGRREEYDVLDKRRGRDPEMGGKPRRKNPQEGLYNELQKDKMAEAYSEIGM<br>KGERRRGKGHDGLYQGLSTATKDTYDALHMQALPPR (SEQ ID NO: 75) |

CAR11

| 105976<br>CAR 11<br>Full-nt | atggctctgcccgtgaccgcactcctcctgccactggctctgctgcttcacgccgctcgcccaca<br>agtccagcttcaagaatcagggcctggtctggtgaagccatctgaagcctctgtccctcacttgca<br>ccgtgagcggagtgtccctcccagactacggagtgagctggattagacagcctcccggaaaggga<br>ctggagtggatcggagtgatttgggggtagcgaaaccacttactataactcttccctgaagtcacg<br>ggtcaccatttcaaaggataactcaaagaatcaagtgagcctcaagctctcatcagtcaccgccg<br>ctgacaccgccgtgtattactgtgccaagcattactactatggagggtcctacgccatggactac<br>tggggccagggaactctggtcactgtgtcatctggtggaggaggtagcggaggaggcggaagtgg<br>tggaggtggctccggaggtggcggaagcgaaatcgtgatgacccagagcctgcaaccctgtccc<br>tttctcccggggaacgggctacccttcttgtcggcatcacaagatatctcaaaataccttcaat<br>tggtatcaacagaagcccggacaggcccctaggcttcttatctaccacacctctcgcctgcatag<br>cgggattcccgcacgctttagcgggtctggaagcgggaccgactacactctgaccatctcatctc<br>tccagcccgaggacttcgccgtctacttctgtccagcagggtaacaccctgccgtacaccttcggc<br>cagggcaccaagcttgagatcaaaaccactactcccgctccaaggccaccaccccctgccccgac<br>catcgcctctcagccgctttccctgcgtccggaggcatgtagacccgcagctggtggggccgtgc<br>atacccgggtcttgacttcgcctgcgatatctacatttgggcccctctggctggtacttgcggg<br>gtcctgctgctttcactcgtgatcactctttactgtaagcgcggtcggaagaagctgctgtacat<br>cttaagcaacccttcatgaggcctgtgcagactactcaagaggaggacggctgttcatgccggt<br>tcccagagaggaggaggaaggcggctgcgaactgcgcgtgaaattcagccgcagcgcagatgctcca<br>gcctacaagcaggggcagaaccagctctacaacgaactcaatcttggtcggagagaggagtacga<br>cgtgctggacaagcggagaggacgggacccagaaatgggcggaagccgcgcagaaagaatcccc<br>aagagggcctgtacaacgagctccaaaaggataagatggcagaagcctatagcgagattggtatg<br>aaaggggaacgcagaagaggcaaaggccacgacggactgtaccagggactcagcaccgccaccaa<br>ggacacctatgacgctcttcacatgcaggccctgccgcctcgg (SEQ ID NO: 76) |

TABLE 13-continued

CD19 CAR Constructs

| Name | Sequence |
|---|---|
| 105976 CAR 11 Full-aa | MALPVTALLLPLALLLHAARPQVQLQESGPGLVKPSETLSLTCTVSGVSLPDYGVSWIRQPPGKG LEWIGVIWGSETTYYNSSLKSRVTISKDNSKNQVSLKLSSVTAADTAVYYCAKHYYYGGSYAMDY WGQGTLVTVSSGGGGSGGGGSGGGGSGGGGSEIVMTQSPATLSLSPGERATLSCRASQDISKYLN WYQQKPGQAPRLLIYHTSRLHSGIPARFSGSGSGTDYTLTISSLQPEDFAVYFCQQGNTLPYTFG QGTKLEIKTTTPAPRPPTPAPTIASQPLSLRPEACRPAAGGAVHTRGLDFACDIYIWAPLAGTCG VLLLSLVITLYCKRGRKKLLYIFKQPFMRPVQTTQEEDGCSCRFPEEEEGGCELRVKFSRSADAP AYKQGQNQLYNELNLGRREEYDVLDKRRGRDPEMGGKPRRKNPQEGLYNELQKDKMAEAYSEIGM KGERRRGKGHDGLYQGLSTATKDTYDALHMQALPPR (SEQ ID NO: 77) |
| | CAR12 |
| 105977 CAR 12-Full-nt | atggcccctccctgtcaccgcctgctgcttccgctggctcttctgctccacgccgctcggcccga aattgtgatgacccagtcacccgccactcttagcctttcaccggtgagcgcgcaaccctgtctt gcagagcctcccaagacatctcaaaatacccttaattggtatcaacagaagcccggacaggctcct cgccttctgatctaccacaccagccggctccattctgaatccctgccaggttcagcggtagcgg atctgggaccgactacaccctcactatcagctcactgcagcagaggacttcgctgtctatttct gtcagcaagggaacaccctgccctacacctttggacagggcaccaagctcgagattaaaggtgga ggtggcagcggaggaggtgggtccggcggtggaggaagccaggtccaactccaagaaagcggacc gggtcttgtgaagccatcagaaactcttttcactgacttgtactgtgagcggagtgtctctcccg attacggggtgtcttggatcagacagccaccgggaagggtctggaatggattggagtgatttgg ggctctgagactacttactacaactcatccctcaagtcacgcgtcaccatctcaaaggacaactc taagaatcaggtgtcactgaaactgtcatctgtgaccgcagccgacaccgccgtgtactattgcg ctaagcattactattatggcgggagctacgcaatggattactggggacagggtactctggtcacc gtgtccagcaccactaccccagcaccgaggcccaccccaccccggctcctaccatcgcctcccagc tctgtccctgcgtccggaggcatgtagacccgcagctggtggggccgtgcatacccggggtcttg acttcgcctgcgatatctacatttgggcccctctggctggtacttgcggggtcctgctgctttca ctcgtgatcactcttactgtaagcgcggtcggaagaagctgctgtacatctttaagcaacccttt catgaggcctgtgcagactactcaagaggaggacggctgttcatgccggttcccagaggaggagg aaggcggctgcgaactgcgcgtgaaattcagccgcagcgatgctccagcctacaagcagggg cagaaccagctctacaacgaactcaatcttggtcggagagaggagtacgacgtgctggacaagcg gagaggacgggacccagaaatgggcgggaagccgcgcagaaagaatccccaagagggcctgtaca acgagctccaaaaggataagatggcagaagcctatagcgagattggtatgaaaggggaacgcaga agaggcaaaggccacgacggactgtaccagggactcagcaccgccaccaaggacacctatgacgc tcttcacatgcaggcccctgccgcctcgg (SEQ ID NO: 78) |
| 105977 CAR 12-Full-aa | MALPVTALLLPLALLLHAARPEIVMTQSPATLSLSPGERATLSCRASQDISKYLNWYQQKPGQAP RLLIYHTSRLHSGIPARFSGSGSGTDYTLTISSLQPEDFAVYFCQQGNTLPYTFGQGTKLEIKGG GSGGGGSGGGGSQVQLQESGPGLVKPSETLSLTCTVSGVSLPDYGVSWIRQPPGKGLEWIGVIW GSETTYYNSSLKSRVTISKDNSKNQVSLKLSSVTAADTAVYYCAKHYYYGGSYAMDYWGQGTLVT VSSTTTPAPRPPTPAPTIASQPLSLRPEACRPAAGGAVHTRGLDFACDIYIWAPLAGTCGVLLLS LVITLYCKRGRKKLLYIFKQPFMRPVQTTQEEDGCSCRFPEEEEGGCELRVKFSRSADAPAYKQG QNQLYNELNLGRREEYDVLDKRRGRDPEMGGKPRRKNPQEGLYNELQKDKMAEAYSEIGMKGERR RGKGHDGLYQGLSTATKDTYDALHMQALPPR (SEQ ID NO: 79) |
| | CTL019 |
| CTL019 Full-nt | atggcctaccagtgaccgccttgctcctgccgctggccttgctgctccacgccgccaggccgga catccagatgacacagactacatcctccctgtctgcctctctgggagacagagtcaccatcagtt gcagggcaagtcaggacattagtaaatatttaaattggtatcagcagaaaccagatggaactgtt aaactcctgatctaccatacatcaagattacactcaggagtcccatcaaggttcagtggcagtgg gtctggaacagattattctctcaccattagcaacctggagcaagaagatattgccacttacttt gccaacagggtaatacgcttccgtacacgttcggaggggggaccaagctggagatcacaggtggc ggtggctcggcggtggtgggtcggtggcggcggatctgaggtgaaactgcaggagtcaggacc tggcctggtggcgccctcacagagcctgtccgtcacatgcactgtctcaggggtctcattaccg actatggtgtaagctggattcgccagcctccacgaaagggtctggagtggctgggagtaatatgg ggtagtgaaaccacatactataattcagctctcaaatccagactgaccatcatcaaggacaactc caagagccaagttttcttaaaaatgaacagtctgcaaactgatgacacagccatttactactgtg ccaaacattattactacggtggtagctatgctatggactactggggtcaaggaacctcagtcacc gtctcctcaaccacgacgccagcgccgcgaccaccaacaccggcgcccaccatcgcgtcgcagcc cctgtccctgcgcccagaggcgtgccggccagcggcggggggcgcagtgcacacgagggggctgg acttcgcctgtgatatctacatctgggcgcccttggccgggacttgtggggtccttctcctgtca ctggttatcacccttactgcaaacgggggcagaaagaaactcctgtatatattcaaacaaccatt tatgagaccagtacaaactactcaagaggaagatggctgtagctgccgatttccagaagaagaag aaggaggatgtgaactgagagtgaagttcagcaggagcgcagacgcccccgcgtacaagcagggc cagaaccagctctataacgagctcaatctaggacgaagagaggagtacgatgttttggacaagag acgtggcgggacctgagatgggggaaagccgagaaggaagaaccctcaggaaggcctgtaca atgaactgcagaaagataagatggcggaggcctacagtgagattgggatgaaaggcgagcgccgg aggggcaaggggcacgatggcctttaccagggtctcagtacagccaccaaggacacctacgacgc ccttcacatgcaggcccctgcccctcgc (SEQ ID NO: 80) |
| CTL019 Full-aa | MALPVTALLLPLALLLHAARPdiqmtqttsslsaslgdrvtiscrasqdiskylnwyqqkpdgtv klliyhtsrlhsgvpsrfsgsgsgtdysltisnleqediatyfcqqgntlpytfggggtkleitgg ggsggggsggggsevklqesgpglvapsqslsvtctvsgvslpdygvswirqppkrglewlgviw gsettyynsalksrltiikdnsksqvflkmnslqtddtaiyycakhyyyggsyamdywgqgtsvt vssttpaprpptpaptiasqplslrpeacrpaaggavhtrgldfacdiyiwaplagtcgvills |

TABLE 13-continued

CD19 CAR Constructs

| Name | Sequence |
|---|---|
| | lvitlyckrgrkkllyifkqpfmrpvqttqeedgcscrfpeeeeggcelrvkfsrsadapaykqg qnqlynelnlgrreeydvldkrrgrdpemggkprrknpqeglynelqkdkmaeayseigmkgerr rgkghdglyqglstatkdtydalhmqalppr (SEQ ID NO: 81) |

CD19 Associated Diseases and/or Disorders

In one aspect, the disclosure provides methods for treating cancer, e.g., a cancer associated with CD19 expression, with a CAR-expressing cell (e.g., T cell, NK cell) therapy. Exemplary cancers include, but are not limited to e.g., one or more acute leukemias including but not limited to, e.g., B-cell acute lymphocytic leukemia ("B-ALL"), T-cell acute lymphocytic leukemia ("T-ALL"), acute lymphocytic leukemia (ALL); one or more chronic leukemias including but not limited to, e.g., chronic myelogenous leukemia (CML), chronic lymphocytic leukemia (CLL). Additional cancers or hematologic conditions associated with expression of CD19 include, but are not limited to, e.g., B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further, a disease associated with CD19 expression include, but not limited to, e.g., atypical and/or non-classical cancers, malignancies, precancerous conditions or proliferative diseases associated with expression of CD19.

In one embodiment, the disclosure provides methods for treating CLL.

In another embodiment, the disclosure provides methods for treating ALL.

In another embodiment, the disclosure provides methods for treating B-cell ALL.

In one aspect, the disclosure provides methods of treating a responder (e.g., a complete responder and partial responder) having cancer (e.g., a hematological cancer such as ALL and CLL) with a CAR-expressing cell (e.g., T cell, NK cell) (e.g., a CD19 CAR-expressing cell (e.g., T cell, NK cell) as described herein, such as, e.g., CTL019). In an embodiment, the disclosure provides methods of treating a responder (e.g., a complete responder and partial responder) with a CAR-expressing cell (e.g., T cell, NK cell) in combination with another therapeutic agent, e.g., another therapeutic agent described herein (e.g., another CAR, e.g., another CAR described herein, an inhibitory CAR, e.g., an inhibitory CAR described herein, a kinase inhibitor (e.g., a kinase inhibitor described herein, e.g., an mTOR inhibitor, a BTK inhibitor), a checkpoint inhibitor, e.g., a checkpoint inhibitor described herein, a standard of care therapy, etc.). The combination can be, e.g., with any agent described herein. In an embodiment, after a CAR-expressing cell (e.g., T cell, NK cell) treatment, e.g., an initial CAR-expressing cell (e.g., T cell, NK cell) treatment, a partial responder is tested by any one of the methods described herein, such as, e.g., a CD19 CAR-expressing cell (e.g., T cell, NK cell) gene set signature, and if status has not changed and/or is down-graded to, e.g., a non-responder, then the subject is administered an alternative therapy, e.g., a standard of care for the particular cancer.

In one aspect, the disclosure provides methods of treating a non-responder having cancer (e.g., a hematological cancer such as ALL and CLL) with a CAR-expressing cell (e.g., T cell, NK cell) (e.g., a CD19 CAR-expressing cell (e.g., T cell, NK cell) as described herein, such as, e.g., CTL019). In an embodiment, the disclosure provides methods of treating a non-responder with a CAR-expressing cell (e.g., T cell, NK cell) in combination with another therapeutic agent, e.g., another therapeutic agent described herein (e.g., another CAR, e.g., another CAR described herein, an inhibitory CAR, e.g., an inhibitory CAR described herein, a kinase inhibitor (e.g., a kinase inhibitor described herein, e.g., an mTOR inhibitor, a BTK inhibitor), a checkpoint inhibitor, e.g., a checkpoint inhibitor described herein, a standard of care therapy, etc.). The combination can be, e.g., with any agent described herein. In an embodiment, after a CAR-expressing cell (e.g., T cell, NK cell) treatment, e.g., an initial CAR-expressing cell (e.g., T cell, NK cell) treatment, a non-responder is tested by any one of the methods described herein, such as, e.g., a CD19 CAR-expressing cell (e.g., T cell, NK cell) gene set signature, and if status has changed and/or is up-graded to, e.g., a partial-responder, e.g., a complete responder, then the subject is administered an alternative therapy described herein.

In an embodiment, the disclosure provides methods of treating cancer (e.g., a hematological cancer such as ALL or CLL) comprising steps of: (1) identifying a partial responder subject and/or non-responder subject, (2) administering to the partial responder subject and/or non-responder subject an mTOR inhibitor described herein, such as, e.g., RAD001 and rapamycin, e.g., at a dose and/or dosing schedule described herein; and (3) administering a CAR (e.g., a CD19 CAR described herein, such as, e.g., CTL019), e.g., subsequent to the administration of the mTOR inhibitor, thus treating the cancer. In an embodiment, the method further includes administering the mTOR inhibitor and/or the CAR in combination with one or more checkpoint inhibitors described here, such as, e.g., a PD1 inhibitor.

In an embodiment, the disclosure provides methods of treating cancer (e.g., a hematological cancer such as ALL or CLL) comprising steps of: (1) identifying a partial responder subject (e.g., patient) and/or non-responder subject (e.g., patient), (2) enriching the T cell population of the partial responder subject and/or non-responder subject by selecting for a less exhausted and/or more naïve T cell population, (3) introducing (e.g., by transforming, transducing, infecting, electroporating, etc.) a CAR (e.g., a CD19 CAR described herein, such as, e.g., CTL019) into said enriched T cell population thus transforming the subject's T cell population; and (4) administering the CAR-expressing T cell population into the partial responder subject and/or non-responder subject, thus treating the cancer.

In an embodiment, the disclosure provides methods of treating cancer (e.g., a hematological cancer such as ALL or CLL) comprising steps of: (1) identifying a partial responder subject (e.g., patient) and/or non-responder subject (e.g., patient), (2) reevaluating a partial responder subject and/or non-responder subject (e.g., patient) at a later time period for naïve T cells and/or less exhausted phenotype, and (3), e.g., if the subject has an increase in naïve T cells and/or a less exhausted phenotype, administering a CAR-expressing cell (e.g., T cell, NK cell) therapy (e.g., a CD19 CAR-expressing cell (e.g., T cell, NK cell) as described herein, such as, e.g., CTL019), thus treating the cancer. In an embodiment, a later time period comprises at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 1 day, at least 2 days, at least 3 days, at least 4 days, at least 5 days, at least 6 days, at least 1 week, at least 2 weeks, at least 3 weeks, at least 1 month, at least 2 months, at least 3 months, at least 4 months, at least 5 months, at least 6 months, at least 7 months at least 8 months, at least 9 months, at least 10 months, at least 11 months, at least 1 year, at least 2 years, at least 3 years, at least 4 years, at least 5 years, at least 6 years, at least 7 years, at least 8 years, at least 9 years, at least 10 years, or 11 years or more.

In an embodiment, the disclosure provides methods of treating cancer (e.g., a hematological cancer such as ALL or CLL) comprising the steps of (1) identifying partial responders and/or non-responders; and (2) treating with an alternative therapy, e.g., a standard of care for the particular cancer (e.g., the standard of care for ALL or CLL). In an embodiment, a partial responder is treated only with the standard of care (e.g., the standard of care for a hematological cancer such as ALL or CLL) in the absence of treatment with a CAR. In an embodiment, a non-responder is treated only with the standard of care (e.g., the standard of care for a hematological cancer such as ALL or CLL) in the absence of treatment with a CAR.

In an embodiment, standard of care for CLL includes, but is not limited to exemplary therapies described herein, e.g., described in Table A, and combinations thereof.

TABLE A

| Exemplary therapies for CLL | | | |
|---|---|---|---|
| | w/o del (11q) or del(17p) | del (17p) | del (11q) |
| First line ≥ 70 yrs with comorbidities | | | |
| Obinutuzumab + chlorambucil | X | X | X |
| Rituxan +chlorambucil | X | X | |
| Rituxan | X | | |
| Chlorambucil | X | | |
| Fludarabine ± Rituxan | X | X | |
| Cladribine | X | | |
| Bendamustine ± Rituxan | X | | X |
| PCR (pentostatin, cyclophosphamide, Rituxan) | X | | X |
| First Line < 70 years without significant comorbidities | | | |
| FCR (Fludarabine, cyclophosphamide, Rituxan) | X | X | X |
| FR (Fludarabine, Rituxan) | X | X | |
| PCR | X | | X |
| Bendamustine ± Rituxan | X | | X |
| Obinutuzumab + chlorambucil | X | X | X |

TABLE A-continued

| Exemplary therapies for CLL | | | |
|---|---|---|---|
| | w/o del (11q) or del(17p) | del (17p) | del (11q) |
| Second line- Relapsed/Refractory ≥ 70 years | | | |
| Imbruvica | X | X | X |
| Reduced-dose FCR | X | | X |
| Reduced-dose PCRR | X | | X |
| Bendamustine ± Rituxan | X | | X |
| Ofatumumab | X | X | X |
| Alemutuzumab + Rituxan | X | X | X |
| High dose methylprednisone (HDMP) + rituximab | X | X | X |
| Lenalidomide + Rituxan | X | X | X |
| Dose dense rituximab | X | | X |
| Second line- Relapsed/Refractory < years without significant comorbiditites | | | |
| Imbruvica | X | X | X |
| FCR (Fludarabine, cyclophosphaide, Rituxan) | X | | X |
| PCR | X | | X |
| Bendamustine ± Rituxan | X | | X |
| Fludarabine + alemtuzumab | X | | X |
| R-CHOP (Rituxan, cyclophosphamide, dosorubicin, vincristine, prednisone) | X | X | X |
| Ofatumumab | X | X | X |
| OFAR (oxaliplatin, Fludara, cytarabine, Rituxan) | X | X | X |
| HDMP + rituximab | X | X | X |
| Lenalidomide + Rituxan | X | X | X |

In an embodiment, standard of care for CLL includes (1) radiation therapy, (2) chemotherapy, (3) surgery (e.g., removal of the spleen), (4) targeted therapy, (5) stem cell transplantation, and combinations thereof. In an embodiment, the standard of care comprises external radiation therapy. In an embodiment, the standard of care comprises internal radiation therapy (e.g., a radioactive substance sealed in needles, wires or catheters, for example, that are placed directly into or near the cancer).

In an embodiment, standard of care for ALL includes, but is not limited to exemplary therapies described herein, e.g., described in Table B, and combinations thereof.

TABLE B

| Exemplary therapies for ALL |
|---|
| First Line |
| RCHOP (Rituxan, cyclophosphamide, doxorubicin, vincristine, prednisone) |
| Dose dense RCHOP 14 (category 3) |
| Dose adjusted EPOCH (etoposide, prednisone, vincristine, cyclophosphamide, doxorubicin) + Rituxan |
| First Line Therapy for subjects with Poor left ventricular function or very frail |
| RCEPP (rituximab, cyclophosphamide, etoposide, prednisone, procarbazine) |
| RCEOP (rituximab, cyclophosphamide, etoposide, vincristine, prednisone) |
| RCNOP (rituximab, cyclophosphamide, mitoxantrone, vincristine, prednisone) |
| RCEOP (rituximab, cyclophosphamide, etoposide, vincristine, prednisone) |
| Dose adjusted EPOCH (etoposide, prednisone, vincristine, cyclophosphamide, doxorubicin) + Rituxan |
| Second line- proceed to high dose therapy with autologous stem cell rescue |
| DHAP (dexamethasone, cisplatin, cytarabine) ± Rituxan |
| ESHAP (etoposide, methylprednisolone, cytarabine, cisplatin) ± Rituxan |
| GDP (gemcitabine, dexamethasone, cisplatin) ± Rituxan |

TABLE B-continued

Exemplary therapies for ALL

GemOx(gemcitabine, oxaliplatin) ± Rituxan
ICE (ifosfamide, carboplatin, etoposide) + Rituxan
MINE (mesna, ifosfamide, mitoxantrone, etoposide) ± Rituxan
Second-line therapy (non-candidates for high-dose therapy)

CEPP (cyclophosphamide, etoposide, prednisone, procarbazine) ± Rituxan
CEOP (cyclophosphamide, etoposide, vincristine, prednisone) ± Rituxan
DA-EPOCH ± Rituxan
Revlimid ± Rituxan
Rituxan
GemOx ± Rituxan
GDP ± Rituxan
Bendamustine + Rituxan In an embodiment, standard of care for ALL includes (1) chemotherapy, (2) radiation therapy, (3) stem cell transplantation, (4) biological therapy, (5) targeted therapy, and combinations thereof.

In an embodiment, the standard of care includes, but is not limited to, fludarabine with cyclophosphamide (FC); fludarabine with rituximab (FR); fludarabine, cyclophosphamide, and rituximab (FCR); cyclophosphamide, doxorubicin, vincristine and prednisone (CHOP); and combinations thereof. General chemotherapeutic agents considered for use include, but are not limited to anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), and combinations thereof.

In an embodiment, chemotherapy comprises an antimetabolite, including, but not limited to, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDR®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), cytarabine liposomal (also known as Liposomal Ara-C, DepoCyt™); decitabine (Dacogen®); hydroxyurea (Hydrea®, Droxia™ and Mylocel™); mercaptopurine (Puri-Nethol®), pralatrexate (Folotyn™) capecitabine (Xeloda®), nelarabine (Arranon®), azacitidine (Vidaza®) and gemcitabine (Gemzar®). Suitable antimetabolites include, e.g., 5-fluorouracil (Adrucil®, Efudex®, Fluoroplex®), floxuridine (FUDF®), capecitabine (Xeloda®), pemetrexed (Alimta®), raltitrexed (Tomudex®) and gemcitabine (Gemzar®), and combinations thereof. In an embodiment, the purine analogue is fludarabine.

In an embodiment, chemotherapy comprises an alkylating agent including, but not limited to nitrogen mustards, ethylenimine derivatives, alkyl sulfonates, nitrosoureas and triazenes, uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®) and combinations thereof. Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); Bendamustine HCl (Treanda®) and combinations thereof. In an embodiment, the alkylating agent is bendamustine. In an embodiment, the alkylating agent is cyclophosphamide.

In an embodiment, the chemotherapeutic agent is a kinase inhibitor, e.g., a tyrosine kinase inhibitor including, but not limited to, erlotinib hydrochloride (Tarceva®); linifanib (N-[4-(3-amino-1H-indazol-4-yl)phenyl]-N'-(2-fluoro-5-methylphenyl)urea, also known as ABT 869, available from Genentech); sunitinib malate (Sutent®); bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); dasatinib (Sprycel®); pazopanib (Votrient®); sorafenib (Nexavar®); zactima (ZD6474); and imatinib or imatinib mesylate (Gilvec® and Gleevec®). In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662). In one embodiment, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In an embodiment, targeted therapy includes, but is not limited to an anti-CD20 antibody or functional fragment thereof, such as, e.g., rituximab (Riuxan® and MabThera®); tositumomab (Bexxar®); and ofatumumab (Arzerra®), and combinations thereof. In one embodiment, the targeted therapy includes, but is not limited to, an anti-CD52 antibody or functional fragment thereof such as, e.g., alemtuzumab (Campath®).

In an embodiment, biologic therapy comprises immunotherapy. Exemplary anthracyclines include, without limitation, doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; desacetylravidomycin and combinations thereof.

In an embodiment, stem cell transplantation comprises an autogeneic stem cell transplant. In an embodiment, stem cell transplantation comprises an allogenic stem cell transplant. In an embodiment, stem cell transplantation comprises allogeneic bone marrow transplantation. In an embodiment, stem cell transplantation comprises a hematopoietic stem cell transplantation (HSCT). In an embodiment, hematopoietic stem cells are derived from various tissues including, but not limited to bone marrow, peripheral blood, umbilical cord blood, and combinations thereof.

In an embodiment, the provided methods comprise determining if the subject is identified as having a statistically significant difference in expression level of one or more markers listed in Table 1A, Table 1B, Table 7A, Table 7B, Table 8, Table 9, Table 10, Table 14, Table 15 and Table 16, or a PD-1 biomarker, LAG-3 biomarker, TIM-3 biomarker, CD57 biomarker CD27 biomarker, CD122 biomarker, CD62L biomarker and a KLRG1 biomarker, relative to a reference level, and administering to the subject a therapeutically effective dose of a CAR-expressing cell, e.g., a T cell or NK cell. In an embodiment, a CAR-expressing cell (e.g., T cell, NK cell) is a CD19 CAR-expressing cell (e.g., T cell, NK cell) described herein such as, e.g., CTL019.

In one aspect, the disclosure provides methods for treating a disease associated with CD19 expression. In one aspect, the invention provides methods for treating a disease wherein part of the tumor is negative for CD19 and part of the tumor is positive for CD19. For example, provided methods are useful for treating subjects that have undergone treatment for a disease associated with elevated expression of CD19, wherein the subject that has undergone treatment for elevated levels of CD19 exhibits a disease associated with elevated levels of CD19.

In one aspect, provided methods comprise a vector comprising CD19 CAR operably linked to promoter for expression in mammalian cells (e.g., T cells or NK cells). In one aspect, provided methods comprise a recombinant cell (e.g., T cell or NK cell) expressing a CD19 CAR for use in treating CD19-expressing tumors, wherein the recombinant T cell expressing the CD19 CAR is termed a CD19 CAR-expressing cell. In one aspect, a CD19 CAR-expressing cell (e.g., T cell, NK cell) administered according to provided methods is capable of contacting a tumor cell with at least one CD19 CAR expressed on its surface such that the CAR-expressing cell targets the tumor cell and growth of the tumor is inhibited.

In one aspect, the disclosure features to a method of inhibiting growth of a CD19-expressing tumor cell, comprising contacting the tumor cell with a CD19 CAR-expressing cell (e.g., T cell, NK cell) described herein such that the CAR-expressing cell is activated in response to the antigen and targets the cancer cell, wherein the growth of the tumor is inhibited.

In one aspect, the disclosure includes a type of cellular therapy where T cells are genetically modified to express a CAR and the CAR-expressing cell (e.g., T cell, NK cell) is infused to a recipient in need thereof. The infused cell is able to kill tumor cells in the recipient. Unlike antibody therapies, CAR-modified cells (e.g., T cells or NK cells) are able to replicate in vivo resulting in long-term persistence that can lead to sustained tumor control. In various aspects, the cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the cell to the patient.

The disclosure also includes a type of cellular therapy where cells (e.g., T cells, NK cells) are modified, e.g., by in vitro transcribed RNA, to transiently express a chimeric antigen receptor (CAR) and the CAR-expressing cell (e.g., T cell, NK cell) is infused to a recipient in need thereof. The infused cell is able to kill tumor cells in the recipient. Thus, in various aspects, the cells administered to the patient, are present for less than one month, e.g., three weeks, two weeks, one week, after administration of the cell (e.g., T cell, NK cell) to the patient.

Without wishing to be bound by any particular theory, the anti-tumor immunity response elicited by the CAR-modified cells (e.g., T cells, NK cells) may be an active or a passive immune response, or alternatively may be due to a direct vs indirect immune response. In one aspect, the CAR transduced T cells exhibit specific proinflammatory cytokine secretion and potent cytolytic activity in response to human cancer cells expressing the CD19, resist soluble CD19 inhibition, mediate bystander killing and mediate regression of an established human tumor. For example, antigen-less tumor cells within a heterogeneous field of CD19-expressing tumor may be susceptible to indirect destruction by CD19-redirected T cells that has previously reacted against adjacent antigen-positive cancer cells.

In one aspect, the fully-human CAR-modified cells (e.g., T cells, NK cells) described herein may be a type of vaccine for ex vivo immunization and/or in vivo therapy in a mammal. In one aspect, the mammal is a human.

With respect to ex vivo immunization, at least one of the following occurs in vitro prior to administering the cell into a subject: i) expansion of the cells, ii) introducing a nucleic acid encoding a CAR to the cells or iii) cryopreservation of the cells.

Ex vivo procedures are well known in the art and are discussed more fully below. Briefly, cells are isolated from a subject (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

Hematologic Cancer

Hematological cancer conditions are types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

The present disclosure provides for compositions and methods for treating cancer. In one aspect, the cancer is a hematologic cancer including but is not limited to a leukemia or a lymphoma. In one aspect, the CAR-expressing cells (e.g., T cells, NK cells) of the invention may be used to treat cancers and malignancies such as, but not limited to, e.g., acute leukemias including but not limited to, e.g., B-cell acute lymphoid leukemia ("B-ALL"), T-cell acute lymphoid leukemia ("T-ALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma (MCL), marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 expression includes, but not limited to, e.g., atypical and/or non-classical cancers, malignancies, precancerous conditions or proliferative diseases expressing CD19.

The present disclosure also provides methods for inhibiting the proliferation or reducing a CD19-expressing cell population, the methods comprising contacting a population of cells comprising a CD19-expressing cell with a CD19 CAR-expressing cell (e.g., T cell, NK cell) described herein that binds to the CD19-expressing cell. In a specific aspect, the disclosure provides methods for inhibiting the proliferation or reducing the population of cancer cells expressing CD19, the methods comprising contacting the CD19-expressing cancer cell population with a CD19 CAR-expressing cell (e.g., T cell, NK cell) described herein that binds to the CD19-expressing cell. In one aspect, the present disclosure provides methods for inhibiting the proliferation or reducing the population of cancer cells expressing CD19, the methods comprising contacting the CD19-expressing cancer cell population with a CD19 CAR-expressing cell (e.g., T cell, NK cell) described herein that binds to the CD19-expressing cell. In certain aspects, the anti-CD19 CAR-expressing cell (e.g., T cell, NK cell) reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with CD19-expressing cells relative to a negative control. In one aspect, the subject is a human.

The present disclosure also provides methods for preventing, treating and/or managing a disease associated with CD19-expressing cells (e.g., a hematologic cancer or atypical cancer expressing CD19), the methods comprising administering to a subject in need a CAR-expressing cell (e.g., T cell, NK cell) described herein that binds to the CD19-expressing cell. In one aspect, the subject is a human. Non-limiting examples of disorders associated with CD19-expressing cells include autoimmune disorders (such as lupus), inflammatory disorders (such as allergies and asthma) and cancers (such as hematological cancers or atypical cancers expressing CD19).

The present disclosure also provides methods for preventing, treating and/or managing a disease associated with CD19-expressing cells, the methods comprising administering to a subject in need a CD19 CAR-expressing cell (e.g., T cell, NK cell) described herein that binds to the CD19-expressing cell. In one aspect, the subject is a human.

The present disclosure provides methods for preventing relapse of cancer associated with CD19-expressing cells (e.g., a hematological cancer such as ALL and CLL), the methods comprising administering to a subject in need thereof a CD19 CAR-expressing cell (e.g., T cell, NK cell) described herein that binds to the CD19-expressing cell. In one aspect, the methods comprise administering to the subject in need thereof an effective amount of a CD19 CAR-expressing cell (e.g., T cell, NK cell) described herein that binds to the CD19-expressing cell in combination with an effective amount of another therapy.

Combination Therapy

It will be appreciated that any cancer therapy as described above and herein, can be administered in combination with one or more additional therapies to treat and/or reduce the symptoms of cancer described herein. The pharmaceutical compositions can be administered concurrently with, prior to, or subsequent to, one or more other additional therapies or therapeutic agents. In an embodiment, a CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation peptide vaccine, such as that described in Izumoto et al. 2008 J NEUROSURG 108:963-971.

In one embodiment, a CAR-expressing cell described herein can be used in combination with a chemotherapeutic agent. Exemplary chemotherapeutic agents include those described in paragraphs 873-874 of International Application WO2015/142675, filed Mar. 13, 2015, which is herein incorporated by reference in its entirety, and combinations thereof.

Exemplary alkylating agents include, without limitation, those described in paragraph 875 of International Application WO2015/142675, filed Mar. 13, 2015, which is herein incorporated by reference in its entirety, and combinations thereof.

Exemplary mTOR inhibitors include, without limitation, RAD001, temsirolimus; ridaforolimus (formally known as deferolimus, (1R,2R,4S)-4-[(2R)-2[(1R,9S,12S,15R,16E, 18R,19R,21R,23S,24E,26E,28Z,30S,32S,35R)-1,18-dihydroxy-19,30-dimethoxy-15,17,21,23,29,35-hexamethyl-2,3, 10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methylpyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartyIL-serine-(SEQ ID NO: 91), inner salt (SF1126, CAS 936487-67-1), XL765 and combinations thereof.

Exemplary immunomodulators include, without limitation, those described in paragraph 882 of International Application WO2015/142675, filed Mar. 13, 2015, which is herein incorporated by reference in its entirety, and combinations thereof.

Exemplary anthracyclines include, without limitation, those described in paragraph 883 of International Application WO2015/142675, filed Mar. 13, 2015, which is herein incorporated by reference in its entirety, and combinations thereof.

Exemplary vinca alkaloids include, without limitation, those described in paragraph 884 of International Application WO2015/142675, filed Mar. 13, 2015, which is herein incorporated by reference in its entirety, and combinations thereof.

Exemplary proteosome inhibitors include, without limitation, those described in paragraph 884 of International Application WO2015/142675, filed Mar. 13, 2015, which is herein incorporated by reference in its entirety, and combinations thereof.

In some embodiments, a CAR-expressing cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse.

In one embodiment, a CAR expressing cell described herein are administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In one embodiment, the GITR binding molecules and/or molecules modulating GITR functions (e.g., GITR agonist and/or Treg depleting GITR antibodies) are administered prior to administration of the CAR-expressing cell. For example, in one embodiment, the GITR agonist can be administered prior to apheresis of the cells. In embodiments, cyclophosphamide is administered to the subject prior to administration (e.g., infusion or re-infusion) of the CAR-expressing cell or prior to apheresis of the cells. In embodiments, cyclophosphamide and an anti-GITR antibody are administered to the subject prior to administration (e.g., infusion or re-infusion) of the CAR-expressing cell or prior to apheresis of the cells. In one embodiment, the subject has cancer (e.g., a solid cancer or a hematological cancer such as ALL or CLL). In an embodiment, the subject has CLL. In embodiments, the subject has ALL. In embodiments, the subject has a solid cancer, e.g., a solid cancer described herein. Exemplary GITR agonists include, without limitation, GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In an embodiment, a CAR expressing cell described herein, such as, e.g., a CD19 CAR-expressing cell (e.g., T cell, NK cell), e.g., CTL019, is administered to a subject, e.g., a subject identified as a partial responder or non-responder, in combination with a GITR agonist, e.g., a GITR agonist described herein. In an embodiment, the GITR agonist is administered prior to the CAR-expressing cell. For example, in an embodiment, the GITR agonist can be administered prior to apheresis of the cells. In an embodiment, the subject has cancer (e.g., a hematological cancer such as ALL and CLL). In an embodiment, the subject has ALL. In an embodiment, the subject has CLL.

In an embodiment, a CAR expressing cell described herein, such as, e.g., a CD19 CAR-expressing cell (e.g., T cell, NK cell), e.g., CTL019 is administered to a subject, e.g., a subject identified as a partial responder or non-responder, in combination with an mTOR inhibitor, e.g., an mTOR inhibitor described herein, e.g., a target of the rapamycin signaling pathway such as RAD001. In an embodiment, the mTOR inhibitor is administered prior to the CAR-expressing cell. For example, in an embodiment, the mTOR inhibitor can be administered prior to apheresis of the cells. In an embodiment, the subject has cancer (e.g., a hematological cancer such as ALL and CLL). In an embodiment, the subject has ALL. In an embodiment, the subject has CLL.

Kinase Inhibitor

In one embodiment, a CAR-expressing cell described herein may be used in a treatment regimen in combination with a kinase inhibitor, e.g., a CDK4 inhibitor, a BTK inhibitor, an MNK inhibitor, an mTOR inhibitor, an ITK inhibitor, etc. In one embodiment, the subject is a complete responder, and the subject is administered a treatment regimen that includes administration of a CAR-expressing cell described herein in combination with a kinase inhibitor, e.g., a kinase inhibitor described herein, e.g., at a dose or dosing schedule described herein. In one embodiment, the subject is a partial responder or a non-responder, and the subject is administered a treatment regimen that includes administration of a CAR-expressing cell described herein in combination with a kinase inhibitor, e.g., a kinase inhibitor described herein, e.g., at a dose or dosing schedule described herein.

In an embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d]pyrimidine. The MNK inhibitor can be, e.g., a MNK1a, MNK1b, MNK2a and/or MNK2b inhibitor.

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1- methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered.

In one embodiment, the kinase inhibitor is an mTOR inhibitor selected from temsirolimus; ridaforolimus (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

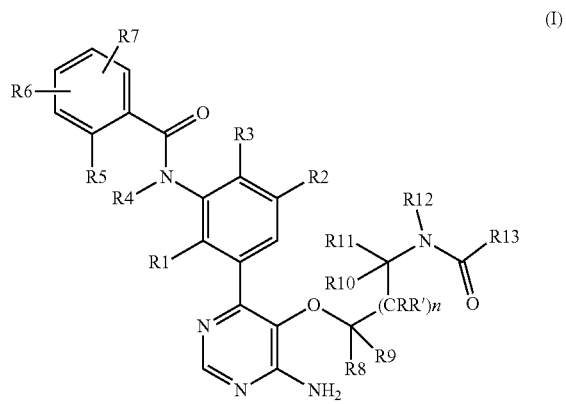

wherein,
R1 is hydrogen, C1-C6 alkyl optionally substituted by hydroxy;
R2 is hydrogen or halogen;
R3 is hydrogen or halogen;
R4 is hydrogen;
R5 is hydrogen or halogen;
or R4 and R5 are attached to each other and stand for a bond, —CH2-, —CH2-CH2-, —CH=CH—, —CH=CH—CH2-; —CH2-CH=CH—; or —CH2-CH2-CH2-;
R6 and R7 stand independently from each other for H, C1-C6 alkyl optionally substituted by hydroxyl, C3-C6 cycloalkyl optionally substituted by halogen or hydroxy, or halogen;
R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;
R12 is hydrogen or C1-C6 alkyl optionally substituted by halogen or C1-C6 alkoxy;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;
n is 0 or 1; and
R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

Low, Immune Enhancing, Dose of an mTOR Inhibitor

Methods described herein can use a low, immune enhancing, dose of an mTOR inhibitor e.g., an allosteric mTOR inhibitor, including rapalogs such as RAD001. Administration of a low, immune enhancing, dose of an mTOR inhibitor (e.g., a dose that is insufficient to completely suppress the immune system, but sufficient to improve immune function) can optimize the performance of immune effector cells, e.g., T cells or CAR-expressing cells, in the subject. Methods for measuring mTOR inhibition, dosages, treatment regimens, and suitable pharmaceutical compositions are described in U.S. Patent Application No. 2015/0140036, filed Nov. 13, 2014, hereby incorporated by reference.

In an embodiment, administration of a low, immune enhancing, dose of an mTOR inhibitor can result in one or more of the following:
i) a decrease in the number of PD-1 positive immune effector cells;
ii) an increase in the number of PD-1 negative immune effector cells;
iii) an increase in the ratio of PD-1 negative immune effector cells/PD-1 positive immune effector cells;
iv) an increase in the number of naive T cells;
v) an increase in the expression of one or more of the following markers: $CD62L^{high}$, $CD127^{high}$, $CD27^+$, and BCL2, e.g., on memory T cells, e.g., memory T cell precursors;
vi) a decrease in the expression of KLRG1, e.g., on memory T cells, e.g., memory T cell precursors; or
vii) an increase in the number of memory T cell precursors, e.g., cells with any one or combination of the following characteristics: increased $CD62L^{high}$ increased $CD127^{high}$, increased $CD27^+$, decreased KLRG1, and increased BCL2;
and wherein any of the foregoing, e.g., i), ii), iii), iv), v), vi), or vii), occurs e.g., at least transiently, e.g., as compared to a non-treated subject.

In another embodiment, administration of a low, immune enhancing, dose of an mTOR inhibitor results in increased or prolonged proliferation of CAR-expressing cells, e.g., in culture or in a subject, e.g., as compared to non-treated CAR-expressing cells or a non-treated subject. In embodiments, increased proliferation is associated with in an increase in the number of CAR-expressing cells. In another embodiment, administration of a low, immune enhancing, dose of an mTOR inhibitor results in increased killing of cancer cells by CAR-expressing cells, e.g., in culture or in a subject, e.g., as compared to non-treated CAR-expressing cells or a non-treated subject. In embodiments, increased killing of cancer cells is associated with in a decrease in tumor volume.

In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001, or a bioequivalent dose thereof.

In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001, or a bioequivalent dose thereof.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, at least 70 but no more than 90%, at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, at least 60 but no more than 80%, at least 5 but no more than 70%, at least 10 but no more than 70%, at least 15, but no more than 70%, at least 20 but no more than 70%, at least 30 but no more than 70%, at least 40 but no more than 70%, at least 50 but no more than 70%, at least 5 but no more than 60%, at least 10 but no more than 60%, at least 15, but no more than 60%, at least 20 but no more than 60%, at least 30 but no more than 60%, at least 40 but no more than 60%, at least 5 but no more than 50%, at least 10 but no more than 50%, at least 15, but no more than 50%, at least 20 but no more than 50%, at least 30 but no more than 50%, at least 40 but no more than 50%, at least 5 but no more than 40%, at least 10 but no more than 40%, at least 15, but no more than 40%, at least 20 but no more than 40%, at least 30 but no more than 40%, at least 35 but no more than 40%, at least 5 but no more than 30%, at least 10 but no more than 30%, at least 15, but no more than 30%, at least 20 but no more than 30%, or at least 25 but no more than 30%.

The extent of mTOR inhibition can be conveyed as, or corresponds to, the extent of P70 S6 kinase inhibition, e.g., the extent of mTOR inhibition can be determined by the level of decrease in P70 S6 kinase activity, e.g., by the decrease in phosphorylation of a P70 S6 kinase substrate. The level of mTOR inhibition can be evaluated by various methods, such as measuring P70 S6 kinase activity by the Boulay assay, as described in U.S. Patent Application No. 2015/01240036, hereby incorporated by reference, or as described in U.S. Pat. No. 7,727,950, hereby incorporated by reference; measuring the level of phosphorylated S6 by western blot; or evaluating a change in the ratio of PD1 negative immune effector cells to PD1 positive immune effector cells.

As used herein, the term "mTOR inhibitor" refers to a compound or ligand, or a pharmaceutically acceptable salt thereof, which inhibits the mTOR kinase in a cell. In an embodiment, an mTOR inhibitor is an allosteric inhibitor. Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity. In an embodiment, an mTOR inhibitor is a catalytic inhibitor.

Rapamycin is a known macrolide antibiotic produced by *Streptomyces hygroscopicus* having the structure shown in Formula A.

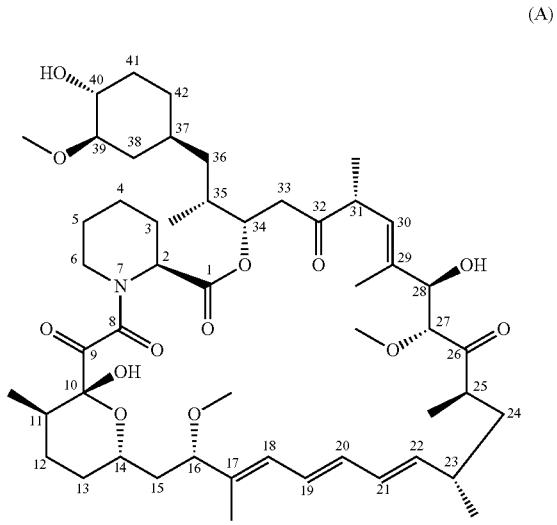 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-0-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethylkapamycin, 40-O-(2-ethoxycarbonylaminoethyl)-rapamycin, 40-O-(2-tolylsulfonamidoethylkapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demethoxy-16-(pent-2-ynyl)oxy-rapamycin, 16-demethoxy-16-(but-2-ynyl)oxy-rapamycin, 16-demethoxy-16-(propargyl)oxy-rapamycin, 16-demethoxy-16-(4-hydroxy-but-2-ynyl)oxy-rapamycin, 16-demethoxy-16-benzyloxy-40-O-(2-hydroxyethyl)-rapamycin, 16-demethoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S,15R,16E,18R,19R,21R, 23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29, 35-hexamethyl-11,36-dioxa-4-aza-tricyclo[30.3.1.04,9] hexatriaconta-16,24,26,28-tetraene-2,3,10,14,20-pentaone Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form. the synthesis of BEZ235 is described in WO2006/122806; CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxyphenyl}-methanol; 3-[2,4-bis[(3S)-3-methylmorpholin-4-yl]pyrido[2,3-d]pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); (E)-N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Inhibitory Molecule Inhibitors/Checkpoint Inhibitors

In one embodiment, the subject can be administered an agent which enhances the activity of a CAR-expressing cell. For example, in one embodiment, the agent can be an agent which inhibits a checkpoint molecule. Checkpoint molecules, e.g., Programmed Death 1 (PD1), can, in some embodiments, decrease the ability of a CAR-expressing cell to mount an immune effector response. Examples of inhibitory molecules, e.g., checkpoint molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta). In embodiments, the CAR-expressing cell described herein comprises a switch costimulatory receptor, e.g., as described in WO 2013/019615, which is incorporated herein by reference in its entirety.

The methods described herein can include administration of a CAR-expressing cell in combination with a checkpoint inhibitor. In one embodiment, the subject is a complete responder. In another embodiment, the subject is a partial responder or non-responder, and, e.g., in some embodiments, the checkpoint inhibitor is administered prior to the CAR-expressing cell, e.g., two weeks, 12 days, 10 days, 8 days, one week, 6 days, 5 days, 4 days, 3 days, 2 days or 1 day before administration of the CAR-expressing cell. In some embodiments, the checkpoint inhibitor is administered concurrently with the CAR-expressing cell.

Inhibition of a checkpoint molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., a siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of a checkpoint molecule in the CAR-expressing cell. In an embodiment, the inhibitor is a shRNA. In an embodiment, the checkpoint molecule is inhibited within a CAR-expressing cell. In these embodiments, a dsRNA molecule that inhibits expression of the checkpoint molecule is linked to the nucleic acid that encodes a component, e.g., all of the components, of the CAR.

In one embodiment, the inhibitor of an inhibitory signal can be, e.g., an antibody or antibody fragment that binds to a checkpoint molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206). In an embodiment, the agent is an antibody or antibody fragment that binds to TIM3. In an embodiment, the agent is an antibody or antibody fragment that binds to LAG3. In an embodiment, the agent is an antibody or antibody fragment that binds to CEACAM.

PD1 is an inhibitory member of the CD28 family of receptors that also includes CD28, CTLA-4, ICOS, and BTLA. PD1 is expressed on activated B cells, T cells and myeloid cells (Agata et al. 1996 INT. IMMUNOL 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 NAT IMMUNOL 2:261-8; Carter et al. 2002 EUR J IMMUNOL 32:634-43). PD-L1 is abundant in human cancers (Dong et al. 2003 J MOL MED 81:281-7; Blank et al. 2005 CANCER IMMUNOL. IMMUNOTHER. 54:307-314; Konishi et al. 2004 CLIN CANCER RES 10:5094). Immune suppression can be reversed by inhibiting the local interaction of PD1 with PD-L1.

Antibodies, antibody fragments, and other inhibitors of PD1, PD-L1 and PD-L2 are available in the art and may be used combination with a CAR described herein, e.g., a CD19 CAR described herein. For example, nivolumab (also referred to as BMS-936558 or MDX1106; Bristol-Myers Squibb) is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. Pidilizumab (CT-011; Cure Tech) is a humanized IgG1k monoclonal antibody that binds to PD1 Pidilizumab and other humanized anti-PD1 monoclonal antibodies are disclosed in WO2009/101611. Lambrolizumab (also referred to as MK03475; Merck) is a humanized IgG4 monoclonal antibody that binds to PD1. Lambrolizumab and other humanized anti-PD1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649.

In one embodiment, the anti-PD-1 antibody or fragment thereof is an anti-PD-1 antibody molecule as described in US 2015/0210769, entitled "Antibody Molecules to PD-1 and Uses Thereof," incorporated by reference in its entirety. In one embodiment, the anti-PD-1 antibody molecule includes at least one, two, three, four, five or six CDRs (or collectively all of the CDRs) from a heavy and light chain variable region from an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1, or a sequence substantially identical (e.g., at least 80%, 85%, 90%, 92%, 95%, 97%, 98%, 99% or higher identical) to any of the aforesaid sequences; or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1; or a sequence substantially identical (e.g., at least 80%, 85%, 90%, 92%, 95%, 97%, 98%, 99% or higher identical) to any of the aforesaid sequences.

TIM3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In one embodiment, the anti-TIM3 antibody or fragment thereof is an anti-TIM3 antibody molecule as described in US 2015/0218274, entitled "Antibody Molecules to TIM3 and Uses Thereof," incorporated by reference in its entirety. In one embodiment, the anti-TIM3 antibody molecule includes at least one, two, three, four, five or six CDRs (or collectively all of the CDRs) from a heavy and light chain variable region from an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-TIM3 antibody molecule comprises at least one, two, three or four variable regions from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10.1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BMS-986016 (Bristol-Myers Squib) is a monoclonal antibody that targets LAW. IMP701 (Immutep) is an antagonist LAG3 antibody and IMP731 (Immutep and GlaxoSmithKline) is a depleting LAG3 antibody. Other LAG3 inhibitors include IN P32 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is a checkpoint molecule, or fragment thereof, and the second domain is a polypeptide that is associated with a positive signal, e.g., a polypeptide comprising an intracellular signaling domain as described herein (also referred to herein as an inhibitory CAR or iCAR). In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express a CAR, e.g., a CD19 CAR.

In one embodiment, the extracellular domain (ECD) of a checkpoint molecule, e.g., a checkpoint molecule described herein such as, e.g., Programmed Death 1 (PD1), can be fused to a transmembrane domain and intracellular signaling domain described herein, e.g., an intracellular signaling domain comprising a costimulatory signaling domain such as, e.g., 41BB OX40, Cd28, CD27, and/or a primary signaling domain, e.g., of CD3 zeta. In one embodiment, the inhibitory CAR, e.g., e.g., PD1 CAR, can be used in combination with another CAR, e.g., CD19CAR (e.g., a CD19RCAR). In one embodiment, the PD1 RCAR (or PD1 CAR) improves the persistence of the T cell. Examples of inhibitory molecules include PD1, PD-L1, PD-L2, CTLA4, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta). In one embodiment, the inhibitory molecule CAR comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR (e.g., TGFRbeta), or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein).

In one embodiment, the inhibitory molecule CAR comprises the extracellular domain (ECD) of PD1 fused to a transmembrane domain and intracellular signaling domains such as 41BB and CD3 zeta (also referred to herein as a PD1 CAR). In one embodiment, the PD1 CAR improves the persistence of the cell CAR-expressing cell. In one embodiment, the PD1 CAR comprises the extracellular domain of PD1 indicated in SEQ ID NO: 44. In one embodiment, the PD1 CAR comprises, the amino acid sequence of SEQ ID NO:40.

In one embodiment, the PD1 CAR comprises the amino acid sequence provided as SEQ ID NO: 41.

In one embodiment, the PD1 CAR, e.g., the PD1 CAR described herein, is encoded by a nucleic acid sequence provided as SEQ ID NO: 42, or at least the comprises the nucleic acid sequence encoding the extracellular domain of PD1 (provided as SEQ ID NO: 101).

In embodiments, the inhibitory extracellular domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human inhibitory molecule, e.g., a naturally occurring human primary stimulatory molecule disclosed herein.

In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR.

In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. In an embodiment, the molecule that modulates or regulates, e.g., inhibits, T-cell function is PD-1.

In embodiments, the agent that enhances the activity of a CAR-expressing cell, e.g., inhibitor of an inhibitory molecule, is administered in combination with an allogeneic CAR, e.g., an allogeneic CAR described herein (e.g., described in the Allogeneic CAR section herein).

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Split CAR

In some embodiments, the CAR-expressing cell uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

Strategies for Regulating Chimeric Antigen Receptors

There are many ways CAR activities can be regulated. In some embodiments, a regulatable CAR (RCAR) where the CAR activity can be controlled is desirable to optimize the safety and efficacy of a CAR therapy. There are many ways CAR activities can be regulated. For example, inducible apoptosis using, e.g., a caspase fused to a dimerization domain (see, e.g., Di Stasa et al., N Engl. J. Med. 2011 Nov. 3; 365(18):1673-1683), can be used as a safety switch in the CAR therapy of the instant invention. In one embodiment, the cells (e.g., T cells or NK cells) expressing a CAR of the present invention further comprise an inducible apoptosis switch, wherein a human caspase (e.g., caspase 9) or a modified version is fused to a modification of the human FKB protein that allows conditional dimerization. In the presence of a small molecule, such as a rapalog (e.g., AP 1903, AP20187), the inducible caspase (e.g., caspase 9) is activated and leads to the rapid apoptosis and death of the cells (e.g., T cells or NK cells) expressing a CAR of the present invention. Examples of a caspase-based inducible apoptosis switch (or one or more aspects of such a switch) have been described in, e.g., US2004040047; US20110286980; US20140255360; WO1997031899; WO2014151960; WO2014164348; WO2014197638; WO2014197638; all of which are incorporated by reference herein.

In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or complement-induced cell death. For example, CAR expressing cells described herein may also express a receptor capable of being targeted by an antibody or antibody fragment. Examples of such receptors include EpCAM, VEGFR, integrins (e.g., integrins αvβ3, α4, αI¾β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain).

For example, a CAR-expressing cell described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8) 853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g., ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In other embodiments, a CAR-expressing cell described herein may also express a target protein recognized by the T cell depleting agent. In one embodiment, the target protein is CD20 and the T cell depleting agent is an anti-CD20 antibody, e.g., rituximab. In such embodiment, the T cell depleting agent is administered once it is desirable to reduce or eliminate the CAR-expressing cell, e.g., to mitigate the CAR induced toxicity. In other embodiments, the T cell depleting agent is an anti-CD52 antibody, e.g., alemtuzumab, as described in the Examples herein.

In other embodiments, an RCAR comprises a set of polypeptides, typically two in the simplest embodiments, in which the components of a standard CAR described herein, e.g., an antigen binding domain and an intracellular signalling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signalling domain. In one embodiment, a CAR of the present invention utilizes a dimerization switch as those described in, e.g., WO2014127261, which is incorporated by reference herein. Additional description and exemplary configurations of such regulatable CARs are provided herein and in, e.g., paragraphs 527-551 of International Publication No. WO 2015/090229 filed Mar. 13, 2015, which is incorporated by reference in its entirety. In some embodiments, an RCAR involves a switch domain, e.g., a FKBP switch domain, as set out SEQ ID NO: 92, or comprise a fragment of FKBP having the ability to bind with FRB, e.g., as set out in SEQ ID NO: 93. In some embodiments, the RCAR involves a switch domain comprising a FRB sequence, e.g., as set out in SEQ ID NO: 94, or a mutant FRB sequence, e.g., as set out in any of SEQ ID Nos. 95-100.

Co-Expression of CAR with a Chemokine Receptor

In embodiments, the CAR-expressing cell described herein further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., J Immunother. 2010 October; 33(8): 780-8 and Kershaw et al., Hum Gene Ther. 2002 Nov. 1; 13(16):1971-80). Thus, without wishing to be bound by theory, it is believed that chemokine receptors expressed in CAR-expressing cells that recognize chemokines secreted by tumors, e.g., solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell described herein include a CXC chemokine receptor (e.g., CXCR1, CXCR2, CXCR3, CXCR4, CXCR5, CXCR6, or CXCR7), a CC chemokine receptor (e.g., CCR1, CCR2, CCR3, CCR4, CCR5, CCR6, CCR7, CCR8, CCR9, CCR10, or CCR11), a CX3C chemokine receptor (e.g., CX3CR1), a XC chemokine receptor (e.g., XCR1), or a chemokine-binding fragment thereof. In one embodiment, the chemokine receptor molecule to be expressed with a CAR described herein is selected based on the chemokine(s) secreted by the tumor. In one embodiment, the CAR-expressing cell described herein further comprises, e.g., expresses, a CCR2b receptor or a CXCR2 receptor. In an embodiment, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

Split CAR

In some embodiments, the CAR-expressing cell uses a split CAR. The split CAR approach is described in more detail in publications WO2014/055442 and WO2014/055657. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates.

When the cell encounters the second antigen, the intracellular signaling domain is activated and cell-killing activity begins. Thus, the CAR-expressing cell is only fully activated in the presence of both antigens.

Pharmaceutical Compositions and Treatments

Pharmaceutical compositions may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions can be, e.g., formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., a contaminant described in paragraph 1009 of International Application WO2015/142675, filed Mar. 13, 2015, which is herein incorporated by reference in its entirety.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the immune effector cells (e.g., T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., NEW ENG. J. OF MED. 319:1676, 1988).

In some embodiments, a dose of CAR cells (e.g., CD19 CAR cells) comprises about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (e.g., CD19 CAR cells) comprises at least about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (e.g., CD19 CAR cells) comprises up to about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (e.g., CD19 CAR cells) comprises about $1.1\times10^6$-$1.8\times10^7$ cells/kg. In some embodiments, a dose of CAR cells (e.g., CD19 CAR cells) comprises about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (e.g., CD19 CAR cells) comprises at least about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (e.g., CD19 CAR cells) comprises up to about $1\times10^7$, $2\times10^7$, $5\times10^7$, $1\times10^8$, $2\times10^8$, $5\times10^8$, $1\times10^9$, $2\times10^9$, or $5\times10^9$ cells.

In certain aspects, it may be desired to administer activated immune effector cells (e.g., T cells, NK cells) to a subject and then subsequently redraw blood (or have an apheresis performed), activate immune effector cells (e.g., T cells, NK cells) therefrom according to the present disclosure, and reinfuse the patient with these activated and expanded immune effector cells (e.g., T cells, NK cells). This process can be carried out multiple times every few weeks. In certain aspects, immune effector cells (e.g., T cells, NK cells) can be activated from blood draws of from 10 cc to 400 cc. In certain aspects, immune effector cells (e.g., T cells, NK cells) are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions described herein are administered to a patient by intradermal or subcutaneous injection. In one aspect, the T cell compositions described herein are administered by i.v. injection. The compositions of immune effector cells (e.g., T cells, NK cells) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs described herein may be introduced, thereby creating a CAR T cell of the present disclosure. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells described herein. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. A suitable daily dose is 1 to 10 mg per day although in some instances larger doses of up to 40 mg per day may be used (described in U.S. Pat. No. 6,120,766).

In one embodiment, the CAR is introduced into immune effector cells (e.g., T cells, NK cells), e.g., using in vitro transcription, and the subject (e.g., human) receives an initial administration of CAR immune effector cells (e.g., T cells, NK cells) of the invention, and one or more subsequent administrations of the CAR immune effector cells (e.g., T cells, NK cells) of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR immune effector cells (e.g., T cells, NK cells) described herein are administered to the subject (e.g., human) per week, e.g., 2, 3, or 4 administrations of the CAR immune effector cells (e.g., T cells, NK cells) of the invention are administered per week. In one embodiment, the subject (e.g., human subject) receives more than one administration of the CAR immune effector cells (e.g., T cells, NK cells) per week (e.g., 2, 3 or 4 administrations per week) (also referred to herein as a cycle), followed by a week of no CAR immune effector cells (e.g., T cells, NK cells) administrations, and then one or more additional administration of the CAR immune effector cells (e.g., T cells, NK cells) (e.g., more than one administration of the CAR immune effector cells (e.g., T cells, NK cells) per week) is administered to the subject. In another embodiment, the subject (e.g., human subject) receives more than one cycle of CAR immune effector cells (e.g., T cells, NK cells), and the time between each cycle is less than 10, 9, 8, 7, 6, 5, 4, or 3 days. In one embodiment, the CAR immune effector cells (e.g., T cells, NK cells) are administered every other day for 3 administrations per week. In one embodiment, the CAR immune effector cells (e.g., T cells, NK cells) described herein are administered for at least two, three, four, five, six, seven, eight or more weeks.

In one aspect, CAR-expressing cells (e.g., T cells, NK cells) as described herein such as, e.g., CD19 CAR-expressing cells, e.g., CTL019 are generated using lentiviral viral vectors, such as lentivirus. CAR-expressing cells generated that way can have stable CAR expression.

In one aspect, CAR-expressing cells (e.g., T cells, NK cells) transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the cell by electroporation.

A potential issue that can arise in patients being treated using transiently expressing CAR cells, e.g., T cells (particularly with murine scFv bearing CAR-expressing cells (e.g., T cells, NK cells)) is anaphylaxis after multiple treatments. Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CAR-expressing cell (e.g., T cell, NK cell) infusion breaks should not last more than ten to fourteen days.

In some embodiments of any of the aforesaid methods, the method further includes administering one or more doses of a cell (e.g., an immune cell containing a CAR nucleic acid or CAR polypeptide as described herein), to a mammal (e.g., a mammal having a cancer, e.g., a mammal that is or is identified as being a responder, complete responder, partial responder, non-responder, relapser, or non-relapser according to the methods herein). In some embodiments, the one or more doses of CAR cells (e.g., CD19 CAR cells) comprises at least about $1 \times 10^6$, $5 \times 10^6$, $1 \times 10^7$, $2 \times 10^7$, $5 \times 10^7$, $1 \times 10^8$, $2 \times 10^8$, $5 \times 10^8$, $1 \times 10^9$, $2 \times 10^9$, or $5 \times 10^9$ cells.

In one embodiment, up to 10, 9, 8, 7, 6, 5, 4, 3, or 2 doses of cells are administered. In other embodiments, one, two, three, four, five or 6 doses of the cells are administered to the mammal, e.g., in a treatment interval of one, two, three, four or more weeks. In one embodiment, up to 6 doses are administered in two weeks. The doses may the same or different. In one embodiment, a lower dose is administered initially, followed by one or more higher doses. In one exemplary embodiment, the lower dose is about $1 \times 10^5$ to $1 \times 10^9$ cells/kg, or $1 \times 10^6$ to $1 \times 10^8$ cells/kg; and the higher dose is about $2 \times 10^5$ to $2 \times 10^9$ cells/kg or $2 \times 10^6$ to $2 \times 10^8$ cells/kg, followed by 3-6 doses of about $4 \times 10^5$ to $4 \times 10^9$ cells/kg, or $4 \times 10^6$ to $4 \times 10^8$ cells/kg.

In one embodiment, the one or more doses of the cells are administered after one or more lymphodepleting therapies, e.g., a lymphodepleting chemotherapy. In one embodiment, the lymphodepleting therapy includes a chemotherapy (e.g., cyclophosphamide).

In one embodiment, the one or more doses is followed by a cell transplant, e.g., an allogeneic hematopoietic stem cell transplant. For example, the allogeneic hematopoietic stem cell transplant occurs between about 20 to about 35 days, e.g., between about 23 and 33 days.

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic. Exemplary biopolymers are described, e.g., in paragraphs 1004-1006 of International Application WO2015/142675, filed Mar. 13, 2015, which is herein incorporated by reference in its entirety.

Exemplary Computer System

Various computer systems can be specially configured to leverage information returned on potential cancer responder status indicators (for example, ALL and CLL responder status indicator as described herein such as, e.g., complete responder, partial responder, non-responder). In some embodiments, the computer system can determine and present information on confidence levels associated with various bio-markers and/or indicators for cancer (e.g. a hematological cancer) such as ALL and CLL. For example, the computer systems can evaluate whether a test conducted on a subject indicates a gene signature of a complete responder, partial responder or non-responder, along with a degree of confidence associated with the subject responder classification. In further examples, the system can provide an indication and/or recommendation on increasing the degree of confidence associated with the predicted responder classification. For example, the system can be configured to evaluate any tests and tested biomarkers and/or indicators of cancer that have been performed for a subject against another characteristic identified as independent and/or additive of the existing data. In an embodiment, the system can be configured to evaluate any tests and tested biomarkers and/or cancer indicators (e.g., a hematological cancer such as CLL and ALL) that have been performed for a subject against another characteristic identified as independent and/or additive of the existing data. The system can determine when an additional biomarker and/or indicator (e.g., gene signature) would increase confidence associated with, for example, a change in responder classification. The system can recommend testing of any identified characteristic accordingly.

In some embodiments, an interactive system for identification, assessment and/or treatment of a subject having cancer (e.g., a hematological cancer such as ALL and CLL) can be provided. In an embodiment, an interactive system for identification, assessment and/or treatment of a subject having cancer (e.g., a hematological cancer such as ALL and CLL) can be provided. According to one embodiment, the system can be configured to accept user input regarding degree of confidence of a subject assessment. Responsive to the user entered degree of confidence, the system can determine test characteristics to include in an evaluation model. In one example, the system includes specification of independent indicators for disease activity in a subject (e.g., patient) population. The system can be configured to estimate a degree of confidence in a determination of disease activity or a prediction of future disease activity based on what independent indicators are used. The system can be further configured to determined and/or recommend various combinations of the determined independent indicators to improve a degree of confidence in an evaluation.

According to another aspect, a computer system can be specially configured to evaluate indicators for cancer (e.g., a hematological cancer such as ALL and CLL). In an embodiment, a computer system can be specially configured to evaluate indicators for ALL and/or CLL. The system can be configured to generate a multivariate model, wherein the multivariate model excludes correlated indicators. In some examples, the system can be configured to identify correlated indicators responsive to evaluating returned test results within a subject (e.g., patient) population having one or more of the indicators. For example, the system can execute regression model analysis to control for various parameters, including, for example, subject age, race, sex, and the presence of other indicators. Responsive to eliminating correlated indicators, the system can generate a model of one or more independent indicators. In some embodiments, the system can be configured to select various combinations of the one or more independent indicators and can further access evaluations (including, for example, evaluating the combination directly) to present information on a confidence level associated with respective selections. The system selected models can be used to generate an expected change in disease activity with the determined confidence level.

In an embodiment, the disclosure provides a system for evaluating cancer (e.g., a hematological cancer such as ALL and CLL) in a subject, comprising:

at least one processor operatively connected to a memory, the at least one processor when executing is configured to:

acquire a value of responder status that comprises a measure of a CD19 CAR-expressing cell (e.g., T cell, NK cell) gene set signature and a combination of one or more of:

a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, a CD27 biomarker, a CD45RO biomarker, a PD-1 biomarker, a LAG-3 biomarker, a TIM-3 biomarker, an IL2RA biomarker, an IL21 biomarker, a CD4 biomarker, a CD8 biomarker, a TH1+ helper T cell gene set signature, a TH2+ helper T cell gene set signature, and a memory T cell (e.g., a CD8+ memory T cell, e.g., a naïve T cell ($T_N$), e.g. a memory stem cell ($T_{SCM}$), e.g. a central memory T cell ($T_{CM}$), e.g. an effector memory T cell ($T_{EM}$)) gene set signature; and responsive to a determination of the value of responder status, perform one, two, three, four or more of:

identify the subject as a complete responder, partial responder, or non-responder;

recommend a CAR-expressing cell (e.g., T cell, NK cell) therapy (e.g., a CD19 CAR-expressing cell (e.g., T cell, NK cell) therapy as described herein, such as, e.g., CTL019);

recommend a selection or alteration of a dosing of a CAR-expressing cell (e.g., T cell, NK cell) therapy; or an alternative therapy, e.g., a standard of care for the particular cancer.

In an embodiment, the invention provides a system for evaluating cancer (e.g., a hematological cancer such as ALL and CLL) in a subject, comprising: at least one processor operatively connected to a memory, the at least one processor when executing is configured to: acquire a value of responder status that comprises a measure of a CD19 CAR-expressing cell (e.g., T cell, NK cell) gene set signature and a combination of one or more of: a biomarker listed in Table 1A, Table 1B, Table 7A, Table 7B, Table 8, Table 9, Table 10, Table 14, Table 15, Table 16 (e.g., CCL20, IL-17a and/or IL-6), Table 17, Table 18, Table 20, PD-1, LAG-3, TIM-3, CD57, CD27, CD122, CD62L, and KLRG1; and responsive to a determination of the value of responder status, perform one, two, three, four or more of: identify the subject as a complete responder, partial responder, or non-responder; recommend a CAR-expressing cell therapy (e.g., a CD19 CAR-expressing cell therapy as described herein, such as, e.g., CTL019); recommend a selection or alteration of a dosing of a CAR-expressing cell therapy; or an alternative therapy.

Figure 16:
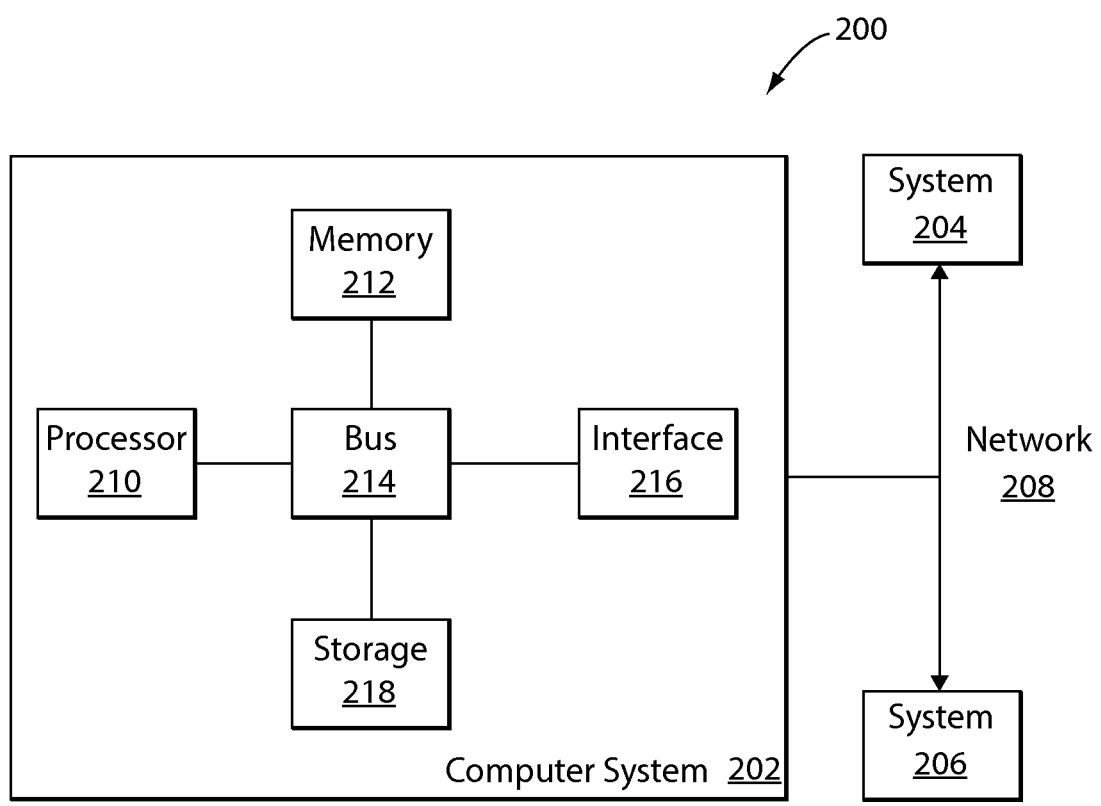
FIG. 16 depicts an exemplary block diagram of a computer system on which various aspects and embodiments may be practiced.

FIG. 16 is a block diagram of a distributed computer system 200, in which various aspects and functions in accord with the present disclosure may be practiced. The distributed computer system 200 may include one or more computer systems. For example, as illustrated, the distributed computer system 200 includes three computer systems 202, 204 and 206. As shown, the computer systems 202, 204 and 206 are interconnected by, and may exchange data through, a communication network 208. The network 208 may include any communication network through which computer systems may exchange data. To exchange data via the network 208, the computer systems 202, 204, and 206 and the network 208 may use various methods, protocols and standards including, among others, token ring, Ethernet, Wireless Ethernet, Bluetooth, radio signaling, infra-red signaling, TCP/IP, UDP, HTTP, FTP, SNMP, SMS, MMS, SS2, JSON, XML, REST, SOAP, CORBA IIOP, RMI, DCOM and Web Services.

According to some embodiments, the functions and operations discussed for identifying, treating or preventing cancer (e.g., a hematological cancer such as ALL and CLL) in a subject can be executed on computer systems 202, 204 and 206 individually and/or in combination. For example, the computer systems 202, 204, and 206 support, for example, participation in a collaborative operations, which may include analyzing treatment data captured on a patient population. In one alternative, a single computer system (e.g., 202) can analyze treatment data captured on a subject (e.g., patient) population to develop characterization models and/or identify independent indicators for disease activity. The computer systems 202, 204 and 206 may include personal computing devices such as cellular telephones, smart phones, tablets, etc., and may also include desktop computers, laptop computers, etc.

Various aspects and functions in accord with the present disclosure may be implemented as specialized hardware or software executing in one or more computer systems including the computer system 202 shown in FIG. 16. In one embodiment, computer system 202 is a computing device specially configured to execute the processes and/or operations discussed above. For example, the system can present user interfaces to end-users that present treatment information, diagnostic information, and confidence levels associated with biomarkers and/or genetic indicators, among other options. As depicted, the computer system 202 includes at least one processor 210 (e.g., a single core or a multi-core processor), a bus 214, a memory 212, a bus 214, input/output interfaces (e.g., 216) and storage 218. The processor 210 may include one or more microprocessors or other types of controllers, and can perform a series of instructions that manipulate data (e.g., treatment data, testing data, etc.). As shown, the processor 210 is connected to other system components, including a memory 212, by an interconnection element (e.g., the bus 214).

The memory 212 and/or storage 218 may be used for storing programs and data during operation of the computer system 202. For example, the memory 212 may be a relatively high performance, volatile, random access memory such as a dynamic random access memory (DRAM) or static memory (SRAM). In addition, the memory 212 may include any device for storing data, such as a disk drive or other non-volatile storage device, such as flash memory, solid state, or phase-change memory (PCM). In further embodiments, the functions and operations discussed with respect to identifying, treating or preventing cancer (e.g., ALL and/or CLL) in a subject can be embodied in an application that is executed on the computer system 202 from the memory 212 and/or the storage 218.

Computer system 202 also includes one or more interfaces 216 such as input devices, output devices, and combination input/output devices. The interfaces 216 may receive input, provide output, or both. The storage 218 may include a computer-readable and computer-writeable non-volatile storage medium in which instructions are stored that define a program to be executed by the processor. The storage system 218 also may include information that is recorded, on or in, the medium, and this information may be processed by the application. A medium that can be used with various embodiments may include, for example, optical disk, magnetic disk or flash memory, SSD, among others.

Further, the invention is not limited to a particular memory system or storage system. Although the computer system 202 is shown by way of example as one type of computer system upon which various functions for identifying, treating or preventing cancer (e.g., a hematological cancer such as ALL and CLL) in a subject may be practiced, aspects of the invention are not limited to being implemented on the computer system, shown in FIG. 16. Various aspects and functions in accord with the present invention may be practiced on one or more computers having different architectures or components than that shown in FIG. 16.

In some embodiments, the computer system 202 may include an operating system that manages at least a portion of the hardware components (e.g., input/output devices, touch screens, cameras, etc.) included in computer system 202. One or more processors or controllers, such as processor 210, may execute an operating system which may be, among others, a Windows-based operating system (e.g., Windows NT, ME, XP, Vista, 2, 8, or RT) available from the Microsoft Corporation, an operating system available from Apple Computer (e.g., MAC OS, including System X), one of many Linux-based operating system distributions (for example, the Enterprise Linux operating system available from Red Hat Inc.), a Solaris operating system available from Sun Microsystems, or a UNIX operating systems available from various sources. Many other operating systems may be used, including operating systems designed for personal computing devices (e.g., iOS, Android, etc.) and embodiments are not limited to any particular operating system.

According to one embodiment, the processor and operating system together define a computing platform on which applications may be executed. Additionally, various functions for identifying, treating or preventing cancer (e.g., a hematological cancer such as ALL and CLL) in a subject may be implemented in a non-programmed environment (for example, documents created in HTML, XML or other format that, when viewed in a window of a browser program, render aspects of a graphical-user interface or perform other functions). Further, various embodiments in accord with aspects of the present disclosure may be implemented as programmed or non-programmed components, or any combination thereof. Thus, the disclosure is not limited to a specific programming language and any suitable programming language could also be used.

EXEMPLIFICATION

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Identification of Novel Transcriptional Gene Signatures that Predict Subject Response to CD19 CAR-Expressing Cell Therapy in Chronic Lymphoid Leukemia (CLL) and Acute Lymphoblastic Leukemia (ALL) Using Whole Genome RNAseq and Unbiased Feature Selection The present Example describes the identification of novel transcriptional gene signatures that predict patient response to CD19 CAR-expressing cell (e.g., T cell, NK cell) therapy (e.g., CTL019 therapy) in Chronic Lymphoid Leukemia (CLL) and Acute Lymphoblastic Leukemia (ALL), for use in accordance with the present invention.

Among other things, the present Example describes novel gene signatures based on mRNA expression levels of selected genes in apheresis and manufactured CD19 CAR-expressing cell (e.g., T cell, NK cell) product samples (e.g., CTL019) prior to re-infusion.

In particular, the present Example describes methods of unbiased feature selection to discover novel gene signatures that predict patient response to CD19 CAR-expressing cell (e.g., T cell, NK cell) therapy (e.g., CTL019) in CLL and ALL, for use in accordance with the present invention.

Novel gene signatures based on mRNA expression levels in apheresis and manufactured CD19 CAR-expressing cell product samples prior to re-infusion have been identified that predict patient response to CD19 CAR-expressing cell therapy in Chronic Lymphoid Leukemia (CLL) and Acute Lymphoblastic Leukemia (ALL). The identified signatures were discovered in a whole genome RNAseq study of manufactured product samples which included 7 ALL subject samples and 21 CLL subject samples. ALL subject samples (7 total) were taken from subjects (e.g., patients) with complete response to CD19 CAR-expressing cell therapy. CLL subject samples (21 total) were stratified as follows: biological samples were taken from 2 patients that were complete responders (CRs) to CTL019 therapy, 6 patients that were partial responders (PRs), and 13 non-responders (NRs). The gene signatures were then investigated in a subset of the above patients where samples were collected at apheresis. Several gene signatures discriminating responders from non-responders in manufactured product and apheresis samples were discovered and are described further in Example 2. Healthy donor samples with manufactured product (i.e., reference samples) were acquired and used as a reference level.

Novel gene signatures were then discovered using various data analytical approaches: 1) unbiased feature selection; 2) gene set analysis; and 3) differential expression analysis of selected genes of interest. Gene set analysis (2) and differential expression analysis (3) are discussed in further detail in Example 2.

Novel gene signatures derived from unbiased feature selection were discovered by determining which genes were differentially expressed between the CRs and NRs and between CRs and PRs. Genes were defined as differentially expressed if their differential expression was statistically significant with a FDR p-value cutoff of 0.1. The gene lists for the CR vs NR comparison (N=128) and CR vs PR comparison (N=34) are tabulated in Table 1A-B.

Figure 3:
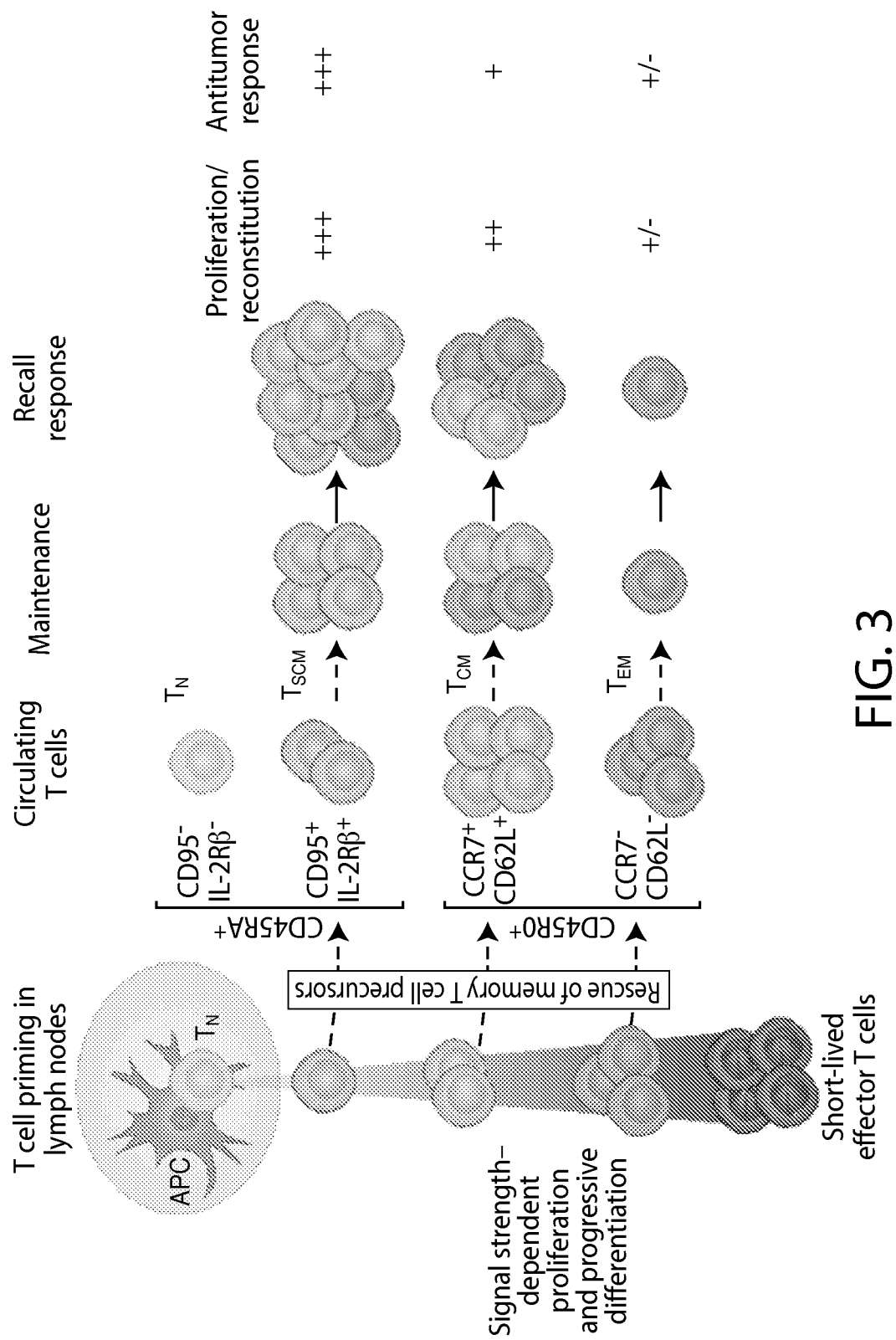
FIG. 3 depicts an exemplary schematic of memory T cell precursors and subsets. Without wishing to be bound by a particular theory, the state of memory T cells in CTL019 samples is likely a major component of response.

Without wishing to be bound by a particular theory, these data indicate that the differentiation state of T cells in apheresis or CD19 CAR-expressing cell (e.g., T cell, NK cell) product (e.g., CTL019) correlate with subject response (i.e., CR, PR, or NR). Gene signatures for T cells from CR are in a more unstimulated/undifferentiated state. In addition, memory T cell subsets are differentially enriched between CRs versus NRs, with CRs showing similarity to naïve T cells ($T_N$) and T memory stem cells ($T_{SCM}$). An exemplary schematic illustrating the progression of a naïve T cell ($T_N$) through the memory T cell subset stages, into an effector memory T cell ($T_{EM}$) is shown in FIG. 3).

Complete responders to CTL019 therapy have a significantly higher % of CD8+ T cells that express the co-stimulatory molecule CD27 but lack the antigen-experienced T cell marker CD45RO compared to the non-responders. In an embodiment, the threshold for this discrimination was 7% CD27+ CD45RO– cells in the CD8+ population. In an embodiment, a complete responder is defined as 7% or greater CD27+ CD45RO– cells in the CD8+ population. Without wishing to be bound by a particular theory, the state of memory T cells in CTL019 samples is likely a major component of response (FIG. 3).

These data demonstrate that CRs are more like resting $T_{EFF}$ cells, resting $T_{REG}$ cells, naïve CD4 cells, unstimulated memory cells and early memory T cells, whereas NRs are more like activated $T_{EFF}$ cells, activated $T_{REG}$ cells, activated TH1 and TH2 cells, stimulated memory cells, and late T memory cells.

TABLE 1A

Comparison of Complete Responders (CR) vs. Non-responders (NR)

| Gene | Unigene | Accession No. | FDR |
|---|---|---|---|
| C16orf74 | Hs.461655 | NM_206967 | 6.47E−05 |
| uc021oxm | | | 1.67E−03 |
| uc021ygq | | | 2.83E−03 |
| uc021oxp | | | 3.31E−03 |
| SNED1 | Hs.471834 | NM_001080437 | 9.55E−03 |
| ADAM19 | Hs.483944 | NM_033274 | 1.34E−02 |
| FAIM2 | Hs.567424 | NM_012306 | 1.82E−02 |
| WHAMMP2 | | | 1.82E−02 |
| LOC730091 | Hs.659905 | | 1.84E−02 |
| TCF7 | Hs.573153 | NM_201633, NM_201632, NM_001134851, NM_001134852. NM_213648, NM_003202, NM_201634 | 1.84E−02 |
| TTLL2 | Hs.520554 | NM_031949 | 1.84E−02 |
| LY9 | Hs.403857 | NM_002348, NM_001033667 | 2.03E−02 |
| uc021tnc | | | 2.13E−02 |
| TRIL | Hs.21572 | NM_014817 | 2.28E−02 |
| uc004crn | | | 2.28E−02 |
| DPEP2 | Hs.372633 | NM_022355 | 2.28E−02 |
| GZMB | Hs.1051 | NM_004131 | 2.35E−02 |
| FAM102A | Hs.568044 | NM_203305, NM_001035254 | 2.35E−02 |
| ALS2CL | Hs.517937 | NM_147129 | 2.35E−02 |
| EPHA4 | Hs.371218 | NM_004438 | 2.35E−02 |
| IKBIP | Hs.252543 | NM_201612, NM_201613, NM_153687 | 2.88E−02 |
| HBEGF | Hs.799 | NM_001945 | 2.88E−02 |
| LHFPL3 | Hs.659164 | NM_199000 | 2.88E−02 |
| RCAN2 | Hs.440168 | NM_005822 | 2.97E−02 |
| MFGE8 | Hs.3745 | NM_005928, NM_001114614 | 2.97E−02 |
| IL24 | Hs.723317, Hs.58831 | NM_006850, NM_181339 | 2.97E−02 |
| FAIM3 | Hs.723317, Hs.58831 | NM 001142472, NM 001142473, NM_005449 | 2.97E−02 |
| CDKN1B | Hs.238990 | NM_004064 | 2.99E−02 |
| AQP3 | Hs.234642 | NM_004925 | 3.06E−02 |
| GPR155 | Hs.516604 | NM_001033045, NM_152529 | 3.06E−02 |
| HS6ST2 | Hs.385956 | NM_147175, NM_001077188 | 3.25E−02 |
| SNORD85 | | | 3.25E−02 |
| uc022cci | | | 3.25E−02 |
| GSTM1 | Hs.301961 | NM_000561, NM_146421 | 3.27E−02 |
| VSIG1 | Hs.177164 | NM_001170553, NM_182607 | 3.86E−02 |
| VIPR1 | Hs.348500 | NM_004624 | 3.86E−02 |
| RCAN3 | Hs.656799 | NM_013441 | 4.45E−02 |
| ADHFE1 | Hs.720023 | NM_144650 | 4.49E−02 |
| HSPH1 | Hs.36927 | NM_006644 | 4.62E−02 |
| ENPP6 | Hs.297814 | NM_153343 | 4.74E−02 |
| RORC | Hs.607993, Hs.256022 | NM_005060, NM_001001523 | 4.83E−02 |
| TRIB2 | Hs.627749, Hs.467751 | NM_021643 | 4.96E−02 |
| LRP8 | Hs.576154 | NM_001018054, NM_004631, NM_033300, NM_017522 | 4.96E−02 |
| RGS17 | Hs.166313 | NM_012419 | 5.05E−02 |
| TAAR3 | Hs.679662 | | 5.18E−02 |
| C5orf41 | Hs.484195 | NM 153607, NM_001168394, NM_001168393 | 5.27E−02 |
| MIR3183 | | | 5.27E−02 |
| LTA | Hs.36 | NM_001159740, NM_000595 | 5.27E−02 |
| KLHL24 | Hs.407709 | NM_017644 | 5.28E−02 |
| PIK3IP1 | Hs.26670 | NM_001135911, NM_052880 | 5.28E−02 |
| MAP3K1 | Hs.653654 | NM_005921 | 5.29E−02 |
| VWC2L | Hs.534834 | NM_001080500 | 5.29E−02 |
| IDI2-AS1 | | | 5.29E−02 |
| DUSP4 | Hs.417962 | NM_001394, NM_057158 | 5.29E−02 |
| SKIL | Hs.581632 | NM 001145098, NM 001145097, NM_005414 | 5.77E−02 |
| uc021oxf | | | 5.86E−02 |
| AMICA1 | Hs.16291 | NM_153206, NM_001098526 | 5.86E−02 |
| TP53INP1 | Hs.492261 | NM_001135733, NM_033285 | 5.86E−02 |
| GDAP1L1 | Hs.517059 | NM_024034 | 6.00E−02 |
| HK2 | Hs.591588, Hs.406266 | NM_000189 | 6.43E−02 |
| CBLL1 | Hs.592271 | NM_024814 | 6.44E−02 |
| PSD3 | Hs.434255 | NM_015310, NM_206909 | 6.44E−02 |

TABLE 1A-continued

Comparison of Complete Responders (CR) vs. Non-responders (NR)

| Table 1A Gene | Unigene | Accession No. | FDR |
|---|---|---|---|
| PUS7 | Hs.520619 | NM_019042 | 6.44E-02 |
| MSMO1 | | | 6.63E-02 |
| IDI1 | Hs.283652 | NM_004508 | 6.63E-02 |
| HRH4 | Hs.287388 | NM_001160166, NM_021624, NM_001143828 | 6.73E-02 |
| FAM19A1 | Hs.655061 | NM_213609 | 6.73E-02 |
| EHD4 | Hs.143703 | NM_139265 | 6.73E-02 |
| PVR | Hs.171844 | NM_001135768, NM_006505, NM_001135770, NM_001135769 | 6.74E-02 |
| MIR1293 | | | 6.74E-02 |
| WDR64 | Hs.723441 | NM_144625 | 6.74E-02 |
| CDKN1A | Hs.370771 | NM_078467, NM_000389 | 6.74E-02 |
| CACNA1I | Hs.125116 | NM_021096, NM_001003406 | 6.75E-02 |
| C21orf63 | Hs.208358 | NM_058187 | 6.75E-02 |
| FLJ41649 | Hs.654837 | | 9.72E-02 |
| MPP7 | Hs.499159 | NM_173496 | 9.82E-02 |
| POP1 | Hs.252828 | NM_001145861, NM_001145860, NM_015029 | 9.82E-02 |
| CALCOCO1 | Hs.156667 | NM_020898, NM_001143682 | 9.82E-02 |
| COL5A3 | Hs.235368 | NM_015719 | 9.82E-02 |
| LHFP | Hs.507798 | NM_005780 | 9.82E-02 |
| CTSO | Hs.75262 | NM_001334 | 9.82E-02 |
| LEF1 | Hs.555947 | NM_001166119, NM_001130713, NM_001130714, NM_016269 | 9.82E-02 |
| RNASET2 | Hs.720966, Hs.529989 | NM_003730 | 9.89E-02 |

TABLE 1B

Comparison of Complete responders (CR) vs. Partial responders (PR)

| Table 1B Gene | Unigene | Acession No. | FDR |
|---|---|---|---|
| uc021oxm | | | 0.000511026 |
| uc021oxp | | | 0.000511026 |
| SPTB | Hs.417303 | NM_000347, NM_001024858 | 0.019052239 |
| ALS2CL | Hs.517937 | NM_147129, NM_182775 | 0.025286191 |
| TCF7 | Hs.573153 | NM_201633, NM_201632, NM_001134851, NM_001134852, NM_213648, NM_003202, NM_201634 | 0.025286191 |
| TRIL | Hs.21572 | NM_014817 | 0.025286191 |
| WDR86 | Hs.647083 | NM_198285 | 0.025286191 |
| ACSM2B | Hs.567879, Hs.298252 | NM_182617, NM_001105069 | 0.044953527 |
| DUSP4 | Hs.417962 | NM_001394, NM_057158 | 0.044953527 |
| EFHC1 | Hs.403171 | NM_018100 | 0.044953527 |
| HS6ST2 | Hs.385956 | NM_147175, NM_001077188 | 0.044953527 |
| TRIB2 | Hs.627749, Hs.467751 | NM_021643 | 0.047492472 |
| SQLE | Hs.71465 | NM_003129 | 0.053797924 |
| PRR5-ARHGAP8 | Hs.720401, Hs.102336 | NM_001017530, NM_181333, NM_181334, NM_181335, NM_015366, NM_001017526, NM_001017529, NM_001017528 | 0.053797924 |
| C16orf74 | Hs.461655 | NM_206967 | 0.056452084 |
| TMIE | Hs.185777 | NM_147196 | 0.056452084 |
| LOC100131176 | Hs.659231 | | 0.056452084 |
| VSIG1 | Hs.177164 | NM_001170553, NM_182607 | 0.056452084 |
| MIR3194 | | | 0.056452084 |
| RAP1GAP2 | Hs.499659 | NM_015085, NM_001100398 | 0.057016164 |
| FLJ13197 | Hs.29725 | | 0.084544923 |
| TSPEAR | | | 0.084544923 |
| uc021zdn | | | 0.084544923 |
| RASA3 | Hs.593075 | NM_007368 | 0.084544923 |
| OLIG3 | Hs.195398 | NM_175747 | 0.084544923 |
| GPR155 | Hs.516604 | NM_001033045, NM_152529 | 0.084544923 |
| uc021ygq | | | 0.084544923 |
| FAM19A1 | Hs.655061 | NM_213609 | 0.084544923 |
| LY9 | Hs.403857 | NM_002348, NM_001033667 | 0.084544923 |
| ANKRD20A5P | | | 0.084544923 |
| C21orf15 | Hs.580910 | | 0.08962672 |
| ADHFE1 | Hs.720023 | NM_144650 | 0.08962672 |
| MIR1293 | | | 0.098706653 |
| LOC730091 | Hs.659905 | | 0.098706653 |

Example 2: Identification of Novel Transcriptional Gene Signatures which Predict Subject Response to CD19 CAR-Expressing Cell Therapy in Chronic Lymphoid Leukemia (CLL) and Acute Lymphoblastic Leukemia (ALL) Using Gene Set Analysis and Differential Expression Analysis The present Example describes the identification of novel transcriptional gene signatures that predict patient response to CD19 CAR-expressing cell (e.g., T cell, NK cell) therapy (e.g., CTL019) in CLL and ALL, for use in accordance with the present invention.

In particular, the present Example describes methods of Gene Set Analysis to discover novel gene signatures, for use in accordance with the present invention.

Figure 2A:
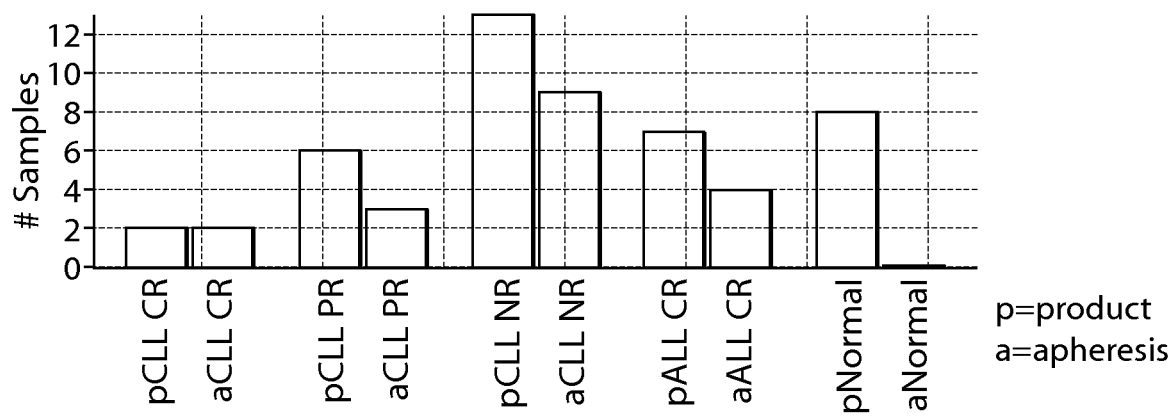
FIG. 2A depicts an exemplary histogram of the number of samples analyzed in the whole genome CTL019 RNAseq analysis described herein. p=product; a=apheresis.

Among other things, the present Example describes novel gene signatures based on Gene Set Analysis, that are predictive of patent response to CD19 CAR-expressing cell (e.g., T cell, NK cell) therapy (e.g., CTL019). Gene set analysis was performed on gene sets described in Example 1, and with gene sets from three additional datasets. FIG. 2A depicts an exemplary histogram comparing the number of samples analyzed in a whole genome CTL019 RNAseq analysis. p=product; a=apheresis. Gene sets were sourced from (1) additional experiments were based on gene sets by Szabo et al. (described herein); (2) gene sets published by Abbas et al. in GENOME RESEARCH 2005; and (3) gene sets published by Gattinoni et al. in NATURE MEDICINE 2011. Each of these gene sets are described in further detail below.

Szabo et al. gene sets that were used in the Gene Set Analysis are provided in Table 2. Human CD4+ T cells were purified from PBMCs (5 normal donors, males, ages 18-28, with no known allergies or infections). CD4+ CD25+(T reg) and CD4+ CD25− (T effector) T cells were isolated and anti-CD3/CD28 stimulated for 0 or 16 hours to yield 4 conditions: (1) T reg 0 hours; (2) T reg 16 hours; (3) T effector 0 hours; and (4) T effector 16 hours. Two gene sets were derived for each condition: one set of genes whose expression levels were up-regulated in that condition relative to all others and another set of genes whose expression levels were downregulated in that condition relative to all others. The number of genes in each gene set was determined by a fold change cutoff (see Table 2).

TABLE 2

| Table 2 Gene | Number of Genes |
|---|---|
| Gene sets comprised of genes up or down regulated in $T_{REG}$ and $T_{EFF}$ at resting and activation (Szabo data set) | |
| Downregulated $T_{REG}$ vs $T_{EFF}$ 0 h (FC3 p < 0.05) | 120 |
| Downregulated $T_{REG}$ vs $T_{EFF}$ 16 h (FC3 p < 0.05) | 139 |
| Downregulated $T_{EFF}$ 16 h vs 0 h (FC7 p < 0.05) | 246 |
| Upregulated $T_{REG}$ vs $T_{EFF}$ 16 h (FC4 p < 0.05) | 254 |
| Upregulated $T_{REG}$ vs $T_{EFF}$ 0 h (FC4 p < 0.05) | 135 |
| Upregulated $T_{EFF}$ 16 h vs 0 h (FC9 p < 0.05) | 347 |
| Upregulated $T_{REG}$ 16 h vs 0 h (FC8 p < 0.05) | 226 |

Exemplary genes according to Table 2 downregulated in Treg compared with Teff at 0 h include ABCB1, ACSL6, ADAMTS10, ADD2, AIF1, AIF1, AIF1, AIF1, AK5, AKR1E2, ALS2CL, ANK3, ANKRD55, APBA2, AREG, ATHL1, AXIN2, B4GALNT4, BACH2, BCL7A, BEND5, BHLHE40, BPGM, C10orf47, C16orf54, C1orf228, C2orf89, CA6, CACHD1, CACNA1I, CCL5, CELA1, CHD7, CHI3L2, COL18A1, COL6A1, CR2, CYB561, CYSLTR1, D4S234E, DACT1, DENND5A, DHRS3, DLG4, DLL1, DPYSL4, DSC1, EDAR, EMR1, EMR4P, ENC1, EPHA1, FCGBP, FHIT, GADD45G, GIPC3, GIPC3, GPR125, GPR160, H1F0, HDGFRP3, HIPK2, IFITM5, KCNQ1, KLF5, KLHL29, KRT72, KRT73, LASS6, LRRC24, MAN1C1, ME3, MMP28, MTUS1, NBL1, NELL2, NEO1, NKG7, NLRP6, NME4, NOG, NOSIP, NPAS2, NRCAM, OBSCN, OSBPL5, PCSK5, PDZD4, PECAM1, PLLP, PLXDC1, PPFIBP2, PRKAR1B, PTK2, RHOB, RMRP, RNF157, SATB1, SCML4, SDK2, SEC14L2, SEC14L2, SLC15A3, SLC22A17, SLC22A23, SLC40A1, SNTB1, SORBS3, SOX8, ST6GALNAC1, TCF7, TCF7, THEMIS, TMIGD2, VIPR1, WNT10B, WNT7A, ZNF467, ZNF516, and ZNF609.

Exemplary genes according to Table 2 downregulated in Treg compared to Teff 16 h include IL2, TNFSF8, NELL2, G0S2, IRF8, IFNG, IGFBP4, GPR125, CD200, GPR81, ADD2, IL21, SNORD86, TMCC2, C1orf228, SLC15A3, IL22, LRRN3, GPR171, FASLG, GZMH, NHS, MCOLN2, BACH2, TAGAP, MPZL2, PRAGMIN, DACT1, CXCL10, SLAMF6, PHGDH, CSF2, PRSS23, UHRF1, PLAC8, ISM1, BTLA, CDC20, GFOD1, HSD11B1, ME3, ZNF704, DHRS3, CXCL13, CCND1, NBL1, CRTAM, MAP6D1, H1F0, CDT1, CCL4, LIF, CD84, TRAT1, MIR155, SLAMF7, AIF1, AIF1, AIF1, AIF1, PRG4, VWCE, CHEK1, SH2D4A, MCM10, RHOU, NPAS2, NFIX, STAP1, DTL, C16orf59, CSDA, GINS2, FAM117B, ABCB1, CLC, PHEX, GDF10, RAB13, BCL7A, MAMLD1, SHF, LPIN2, AHI1, CCND3, HDGFRP3, MIR155HG, PVR, CDCA5, RRAS2, SIPA1L2, RASL10B, GAL, SNORD88C, SNORD18B, CDC6, SRD5A3, ORC6L, B3GNT5, ANK3, MCM2, MIR25, RHOBTB3, TNF, TERT, CSDAP1, CCDC64, CDC25A, ZNF367, MCM7, CASP10, LTA, MCM4, AFF3, FMNL2, TNFRSF21, AXIN2, CHD7, FABP5, XRCC2, CGREF1, CCL4L1, CCL4L2, B4GALNT4, DSCC1, CD97, PTPRK, RAD54L, EPB41L3, MYO1B, ORC1L, CHML, ZWINT, MAD2L1, NDST1, C11orf82, BEGAIN, CD55, and FABP5L3.

Exemplary genes according to Table 2 downregulated in Teff at 16 h vs 0 h include ABCA7, ABCG1, ABTB1, ACCS, ADAMTS10, ADD3, AK5, ALS2CL, AMT, ANKRD55, ANXA1, AQP3, AREG, ARL4C, ARRDC2, ARRDC3, BBC3, BCL9L, BIN2, BNIP3L, BTG1, BTN3A1, C10orf110, C11orf21, C11orf35, C14orf181, C16orf54, C16orf74, C17orf108, C1orf162, C1QTNF6, C20orf111, C20orf112, C5orf39, C5orf41, C5orf41, CACNA1I, CAPS, CBX4, CCNL1, CDC14A, CDC42BPG, CECR1, CFP, CHI3L2, CITED4, CLK1, CRIP2, CSGALNACT1, CTSF, CTSW, CXCR4, CYTH4, DCHS1, DDIT3, DDX60L, DISC1, DISC1, DISC1, DISC1, DPEP2, DPYD, DUSP1, DUSP8, EDAR, EMR4P, EPHA4, EPHX1, EPHX2, ERMN, ERP27, EVI2B, FAM13A, FAM13AOS, FAM46C, FAM65B, FBXO32, FHIT, FLT3LG, FOS, FOSB, FRAT1, FYB, GABARAPL1, GABARAPL3, GADD45B, GOLGA7B, GPA33, GPRASP1, GRASP, GSTM2, GZMA, GZMK, HBP1, HERPUD2, HIST1H1C, HIST1H3A, HPCAL4, HSD17B11, ID1, IDUA, IER2, IFI44, IL10RA, IL11RA, IRF2BP2, IRS2, ITGA6, JMY, JUN, JUNB, JUND, KCNQ1, KIAA1370, KIAA1683, KLF2, KLF3, KLF4, KLF5, KLF6, KLHL24, KLHL3, KLRB1, KRT72, KRT73, LIME1, LOC100128071, LOC100289511, LOC282997, LOC283070, LOC338799, LOC728392, LTBP3, MAL, MAP2K6, MDS2, MEGF6, MEGF6, MFGE8, MIR1909, MMP28, MOAP1, MXD4, MYADM, MYLIP, MYO15B, NFKBIZ, NLRC3, NLRP1, NOG, NR1D2, NR1D2, NR3C2, P2RY8, PBXIP1, PCSK5, PDE4D, PDZD4, PER1, PGAM2, PGCP, PHF1, PHF1, PIK3IP1, PIK3R5, PIM1, PION, PLCD1, PLCH2, PLCL1, PLEKHB1, PLK2, PLXDC1, PNRC1, PPP1R15A, Pro-SAPiP1, RAB37, RAP1GAP2, RARRES3, RASA3, RASGRP2, REM2, RGS1, RGS2, RNF125, SAMD3, SCML4, SEC31B, SIGIRR, SIK1, SLC2A3, SLC2A4RG, SLC2A4RG, SLC9A9, SLFN5, SMAD7, SMPD1, SNORA11, SORL1, SOX4, SULT1B1, SYNE1, SYTL1, TCEA3, TCF7, TCF7, TCP11L2, THEMIS, TMC8, TMEM63A, TMEM71, TMIGD2, TNFAIP3, TNNT3, TP53INP2, TPM2, TRANK1, TRIB2, TSC22D3, TSPAN18, TSPAN18, TSPAN32, TSSK3, TXK, TXNIP, UNC84B, UTRN, VIPR1, VSIG1, VSIG1, WHAMM, WNT10B, WNT7A, XAF1, XYLT1, XYLT1, YPEL2, YPEL3, YPEL5, ZBP1, ZBTB10, ZFP36, ZFP36L2, ZMAT1, ZNF331, and ZNF815.

Exemplary genes according to Table 2 upregulated in Treg v Teff at 16 h FC include ZBTB32, LRRC32, STAMBPL1, SNX10, LOC389333, ZNF193, GCNT1, FAS, GK3P, NTRK1, FREQ, IL1R1, CRADD, GNA15, RAB33A, IL18R1, CX3CR1, TNFRSF1B, APOBEC3G, FOXP3, SEPT11, CD70, IL1RL1, NIPA1, PANX2, CHST2, NEDD9, ACOT9, PDGFA, MAST4, TNFRSF8, PHLPP1, IL2RB, CTLA4, SYTL3, ZC3H12C, PTPRJ, UBASH3B, METRNL, PRDM1, SEPT3, TNFRSF18, WNT10A, CCR8, C18orf1, CSF1, CD80, GALNT4, GALNT4, IL1RL2, ADPRH, ZNF282, APOBEC3C, HS3ST3B1, EPAS1, RBKS, KAT2B, C9orf167, TYMP, IL1RAP, C2CD4A, CD68, ABHD4, MICAL2, C6orf145, DUSP16, LRIG1, CASK, EPSTI1, TNFRSF12A, IGSF3, SPATS2L, SPATS2L, MAF, CD58, KLHDC7B, ZBTB38, LAYN, IL1R2, HIP1, ITGB8, ITGB8, IKZF2, LGMN, XIRP1, GPR19, SAMD9L, PRF1, JAKMIP1, MGC29506, ADAMS, HLF, COL9A2, NDRG1, SAMHD1, AKAP5, RNF213, RNF213, APAF1, STX1A, SSH1, SSH1, CCRL2, CCR6, CSF2RB, HAVCR2, KLF5, MX1, ACTA2, OAS3, EMP1, CTNNAL1, MGC12916, CCL17, FOSL2, SAT1, TRPV2, PRIC285, SOCS2, ETV7, TIGIT, RASAL1, OPTN, MGST2, GPR68, MYO1G, PTPLA, TNFRSF11A, ANXA2, IRF5, C14orf139, CAPN2, LFNG, IL12RB1, MYO1E, GLRX, DENND3, ANXA2P2, NQO1, C10orf128, ANTXR2, ANTXR2, SLC26A11, FLVCR2, PREX1, SLC2A8, CDKN2A, TMEM149, SYT11, TOX, TOX2, FUT7, ANXA2P1, FAM129B, DFNB31, TMPRSS6, IL1RN, ISG15, CDKN1B, FAM129A, TST, HDAC9, TMEM110, SMPD1, CDKN1A, C17orf67, ANXA2P3, MPST, IRF7, LMCD1, SNX24, HMOX1, ATP2B4, FCER2, HPGD, RASGRP4, FAM164A, IFI6, FAM110C, XKRX, PBX4, NTNG2, CST7, BASP1, C14orf49, GLIPR1, DHRS2, TWIST1, SPSB1, CYTH4, CADM1, ITIH4, L00541471, CGA, LOC645166, PARP12, NINJ2, MICAL1, OAS1, HLA-DRB4, LGALS3, OASL, CORO2A, HLA-DRB3, KIAA1370, HERC6, STAC, MSC, CCR5, SUOX, RHOC, HLA-DQB2, PDE4A, LOC100302650, XAF1, FCRL3, RTKN2, GLIPR2, HLA-DRB1, IL13, P2RY10, IL10, CXCR6, LSP1, ACP5, SLC1A4, FXYD7, TRIB2, LMNA, HLA-DPA1, MEOX1, LGALS1, HLA-DRB5, IL10RA, HLA-DRA, CARD16, IL5, RGS1, HLA-DQA2, AKR1C3, IL4, HLA-DMA, GPR55, AQP3, MUSTN1, P2RY8, FANK1, IL9, CCNG2, ADAM12, LOC654342, IL17A, PPP2R2B, and FAM46C.

Exemplary genes according to Table 2 upregulated Treg vs Teff at 0h FC4 include C12orf75, SELPLG, SWAP70, RGS1, PRR11, SPATS2L, SPATS2L, TSHR, C14orf145, CASP8, SYT11, ACTN4, ANXA5, GLRX, HLA-DMB, PMCH, RAB11FIP1, IL32, FAM160B1, SHMT2, FRMD4B, CCR3, TNFRSF13B, NTNG2, CLDND1, BARD1, FCER1G, TYMS, ATP1B1, GJB6, FGL2, TK1, SLC2A8, CDKN2A, SKAP2, GPR55, CDCA7, S100A4, GDPD5, PMAIP1, ACOT9, CEP55, SGMS1, ADPRH, AKAP2, HDAC9, IKZF4, CARD17, VAV3, OBFC2A, ITGB1, CIITA, SETD7, HLA-DMA, CCR10, KIAA0101, SLC14A1, PTTG3P, DUSP10, FAM164A, PYHIN1, MYO1F, SLC1A4, MYBL2, PTTG1, RRM2, TP53INP1, CCR5, ST8SIA6, TOX, BFSP2, ITPRIPL1, NCAPH, HLA-DPB2, SYT4, NINJ2, FAM46C, CCR4, GBP5, C15orf53, LMCD1, MKI67, NUSAP1, PDE4A, E2F2, CD58, ARHGEF12, LOC100188949, FAS, HLA-DPB1, SELP, WEE1, HLA-DPA1, FCRL1, ICA1, CNTNAP1, OAS1, METTL7A, CCR6, HLA-DRB4, ANXA2P3, STAM, HLA-DQB2, LGALS1, ANXA2, PI16, DUSP4, LAYN, ANXA2P2, PTPLA, ANXA2P1, ZNF365, LAIR2, L00541471, RASGRP4, BCAS1, UTS2, MIAT, PRDM1, SEMA3G, FAM129A, HPGD, NCF4, LGALS3, CEACAM4, JAKMIP1, TIGIT, HLA-DRA, IKZF2, HLA-DRB1, FANK1, RTKN2, TRIB1, FCRL3, and FOXP3.

Exemplary genes according to Table 2 upregulated in Teff at 16 h v 0 h include AARS, ABCF2, ACOT7, ACTL6A, AHSA1, AIM2, AIMP2, ALAS1, ALDH1B1, ANKRD13B, APOL1, ARMCX3, ASPHD2, B3GNT5, B4GALT2, B4GALT5, BATF, BATF3, BCAT2, BCL2L1, BOP1, BTLA, BYSL, C11orf75, C15orf23, C15orf63, C16orf59, C17orf79, C17orf96, C1orf163, C3orf26, C4orf43, C8orf30A, C9orf64, CAD, CBR1, CCDC56, CCDC86, CCL20, CCL3, CCL3L1, CCL3L3, CCL4, CCL4L1, CCL4L2, CCNB1, CCND2, CCT3, CCT5, CCT6A, CCT7, CD109, CD200, CD274, CD3EAP, CD40LG, CD82, CDC20, CDC45L, CDC6, CDK4, CDT1, CENPM, CETN3, CHAC2, CHEK1, CISD1, CISH, CKS1B, COPB2, CORO1C, CSF2, CTNNA1, CTPS, CTTN, DARS2, DCAF12, DCTPP1, DHCR24, DKC1, DTL, E2F1, EBNA1BP2, ECE2, EDARADD, EEF1E1, EGR2, EIF2B3, EIF2S1, EIF5B, EIF6, ENO1, ESPL1, EXOSC3, EXOSC4, F5, F5, FABP5, FABP5L3, FADS1, FAM40B, FARSA, FASLG, FDPS, FKBP4, FKBP4, FOSL1, FREQ, GOS2, G3BP1, GALE, GAR1, GART, GEM, GEMIN6, GEMINI, GFOD1, GINS1, GINS2, GLRX2, GNG8, GNPDA1, GPATCH4, GPN3, GPR171, GTF2H2D, HIVEP3, HMGCS1, HN1L, HNRNPAB, HSPD1, HSPE1, HYAL2, IARS, IER3, IFNG, IFRD2, IGFBP4, IL12RB2, IL15RA, IL17F, IL2, IL21, IL22, IL2RA, IL3, IRF4, IRF8, ISOC2, KCNK5, KEAP1, KIAA0020, KIAA0664, LAG3, LAPTM4B, LARP4, LIF, LOC286016, LOC344967, LOC442308, LOC728402, LRP8, LSM2, LTA, LYAR, MANF, MATK, MCM10, MCM2, MCM3, MCM4, METTL13, MIR1182, MIR155, MIR155HG, MIR621, MPV17L2, MPZL2, MRM1, MRPL12, MRPL15, MRPL17, MRPL35, MRPL51, MRPS17, MRPS23, MRTO4, MTCH2, MTHFD1L, MTHFD2, MYOF, NAB2, NDFIP2, NDUFAF1, NFE2L3, NFKBIL2, NLN, NME1, NME1-NME2, NOLC1, NOP16, NPTX1, NT5DC2, NUDCD1, NUP43, NUP62, OTUD7B, PACSIN3, PAICS, PAK1IP1, PAM, PDCD1, PDCD2L, PDIA4, PDIA6, PEA15, PFAS, PFDN6, PFDN6, PFKM, PFKP, PGAM1, PGAM4, PHB, PHF6, PKM2, PLAGL2, PNPO, POLD2, POLE2, POLR3K, POP1, PPIL1, PPP1R14B, PRDX1, PRDX3, PRDX4, PRMT1, PRMT5, PRSS23, PSAT1, PSMA3, PSMA5, PSMA6, PSMB3, PSMB5, PSMD1, PSMD11, PSMD14, PTGFRN, PTMS, PTRH1, PTRH2, PUS7, PYCR1, PYCRL, RARS, RBBP8, RCC1, RPF2, RPP25, RRP1, RRP9, RUVBL1, RUVBL2, SAMD4A, SCD, SDC4, SECTM1, SEH1L, SEMA7A, SFT2D1, SFXN1, SH2D2A, SHF, SHMT2, SIPA1L2, SLAMF1, SLC1A5, SLC27A2, SLC27A4, SLC29A1, SLC38A5, SLC39A14, SLC43A3, SLC6A9, SLCO4A1, SNORA18, SNORD17, SORD, SPR, SQLE, SRM, SRXN1, STIP1, STT3A, TALDO1, TAP1, TBKBP1, TBL3, TBX21, TIMM8B, TIMM8B, TIPIN, TMCC2, TMEM165, TMEM194A, TMEM208, TMEM97, TNF, TNFAIP8L2, TNFRSF4, TNFRSF9, TNFSF14, TOMM40, TPI1, TRIP10, TRIP13, TTLL12, TUBA1B, TUBB, TUBB, TUBB, TUBG1, TXN, TXNDC5, UBE2T, UCK2, UGDH, UHRF1, UMPS, UTP6, VDAC1, VDR, WARS, WDR12, WDR18, WDR3, WDR4, WDR77, YIF1A, YWHAG, ZBED2, ZDHHC16, ZNF593, ZNF607, and ZWINT.

Exemplary genes according to Table 2 upregulated in Treg 16h vs 0h Fc8 include AARS, ACOT7, AGRN, AHSA1, AIM2, AIMP2, ALAS1, ALDH1B1, APOL1, APOL2, B4GALT2, BATF, BATF3, BCL2A1, BCL2L1, BOP1, BYSL, C17orf96, C2CD4A, C5orf32, C9orf64, CCDC86, CCL17, CCL20, CCT5, CD3EAP, CD40LG, CD68, CD7, CDK2AP2, CDK4, CHAC2, CHPF, CISD1, CISH, COPB2, CRIM1, CSF1, CTLA4, CTSL1, CTTN, DCTPP1, DHCR24, EBI3, EBNA1BP2, ECE2, EDARADD, EGR2, EMP1, ENO1, EPAS1, EXOSC4, FABP5, FAH, FAM40B, FARSA, FKBP4, FKBP4, FLT1, FLT1, FOSL1, FREQ, G6PD, GALE, GART, GCLM, GEM, GK, GNPDA1, GPR56, HIVEP3, HMGCS1, HMOX1, HN1L, HSPA1A, HSPA1B, HSPD1, HSPE1, HYAL2, IER3, IFRD1, IKBIP, IL10, IL12RB2, IL13, IL15RA, IL17A, IL1R1, IL1R2, IL1RL2, IL1RN, IL2RA, IL3, IL4, IL4I1, IL5, IL9, IRF4, KCNK5, LAG3, LAPTM4B, LIF, LOC344967, LOC389333, LOC442308, LRRC32, LRRC61, LTA, LYAR, MANF, MATK, METRNL, METTL13, MGC29506, MICAL2, MIR1182, MIR155, MIR155HG, MLEC, MRPL12, MRTO4, MTHFD1L, MYOF, NAB2, NDFIP2, NDUFAF1, NKG7, NLN, NME1, NME1-NME2, NOP16, NPM3, NUDCD1, PAICS, PANX2, PDCD1, PDGFA, PDIA4, PDIA6, PFAS, PGAM4, PHB, PNPO, POP1, PPIL1, PPPDE2, PRDX1, PRDX3, PRDX4, PRKAR1B, PRMT1, PRMT5, PSAT1, PSMB5, PSMD1, PSMD11, PTGFRN, PTRH1, PUS7, PYCR1, RASAL1, RBBP8, RCC1, SC4MOL, SCD, SDC4, SECTM1, SEH1L, SEMA7A, SETP11, SERPINE2, SERPINH1, SH2D2A, SLC16A13, SLC16A3, SLC1A5, SLC27A2, SLC27A4, SLC29A1, SLC38A5, SLC39A1, SLC39A14, SLC43A3, SLCO4A1, SOCS1, SPHK1, SPINT1, SQLE, SRM, SRXN1, STIP1, STT3A, TBKBP1, TBX21, TMPRSS6, TNF, TNFRSF11A, TNFRSF12A, TNFRSF18, TNFRSF1B, TNFRSF4, TNFRSF8, TNFRSF9, TNFSF14, TOMM40, TRIP10, TTLL12, TUBB, TUBB, TUBB, TXN, TYMP, UCK2, UGDH, VDR, VTRNA1-3, WARS, WDR12, WDR4, WDR77, XIRP1, YWHAG, ZBED2, ZBTB32, ZDHHC16, and ZNF282.

An exemplary list of the $T_{REG}$ genes upregulated at 16h include AIM2, ALAS1, BATF, C5orf32, CCL17, CD40LG, CHAC2, CSF1, CTSL1, EBNA1BP2, EDARADD, EMP1, EPAS1, FABP5, FAM40B, FKBP4, FOSL1, GCLM, GK, GPR56, HMOX1, HSPD1, HSPE1, IKBIP, IL10, IL13, IL15RA, IL1RN, IL2RA, IL3, IL4, IL5, IL9, KCNK5, LTA, MANF, MIR1182, MIR155, MIR155HG, MYOF, NDUFAF1, NLN, NME1, NME1-NME2, PANX2, PDIA6, PGAM4, PPIL1, PPPDE2, PRDX4, PRKAR1B, PSMD1, PSMD11, PUS7, RBBP8, SLC27A2, SLC39A14, SLC43A3, SRXN1, STIP1, STT3A, TBX21, TNFRSF11A, TNFRSF1B, TNFRSF8, TNFRSF9, TXN, UCK2, VDR, VTRNA1-3, WDR12, YWHAG, ZDHHC16, and ZNF282. The upregulated expression may be determined, e.g., by measuring RNA levels for the indicated genes.

An exemplary list of the $T_{EFF}$ genes upregulated at 16h include AIM2, ALAS1, B4GALT5, BATF, C3orf26, C4orf43, CCL3, CCL4, CCT3, CCT7, CD40LG, CHAC2, CSF2, CTNNA1, EBNA1BP2, EDARADD, EEF1E1, EIF2B3, EIF2S1, FABP5, FAM40B, FKBP4, FOSL1, GFOD1, GLRX2, HSPD1, HSPE1, IFNG, IL15RA, IL21, IL2RA, IL3, KCNK5, KIAA0020, LARP4, LRP8, LTA, MANF, MIR1182, MIR155, MIR155HG, MTCH2, MYOF, NDUFAF1, NLN, NME1, NME1-NME2, OTUD7B, PAM, PDIA6, PEA15, PFKM, PGAM1, PGAM4, PPIL1, PRDX4, PRSS23, PSMD1, PSMD11, PSMD14, PTRH2, PUS7, RBBP8, RPF2, RPP25, SFXN1, SLC27A2, SLC39A14, SLC43A3, SORD, SPR, SRXN1, STIP1, STT3A, TBX21, TMCC2, TMEM165, TNFRSF9, TXN, TXNDC5, UCK2, VDR, WDR12, YWHAG, and ZDHHC16.

The Abbas gene sets compared the expression profiles of 17 immune cell types and identified genes uniquely expressed in certain cell types relative to others. The select Abbas gene sets that were included in the Gene Set Analysis are listed in Table 3 and include CD4+ T cells naïve and resting, CD8+ T cells naïve and resting, helper Th1 at 12 hours, helper Th1 at 48 hours, helper Th2 at 12 hours, helper Th2 at 48 hours, memory T resting (naïve) cells, and memory T activated cells.

TABLE 3

Gene sets comprised of gene up or down regulated resting and activated T-cell subtypes (Abbas data set)

| Gene Set | Number of genes |
|---|---|
| Downregulated CD8 vs CD4 Naïve T-cells | 200 |
| Downregulated Naïve CD4 vs 12 H activated Th1 | 200 |
| Downregulated Naïve CD4 vs 48 H activated Th1 | 200 |
| Downregulated Naïve CD4 vs 12 H activated Th2 | 200 |
| Downregulated Naïve CD4 vs 48 H activated Th2 | 200 |
| Downregulated Th1 vs Th2 12 H activated | 200 |
| Downregulated Th1 vs Th2 48 H activated | 200 |
| Downregulated unstimulated vs stimulated memory T-cells | 200 |
| Upregulated CD8 vs CD4 Naïve T-cells | 200 |
| Upregulated Naïve CD4 vs 12 H activated Th1 | 200 |
| Upregulated Naïve CD4 vs 48 H activated Th1 | 200 |
| Upregulated Naïve CD4 vs 12 H activated Th2 | 200 |
| Upregulated Naïve CD4 vs 48 H activated Th2 | 200 |
| Upregulated Th1 vs Th2 12 H activated | 200 |
| Upregulated Th1 vs Th2 48 H activated | 200 |
| Upregulated unstimulated vs stimulated memory T-cells | 200 |

The Gattinoni gene sets compared the expression profiles of various CD8+ memory T cell subsets. Specifically, immune cells were isolated from healthy donors and the following CD8+ T memory subsets were purified: $T_N$ (naïve), $T_{SCM}$ (memory stem cells), $T_{CM}$ (central memory), $T_{EM}$ (effector memory). Gene sets were defined by comparing between all pairs of groups (e.g. $T_{SCM}$ vs. $T_N$) and by identifying those genes that either progressively increased or decreased across the 4 conditions in order from $T_N \rightarrow T_{SCM} \rightarrow T_{CM} \rightarrow T_{EM}$. The select gene sets from Gattinoni et al. that were considered in the Gene Set Analysis are tabulated in Table 4.

TABLE 4

Gene sets comprised of gene up or down regulated resting and activated T-cell subtypes (Gattinoni data set)
Table 4

| Gene Set | Number of genes |
|---|---|
| $T_{CM}$ vs $T_{EM}$ | 29 |
| $T_N$ vs $T_{CM}$ | 148 |

TABLE 4-continued

Gene sets comprised of gene up or down regulated resting
and activated T-cell subtypes (Gattinoni data set)
Table 4

| Gene Set | Number of genes |
| --- | --- |
| $T_N$ vs $T_{EM}$ | 212 |
| $T_{SCM}$ vs $T_{CM}$ | 19 |
| $T_{SCM}$ vs $T_{EM}$ | 75 |
| $T_{SCM}$ vs $T_N$ | 73 |
| Progressively down | 208 |
| Progressively up | 32 |

Each gene set (e.g., ALL and CLL RNAseq gene sets, Szabo gene sets, Abbas gene sets, and Gattinoni gene sets) was evaluated to determine its association with subject response (i.e., CR, PR, or NR) in the following manner: a meta-gene was calculated for each subject, where the meta-gene score for subject j was defined as $$m_j = \sum_{i=G}^{1} x_{ij} - \mu(x_{\cdot j})/\sigma(x_{\cdot j})$$

where $x_{ij}$ is the expression value of gene i in subject j for a given gene set n=1, . . . , G; $\mu(x_{\cdot j})$ is the mean of genes 1, . . . , G in subject j; and $\sigma(x_{\cdot j})$ is the standard deviation of genes 1, . . . , G in subject j.

A 3-group statistical model was applied to each gene set to determine whether the meta-gene was statistically different between the CLL product CRs, PRs, and NRs. A schematic illustrating this approach is given in FIG. 2B. CRs are more like resting $T_{EFF}$ cells, whereas NR are more like activated $T_{EFF}$ cells. CTL019 NR samples are in a more activated state than CR samples. Gene sets that were found to be significantly altered and predictive of patient response to CD19 CAR-expressing cell (e.g., T cell, NK cell) therapy (e.g., CTL019) are listed in Table 5.

TABLE 5

Gene sets that are enriched in CLL samples
Table 5

| Gene Set | Source | CRs | NRs | Product | Apheresis |
| --- | --- | --- | --- | --- | --- |
| $T_{EFF}$ 16 h vs 0 h | Szabo | $T_{EFF}$ oh | $T_{EFF}$ 16 h | X | X |
| $T_{REG}$ 16 h vs 0 h | Szabo | $T_{REG}$ oh | $T_{REG}$ 16 h | X | X |
| $T_{REG}$ vs $T_{EFF}$ 16 h | Szabo | $T_{EFF}$ | $T_{REG}$ | X | X |
| Naïve CD4 vs 12 H act Th1 | Abbas | Naïve CD4 | Th1 | X | X |
| Naïve CD4 vs 12 H act Th2 | Abbas | Naïve CD4 | Th2 | X | X |
| Naïve CD4 vs 48 H act Th1 | Abbas | Naïve CD4 | Th1 | X | X |
| Naïve CD4 vs 48 H act Th2 | Abbas | Naïve CD4 | Th2 | X | X |
| Unstim vs stim memory | Abbas | Unstimulated | Stimulated | X | |
| $T_{SCM}$ vs $T_{EM}$ | Gattinoni | $T_{SCM}$ | $T_{EM}$ | X | |
| $T_{SCM}$ vs $T_{CM}$ | Gattinoni | $T_{SCM}$ | $T_{CM}$ | X | |
| $T_{CM}$ vs $T_{EM}$ | Gattinoni | $T_{EM}$ | $T_{CM}$ | X | |
| Progressively down | Gattinoni | Early stage | Late stage | X | X |

FIG. 3 depicts an exemplary schematic of memory T cell precursors and subsets. Without wishing to be bound by a particular theory, the state of memory T cells in CTL019 samples is likely a major component of response.

For a subset of the patients in the manufactured product study described in Example 1, whole genome RNAseq was also performed on T cells collected by apheresis. The gene sets described above were evaluated in these 14 apheresed samples (2 CRs, 3 PRs, and 9 NRs). Gene sets that were found to be significantly altered and predictive of patient response to CTL019 therapy are tabulated in Table 5.

Whole genome RNAseq was performed on 7 ALL manufactured product CR samples and 4 ALL apheresis CR samples. Meta-gene scores for each gene set were calculated for the ALL samples as described above for the CLL samples. Gene sets with meta-gene scores correlating with the expected pattern of response in product and apheresis samples (ALL→CLL CR→CLL PR→CLL NR) are tabulated in Table 6. Gene sets marked with * in Table 6 are also correlated with response in apheresis samples.

TABLE 6

Gene sets correlating to response over product ALL and
CLL samples (ALL → CLL CR → CLL PR → CLL NR)
Table 6

Gene Set

Figure 4:
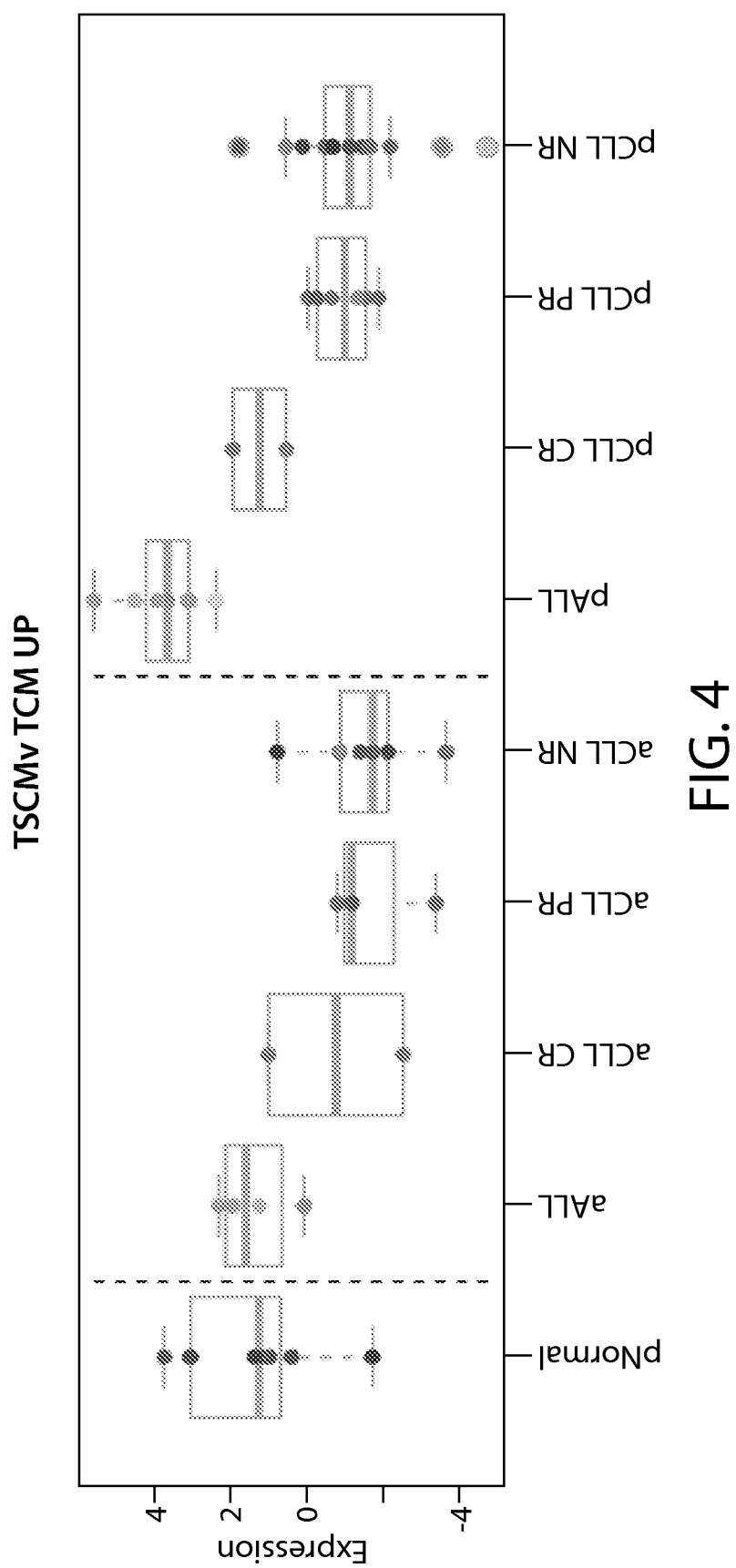
FIG. 4 depicts an exemplary result illustrating meta-gene scores for the $T_{SCM}$ vs $T_{CM}$ upregulated gene set. The x-axis is samples by response group where a=apheresis and p=product. The y-axis is normalized meta-gene expression scores. Gene sets enriched in CLL CRs (e.g., CTL019 CRs) are also enriched in acute lymphoblastic leukemias (ALLs). ALL and CLL CRs are enriched in T stem cell ($T_{SCM}$) subset specific genes, whereas CLL PRs and NRs are enriched in T central memory ($T_{CM}$) subset genes. The same pattern is seen in apheresis as in product samples. ALL expression patters are most similar to CLL CRs and are even more extreme in the direction of resting/unstimulated/early memory T cells.

Downregulated Treg vs Teff 0 h (FC3 p < 0.05)*
Downregulated Treg vs Teff 16 h (FC3 p < 0.05)
Upregulated Treg vs Teff 0 h (FC4 p < 0.05)*
Upregulated Treg vs Teff 16 h (FC4 p < 0.05)
TCMvsTEM down gene set
TCMvsTEM up gene set
TNvsTCM down gene set*
TNvsTCM up gene set*
TNvsTEM down gene set*
TNvsTEM up gene set*
TSCMvsTCM down gene set*
TSCMvsTCM up gene set*
TSCMvsTEM up gene set*
TSCMvsTN down gene set*
TSCMvsTN up gene set*
Progressively down*
Progressively up*
Downregulated CD8 vs CD4 Naïve T-cells*
Upregulated Naïve CD4 vs 12 H activated Th1
Upregulated Naïve CD4 vs 48 H activated Th1
Upregulated Naïve CD4 vs 12 H activated Th2
Upregulated Naïve CD4 vs 48 H activated Th2*
Downregulated Th1 vs Th2 12 H activated For example, the meta-gene score for the gene set comprised of genes upregulated in $T_{SCM}$ in comparison to $T_{CM}$ is found to be correlated with response in both apheresis and product samples, FIG. 4. The meta-gene scores from healthy donor samples with manufactured product are included in the plot to serve as a reference point. The x-axis is samples by response group where a=apheresis and p=product. The y-axis is normalized meta-gene expression scores. Gene sets enriched in CLL CRs (e.g., CTL019 CRs) are also enriched in acute lymphoblastic leukemias (ALLs). ALL and CLL CRs are enriched in T stem cell ($T_{SCM}$) subset specific genes, whereas CLL PRs and NRs are enriched in T central memory ($T_{CM}$) subset genes. The same pattern is seen in apheresis as in product samples. ALL expression patters are most similar to CLL CRs and are even more extreme in the direction of resting/unstimulated/early memory T cells.

Figure 5A:
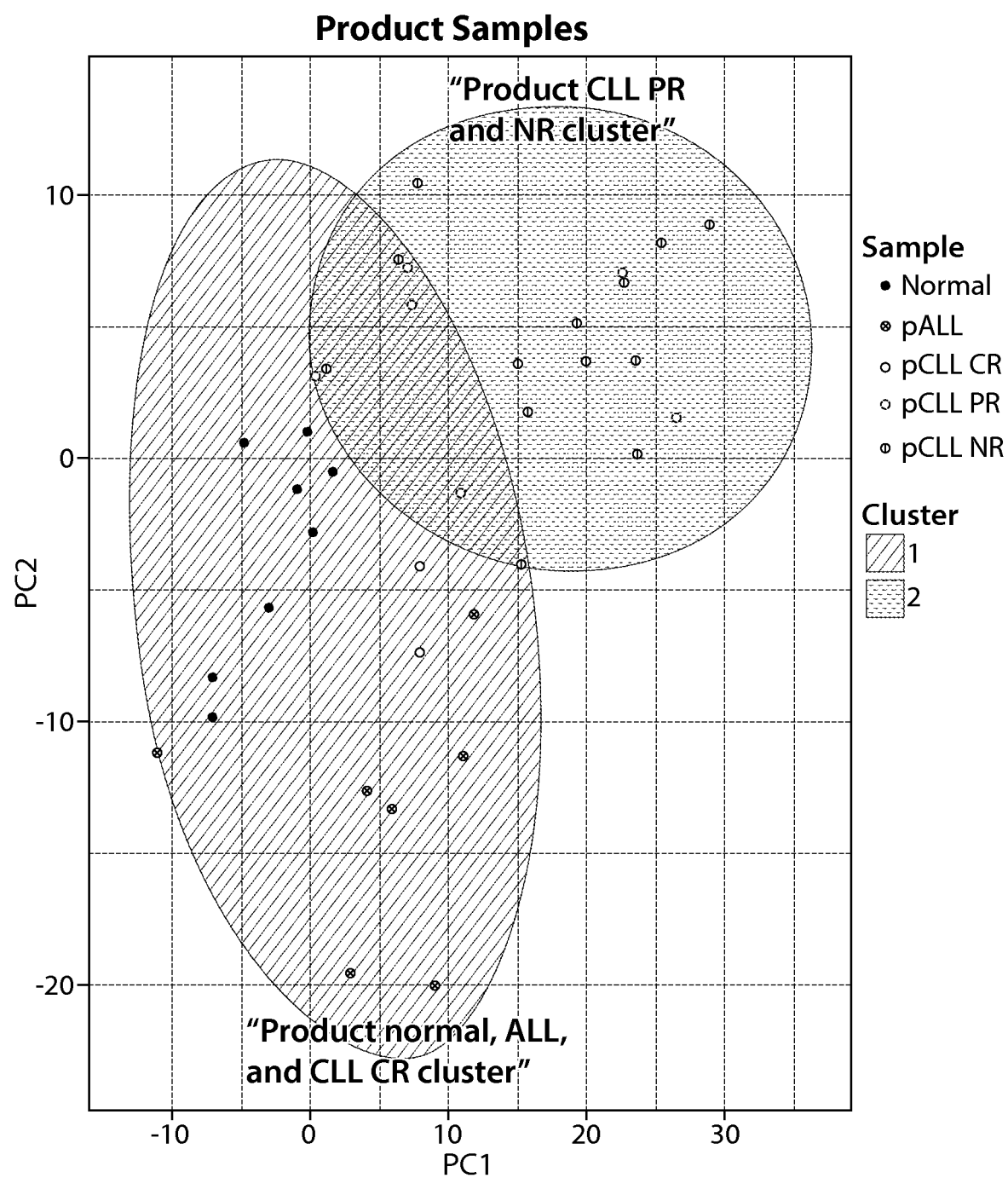
FIG. 5A depicts an exemplary result from a Principle Component Analysis (PCA) of CTL019 samples. This exemplary PCA result illustrates that CRs, ALL and Normal samples cluster separately from PRs and NRs.
Figure 5B:
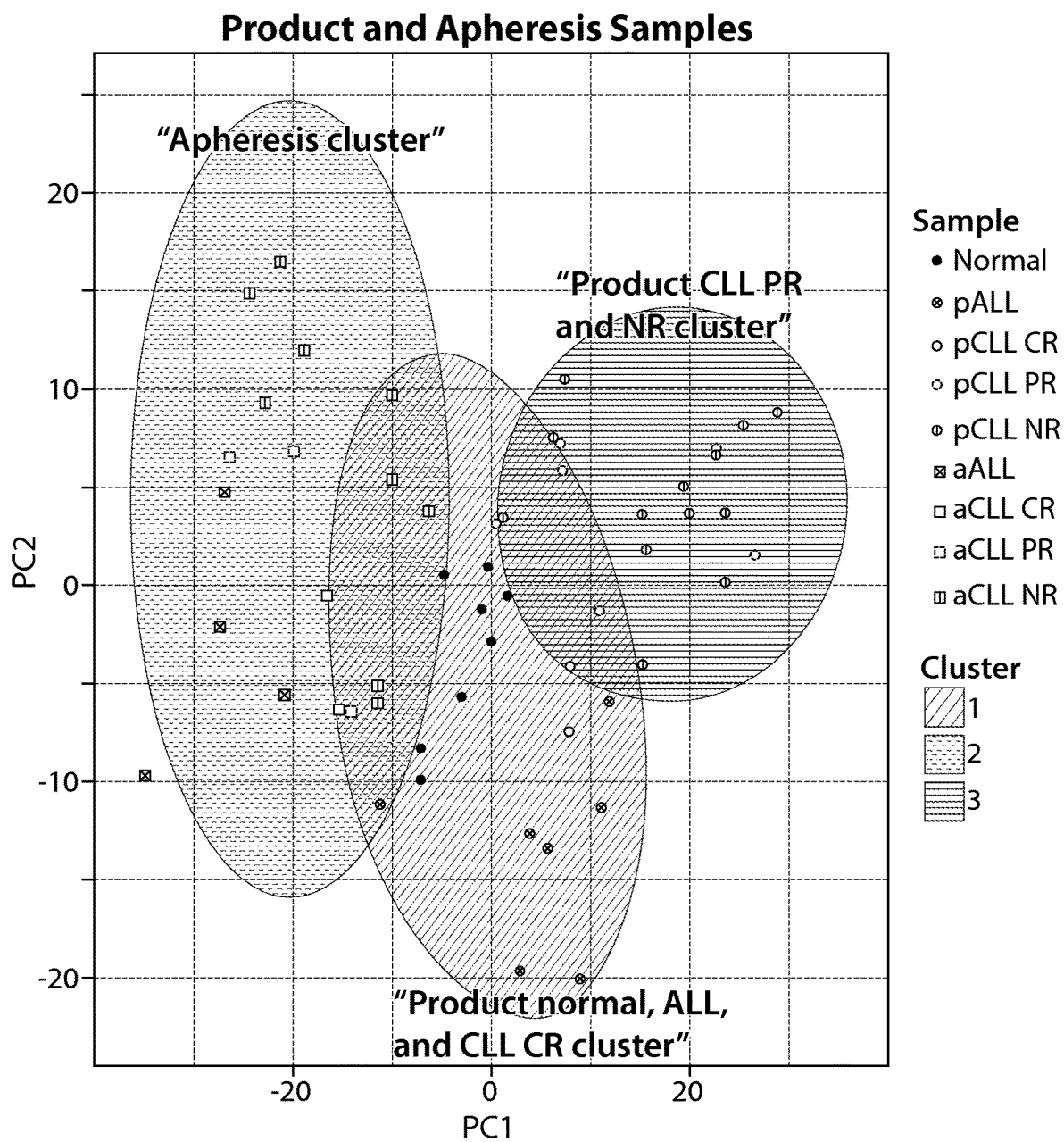
FIG. 5B depicts an exemplary result from a PCA of CTL019 and apheresis samples. This exemplary PCA result illustrates that CRs, ALL and Normal samples cluster separately from PRs and NRs and from the apheresis cluster.

FIG. 5A depicts an exemplary result from a Principle Component Analysis (PCA) of CTL019 samples. This exemplary PCA result illustrates that CRs, ALL and Normal samples cluster separately from PRs and NRs. FIG. 5B depicts an exemplary result from a PCA of CTL019 and apheresis samples. This exemplary PCA result illustrates that CRs, ALL and Normal samples cluster separately from PRs and NRs and from the apheresis cluster.

Figure 6:
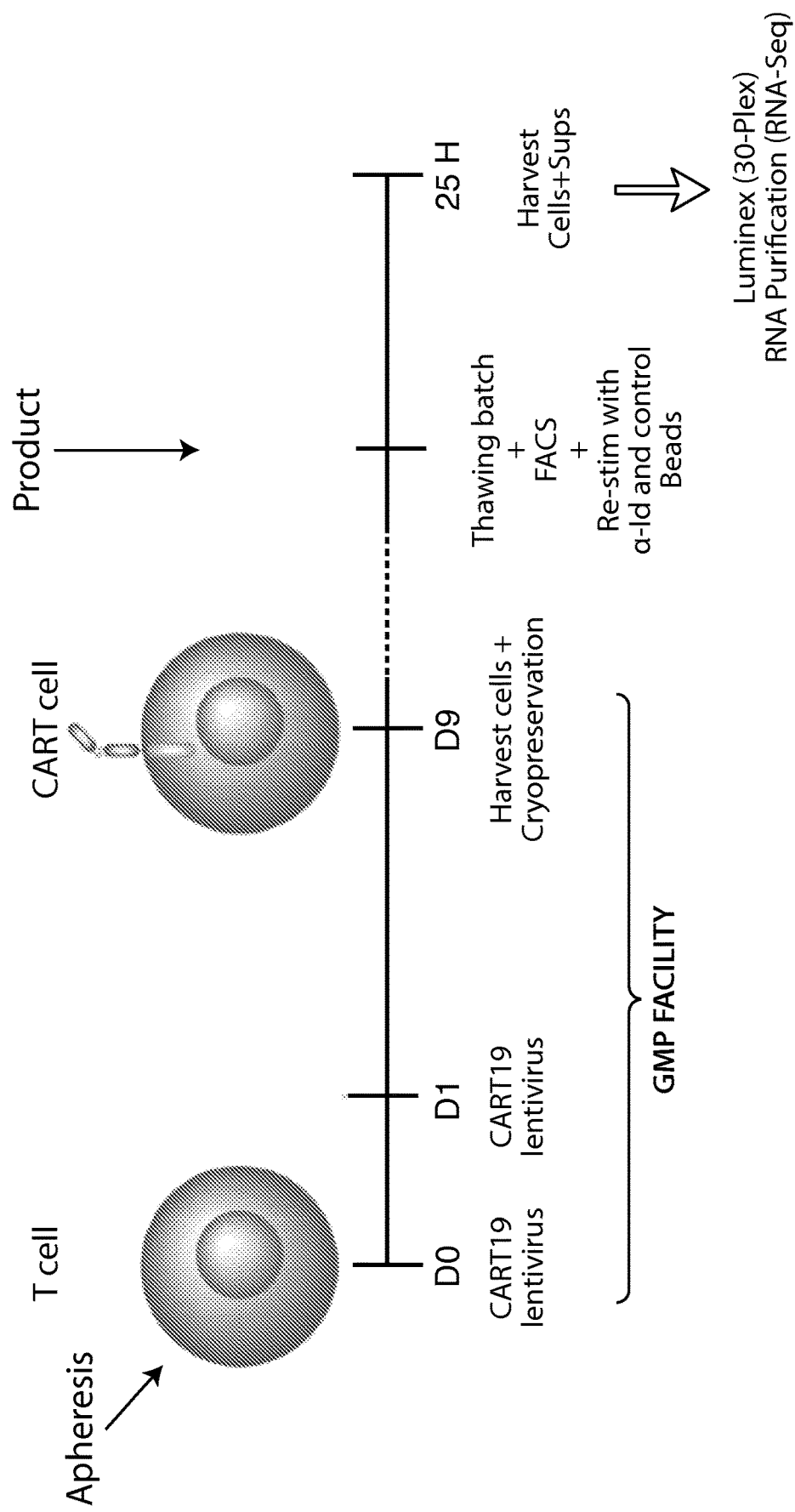
FIG. 6 depicts an exemplary schematic depicting immunophenotyping of apheresis and product samples.

FIG. 6 depicts an exemplary schematic depicting immunophenotyping of apheresis and product samples.

Manufactured CTL019 product (e.g., genetically engineered CAR19-expressing T cells obtained from CLL patients) classified as complete responders (CR), partial responders (PR), non-responders (NR), or pending were assessed for expression of immune checkpoint inhibitor molecules, such as PD-1, LAG3, and TIM3.

CD 19 CAR-expressing cells (e.g., T cells, NK cells) from CLL patients (e.g., manufactured product) with different responses to CAR-expressing cell therapy were analyzed by flow cytometery to determine percentages of CD4+ and CD8+ T cells. The CD19 CAR-expressing cells were from: patients that responded to CAR-expressing cell therapy (CR) (n=5); patients that partially responded to CAR-expressing cell therapy (n=8), patients that did not respond to CAR-expressing cell therapy (NR) (n=19); and patients that were pending, e.g., not yet assigned to a group (NA) (n=3). Cells were labeled with antibodies that specifically recognize CD4, CD8, the CAR19 molecule, and immune checkpoint molecules PD-1, LAG3, and TIM3, and secondary antibodies conjugated to fluoresceins, according to standard methods for flow cytometry analysis known in the art. Expression of each marker, e.g., CD4+, CD8+, etc., was determined by flow cytometry analysis software, and subpopulations (e.g., CD4+ T cells, CD8+ T cells, or CAR19-expressing T cells) were further analyzed fro the expression of immune checkpoint molecules PD-1, LAG3, and TIM3.

Figure 7A:
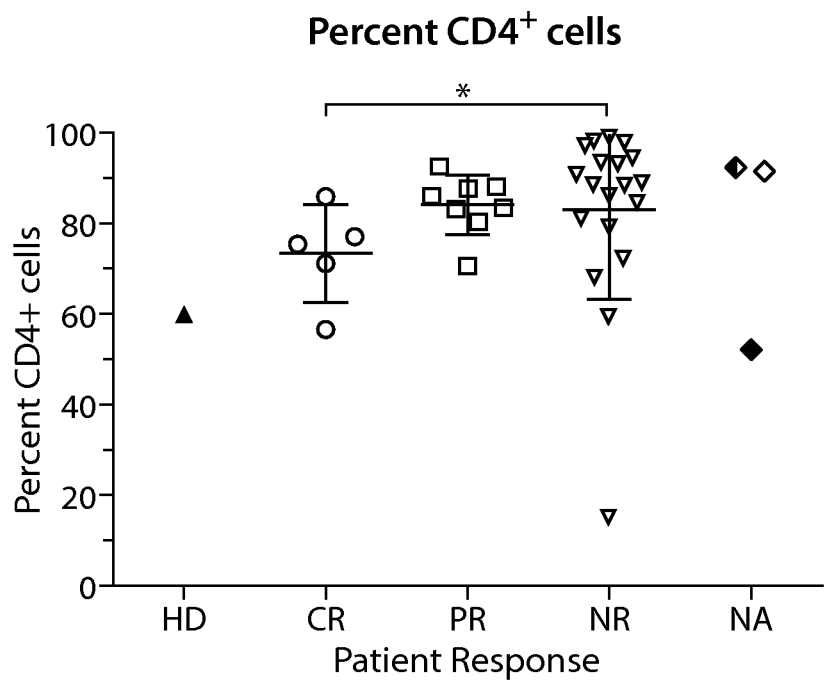
FIG. 7A and FIG. 7B depict exemplary multi-color flow cytometry analysis results identifying correlates of response in product samples. 36 manufactured CTL019 samples from CLL patients were analyzed. Samples included 5 CR, 8 PR, 19NR and 3 pending.
Figure 7B:
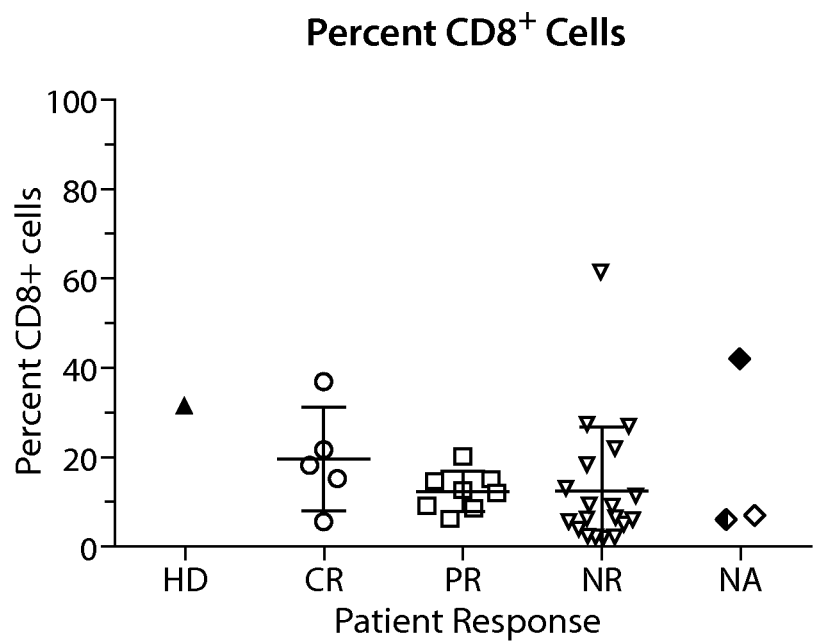

Using the methods and analysis described above, the percentage of CD4-expressing cells and CD8-expressing cells was determined for each patient in each response group. As described above, 36 manufactured CTL019 samples from CLL patients were analyzed, and included 5 CR, 8 PR, 19NR and 3 pending. FIG. 7A depicts an exemplary result illustrating percent CD4+ cells and patient response. Partial responders were shown to have a statistically significant greater percentage of CD4+ cells. FIG. 7B depicts an exemplary result illustrating percent CD8+ cells and patient response. Complete responders were shown to have a statistically significant great percentage of CD8+ cells.

Figure 8B:
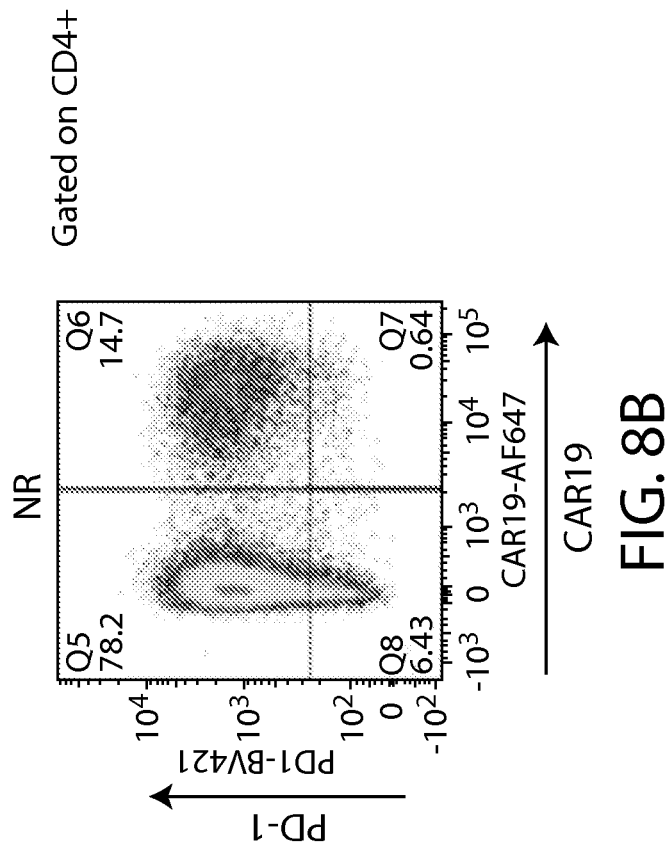
FIG. 8A, FIG. 8B, FIG. 8C and FIG. 8D depicts an exemplary flow cytometry analysis of PD1 and CAR19 expression on T cells.
Figure 8A:
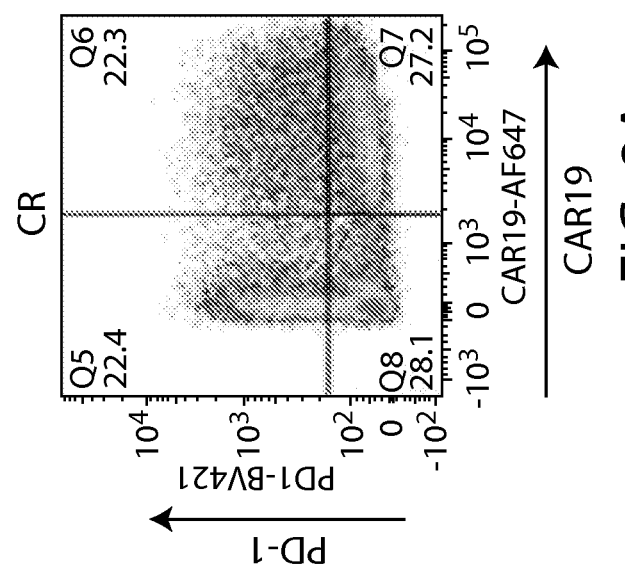

An example of the flow cytometry profiles analysis used to determine surface marker expression is shown in FIGS. 8A and 8B. Cells expressing CD4+ were determined using flow cytometry, and were further analyzed for CAR19 and PD-1 expression, such that the x-axis of the profiles indicate CAR19 expression (the top left (Q5) and bottom left (Q8) quadrants show the CAR19-negative CD4+ cells, while the top right (Q6) and bottom right (Q7) quadrants show the CAR19-expressing CD4+ cells) and the y-axis shows PD-1 expression (the bottom left (Q8) and right (Q7) quadrants show the PD-1 negative CD4+ cells and the top left (Q5) and right (Q6) quadrants show the PD-1– expressing CD4+ cells). In the CD4+ population from a CAR-expressing cell (e.g., T cell, NK cell) responder, 44.7% of the CD4+ cells overall expressed PD-1, and about 22.3% of the CAR19-expressing cells were PD-1 positive, while 27.2% of CAR19-expressing cells were PD-1 negative (FIG. 8A). In contrast, in the CD4+ population from a non-responder, there was a significant decrease in CAR19-expressing cells overall (about 15.3% compared to the 49.5% in CR), with 14.7% of the CAR19-expressing cells being PD-1 positive while only 0.64% were PD-1 negative (FIG. 8B). Comparison between the profiles in FIG. 8A and FIG. 8B shows that a much higher percentage of the CD4+ cells from a non-responder express PD-1 (about 92.9%) compared to the CAR-expressing cell responder (about 44.7%).

Figure 8D:
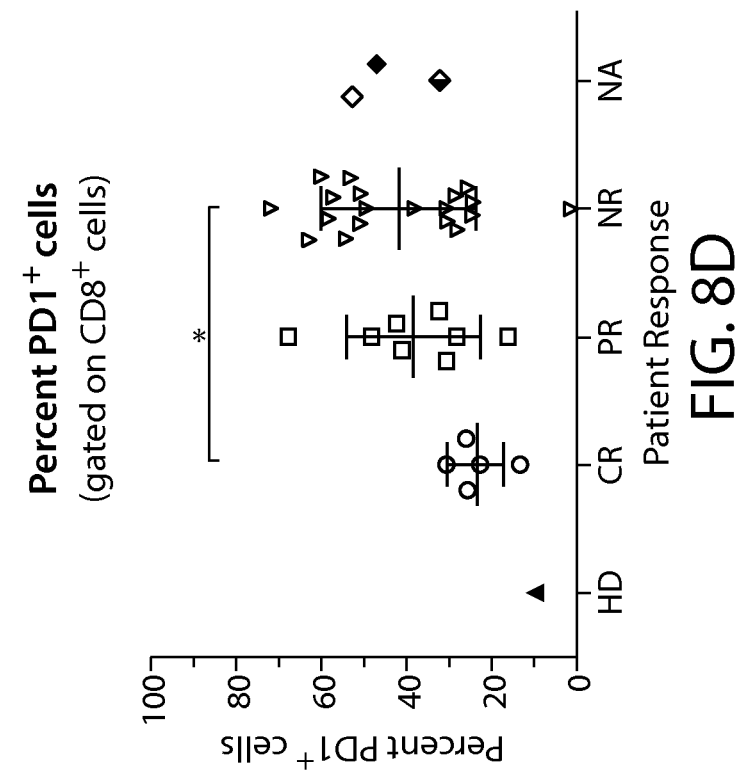
Figure 8C:
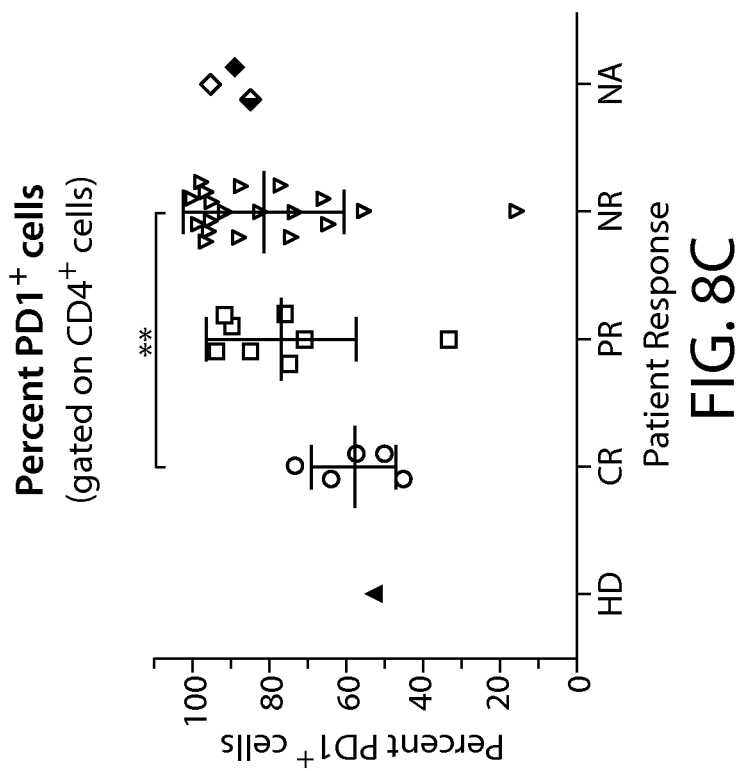

Using the methods and analysis described above, the percentage of PD-1 expressing (PD-1+) cells of the CD4+ population and the CD8+ population was determined for each patient in each response group. Non-responders were shown to have a greater percentage of PD-1+ cells in both the CD4+ (FIG. 8C) and CD8+ (FIG. 8D) populations compared to those that responded to CAR therapy (CR); the increase of average PD-1 percentage was statistically significant for both CD4+ and CD8+ populations. Partial responders (PR) exhibited higher percentages of PD-1+ cells than responders (CR) in both CD4+ (FIG. 8C) and CD8+ (FIG. 8D) populations.

Figures 9A, 9B:
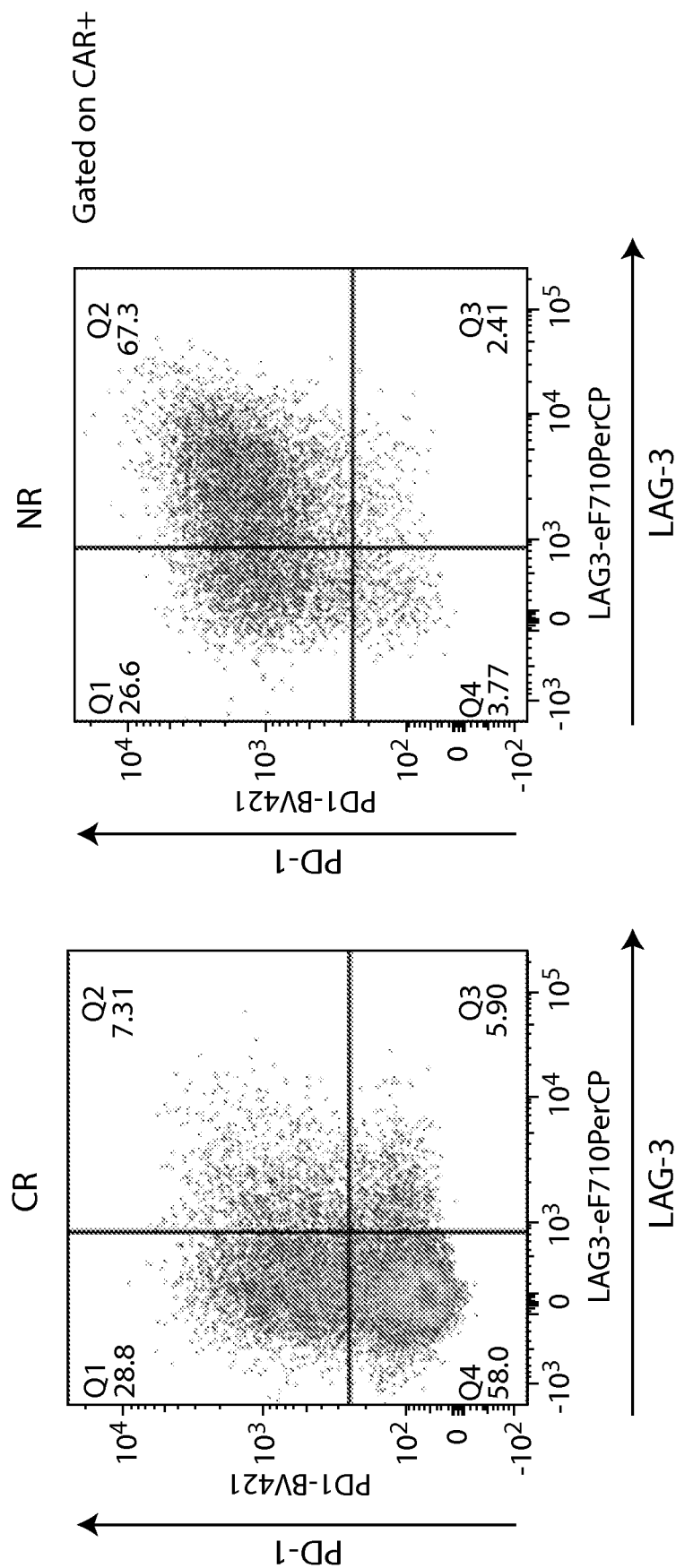
FIG. 9A and FIG. 9B depict an exemplary flow cytometry analysis of PD1, CAR 19, and LAG-3 expression on T cells from subjects that are complete responders (CR) or non-responders (NR) to CAR-expressing cell therapy.
Figure 9C:
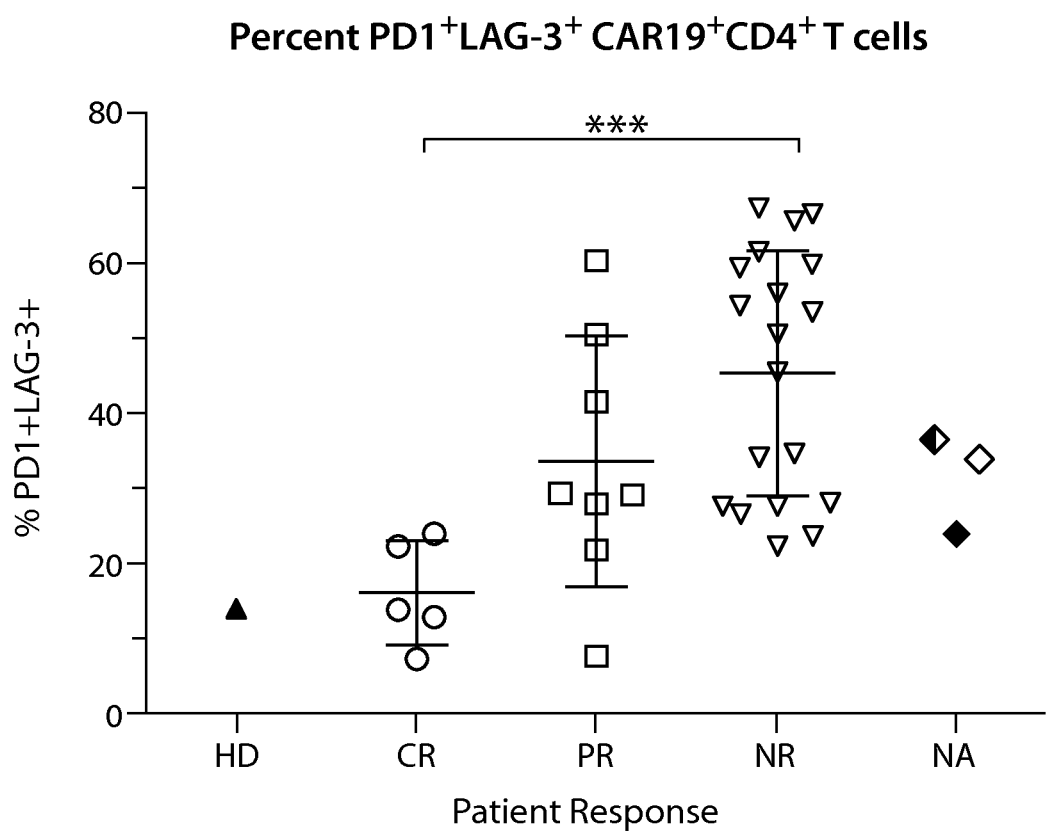
FIG. 9C depicts exemplary results that show the distribution of PD1 and LAG-3 expression from groups of subjects with different responses to CAR-expressing cell therapy. Non-responder (NR) products have higher percentages of PD1+ CAR19+ LAG3+ T cells than CRs. These data demonstrate that NR products exhibit an exhausted phenotype of PD1+ CAR+ and co-expression of LAG3.
Figures 10A, 10B:
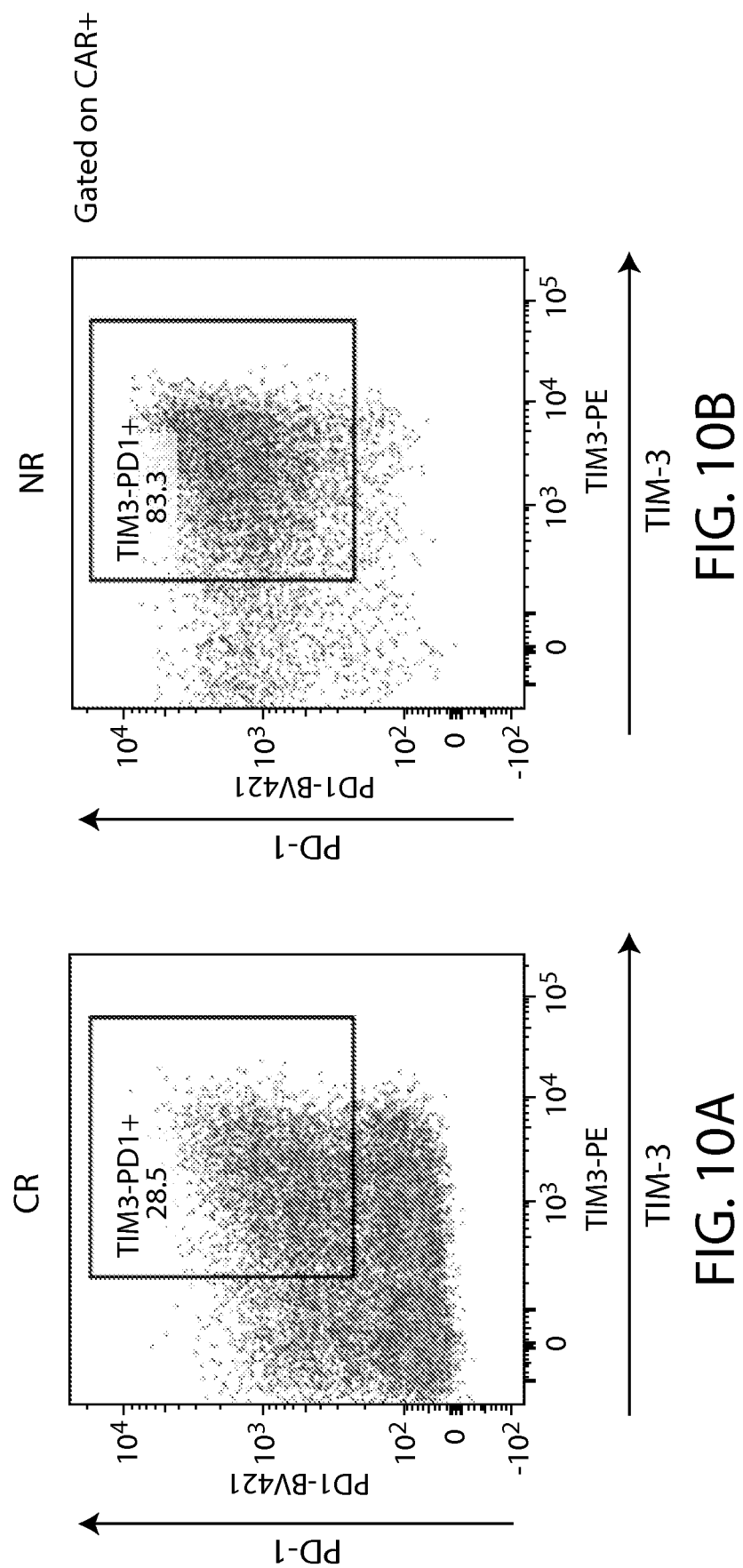
FIG. 10A and FIG. 10B depict an exemplary flow cytometry analysis of PD1, CAR 19, and TIM-3 expression on T cells from subjects that are complete responders (CR) or non-responders (NR) to CAR-expressing cell therapy.
Figure 10C:
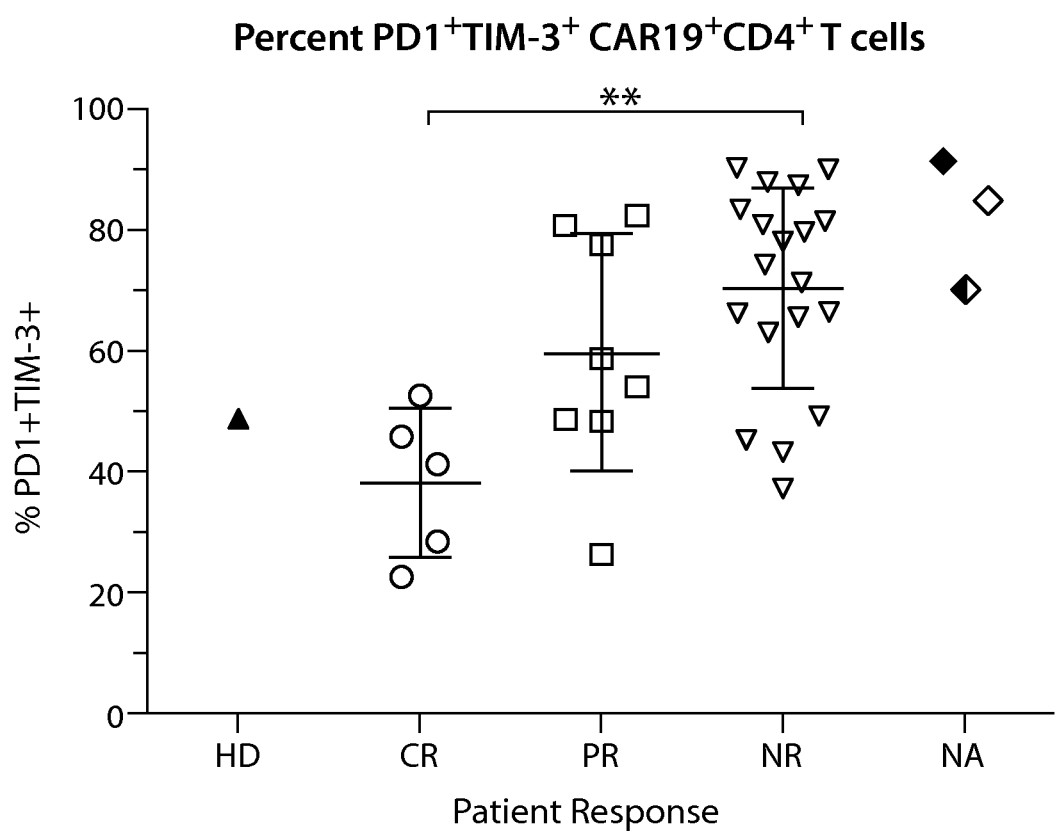
FIG. 10C depicts exemplary results that show the distribution of PD1 and TIM-3 expression from groups of subjects with different responses to CAR-expressing cell therapy. Non-responder (NR) products have higher percentages of CAR19+ PD1+ TIM3+ cells than CRs. These data demonstrate that NR products exhibit an exhausted phenotype of PD1+ CAR+ and co-expression of TIM3.

Further analysis was performed to determine the distribution of cells expressing PD-1, LAG3, and TIM3 from patients with different responses to CAR therapy. Representative cell profile analysis for PD-1, LAG3, and TIM3 expression in the CD4+ population are shown in FIG. 9 and FIG. 10. The cell populations were first analyzed for CAR19+ expression. The CAR19+ population was then analyzed for PD-1 and LAG3 expression (FIG. 9) or PD-1 and TIM-3 expression (FIG. 10). In the LAG3+ population from a CAR-expressing cell (e.g., T cell, NK cell) responder, 36.1% of the CAR19+ cells overall expressed PD-1, and about 7.3% of the LAG3-expressing cells were PD-1 positive, while 5.9% of LAG3-expressing cells were PD-1 negative (FIG. 9). In contrast, in the CAR19+ population from a non-responder, there was a significant increase in LAG3-expressing cells overall (about 69.7% compared to the 13.2% in CR), with 67.3% of the LAG3-expressing cells being CAR19+ positive while only 2.41% were PD-1 negative (FIG. 9). Comparison between the CR and NR flow cytometry profiles in FIG. 9 show that a much higher percentage of the LAG3+ cells from a non-responder express PD-1 (about 67.3%) compared to the CAR-expressing cell (e.g., T cell, NK cell) responder (about 7.3%).

Using the methods and analysis described above, the percentage of PD-1 and LAG-3 expressing (PD-1+/LAG-3+) cells of the CAR19+ population was determined for each patient in each response group. Non-responders were shown to have a greater percentage of PD-1+/LAG-3+ cells in the CAR19+ populations compared to those that responded to CAR therapy (CR) (FIG. 9); the increase of average PD-1/LAG-3 percentage was statistically significant for the CAR19+ population. Partial responders (PR) exhibited higher percentages of PD-1+/LAG-3+ cells than responders (CR) in the CAR19+ (FIG. 9) population. In an embodiment, NR products exhibit an exhausted phenotype of PD1+ CAR+ and co-expression of LAG3.

Next, the CAR19+ population was analyzed for PD-1 and TIM-3 expression (FIG. 10). In the TIM+ population from a CAR-expressing cell (e.g., T cell, NK cell) responder, 28.5% of the CAR19+ cells overall expressed PD-1 (FIG. 10). In contrast, in the CAR19+ population from a non-responder, there was a significant increase in TIM3+/PD1+ cells, with 83.3% of the CAR19+-expressing cells being TIM3+/PD1+ (FIG. 10).

Using the methods and analysis described above, the percentage of PD-1 and TIM-3 expressing (PD-1+/TIM-3+) cells of the CAR19+ population was determined for each patient in each response group. Non-responders were shown to have a greater percentage of PD-1+/TIM-3+ cells in the CAR19+ populations compared to those that responded to CAR therapy (CR) (FIG. 10); the increase of average PD-1/TIM-3 percentage was statistically significant for the CAR19+ population. Partial responders (PR) exhibited higher percentages of PD-1+/TIM-3+ cells than responders (CR) in the CAR19+ (FIG. 10) population. In an embodiment, NR products exhibit an exhausted phenotype of PD1+ CAR+ and co-expression of TIM3.

Figure 11:
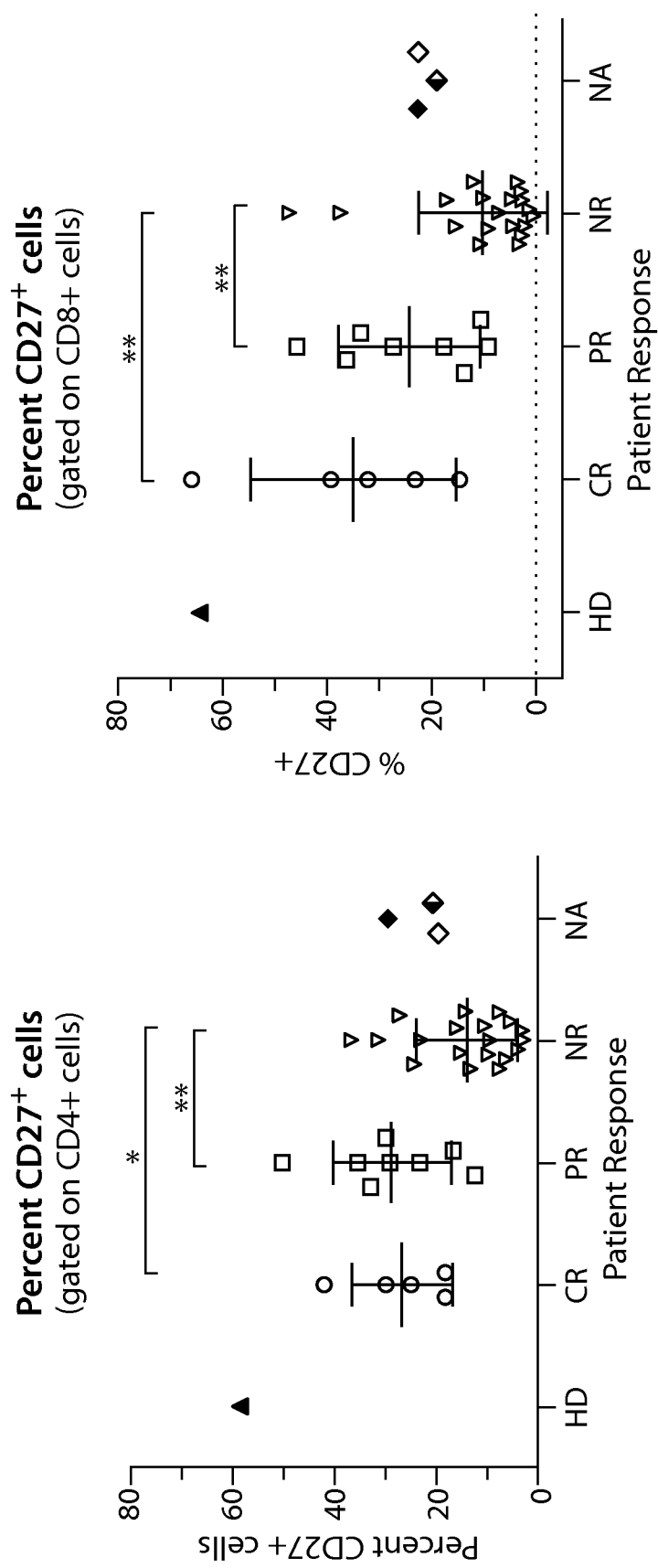
FIG. 11 depicts an exemplary result illustrating that CD27 levels in the CAR product correlate with patient response. CRs CD8+ cells displayed a higher percentage of CD27+ cells as compared to PRs and NRs.

Cells expressing CD4+ and CD8+ were determined using flow cytometry, and were further analyzed for CD27+ expression. Using the methods and analysis described above, the percentage of CD27 expressing (CD27+) cells of the CD4+ population and the CD8+ population was determined for each patient in each response group. Complete responders (CR) and partial responders (PR) were shown to have a greater percentage of CD27+ cells in both the CD4+ (FIG. 11A) and CD8+ (FIG. 11B) populations compared to non-responders (NR); the increase of average CD27 percentage was statistically significant for both CD4+ and CD8+ populations. Partial responders (PR) exhibited higher percentages of CD27+ cells than complete responders (CR) in CD4+ (FIG. 11A) populations. Complete responders (CR) exhibited higher percentages of CD27+ cells than partial responders (PR) in CD8+ (FIG. 11B) populations. In an embodiment, CD27 levels in a CAR product correlate with patient response. In an embodiment, CRs CD8+ cells display higher percentages of CD27+ cells as compared to PRs and NRs.

Figure 12:
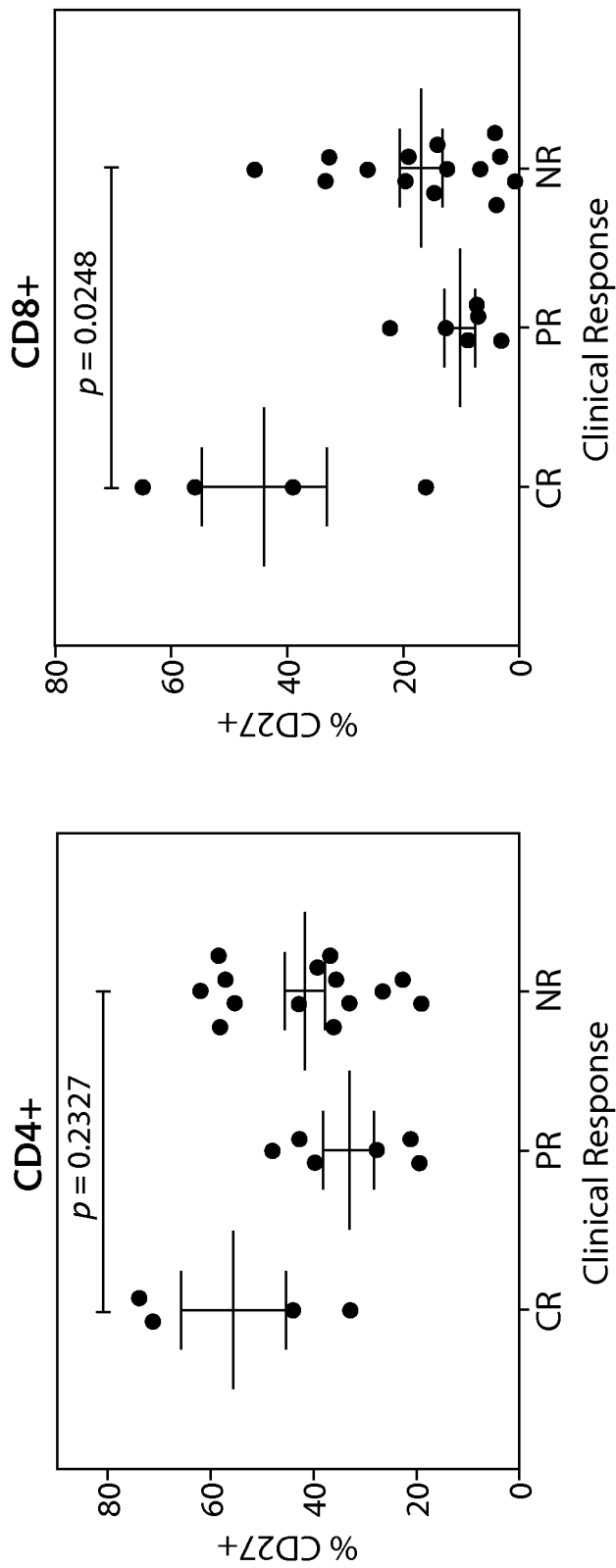
FIG. 12 depicts an exemplary multi-color flow cytometry analysis result identifying correlates of response in apheresis samples. 26 apheresed samples from CLL patients were analyzed. Samples included 4 CR, 6 PR, 14NR and 1 patient was not infused.

FIG. 12 depicts an exemplary multi-color flow cytometry analysis result identifying correlates of response in apheresis samples. 26 apheresed samples from CLL patients were analyzed. Samples included 4 CR, 6 PR, 14NR and 1 patient was not infused.

Figure 13:
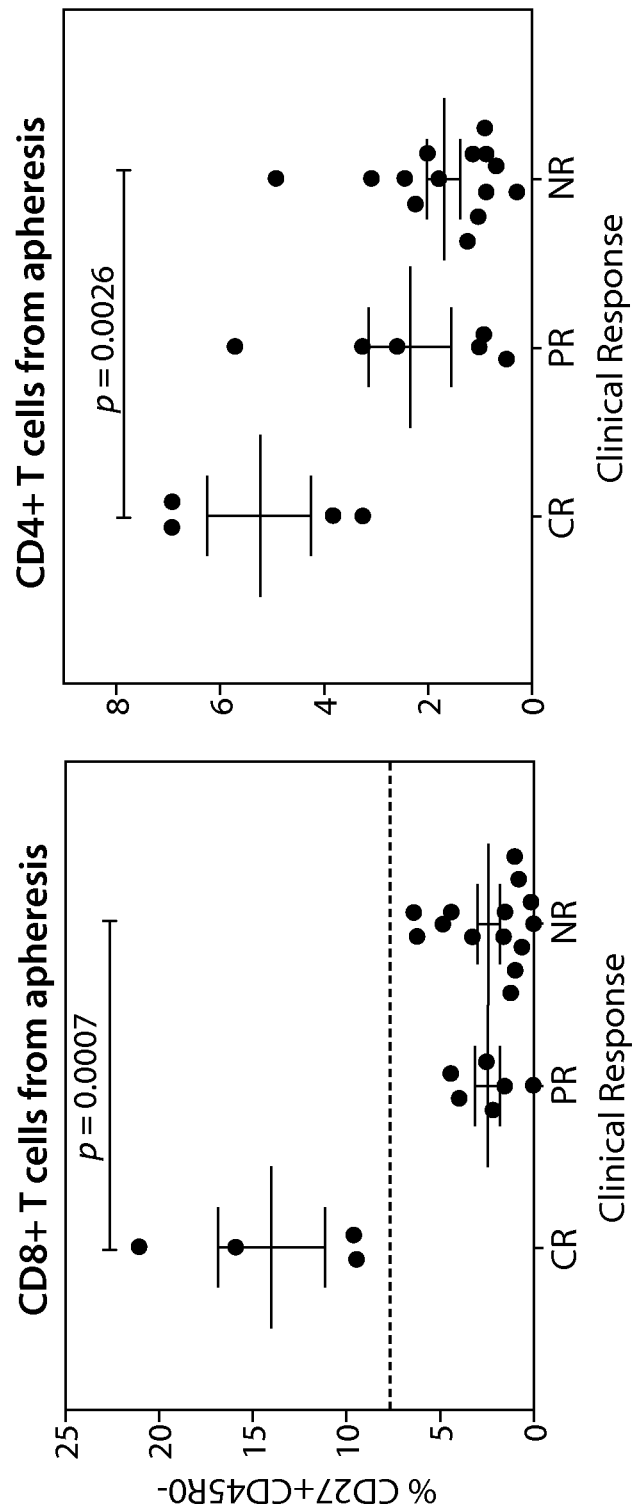
FIG. 13 depicts an exemplary multi-color flow cytometry analysis result illustrating a correlation between a younger T cell phenotype and response to CTL019 therapy. These data demonstrate that the percentage of CD27+ CD45RO− in CD8+ T cells is predictive of which CLL patients will undergo a complete response to CTL019.

FIG. 13 depicts an exemplary multi-color flow cytometry analysis result illustrating a correlation between a younger T cell phenotype and response to CTL019 therapy. These data demonstrate that the percentage of CD27+ CD45RO− in CD8+ T cells is predictive of which CLL patients will undergo a complete response to CTL019.

Figure 14:
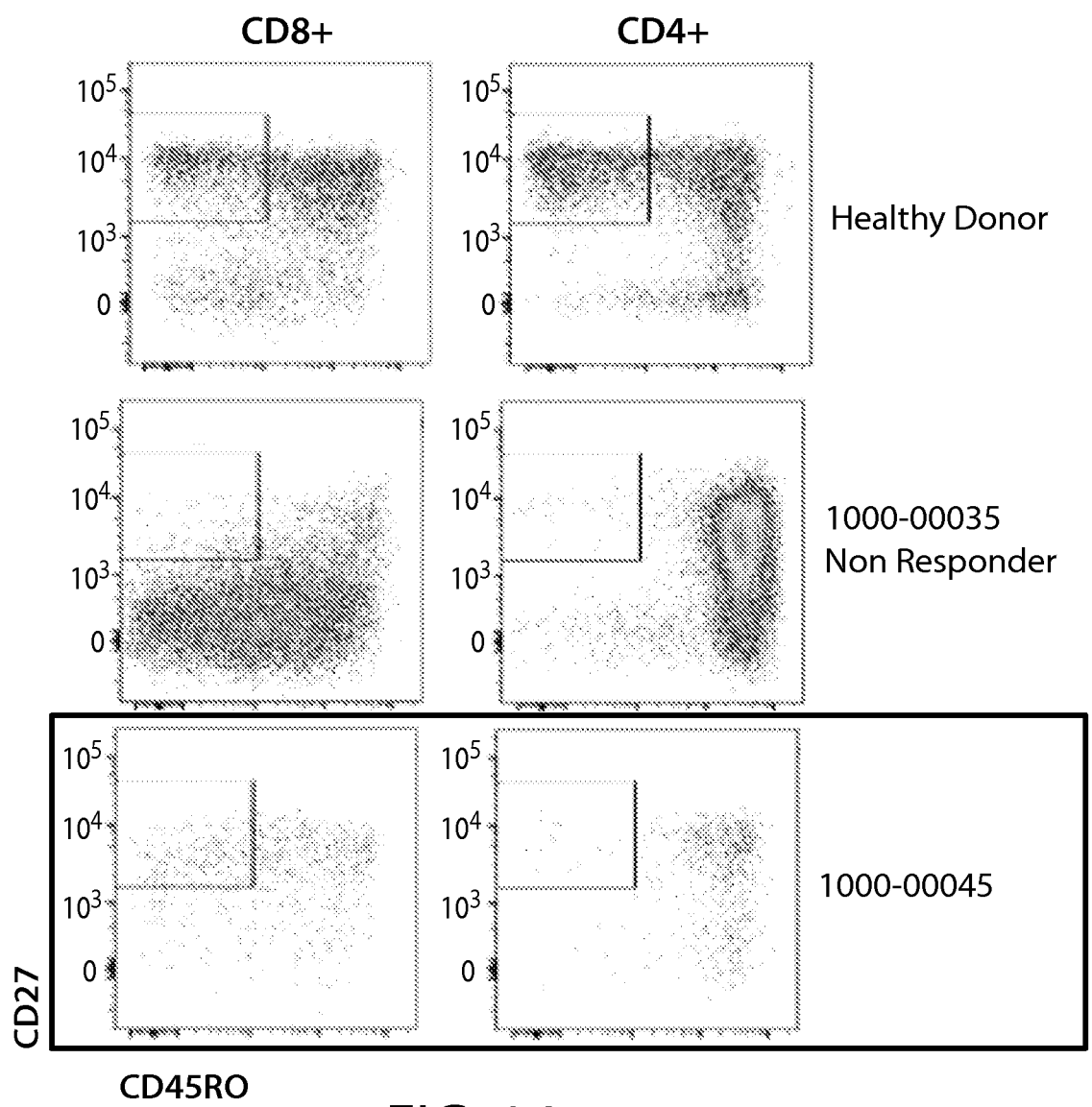
FIG. 14 depicts an exemplary analysis of apheresis in a human patient prior to CTL019 therapy. Exemplary results illustrate that while patient 1000-00045 presented with very few T cells, 27% of the T cells were CD8+ CD27+ CD45RO−.

FIG. 14 depicts an exemplary analysis of apheresis in a human patient prior to CTL019 therapy. Exemplary results illustrate that while patient 1000-00045 presented with very few T cells, 27% of the T cells were CD8+ CD27+ CD45RO−.

Figure 15:
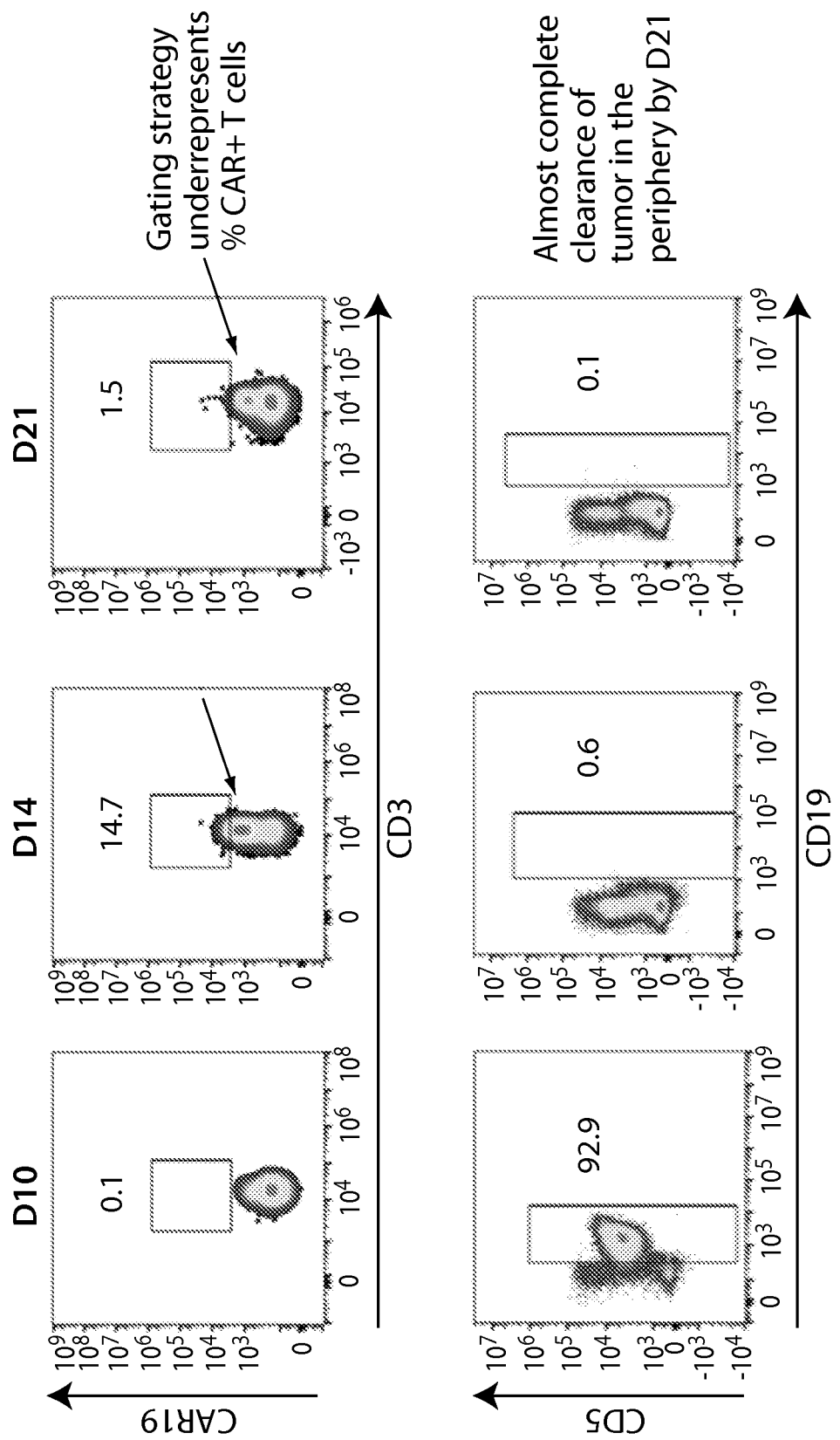
FIG. 15 depicts an exemplary result of a patient response (patient 1000-00045) to CTL019 therapy. CD8+ CD27+ CD45RO− T cells were a positive predictor of the patient response to CTL019 therapy. These exemplary results illustrate that a good prognostic phenotype in apheresis is a high percentage of CD8+ CD27+ CD45RO− T cells (naïve or $T_{SCM}$ phenotype). A poor prognostic phenotype in CTL019 product is a high percentage of PD1+ CAR+ and LAG3+ or TIM3+ T cells (exhausted phenotype).

FIG. 15 depicts an exemplary result of a patient response (patient 1000-00045) to CTL019 therapy. CD8+ CD27+ CD45RO− T cells were a positive predictor of the patient response to CTL019 therapy. These exemplary results illustrate that a good prognostic phenotype in apheresis is a high percentage of CD8+ CD27+ CD45RO− T cells (young phenotype). A poor prognostic phenotype in CTL019 product is a high percentage of PD1+ CAR+ and LAG3+ or TIM3+ T cells (exhausted phenotype).

Significant gene sets from the analyses above were refined to a subset of genes within the gene sets that are significantly differentially expressed between ALL CRs/CLL CRs and CLL NRs as well as following the expected expression pattern of increasing or decreasing from ALL→CLL CR→CLL PR→CLL NR. An exemplary listing of genes that were significantly differentially expressed are listed in Table 7A. Table 7A is an exemplary list of biomarkers whose expression values predict patient response to CTL019 therapy. Table 7A was further refined to produce a flow cytometry biomarker gene panel by selecting for genes that are cell surface markers. Exemplary cell surface genes that predict patient response to CTL019 therapy are shown in Table 8.

TABLE 7A

Exemplary genes that predict patient response to CTL019 therapy
Table 7A

| Gene | Unigene | Accession No. |
|---|---|---|
| ABCA7 | Hs.134514 | NM_019112 |
| ABTB1 | Hs.107812 | NM_172027, NM_172028, NM_032548 |
| ACOT9 | Hs.298885 | NM_001037171, NM_001033583 |
| ACTA2 | Hs.500483 | NM_001141945, NM_001613 |
| ADAMTS10 | Hs.657508 | NM_030957 |
| ADD3 | Hs.501012 | NM_016824, NM_019903, NM_001121 |
| ADPRH | Hs.99884 | NM_001125 |
| AEBP1 | Hs.439463 | NM_001129 |
| AES | Hs.515053 | NM_198970, NM_198969, NM_001130 |
| AIM2 | Hs.281898 | NM_004833 |
| ALAS1 | Hs.476308 | NM_199166, NM_000688 |
| ALPK1 | Hs.652825 | NM_025144, NM_001102406 |
| ALS2CL | Hs.517937 | NM_147129, NM_182775 |
| AMD1 | Hs.159118 | NM_001634, NM_001033059 |
| ANKRD55 | Hs.436214 | NM_024669, NM_001039935 |
| ANKZF1 | Hs.437647 | NM_018089, NM_001042410 |
| ANTXR2 | Hs.162963, Hs.720941 | NM_001145794, NM_058172 |
| ANXA2 | Hs.591361, Hs.546235, Hs.511605 | NM_004039, NM_001136015, NM_001002858, NM_001002857 |
| ANXA2P2 | Hs.534301 | |
| AP1G2 | Hs.343244 | NM_003917 |
| AP1M1 | Hs.71040 | NM_032493, NM_001130524 |
| AP2A2 | Hs.19121 | NM_012305 |
| APAF1 | Hs.552567 | NM_181869, NM_181868, NM_013229, NM_001160, NM_181861 |
| APBA2 | Hs.721380, Hs.618112 | NM_001130414, NM_005503 |
| APBB3 | Hs.529449 | NM_133174, NM_133173, NM_133172, NM_006051 |
| AQP3 | Hs.234642 | NM_004925 |
| ARFGAP2 | Hs.436204 | NM_032389 |
| ARHGAP33 | Hs.515364 | NM_052948 |
| ARHGEF1 | Hs.631550 | NM_004706, NM_199002, NM_198977 |
| ARHGEF11 | Hs.516954 | NM_198236, NM_014784 |
| ARHGEF18 | Hs.465761 | NM_001130955, NM_015318 |
| ARL4C | Hs.723194, Hs.111554 | NM_005737 |
| ARPC5L | Hs.132499 | NM_030978 |
| ARRB1 | Hs.625320, Hs.503284 | NM_020251, NM_004041 |
| ARRDC2 | Hs.515249 | NM_015683, NM_001025604 |
| ARSB | Hs.604199, Hs.149103 | NM_000046, NM_198709 |
| ATOX1 | Hs.125213 | NM_004045 |
| ATP13A3 | Hs.529609 | NM_024524 |
| ATP1B3 | Hs.477789 | NM_001679 |
| ATP2A2 | Hs.506759 | NM_001135765, NM_170665, NM_001681 |
| ATP2B4 | Hs.343522, Hs.511311 | NM_001001396, NM_001684 |
| ATP8B4 | Hs.511311 | NM_024837 |
| ATXN7L3B | Hs.744849 | NM_001136262 |
| AVEN | Hs.555966 | NM_020371 |
| B4GALT5 | Hs.370487 | NM_004776 |
| BATF | Hs.509964 | NM_006399 |
| BCL9L | Hs.414740 | NM_182557 |
| BENDS | Hs.475348 | NM_024603 |
| BEX4 | Hs.184736 | NM_001080425, NM_001127688 |
| BIN1 | Hs.193163 | NM_139350, NM_139348, NM_139349, NM_139343, NM_004305, NM_139345, NM_139344, NM_139347, NM_139351, NM_139346 |
| BNIP3L | Hs.131226 | NM_004331 |
| BTN3A1 | Hs.191510 | NM_001145008, NM_007048, NM_194441, NM_001145009 |
| C10orf128 | Hs.385493 | NM_001010863 |
| C11orf10 | Hs.437779 | NM_014206 |
| C11orf21 | Hs.559181 | NM_001142946 |
| C11orf35 | Hs.669395 | NM_173573 |
| C12orf5 | Hs.504545 | NM_020375 |
| C16orf54 | Hs.331095 | NM_175900 |

TABLE 7A-continued

Exemplary genes that predict patient response to CTL019 therapy
Table 7A

| Gene | Unigene | Accession No. |
|---|---|---|
| C16orf74 | Hs.461655 | NM_206967 |
| C17orf48 | Hs.47668 | NM_020233 |
| C17orf67 | Hs.658949 | NM_001085430 |
| C19orf29 | Hs.267446 | NM_001080543, NM_021231 |
| C1QBP | Hs.555866 | NM_001212 |
| C20orf11 | Hs.353013 | NM_017896 |
| C20orf112 | Hs.516978 | NM_080616 |
| C21orf2 | Hs.517331 | NM_004928 |
| C2orf67 | Hs.591638, Hs.282260 | NM_152519 |
| C3orf26 | | NM_001167924, NM_032359 |
| C4orf43 | | NM_018352 |
| C5orf13 | Hs.483067, Hs.36053, Hs.694860 | NM_001142475, NM_001142476, NM_004772, NM_001142482, NM_001142477, NM_001142483, NM_001142478, NM_001142474, NM_001142481, NM_001142479, NM_001142480 |
| C5orf30 | Hs.482976 | NM_033211 |
| C5orf32 | Hs.529798 | NM_032412 |
| C5orf39 | Hs.529385, Hs.721020 | NM_001014279 |
| CABIN1 | Hs.517478 | NM_012295 |
| CACHD1 | Hs.443891 | NM_020925 |
| CADM1 | Hs.370510 | NM_014333, NM_001098517 |
| CAPG | Hs.516155 | NM_001747 |
| CAPS | Hs.584744 | NM_004058, NM_080590 |
| CASK | Hs.495984 | NM_001126054, NM_001126055, NM_003688 |
| CBX4 | Hs.405046 | NM_003655 |
| CCDC47 | Hs.202011 | NM_020198 |
| CCL17 | Hs.546294 | NM_002987 |
| CCL3 | Hs.514107 | NM_002983 |
| CCL4 | Hs.75703 | NM_002984 |
| CCR1 | Hs.301921 | NM_001295 |
| CCT2 | Hs.189772 | NM_006431 |
| CCT3 | Hs.491494 | NM_001008800, NM_005998, NM_001008883 |
| CCT7 | Hs.368149 | NM_001009570, NM_006429, NM_001166284, NM_001166285 |
| CD248 | Hs.195727 | NM_020404 |
| CD40LG | Hs.592244 | NM_000074 |
| CD58 | Hs.34341 | NM_001144822, NM_001779 |
| CD70 | Hs.715224, Hs.501497 | NM_001252 |
| CD80 | Hs.838 | NM_005191 |
| CDC123 | Hs.412842 | NM_006023 |
| CDC25B | Hs.153752 | NM_004358, NM_021872, NM_021873 |
| CDC42BPG | Hs.293590 | NM_017525 |
| CDK7 | Hs.184298 | NM_001799 |
| CDKN1A | Hs.370771 | NM_078467, NM_000389 |
| CDKN2A | Hs.512599 | NM_058197, NM_058195, NM_000077 |
| CERK | Hs.200668 | NM_022766 |
| CFP | Hs.53155 | NM_001145252, NM_002621 |
| CHAC2 | Hs.585944 | NM_001008708 |
| CHI3L2 | Hs.514840 | NM_001025199, NM_001025197, NM_004000 |
| CHMP7 | Hs.5019 | NM_152272 |
| CLDND1 | Hs.531371 | NM_001040181, NM_001040183, NM_001040200, NM_001040199, NM_001040182, NM_019895 |
| CLTC | Hs.491351 | NM_004859 |
| CNN3 | Hs.483454 | NM_001839 |
| CNOT8 | Hs.26703 | NM_004779 |
| CNPY3 | Hs.414099 | NM_006586 |
| COQ3 | Hs.713623 | NM_017421 |
| CSF1 | Hs.591402 | NM_000757, NM_172212, NM_172211, NM_172210 |
| CSF2 | Hs.1349 | NM_000758 |
| CSNK2A1 | Hs.654675, Hs.644056 | NM_001895, NM_177560, NM_177559 |
| CST7 | Hs.143212 | NM_003650 |
| CTC1 | Hs.156055 | NM_025099 |
| CTDSP1 | Hs.444468 | NM_182642, NM_021198 |
| CTDSP2 | Hs.524530 | XM_001720210, XM_001722552, XM_002344384, XM_001725997, NM_005730 |
| CTNNA1 | Hs.656653, Hs.445981 | NM_001903 |
| CTSL1 | Hs.418123 | NM_001912, NM_145918 |
| CUL9 | Hs.485434 | NM_015089 |
| CUTA | Hs.520070 | NM_001014433, NM_001014840, NM_015921, NM_001014838, NM_001014837 |
| CYFIP1 | Hs.26704 | NM_014608, NM_001033028 |
| CYP2J2 | Hs.152096 | NM_000775 |
| DBP | Hs.414480, Hs.528006 | NM_001352 |
| DCAF11 | Hs.525251 | NM_001163484, NM_181357, NM_025230 |
| DCBLD2 | Hs.203691 | NM_080927 |
| DCHS1 | Hs.199850 | NM_003737 |
| DCTN6 | Hs.158427 | NM_006571 |
| DDX10 | Hs.591931 | NM_004398 |
| DENND2D | Hs.557850 | NM_024901 |
| DENND5A | Hs.501857 | NM_015213 |
| DERL1 | Hs.241576 | NM_001134671, NM_024295 |
| DFNB31 | Hs.93836 | NM_001083885, NM_015404 |
| DGKD | Hs.471675 | NM_152879, NM_003648 |
| DGKZ | Hs.502461 | NM_001105540, NM_003646, NM_201533, NM_201532 |
| DHRS2 | Hs.272499 | NM_182908, NM_005794 |
| DIABLO | Hs.169611 | NM_138929, NM_019887 |
| DNAJB6 | Hs.490745 | NM_005494, NM_058246 |
| DPEP2 | Hs.372633 | NM_022355 |
| DUSP22 | Hs.29106 | NM_020185, XM_001718070 |
| E2F6 | Hs.603093 | NM_198256 |
| EBNA1BP2 | Hs.346868 | NM_006824, NM_001159936 |
| EDARADD | Hs.352224 | NM_080738, NM_145861 |
| EED | Hs.503510 | NM_152991, NM_003797 |
| EEF1E1 | Hs.602353, Hs.723203 | NM_004280, NM_001135650 |
| EGFL6 | Hs.12844 | NM_001167890, NM_015507 |
| EHD1 | Hs.523774 | NM_006795 |
| EIF2B3 | Hs.533549 | NM_001166588, NM_020365 |
| EIF2S1 | Hs.151777 | NM_004094 |
| ELL2 | Hs.708710, Hs.192221 | NM_012081 |
| EMP1 | Hs.436298 | NM_001423 |
| EPAS1 | Hs.468410 | NM_001430 |
| EPHA4 | Hs.371218 | NM_004438 |
| EPHX1 | Hs.89649 | NM_001136018, NM_000120 |
| EPPK1 | Hs.200412 | NM_031308 |
| ERGIC2 | Hs.339453 | NM_016570 |
| ERGIC3 | Hs.472558 | NM_015966, NM_198398 |
| ERP29 | Hs.75841 | NM_001034025, NM_006817 |
| ETFA | Hs.39925 | NM_001127716, NM_000126 |
| ETNK1 | Hs.29464 | NM_001039481, NM_018638 |
| ETV7 | Hs.272398 | NM_016135 |
| FAAH | Hs.720143 | NM_001441 |
| FABP5 | Hs.408061 | NM_001444 |
| FAF2 | Hs.484242 | NM_014613 |
| FAIM3 | Hs.723317, Hs.58831 | NM_001142472, NM_001142473, NM_005449 |
| FAM117B | Hs.471130 | NM_173511 |
| FAM134B | Hs.711125 | NM_001034850, NM_019000 |
| FAM13A | Hs.97270 | NM_014883, NM_001015045 |
| FAM193B | Hs.484289 | NM_019057 |
| FAM40B | Hs.489988 | NM_020704, NM_001134336 |
| FAM63A | Hs.723127 | NM_018379, NM_001163260, NM_001163259, NM_001163258, NM_001040217 |
| FAM65B | Hs.559459 | NM_014722, NM_015864 |
| FANCL | Hs.720331 | NM_001114636, NM_018062 |
| FANK1 | Hs.352591 | NM_145235 |
| FAR2 | Hs.298851 | NM_018099 |
| FAU | Hs.387208 | NM_001997 |
| FCER1G | Hs.433300 | NM_004106 |

TABLE 7A-continued

Exemplary genes that predict patient
response to CTL019 therapy
Table 7A

| Gene | Unigene | Accession No. |
|---|---|---|
| FCER2 | Hs.465778 | NM_002002 |
| FCGBP | Hs.111732 | NM_003890, XM_001717543 |
| FCHO1 | Hs.96485 | NM_001161358, NM_001161357, NM_001161359, NM_015122 |
| FCRL3 | Hs.292449 | NM_052939 |
| FGD3 | Hs.411081 | NM_033086, NM_001083536 |
| FGF9 | Hs.111 | NM_002010 |
| FKBP4 | Hs.713721, Hs.524183 | NM_002014 |
| FLOT2 | Hs.514038 | NM_004475 |
| FLT3LG | Hs.428 | NM_001459 |
| FLVCR2 | Hs.615289, Hs.509966 | NM_017791 |
| FOSL1 | Hs.283565 | NM_005438 |
| FOSL2 | Hs.596972, Hs.220971 | NM_005253 |
| FRAT1 | Hs.126057 | NM_005479 |
| GAL3ST4 | Hs.44856 | NM_024637 |
| GALNT4 | Hs.713979, Hs.25130 | NM_003774 |
| GCLM | Hs.315562 | NM_002061 |
| GCNT1 | Hs.521568 | NM_001490, NM_001097633, NM_001097635, NM_001097634, NM_001097636 |
| GFOD1 | Hs.484686 | NM_018988 |
| GFPT1 | Hs.580300 | NM_002056 |
| GIPC3 | Hs.266873 | NM_133261 |
| GK | Hs.1466, Hs.654557 | NM_001128127, NM_000167, NM_203391 |
| GLRX2 | Hs.458283 | NM_016066, NM_197962 |
| GMEB2 | Hs.473286 | NM_012384 |
| GNAI1 | Hs.134587 | NM_002069 |
| GPA33 | Hs.651244 | NM_005814 |
| GPD1L | Hs.82432 | NM_015141 |
| GPKOW | Hs.503666 | NM_015698 |
| GPR125 | Hs.99195 | NM_145290 |
| GPR56 | Hs.513633 | NM_001145773, NM_001145774, NM_001145771, NM_001145772, NM_005682, NM_201525, NM_001145770, NM_201524 |
| GPSM3 | Hs.520046 | NM_022107 |
| GRAP | Hs.567416 | NM_006613 |
| GRASP | Hs.407202 | NM_181711 |
| GTF2A2 | Hs.512934 | NM_004492 |
| HAVCR1 | Hs.129711 | NM_001099414, NM_012206 |
| HBS1L | Hs.378532 | NM_001145207, NM_001145158, NM_006620 |
| HDAC9 | Hs.196054 | NM_014707, NM_178423, NM_178425, NM_058176, NM_058177 |
| HIGD1A | Hs.711098, Hs.593134, Hs.7917 | NM_014056, NM_001099669, NM_001099668 |
| HIP1 | Hs.329266, Hs.619089 | NM_005338 |
| HLA-DMA | Hs.351279 | NM_006120 |
| HLA-DPA1 | Hs.347270 | NM_033554 |
| HLA-DQA2 | Hs.591798 | NM_020056 |
| HLA-DQB2 | Hs.719990 | NM_001198858, NM_001300790 |
| HLA-DRA | Hs.520048 | NM_019111 |
| HLA-DRB1 | Hs.716081, Hs.696211, Hs.723344, Hs.534322 | NM_002124, NM_021983, XM_002346251 |
| HLA-DRB5 | Hs.534322 | NM_002125 |
| HLF | Hs.196952 | NM_002126 |
| HMOX1 | Hs.517581 | NM_002133 |
| HSPD1 | Hs.595053, Hs.723164 | NM_199440, NM_002156 |
| HSPE1 | Hs.1197 | NM_002157 |
| HYI | Hs.709864 | NM_031207 |
| ICAM3 | Hs.654563 | NM_002162 |
| IDUA | Hs.89560 | NM_000203 |
| IER2 | Hs.501629 | NM_004907 |
| IFNAR2 | Hs.708195 | NM_207584, NM_207585, NM_000874 |
| IFNG | Hs.856 | NM_207585 |
| IGF1R | Hs.643120, Hs.714012 | NM_000875 |
| IGSF3 | Hs.171057 | NM_001007237, NM_001542 |
| IGSF9B | Hs.204121 | NM_014987 |
| IKBIP | Hs.252543 | NM_201612, NM_201613, NM_153687 |
| IL10 | Hs.193717 | NM_000572 |
| IL11RA | Hs.591088 | NM_004512, NM_147162, NM_001142784 |
| IL13 | Hs.845 | NM_002188 |
| IL15RA | Hs.524117 | NM_002189, NM_172200 |
| IL1RAP | Hs.478673 | NM_134470, NM_001167930, NM_001167928, NM_001167929, NM_002182 |
| IL1RL1 | Hs.66 | NM_003856, NM_016232 |
| IL1RN | Hs.81134 | NM_000577, NM_173841, NM_173842, NM_173843 |
| IL21 | Hs.567559 | NM_021803 |
| IL2RA | Hs.231367 | NM_000417 |
| IL2RB | Hs.474787 | NM_000878 |
| IL3 | Hs.694 | NM_000588 |
| IL4 | Hs.73917 | NM_000589, NM_172348 |
| IL5 | Hs.2247 | NM_000879 |
| IL6ST | Hs.532082 | NM_002184, NM_175767 |
| IL9 | Hs.960 | NM_000590 |
| ING4 | Hs.524210 | NM_001127583, NM_001127582, NM_001127586, NM_001127585, NM_001127584, NM_016162 |
| INPP5A | Hs.523360, Hs.715308 | NM_005539 |
| INTS1 | Hs.532188 | NM_001080453 |
| IRF2BP2 | Hs.350268 | NM_001077397, NM_182972 |
| ISOC1 | Hs.483296 | NM_016048 |
| ITGA6 | Hs.133397 | NM_001079818, NM_000210 |
| ITPKB | Hs.528087, Hs.659396 | NM_002221 |
| ITPR3 | Hs.65758 | NM_002224 |
| JAKMIP1 | Hs.479066 | NM_144720, NM_001099433 |
| KAT8 | Hs.533803 | NM_032188, NM_182958 |
| KCNK5 | Hs.444448 | NM_003740 |
| KCTD12 | Hs.644125 | NM_138444 |
| KIAA0020 | Hs.493309 | NM_014878 |
| KIAA0141 | Hs.210532 | NM_014773, NM_001142603 |
| KIAA0664L3 | Hs.715792 | |
| KIAA0748 | Hs.33187 | NM_001098815, NM_001136030 |
| KIAA1257 | Hs.518247 | NM_020741 |
| KIAA1279 | Hs.279580 | NM_015634 |
| KIAA1683 | Hs.313471 | NM_025249, NM_001145305, NM_001145304 |
| KIAA1797 | Hs.136247 | NM_017794 |
| KIF3A | Hs.43670 | NM_007054 |
| KIT | Hs.479754 | NM_001093772, NM_000222, XM_001724747, XM_936229 |
| KLF2 | Hs.107740 | NM_016270 |
| KLF3 | Hs.298658 | NM_016531 |
| KPNA3 | Hs.527919 | NM_002267 |
| KRT72 | Hs.662013 | NM_080747, NM_001146226, NM_001146225 |
| KRT73 | Hs.55410 | NM_175068 |
| LAIR1 | Hs.572535 | NM_002287, NM_021706 |
| LARP4 | Hs.26613 | NM_199188, NM_199190, NM_052879, NM_001170808, NM_001170803, NM_001170804 |
| LDLRAP1 | Hs.590911 | NM_015627 |
| LEF1 | Hs.555947 | NM_001166119, NM_001130713, NM_001130714, NM_016269 |
| LGMN | Hs.18069 | NM_001008530, NM_005606 |
| LIMA1 | Hs.525419 | NM_001113547, NM_001113546, NM_0016357, NM_017806 |
| LIME1 | Hs.233220 | NM_017806 |
| LMBR1L | Hs.272838 | NM_018113 |
| LMNA | Hs.594444 | NM_005572, NM_170708, NM_170707 |
| LMO7 | Hs.207631 | NM_015842, NM_005358 |

TABLE 7A-continued

Exemplary genes that predict patient
response to CTL019 therapy
Table 7A

| Gene | Unigene | Accession No. |
|---|---|---|
| LOC100289511 | Hs.729250 | XM_002347442, XM_002343308, XM_002344795 |
| LOC100302650 | Hs.729719 | |
| LOC282997 | Hs.599931 | |
| LOC283174 | Hs.504370 | |
| LOC338799 | Hs.524804 | |
| LOC541471 | Hs.652166, Hs.652426, Hs.560805 | |
| LOC728392 | Hs.104305 | NM_001162371 |
| LRCH4 | Hs.719669, Hs.125742 | NM_002319 |
| LRP8 | Hs.576154 | NM_001018054, NM_004631, NM_0033300, NM_017522 |
| LRRN1 | Hs.163244 | NM_020873 |
| LSM14B | Hs.105379 | NM_144703 |
| LTA | Hs.36 | NM_001159740, NM_000595 |
| LTBP3 | Hs.289019 | NM_001130144, NM_001164266, NM_021070 |
| LYPD3 | Hs.631594 | NM_014400 |
| MAF | Hs.134859 | NM_005360, NM_001031804 |
| MAL | Hs.80395 | NM_022438, NM_022439, NM_0002371, NM_022440 |
| MAMLD1 | Hs.20136 | NM_005491 |
| MANF | Hs.436446 | NM_006010 |
| MAP2K6 | Hs.463978 | NM_002758 |
| MAP4K2 | Hs.534341 | NM_004579 |
| MARCKSL1 | Hs.75061 | NM_023009 |
| MCF2L | Hs.170422, Hs.597691 | NM_001112732, NM_024979 |
| MDS2 | Hs.523369 | |
| MED28 | Hs.434075, Hs.644788 | NM_025205 |
| MED6 | Hs.497353 | NM_005466 |
| MEGF6 | Hs.593645 | NM_001409 |
| MEOX1 | Hs.438 | NM_001040002, NM_013999, NM_004527 |
| MFGE8 | Hs.3745 | NM_005928, NM_001114614 |
| MINPP1 | Hs.121260 | NM_004897 |
| MIR1182 | | |
| MIR155 | | |
| MIR155HG | Hs.697120 | |
| MLXIP | Hs.721711, Hs.437153 | NM_014938 |
| MOB1A | Hs.602092 | NM_018221 |
| MPI | Hs.75694 | NM_002435 |
| MPRIP | Hs.462341, Hs.646854 | NM_201274, NM_015134 |
| MRPL13 | Hs.333823 | NM_014078 |
| MRPL22 | Hs.483924 | NM_014180, NM_001014990 |
| MRPL33 | Hs.515879 | NM_145330, NM_004891 |
| MRPL39 | Hs.420696 | NM_017446, NM_080794 |
| MRPL42 | Hs.199579 | NM_014050, NM_172177, NM_172178 |
| MRPS28 | Hs.521124 | NM_014018 |
| MSC | Hs.442619 | NM_005098 |
| MSL1 | Hs.532786 | NM_001012241 |
| MTCH2 | Hs.269944 | NM_014342 |
| MYADM | Hs.380906 | NM_001020819, NM_001020818, NM_001020821, NM_001020820, NM_138373 |
| MYCBP2 | Hs.591221 | NM_015057 |
| MYO15B | Hs.390817 | |
| MYOF | Hs.602086 | NM_013451, NM_133337 |
| MZF1 | Hs.399810 | NM_198055, NM_003422 |
| NAA50 | Hs.596074 | NM_025146 |
| NCKAP1 | Hs.603732 | NM_205842, NM_013436 |
| NDRG2 | Hs.525205 | NM_201540, NM_201541, NM_201539, NM_201538, NM_201537, NM_201536, NM_201535, NM_016250 |
| NDUFAB1 | Hs.189716 | NM_005003 |
| NDUFAF1 | Hs.106529 | NM_016013 |
| NDUFV2 | Hs.464572 | NM_021074 |
| NEDD9 | Hs.37982 | NM_182966, NM_001142393, NM_006403 |
| NEK7 | Hs.723303, Hs.24119 | NM_133494 |
| NELL2 | Hs.505326 | NM_006159, NM_001145110, NM_001145108, NM_001145109, NM_001145107 |
| NFATC1 | Hs.701518, Hs.534074 | NM_172388, NM_172387, NM_172389, NM_006162, NM_172390 |
| NIPA1 | Hs.511797 | NM_144599, NM_001142275 |
| NIPAL3 | Hs.523442 | NM_020448 |
| NLN | Hs.247460 | NM_020726 |
| NME1 | Hs.463456 | NM_198175, NM_001018138, NM_000269, NM_001018139, NM_002512, NM_001018137, NM_001018136 |
| NME1-NME2 | Hs.463456 | NM_198175, NM_001018138, NM_001018139, NM_001018137, NM_001018136, NM_000269, NM_002512 |
| NME7 | Hs.706952 | NM_013330, NM_197972 |
| NPEPPS | Hs.443837, Hs.449880 | NM_006310, XM_001725441, XM_001725426 |
| NQO1 | Hs.406515 | NM_001025434, NM_001025433, NM_000903 |
| NRCAM | Hs.21422 | NM_001037132, NM_001037133, NM_005010 |
| NSDHL | Hs.57698 | NM_015922, NM_001129765 |
| NSMAF | Hs.372000 | NM_003580, NM_001144772 |
| NT5DC3 | Hs.48428 | NM_001031701 |
| NUBP1 | Hs.81469 | NM_002484 |
| NUCB2 | Hs.654599 | NM_005013 |
| NUMA1 | Hs.325978 | NM_006185 |
| NUP153 | Hs.601591, Hs.718703 | NM_005124 |
| OASL | Hs.118633 | NM_198213, NM_003733 |
| ODC1 | Hs.467701 | NM_002539 |
| OLFM2 | Hs.169743 | NM_058164 |
| OSBPL7 | Hs.463320 | NM_145798 |
| OTUD7B | Hs.98322 | NM_020205 |
| P2RY8 | Hs.111377 | NM_178129 |
| P4HA2 | Hs.519568 | NM_001017974, NM_001017973, NM_001142598, NM_001142599, NM_004199 |
| PAM | Hs.369430 | NM_138766, NM_000919, NM_138822, NM_138821 |
| PAN2 | Hs.273397 | NM_014871, NM_001166279, NM_001127460 |
| PANX2 | Hs.440092 | NM_001160300, NM_052839 |
| PAPD7 | Hs.481542 | NM_006999, NM_001171806, NM_001171805 |
| PARK7 | Hs.419640 | NM_007262, NM_001123377 |
| PBX4 | Hs.466257 | NM_025245 |
| PCIF1 | Hs.716563 | NM_022104 |
| PCSK5 | Hs.368542 | NM_006200 |
| PDE4A | Hs.89901 | NM_001111308, NM_006202, NM_001111307, NM_001111309 |
| PDIA6 | Hs.212102 | NM_005742 |
| PDK1 | Hs.470633 | NM_002610 |
| PEA15 | Hs.517216 | NM_003768 |
| PFKM | Hs.75160 | NM_001166688, NM_001166686, NM_001166687, NM_000289 |
| PGAM1 | Hs.592599, Hs.632918 | NM_002629 |
| PGAM2 | Hs.632642 | NM_000290 |
| PGAM4 | Hs.632822 | NM_001029891 |
| PHKA2 | Hs.54941 | NM_000292 |
| PHLPP1 | Hs.465337 | NM_194449 |
| PHLPP2 | Hs.709458 | NM_015020 |
| PICALM | Hs.163893 | NM_001008660, NM_007166 |
| PIK3R5 | Hs.278901 | NM_001142633, NM_014308 |
| PIP4K2A | Hs.57079 | NM_005028 |
| PITPNM2 | Hs.272759 | NM_020845 |
| PLAA | Hs.27182 | NM_001031689 |
| PLCG1 | Hs.268177 | NM_182811, NM_002660 |
| PLCH2 | Hs.170156 | NM_014638 |

TABLE 7A-continued

Exemplary genes that predict patient response to CTL019 therapy
Table 7A

| Gene | Unigene | Accession No. |
|---|---|---|
| PNISR | Hs.520287, Hs.644863 | NM_015491, NM_032870, |
| POMP | Hs.268742 | NM_015932 |
| PPFIBP2 | Hs.655714 | NM_003621 |
| PPIL1 | Hs.27693 | NM_016059 |
| PPP2R1B | Hs.584790 | NM_002716, NM_181699 |
| PPP2R2B | Hs.655213 | NM_181676, NM_181675, NM_181674, NM_181678, NM_181677, NM_004576, NM_001127381 |
| PPP6R2 | Hs.449098, Hs.733531, Hs.740776 | NM_001242898, NM_001242899, NM_001242900, NM_014678 |
| PPPDE2 | Hs.570455 | NM_015704 |
| PRDM1 | Hs.436023 | NM_182907, NM_001198 |
| PRDX4 | Hs.83383 | NM_006406 |
| PREP | Hs.436564 | NM_002726 |
| PRKAR1B | Hs.520851 | NM_001164760, NM_002735, NM_001164758, NM_001164759, NM_001164762, NM_001164761 |
| PRKCZ | Hs.496255 | NM_001033581, NM_002744, NM_001033582 |
| PRR5 | Hs.720401, Hs.102336 | NM_001017530, NM_181333, NM_181334, NM_181335, NM_015366, NM_001017526, NM_001017529, NM_001017528 |
| PRSS23 | Hs.25338 | NM_007173 |
| PSMA1 | Hs.102798 | NM_001143937, NM_148976, NM_002786 |
| PSMB1 | Hs.352768 | NM_002793 |
| PSMC2 | Hs.437366 | NM_002803 |
| PSMD1 | Hs.3887 | NM_002807 |
| PSMD11 | Hs.655396 | NM_002815 |
| PSMD14 | Hs.567410 | NM_005805 |
| PSMD5 | Hs.193725 | NM_005047 |
| PTP4A3 | Hs.43666 | NM_007079, NM_032611 |
| PTPLA | Hs.114062 | NM_014241 |
| PTPN6 | Hs.63489 | NM_002831, NM_080548, NM_080549 |
| PTRH2 | Hs.12677 | NM_016077 |
| PUS7 | Hs.520619 | NM_019042 |
| PYCARD | Hs.499094 | NM_145182, NM_013258 |
| R3HDM2 | Hs.443673 | NM_014925 |
| RAB1A | Hs.310645 | NM_004161, NM_015543 |
| RAB21 | Hs.524590 | NM_014999 |
| RAB23 | Hs.555016 | NM_016277, NM_183227 |
| RAB33A | Hs.654356 | NM_004794 |
| RAB37 | Hs.351413 | NM_001163990, NM_001163989, NM_175738, NM_001006638 |
| RAB43 | Hs.546542, Hs.723723 | NM_001723593, XM_001720383, XM_001724346, NM_198490, XM_002342369 |
| RABGGTB | Hs.78948 | NM_004582 |
| RAD50 | Hs.655835 | NM_133482, NM_005732 |
| RAPGEF6 | Hs.483329 | NM_001164386, NM_001164387, NM_001164388, NM_001164389, NM_001164390, NM_016340 |
| RASA3 | Hs.593075 | NM_007368 |
| RASGRP2 | Hs.99491 | NM_153819, NM_001098670, NM_001098671 |
| RBBP8 | Hs.546282 | NM_002894, NM_203292, NM_203291 |
| RBKS | Hs.11916 | NM_022128 |
| REEP5 | Hs.429608 | NM_005669 |
| RGS1 | Hs.75256 | NM_002922 |
| RGS14 | Hs.9347 | NM_006480 |
| RHOT2 | Hs.513242 | NM_138769 |
| RNF19A | Hs.292882 | NM_015435, NM_183419 |
| RNF213 | Hs.195642 | NM_020914, NM_020954, NM_002343588 |
| RNF34 | Hs.292804 | NM_194271, NM_025126 |
| RPF2 | Hs.372265 | NM_032194 |
| RPP25 | Hs.8562 | NM_017793 |
| RYBP | Hs.7910 | NM_012234 |
| S1PR1 | Hs.154210 | NM_001400 |
| S1PR4 | Hs.662006 | NM_003775 |
| SCML4 | Hs.486109 | NM_198081 |
| SDHB | Hs.465924 | NM_003000 |
| SDK2 | Hs.435719 | NM_001144952 |
| SEC24D | Hs.189641 | NM_014822 |
| SEC31B | Hs.18889 | NM_015490 |
| SELL | Hs.728756 | NM_000655 |
| SELP | Hs.73800 | NM_003005 |
| SEPT11 | Hs.128199 | NM_018243 |
| SEPT3 | Hs.120483 | NM_019106, NM_145733 |
| SEPT9 | Hs.440932 | NM_001113491, NM_001113492, NM_001113493, NM_001113494, NM_001113495, NM_001113496, NM_001293695, NM_001293696, NM_001293697, NM_001293698, NM_006640, |
| SERPINF1 | Hs.532768 | NM_002615 |
| SERPINF2 | Hs.159509 | NM_001165920, NM_001165921, NM_000934 |
| SF1 | Hs.502829 | NM_004630, NM_201995, NM_201997, NM_201998 |
| SFXN1 | Hs.369440 | NM_022754 |
| SH2B1 | Hs.723196 | NM_001145797, NM_015503, NM_001145795, NM_001145796, NM_001145812 |
| SHC1 | Hs.433795 | NM_001130040, NM_003029, NM_001130041, NM_183001 |
| SIGIRR | Hs.501624 | NM_021805, NM_001135054, NM_001135053 |
| SIRPG | Hs.590883 | NM_080816, NM_018556, NM_001039508 |
| SLC16A1 | Hs.75231 | NM_001166496, NM_003051 |
| SLC16A10 | Hs.591327 | NM_018593 |
| SLC1A4 | Hs.654352 | NM_003038, NM_001135581 |
| SLC24A6 | Hs.286194 | NM_024959 |
| SLC25A17 | Hs.474938 | NM_006358 |
| SLC25A32 | Hs.607819 | NM_030780 |
| SLC26A11 | Hs.4866 | NM_173626, NM_001166348, NM_001166347, NM_001166349 |
| SLC27A2 | Hs.720807 | NM_003645, NM_001159629 |
| SLC2A1 | Hs.473721 | NM_006516 |
| SLC2A4RG | Hs.435126 | NM_020062 |
| SLC2A8 | Hs.179522 | NM_014580 |
| SLC35F2 | Hs.524014 | NM_017515 |
| SLC39A14 | Hs.491232 | NM_001128431, NM_015359, NM_001135153, NM_001135154 |
| SLC39A8 | Hs.288034 | NM_022154, NM_001135148, NM_001135147, NM_001135146 |
| SLC40A1 | Hs.643005 | NM_014585 |
| SLC43A3 | Hs.99962 | NM_199329, NM_017611, NM_014096 |
| SLIRP | Hs.655105 | NM_001267863, NM_001267864, NM_031210 |
| SNPH | Hs.713451, Hs.323833 | NM_014723, NM_001136566 |
| SNRK | Hs.476052 | NM_017719, NM_001100594 |
| SNRPG | Hs.631639, Hs.654528, Hs.516076, Hs.465167 | NM_003096, XM_002347904, NM_001146693, XM_002343626, XM_001723258 |
| SNX24 | Hs.483200 | NM_014035 |
| SOAT1 | Hs.496383 | NM_003101 |
| SORD | Hs.878, Hs.633539 | NM_003104 |
| SOX4 | Hs.643910 | NM_003107 |
| SP140L | Hs.662198 | NM_138402 |
| SPATS2L | Hs.120323 | NM_001100424, NM_001100423, NM_001100422, NM_015535 |
| SPG7 | Hs.185597 | NM_003119, NM_199367 |
| SPR | Hs.301540 | NM_003124 |
| SPSB3 | Hs.592080 | NM_080861 |
| SPTBN1 | Hs.503178, Hs.705692 | NM_003128, NM_178313 |
| SRGN | Hs.1908 | NM_002727 |
| SRSF5 | Hs.632326 | NM_001039465, NM_006925 |
| SRXN1 | Hs.719997, Hs.516830 | NM_080725 |

TABLE 7A-continued

Exemplary genes that predict patient response to CTL019 therapy
Table 7A

| Gene | Unigene | Accession No. |
|---|---|---|
| SSH1 | Hs.199763 | NM_001161331, NM_001161330, NM_018984 |
| ST8SIA4 | Hs.308628 | NM_175052, NM_005668 |
| STAC | Hs.56045 | NM_003149 |
| STAT6 | Hs.524518 | NM_003153 |
| STIP1 | Hs.337295 | NM_006819 |
| STMN3 | Hs.639609 | NM_015894 |
| STRAP | Hs.504895 | NM_007178 |
| STT3A | Hs.504237 | NM_152713 |
| STX16 | Hs.307913 | NM_001134772, NM_001134773, NM_003763, NM_001001433 |
| SULT1B1 | Hs.129742 | NM_014465 |
| SUN1 | Hs.438072 | NM_001171944, NM_001171946, NM_001171945, NM_001130965, NM_025154 |
| SUN2 | Hs.517622 | NM_015374 |
| SVIL | Hs.499209 | NM_003174, NM_021738 |
| SYT11 | Hs.32984 | NM_152280 |
| SYTL1 | Hs.469175 | NM_032872 |
| SYTL3 | Hs.436977 | NM_001009991 |
| TACC3 | Hs.104019 | NM_006342 |
| TANK | Hs.132257 | NM_004180, NM_133484 |
| TBCC | Hs.75064 | NM_003192 |
| TBX21 | Hs.272409 | NM_013351 |
| TCEA3 | Hs.446354 | NM_003196 |
| TCF20 | Hs.475018 | NM_181492, NM_005650 |
| TCF7 | Hs.573153 | NM_201633, NM_201632, NM_001134851, NM_001134852, NM_213648, NM_003202, NM_201634 |
| TFRC | Hs.529618 | NM_001128148, NM_003234 |
| THNSL1 | Hs.645274 | NM_024838 |
| TIGIT | Hs.421750 | NM_173799 |
| TIMD4 | Hs.334907 | NM_001146726, NM_138379 |
| TJP3 | Hs.25527 | NM_014428 |
| TMC6 | Hs.632227 | NM_001127198, NM_007267 |
| TMC8 | Hs.592102 | NM_152468 |
| TMCC2 | Hs.6360 | NM_014858 |
| TMED2 | Hs.75914, Hs.592682 | NM_006815 |
| TMEM110 | Hs.556077, Hs.705605 | NM_198563, NM_205853 |
| TMEM123 | Hs.503709 | NM_052932 |
| TMEM165 | Hs.479766 | NM_018475 |
| TMEM220 | Hs.462230 | NM_001004313 |
| TMEM33 | Hs.31082 | NM_018126 |
| TMEM63A | Hs.119387 | NM_014698 |
| TMEM66 | Hs.521487 | NM_016127 |
| TMEM70 | Hs.106650 | NM_017866, NM_001040613 |
| TMEM71 | Hs.293842 | NM_144649, NM_001145153 |
| TMIGD2 | Hs.263928 | NM_001169126, NM_144615 |
| TNFRSF11A | Hs.204044 | NM_003839 |
| TNFRSF1B | Hs.256278 | NM_001066 |
| TNFRSF8 | Hs.1314 | NM_152942, NM_001243 |
| TNFRSF9 | Hs.654459 | NM_001561 |
| TNNT3 | Hs.73454 | NM_006757, NM_001042782, NM_001042780, NM_001042781 |
| TOP2B | Hs.475733 | NM_001068 |
| TPM2 | Hs.300772 | NM_213674, NM_003289, NM_001145822 |
| TRAPPC6A | Hs.466929 | NM_024108 |
| TRIB2 | Hs.627749, Hs.467751 | NM_021643 |
| TRIM22 | Hs.501778, Hs.684559 | NM_006074 |
| TRIP12 | Hs.591633 | NM_004238 |
| TRMT5 | Hs.380159 | NM_020810 |
| TSC2 | Hs.90303 | NM_001077183, NM_001114382, NM_000548 |
| TSPAN18 | Hs.592575, Hs.385634 | NM_001031730, NM_130783 |
| TSPAN32 | Hs.271954 | NM_139022 |
| TTC4 | Hs.720251 | NM_004623 |
| TTC9 | Hs.79170 | NM_015351 |
| TTN | Hs.134602 | NM_133432, NM_133379, NM_133378, NM_133437, NM_003319 |
| TWIST1 | Hs.66744 | NM_000474 |
| TXK | Hs.479669 | NM_003328 |
| TXN | Hs.435136 | NM_003329 |
| TXNDC5 | Hs.719272, Hs.150837 | NM_001145549, NM_201280, NM_030810 |
| UBASH3B | Hs.444075 | NM_032873 |
| UBE2E2 | Hs.595802, Hs.475688 | NM_152653 |
| UBE2Z | Hs.514297 | NM_023079 |
| UCHL3 | Hs.162241 | NM_006002 |
| UCK2 | Hs.458360 | NM_012474 |
| UHRF1BP1L | Hs.620701 | NM_001006947, NM_015054 |
| USP19 | Hs.255596 | NM_006677 |
| USP53 | Hs.595368, Hs.431081 | NM_019050 |
| UXS1 | Hs.469561 | NM_025076 |
| UXT | Hs.172791 | NM_004182, NM_153477 |
| VDR | Hs.524368 | NM_001017535, NM_000376 |
| VILL | Hs.103665 | NM_015873 |
| VIPR1 | Hs.348500 | NM_004624 |
| VSIG1 | Hs.177164 | NM_001170553, NM_182607 |
| VTRNA1-3 | | |
| WDR12 | Hs.73291 | NM_018256 |
| WNT7A | Hs.72290 | NM_004625 |
| WRB | Hs.198308 | NM_001146218, NM_004627 |
| XAF1 | Hs.441975 | NM_017523, NM_199139 |
| YPEL3 | Hs.513491 | NM_031477, NM_001145524 |
| YWHAE | Hs.591239, Hs.513851 | NM_006761 |
| YWHAG | Hs.520974 | NM_012479 |
| ZBTB22 | Hs.206770 | NM_005453, NM_001145338 |
| ZBTB38 | Hs.723156 | NM_001080412 |
| ZC3H12C | Hs.376289 | NM_033390 |
| ZDHHC16 | Hs.76662 | NM_032327, NM_198046, NM_198045, NM_198044, NM_198043 |
| ZFP36L2 | Hs.503093 | NM_006887 |
| ZGPAT | Hs.590868 | NM_181485, NM_001083113, NM_032527 |
| ZMAT1 | Hs.496512 | NM_032441, NM_001011657 |
| ZNF193 | Hs.100921 | NM_006299 |
| ZNF238 | Hs.69997 | NM_205768, NM_006352 |
| ZNF282 | Hs.657701 | NM_003575 |
| ZNF331 | Hs.185674 | NM_018555, NM_001079907, NM_001079906 |
| ZNF506 | Hs.351906 | NM_001145404, NM_001099269 |
| ZNF542 | Hs.467326 | |
| ZNF673 | Hs.632800 | NM_017776, NM_001129900, NM_001129898, NM_001129899 |
| ZNF688 | Hs.301463, Hs.513509 | NM_152458, NM_145271, NM_001024683 |
| ZNF710 | Hs.459311 | NM_198526 |
| ZNF83 | Hs.710125, Hs.665751, Hs.467210, Hs.659798 | NM_018300, NM_001105550, NM_001105552, NM_001105551, NM_001105554, NM_001105553, NM_001105549 |
| ZSWIM1 | Hs.517075 | NM_080603 |

The most significant genes in Table 7A were defined as those with 1) an absolute fold change between ALL CRs/CLL CRs and CLL NRs of greater than 2 and 2) a p-value on the correlation of response and expression of less than 0.01. Thirty-four genes, listed in Table 7B below, met this criteria and the expression of these genes were measured on four additional platforms to compare and validate the findings from RNAseq. The four platforms were OpenArray, Fluidigm, Nanostring, and qPCR. Results from this cross-platform comparison experiment confirmed the results and conclusions described herein. Table 7B also indicates whether each gene is upregulated in complete responders (CR) relative to non-responders, or upregulated in non-responders (NR) relative to complete responders. An exemplary publication disclosing the sequence of each gene is also given in Table 7B, and each publication is incorporated by reference in its entirety, including all nucleic acid and protein sequences therein.

TABLE 7B

Selected genes from Table 7A
Table 7B

| Gene | Unigene | Accession No. | Exemplary publication | Upregulated in CR or NR |
|---|---|---|---|---|
| ALS2CL | Hs.517937 | NM_147129, NM_182775 | Jouan et al., Behav Brain Funct 9, 9 (2013) | CR |
| AQP3 | Hs.234642 | NM_004925 | Xie et al., Arch. Dermatol. Res. 305 (5), 397-406 (2013) | CR |
| C16orf74 | Hs.461655 | NM_206967 | Kim et al., PLoS ONE 5 (12), E15260 (2010) | CR |
| CCL17 | Hs.546294 | NM_002987 | Lee et al, Pediatr. Res. 74 (5), 545-551 (2013) | NR |
| CD248 | Hs.195727 | NM_020404 | Kontsekova et al., Int. J. Oncol. 41 (4), 1365-1372 (2012) | CR |
| CSF2 | Hs.1349 | NM_000758 | Sawada et al., J. Exp. Med. 211 (2), 263-280 (February 2014) | NR |
| DHRS2 | Hs.272499 | NM_182908, NM_005794 | Prunotto et al., J Proteomics 82, 193-229 (2013) | NR |
| DPEP2 | Hs.372633 | NM_022355 | Willer et al., Nat. Genet. 40 (2), 161-169 (2008) | CR |
| EPAS1 | Hs.468410 | NM_001430 | Mathew et al., Proc. Natl. Acad. Sci. U.S.A. 111 (1), 291-296 (January 2014) | NR |
| EPHA4 | Hs.371218 | NM_004438 | Xu et al., Proc. Natl. Acad. Sci. U.S.A. 110 (36), 14634-14639 (2013) | CR |
| FAIM3 | Hs.723317, Hs.58831 | NM_001142472, NM_001142473, NM_005449 | Murakami et al., J. Immunol. 189 (2), 587-597 (2012) | CR |
| FAM134B | Hs.711125 | NM_001034850, NM_019000 | Murphy et al., J. Neurol. Neurosurg. Psychiatr. 83 (1), 119-120 (2012) | CR |
| GPA33 | Hs.651244 | NM_005814 | Deng et al. PLoS ONE 8 (11), E79629 (2013) | CR |
| IL13 | Hs.845 | NM_002188 | Jiang et al., Am. J. Physiol. Endocrinol. Metab. 305 (11), E1359-E1366 (2013) | NR |
| IL3 | Hs.694 | NM_000588 | Miyake et al., Cytokine 64 (1), 86-89 (2013) | NR |
| IL9 | Hs.960 | NM_000590 | Jabeen et al., J. Clin. Invest. 123 (11), 4641-4653 (2013) | NR |
| KRT72 | Hs.662013 | NM_080747, NM_001146226, NM_001146225 | Principe et al., Proteomics 13 (10-11), 1667-1671 (2013) | CR |
| KRT73 | Hs.55410 | NM_175068 | De Mateo et al., Proteomics 11 (13), 2714-2726 (2011) | CR |
| LTA | Hs.36 | NM_001159740, NM_000595 | Stuart et al., Twin Res Hum Genet 16 (6), 1079-1086 (2013) | NR |
| MCF2L | Hs.170422, Hs.597691 | NM_001112732, NM_024979 | Valdes et al., Ann. Rheum. Dis. 71(9), 1537-1540 (2012) | CR |
| MDS2 | Hs.523369 | | Meyer et al., PLoS Genet. 6 (8) (2010) | CR |
| MEGF6 | Hs.593645 | NM_001409 | Nakayama et al. Genomics 51 (1), 27-34 (1998) | CR |
| MIR155 | | | Weber et al., FEBS J. 272 (1), 59-73 (2005) | NR |
| PPFIBP2 | Hs.655714 | NM_003621 | Bohm et al., Oncol. Rep. 28 (2), 429-438 (2012) | CR |
| SCML4 | Hs.486109 | NM_198081 | Vieira et al., Genet. Med. 10 (9), 668-674 (2008) | CR |
| SDK2 | Hs.435719 | NM_001144952 | Otowa et al., J. Hum. Genet. 54 (2), 122-126 (2009) | CR |
| SPR | Hs.301540 | NM_003124 | Yang et al., J. Biol. Chem. 288 (26), 19221-19237 (2013) | NR |
| SULT1B1 | Hs.129742 | NM_014465 | Ross et al., Nat. Genet. 41 (12), 1345-1349 (2009) | CR |
| TCF7 | Hs.573153 | NM_201633, NM_201632, NM_001134851, NM_001134852, NM_213648, | Nikuseva-Martic et al., Pathol. Oncol. Res. 19 (3), 545-551 (2013) | CR |

TABLE 7B-continued

Selected genes from Table 7A
Table 7B

| Gene | Unigene | Accession No. | Exemplary publication | Upregulated in CR or NR |
|---|---|---|---|---|
| TNFRSF8 | Hs.1314 | NM_003202, NM_201634, NM_152942, NM_001243 | Yao et al., Am. J. Surg. Pathol. 37 (9), 1407-1412 (2013) | NR |
| TSPAN18 | Hs.592575, Hs.385634 | NM_001031730, NM_130783 | Yuan et al., PLoS ONE 8 (3), E58785 (2013) | CR |
| TWIST1 | Hs.66744 | NM_000474 | Zhou et al., J. Exp. Clin. Cancer Res. 33, 12 (January 2014) | NR |
| VIPR1 | Hs.348500 | NM_004624 | Bono et al., Cancer Cell 23 (4), 477-488 (2013) | CR |
| VSIG1 | Hs.177164 | NM_001170553, NM_182607 | Chen et al., J Surg Oncol 106 (3), 286-293 (2012) | CR |

Cell surface markers differentiating memory T cell subsets that are described in Maus et al. (ANNU. REV. IMMUNOL. 2014) and were not included in the Gattinoni gene sets were also evaluated. Among other things, KLRG1 was identified as a gene whose expression increases in apheresis samples from ALL→CLL CR→CLL PR→CLL NR. KLRG1 expression values predict patient response to CTL019 therapy. At least CD57, CD27, CD122, and CD62L were identified as biomarkers of response in the product samples. Among other things CD57, CD27, CD122, and CD62L expression values predict patient response to CTL019 therapy.

In an embodiment, a complete responder (CR) gene signature comprises one or more biomarker profiles described in Table 9.

TABLE 9

Exemplary biomarker profile of a complete responder to CAR19 therapy
Table 9: Exemplary biomarker profile of a complete responder to CAR19 therapy

| CD27+ | PD1− |
|---|---|
| CD8+ | LAG3− |
| | TIM3− |
| | KLRG1− |

Exemplary CR cell-types

Resting T effector cells ($T_{EM}$)
Resting $T_{REG}$
Naïve CD4+
Unstimulated memory T cells ($T_{SCM}$)
Early memory T cells In an embodiment, a non-responder (NR) gene signature comprises one or more biomarker profiles described in Table 10.

TABLE 10

Exemplary biomarker profile of a non-responder to CAR19 therapy
Table 10: Exemplary biomarker profile of a non-responder to CAR19 therapy

| PD1+ | CD27− |
|---|---|
| LAG3+ | |
| TIM3+ | |
| KLRG1+ | |

Exemplary NR cell-types

Activated T effector cells ($T_{EM}$)
Activated $T_{REG}$
Activated $T_{H1}$
Resting $T_{H2}$
Stimulated memory T cells ($T_{SCM}$)
Late memory T cells Based on the biological understanding, combinations of genes from unbiased feature selection, gene sets, and selected genes of interest could be used to further differentiate NR's, PR's, and CR's.

The previously described work was expanded upon in a study of 35 CLL subject samples. This group of 35 subjects includes the 21 CLL subjects in the previous study, for a total of 5 CRs, 9 PRs, and 21 NRs. In this study manufactured CD19 CAR-expressing cell product samples were collected and cultured overnight with control beads. Novel gene signatures based on mRNA expression levels have been identified that predict patient response. The gene lists for the CR vs NR comparison (N=185) is tabulated in Table 18.

TABLE 18

Gene lists for the CR vs NR comparison

| Gene | Unigene | Accession No. | FDR |
|---|---|---|---|
| ABCB1 | Hs.489033 | NM_000927 | 0.0492 |
| ACSL1 | Hs.406678 | NM_001995, NM_001286711, NM_001286708, NM_001286710, NM_001286712 | 0.0362 |
| ADAM12 | | NM_003474, NM_001288973, NM_021641, NM_001288974, NM_001288975 | 0.0089 |
| ADAM23 | | NM_003812 | 0.0185 |
| ADCY1 | Hs.192215 | NM_001281768, NM_021116 | 0.0203 |
| AFAP1 | Hs.529369 | NM_198595, NM_001134647 | 0.0884 |
| AGRN | Hs.273330 | NM_198576, NM_001305275 | 0.0212 |

TABLE 18-continued

Gene lists for the CR vs NR comparison

| Gene | Unigene | Accession No. | FDR |
|---|---|---|---|
| ANKRD33B | Hs.26039 | NM_001164440 | 0.0097 |
| APLP2 | Hs.370247 | NM_001142277, NM_001642, NM_001142278, NM_001142276, NM_001243299 | 0.0429 |
| AQPEP | | | 0.0615 |
| ARHGAP32 | Hs.440379 | NM_001142685, NM_014715 | 0.0675 |
| ART3 | Hs.731997 | NM_001130017, NM_001130016, NM_001130016, NM_001179 | 0.0890 |
| ATN1 | Hs.143766 | NM_001007026, NM_001940 | 0.0675 |
| ATP9A | Hs.649234 | NM_006045 | 0.0029 |
| B4GALNT1 | Hs.159481 | NM_001478, NM_001276468, NM_001276469 | 0.0104 |
| B4GALT6 | | NM_004775 | 0.0965 |
| C1orf198 | Hs.520494 | NM_032800, NM_001136494, NM_001136495 | 0.0047 |
| C21orf63 | | | 0.0029 |
| C5orf39 | | | 0.0047 |
| C9orf142 | | NM_183241 | 0.0870 |
| CACNB2 | Hs.59093 | NM_201596, NM_201593, NM_201597, NM_201571, NM_001167945, NM_201572, NM_000724, NM_201590, NM_201570 | 0.0615 |
| CAMK2G | | NM_001222, NM_172173, NM_172169, NM_172170, NM_001204492, NM_172171 | 0.0675 |
| CAMSAP2 | Hs.23585 | NM_203459, NM_001297708, NM_001297707 | 0.0797 |
| CCDC74A | Hs.351461 | NM_138770, NM_001258304, NM_001258306, NM_001258305 | 0.0492 |
| CCL22 | Hs.534347 | NM_002990 | 0.0666 |
| CCL5 | | NM_002985, NM_001278736 | 0.0615 |
| CD109 | Hs.399891 | NM_133493, NM_001159588, NM_001159587 | 0.0423 |
| CD200 | | NM_001004196, NM_005944 | 0.0299 |
| CD27 | Hs.355307 | NM_001242 | 0.0225 |
| CD52 | | NM_001803 | 0.0172 |
| CDKN1A | Hs.370771 | NM_000389, NM_001220778, NM_001220777, NM_078467 | 0.0450 |
| CERS6 | Hs.743222 | NM_203463, NM_001256126 | 0.0384 |
| CHST2 | Hs.8786 | NM_004267 | 0.0063 |
| CNTNAP2 | Hs.655684 | NM_014141 | 0.0872 |
| CPA5 | Hs.567642 | NM_001127442, NM_080385, NM_001127441 | 0.0433 |
| CPM | Hs.654387 | NM_001005502, NM_198320, NM_001874, NM_001005502, NM_198320, NM_001874 | 0.0466 |
| CR1 | | NM_000573, NM_000651 | 0.0891 |
| CTNNA1 | Hs.445981, Hs.740112 | NM_001903, NM_001290310, NM_001290309, NM_001290307, NM_001290312 | 0.0148 |
| CXCL9 | Hs.77367 | NM_002416 | 0.0299 |
| CXCR5 | | NM_001716 | 0.0939 |
| DBN1 | | NM_004395, NM_080881 | 0.0492 |
| DEPDC7 | Hs.280990 | NM_001077242, NM_139160 | 0.0256 |
| DIRC3 | | | 0.0890 |
| DLG2 | Hs.367656 | NM_001364, NM_001142702, NM_001142699, NM_001142700, NM_001300983, NM_001206769 | 0.0085 |
| DNAJC12 | Hs.260720 | NM_021800, NM_201262 | 0.0891 |
| DRAM1 | Hs.525634 | NM_018370 | 0.0376 |
| DSG2 | Hs.412597 | NM_001943 | 0.0384 |
| DUSP4 | | NM_001394, NM_057158 | 0.0148 |
| EBI3 | | NM_005755 | 0.0063 |
| EEF1A2 | Hs.433839 | NM_001958 | 0.0497 |
| EEF1DP3 | | | 0.0939 |
| EHD4 | | NM_139265 | 0.0415 |
| EMP1 | | NM_001423 | 0.0541 |
| ENPP2 | Hs.190977 | NM_006209, NM_001130863, NM_001040092 | 0.0870 |
| EPAS1 | Hs.468410 | NM_001430 | 0.0149 |
| ERP29 | | NM_006817, NM_001034025 | 0.0615 |
| EVC | Hs.646899 | NM_001306090, NM_153717, NM_001306092 | 0.0666 |
| EVI5 | Hs.594434 | NM_005665, NM_001308248 | 0.0373 |
| FADS2 | | NM_001281501, NM_001281502, NM_004265 | 0.0764 |
| FAM134B | Hs.481704 | NM_019000, NM_001034850 | 0.0452 |
| FAM40B | | | 0.0148 |
| FAM65C | Hs.372578 | NM_001290268, NM_080829 | 0.0615 |
| FASN | Hs.83190 | NM_004104 | 0.0884 |
| FKBP11 | | NM_001143781, NM_016594, NM_001143782 | 0.0407 |
| FLT1 | Hs.594454 | NM_002019, NM_001160030, NM_001159920, NM_001160031 | 0.0699 |
| FLT3LG | | NM_001204502, NM_001459, NM_001278637, NM_001278638, NM_001204503 | 0.0408 |
| FOXP1 | | NM_032682, NM_001244816, NM_001244815, NM_001244814, NM_001244808, NM_001244812, NM_001012505, NM_001244813, NM_001244810 | 0.0615 |
| FSCN1 | Hs.118400 | NM_003088 | 0.0694 |
| GAS8 | Hs.431792, Hs.739124 | NM_001481, NM_001286209, NM_001286205, NM_001286208 | 0.0811 |

TABLE 18-continued

Gene lists for the CR vs NR comparison

| Gene | Unigene | Accession No. | FDR |
|---|---|---|---|
| GEM | Hs.654463 | NM_181702, NM_005261 | 0.0275 |
| GNA12 | Hs.487341 | NM_007353, NM_001282441, NM_001282440 | 0.0360 |
| GPR56 | | | 0.0122 |
| GZMA | | NM_006144 | 0.0805 |
| HCST | | NM_014266, NM_001007469 | 0.0212 |
| HDC | Hs.1481 | NM_002112, NM_001306146 | 0.0890 |
| HSH2D | Hs.631617 | NM_032855 | 0.0243 |
| IL1A | | NM_000575 | 0.0148 |
| IL1RN | | NM_173843, NM_173841, NM_000577, NM_173842 | 0.0615 |
| IL26 | Hs.272350 | NM_018402 | 0.0718 |
| ILDR2 | Hs.133153, Hs.730291 | NM_199351 | 0.0860 |
| KLRB1 | Hs.169824 | NM_002258 | 0.0074 |
| KLRC3 | Hs.654362 | NM_002261, NM_007333 | 0.0035 |
| LHFP | Hs.507798 | NM_005780 | 0.0053 |
| LIFR | Hs.133421, Hs.616721 | NM_002310, NM_001127671 | 0.0362 |
| LINC00476 | | | 0.0299 |
| LMCD1 | | NM_014583, NM_001278235, NM_001278233, NM_001278234 | 0.0423 |
| LMNA | Hs.594444 | NM_001282625, NM_005572, NM_170707, NM_001282626, NM_001257374, NM_001282624, NM_170708 | 0.0677 |
| LOC347411 | | | 0.0407 |
| LOC619207 | | | 0.0407 |
| LRIG3 | | NM_001136051, NM_153377 | 0.0746 |
| LRP1B | Hs.656461 | NM_018557 | 0.0615 |
| LRRC4C | Hs.745123 | NM_001258419, NM_020929 | 0.0733 |
| LY9 | Hs.403857 | NM_001261456, NM_001261457, NM_002348, NM_001033667 | 0.0615 |
| MAST2 | Hs.319481 | NM_015112 | 0.0959 |
| MGAT4A | Hs.177576 | NM_001160154, NM_012214 | 0.0085 |
| MOB1B | Hs.691454 | NM_173468, NM_001244766 | 0.0441 |
| MRPL54 | | NM_172251 | 0.0910 |
| MYOF | Hs.602086 | NM_133337, NM_013451 | 0.0615 |
| NAB2 | Hs.159223 | NM_005967 | 0.0373 |
| NCDN | Hs.121870 | NM_001014841, NM_001014839, NM_014284 | 0.0876 |
| NCKAP1 | Hs.603732 | NM_013436, NM_205842 | 0.0299 |
| NCR3 | | NM_147130, NM_001145466, NM_001145467 | 0.0595 |
| NDUFA12 | Hs.674965 | NM_018838, NM_001258338 | 0.0936 |
| NEDD4L | Hs.185677 | NM_001243960, NM_001144967, NM_015277, NM_001144971, NM_001144968, NM_001144969, NM_001144970, NM_001144966, NM_001144964, NM_001144965 | 0.0333 |
| NEURL3 | Hs.149219 | NM_001285485, NM_001285486 | 0.0821 |
| NINL | Hs.631508 | NM_025176 | 0.0709 |
| NOSIP | Hs.7236 | NM_001270960, NM_015953 | 0.0001 |
| NRP2 | Hs.471200 | NM_201266, NM_201264, NM_201267, NM_003872, NM_018534, NM_201279 | 0.0926 |
| OSMR | Hs.120658 | NM_001168355, NM_003999 | 0.0432 |
| PANX2 | Hs.440092 | NM_001160300, NM_052839 | 0.0376 |
| PCBP3 | Hs.736936 | NM_020528, NM_001130141 | 0.0089 |
| PHKA1 | Hs.201379 | NM_002637, NM_001122670, NM_001172436 | 0.0130 |
| PITPNC1 | Hs.591185 | NM_181671, NM_012417 | 0.0373 |
| PLXNB2 | Hs.3989 | NM_012401 | 0.0148 |
| PLXNB3 | Hs.632833 | NM_005393, NM_001163257 | 0.0981 |
| PMCH | | NM_002674 | 0.0383 |
| POU2AF1 | Hs.654525, Hs.733573, Hs.739353 | NM_006235 | 0.0376 |
| PPARG | Hs.162646 | NM_138712, NM_005037, NM_138711, NM_015869 | 0.0821 |
| PPCDC | Hs.458922, Hs.640486 | NM_021823, NM_001301103, NM_001301101, NM_001301102, NM_001301104, NM_001301105 | 0.0224 |
| PRDM1 | Hs.436023 | NM_001198, NM_182907 | 0.0376 |
| PRKCDBP | | NM_145040 | 0.0615 |
| PRR5 | | NM_015366, NM_001198721, NM_181333, NM_001017528, NM_001017530, NM_001017529 | 0.0384 |
| PSEN2 | Hs.25363 | NM_000447, NM_012486 | 0.0299 |
| PTPN6 | Hs.63489 | NM_080548, NM_002831, NM_080549 | 0.0733 |
| PTPRCAP | | NM_005608 | 0.0521 |
| PTPRD | Hs.446083 | NM_002839, NM_130391, NM_001171025, NM_130393, NM_001040712, NM_130392 | 0.0141 |
| PVR | | NM_006505, NM_001135769, NM_001135768, NM_001135770 | 0.0149 |
| RABL3 | Hs.444360 | NM_173825 | 0.0733 |
| RBMY1E | | NM_001006118 | 0.0089 |

TABLE 18-continued

Gene lists for the CR vs NR comparison

| Gene | Unigene | Accession No. | FDR |
|---|---|---|---|
| RGL1 | Hs.497148 | NM_001297669, NM_015149, NM_001297670, NM_001297671, NM_001297672 | 0.0891 |
| RNASE4 | | NM_001282193, NM_001282192, NM_002937, NM_194431 | 0.0860 |
| RORC | Hs.256022 | NM_001001523, NM_005060 | 0.0027 |
| RPS28 | | NM_001031 | 0.0763 |
| S100A4 | | NM_019554, NM_002961 | 0.0047 |
| SCARB1 | | NM_001082959, NM_005505 | 0.0327 |
| SCD | Hs.558396 | NM_005063 | 0.0870 |
| SCML4 | | NM_001286408, NM_001286409, NM_198081 | 0.0860 |
| SDC1 | Hs.224607 | NM_002997, NM_001006946 | 0.0299 |
| SDK2 | Hs.435719 | NM_001144952 | 0.0981 |
| SEPT3 | Hs.120483 | NM_145733, NM_019106 | 0.0582 |
| SEPT5-GP1BB | | | 0.0107 |
| SGPP2 | Hs.591604 | NM_152386 | 0.0347 |
| SH2B2 | Hs.489448 | NM_020979 | 0.0373 |
| SH3TC1 | Hs.479116, Hs.630085 | NM_018986 | 0.0205 |
| SKAP1 | Hs.316931 | NM_003726, NM_001075099 | 0.0661 |
| SLC13A3 | Hs.655498 | NM_022829, NM_001193340, NM_001193339, NM_001193342, NM_001011554 | 0.0254 |
| SLC22A17 | Hs.373498 | NM_001289050, NM_016609, NM_020372 | 0.0944 |
| SLC27A2 | Hs.11729 | NM_003645, NM_001159629 | 0.0811 |
| SLC29A1 | Hs.25450 | NM_001304463, NM_001078175, NM_001078177, NM_001304465, NM_001304466, NM_001304462 | 0.0150 |
| SLC41A2 | | NM_032148 | 0.0936 |
| SLC43A3 | Hs.99962 | NM_014096, NM_001278201, NM_199329, NM_017611, NM_001278206 | 0.0423 |
| SLC4A10 | Hs.333958 | NM_022058, NM_001178015, NM_001178016 | 0.0376 |
| SOAT2 | Hs.656544 | NM_003578 | 0.0130 |
| SORCS3 | Hs.671950 | NM_014978 | 0.0876 |
| SPIRE1 | Hs.515283 | NM_001128626, NM_020148, NM_001128627 | 0.0615 |
| SPNS3 | | NM_182538 | 0.0001 |
| SPOCK1 | Hs.582184, Hs.596136 | NM_004598 | 0.0718 |
| SRCIN1 | Hs.448872 | NM_025248 | 0.0661 |
| SSBP3 | Hs.733025 | NM_145716, NM_001009955, NM_018070 | 0.0376 |
| STX8 | | NM_004853 | 0.0937 |
| SULT2B1 | Hs.369331 | NM_177973, NM_004605 | 0.0150 |
| TERT | Hs.492203 | NM_198253, NM_001193376, NM_005424 | 0.0765 |
| TIE1 | Hs.78824 | NM_005424, NM_001253357 | 0.0931 |
| TLE4 | | NM_007005, NM_001282760, NM_001282748, NM_001282749, NM_001282753 | 0.0891 |
| TMOD1 | Hs.404289 | NM_003275, NM_001166116 | 0.0308 |
| TNFRSF19 | | NM_148957, NM_018647, NM_001204458, NM_001204459 | 0.0224 |
| TNFRSF4 | Hs.129780 | NM_003327 | 0.0884 |
| TOB1 | Hs.744946 | NM_005749, NM_001243885, NM_001243877 | 0.0945 |
| TOX2 | Hs.26608 | NM_001098797, NM_001098796, NM_032883, NM_001098798 | 0.0347 |
| TRIB2 | Hs.467751 | NM_021643 | 0.0666 |
| TSKU | Hs.8361 | NM_015516, NM_001258210 | 0.0027 |
| TSPAN13 | | NM_014399 | 0.0376 |
| TTBK1 | Hs.485436 | NM_032538 | 0.0027 |
| TTC39C | Hs.733420 | NM_153211, NM_001243425, NM_001135993, NM_001292030 | 0.0172 |
| TUBB6 | Hs.193491, Hs.744066 | NM_001303524, NM_032525, NM_001303529, NM_001303526, NM_001303525 | 0.0271 |
| uc001acl | | | 0.0212 |
| uc004aex | | | 0.0299 |
| uc010eif | | | 0.0243 |
| uc021oxp | | | 0.0595 |
| USP44 | | NM_032147, NM_001042403, NM_001278393 | 0.0666 |
| XYLT1 | Hs.22907 | NM_022166 | 0.0890 |
| ZBTB20 | | NM_001164343, NM_001164347, NM_001164345, NM_001164342, NM_015642, NM_001164344, NM_001164346 | 0.0148 |
| ZBTB32 | Hs.99430, Hs.736841 | NM_014383 | 0.0384 |
| ZNF219 | Hs.250493 | NM_016423, NM_001102454, NM_001101672 | 0.0860 |
| ZNF683 | Hs.353208 | NM_001114759, NM_173574, NM_001307925 | 0.0205 |

Gene set analyses were performed to predict patient response to CD19 CAR-expressing cell therapy (e.g., CTL019). Gene set analysis was performed on gene sets described in Example 1, and with gene sets from three additional datasets described in Example 2 (Szabo et al., Abbas et al., and Gattinoni et al.). Each gene set was evaluated to determine its association with subject response (i.e. CR, PR, or NR) as described in Example 2. Gene sets found to be significantly altered and predictive of patient response to CD19 CAR-expressing cell therapy (e.g., CTL019) are listed in Table 19.

TABLE 19

Gene sets predictive of patient response to CAR therapy

| Gene Set | Source | CRs | NRs |
|---|---|---|---|
| Treg vs Teff 0 h | Szabo | Teff 0 h | Treg 0 h |
| Treg vs Teff 16 h | Szabo | Teff 16 h | Treg 16 h |
| Teff 16 h vs 0 h | Szabo | Teff 0 h | Teff 16 h |
| Treg 16 h vs 0 h | Szabo | Treg 0 h | Treg 16 h |
| Naïve CD4 vs 12 h act Th2 | Abbas | Naïve CD4 | Th2 |
| Naïve CD4 vs 48 h act Th2 | Abbas | Naïve CD4 | Th2 |
| Naïve CD4 vs 12 h act Th1 | Abbas | Naïve CD4 | Th1 |

TABLE 19-continued

Gene sets predictive of patient response to CAR therapy

| Gene Set | Source | CRs | NRs |
|---|---|---|---|
| Unstim vs stim memory | Abbas | Unstimulated | Stimulated |
| Progressively down | Gattinoni | Early stage | Late stage |

Significant gene sets from the analyses above were refined to a subset of genes within the gene sets that are significantly differentially expressed between the CRs and NRs. An exemplary listing of genes that were significantly differentially expressed are listed in Table 20. Table 20 is an exemplary list of biomarkers whose expression values predict patient response to CTL019 therapy. Table 20 can be further refined into a smaller list of high confidence biomarkers by setting a stricter FDR. For instance, using a FDR of 0.10 will results in a list of 265 genes and a FDR of 0.01 will result in a list of 27 genes.

TABLE 20

Exemplary biomarkers for predicting patient response to CAR therapy

| Gene | Unigene | Accession No. | FDR |
|---|---|---|---|
| ABCB1 | Hs.489033 | NM_000927 | 0.0147 |
| ABTB1 | Hs.107812 | NM_172027, NM_032548 | 0.156 |
| ACACA | | NM_198834, NM_198837, NM_198836, NM_198839, NM_198838 | 0.226 |
| ACSL1 | Hs.406678 | NM_001995, NM_001286711, NM_001286708, NM_001286710, NM_001286712 | 0.0211 |
| ACSS2 | Hs.517034 | NM_001242393, NM_018677, NM_001076552 | 0.189 |
| ACTN1 | Hs.509765 | NM_001102, NM_001130004, NM_001130005 | 0.137 |
| ADAM12 | | NM_003474, NM_001288973, NM_021641, NM_001288974, NM_001288975 | 0.00259 |
| ADAM7 | Hs.116147 | NM_003817 | 0.249 |
| ADD3 | | NM_019903, NM_016824, NM_001121 | 0.243 |
| ADH7 | Hs.389 | NM_001166504, NM_000673 | 0.179 |
| AES | Hs.515053 | NM_198969, NM_001130, NM_198970 | 0.0307 |
| AGRN | Hs.273330 | NM_198576, NM_001305275 | 0.00795 |
| AHCYL1 | Hs.743973 | NM_006621, NM_001242675, NM_001242676, NM_001242673, NM_001242674 | 0.24 |
| AHI1 | | NM_001134830, NM_017651, NM_001134831, NM_001134832 | 0.106 |
| AIM2 | | NM_004833 | 0.224 |
| AK5 | Hs.559718 | NM_174858, NM_012093 | 0.21 |
| AKR1C3 | | NM_003739, NM_001253908 | 0.212 |
| ALDH18A1 | Hs.500645 | NM_002860, NM_001017423 | 0.234 |
| ALG5 | | NM_013338, NM_001142364 | 0.171 |
| ALOX5AP | | NM_001629, NM_001204406 | 0.0878 |
| ALPP | Hs.284255 | NM_001632 | 0.218 |
| ANAPC13 | Hs.106909 | NM_001242374, NM_015391, NM_001242375 | 0.246 |
| ANKRD10 | | NM_017664, NM_001286721 | 0.229 |
| ANKRD6 | | NM_001242813, NM_001242809, NM_014942, NM_001242811, NM_001242814 | 0.0842 |
| ANXA2P3 | | | 0.219 |
| AP1G2 | Hs.343244, Hs.740123 | NM_001282475, NM_001282474, NM_003917 | 0.0756 |
| APOA2 | | NM_001643 | 0.0265 |
| APOBEC3C | | NM_014508 | 0.11 |
| APP | Hs.434980 | NM_000484, NM_001136129, NM_201414, NM_001204303, NM_201413, NM_001204302, NM_001136016, NM_001136130, NM_001204301, NM_001136131 | 0.129 |
| AQP3 | Hs.234642 | NM_004925 | 0.0645 |
| ARFRP1 | Hs.389277, Hs.661969 | NM_001267549, NM_001134758, NM_001267544, NM_001267546, NM_001267545, NM_001267547, NM_003224, NM_001267548 | 0.112 |
| ARHGEF18 | Hs.465761 | NM_015318, NM_001130955 | 0.207 |
| ARID5A | | NM_212481 | 0.184 |
| ARL4C | Hs.111554, Hs.730678 | NM_001282431, NM_005737 | 0.091 |
| ARNTL2 | | NM_001248003, NM_001248005, NM_001248002, NM_001248004, NM_020183 | 0.0709 |
| ARRDC2 | Hs.515249 | NM_001025604, NM_001286826, NM_015683 | 0.248 |
| ATF7IP2 | Hs.513343, Hs.742019 | NM_024997, NM_001256160 | 0.0661 |

TABLE 20-continued

Exemplary biomarkers for predicting patient response to CAR therapy

| Gene | Unigene | Accession No. | FDR |
|---|---|---|---|
| ATP6V1B2 | Hs.295917 | NM_001693 | 0.171 |
| ATP8A2 | | NM_016529 | 0.222 |
| AURKAIP1 | | NM_017900, NM_001127230, NM_001127229 | 0.207 |
| AUTS2 | Hs.21631 | NM_001127231, NM_015570, NM_001127232 | 0.158 |
| B4GALT7 | Hs.455109 | NM_007255 | 0.115 |
| BACH2 | Hs.269764 | NM_021813, NM_001170794 | 0.115 |
| BANP | Hs.461705, Hs.690969 | NM_001173541, NM_079837, NM_001173540, NM_017869, NM_001173543, NM_001173539, NM_001173542 | 0.236 |
| BARD1 | | NM_000465, NM_001282549, NM_001282543, NM_001282548, NM_001282545 | 0.232 |
| BASP1 | Hs.201641 | NM_006317, NM_001271606 | 0.137 |
| BCL11B | Hs.709690 | NM_001282237, NM_138576, NM_001282238, NM_022898 | 0.134 |
| BCOR | | NM_017745, NM_001123384, NM_001123385, NM_001123383 | 0.22 |
| BEX4 | Hs.184736 | NM_001080425, NM_001127688 | 0.218 |
| BFSP1 | Hs.129702 | NM_001195, NM_001161705, NM_001278607, NM_001278606, NM_001278608 | 0.186 |
| BHLHE40 | | NM_003670 | 0.224 |
| BIN1 | Hs.193163 | NM_139344, NM_139348, NM_139351, NM_139346, NM_139347, NM_139349, NM_139345, NM_004305, NM_139343, NM_139350 | 0.192 |
| BIN2 | Hs.14770 | NM_001290008, NM_001290009, NM_016293, NM_001290007 | 0.094 |
| BIRC3 | | NM_182962, NM_001165 | 0.127 |
| BUB1 | Hs.469649 | NM_001278617, NM_004336, NM_001278616 | 0.141 |
| C11orf21 | Hs.559181 | NM_001142946 | 0.0679 |
| C11orf48 | | | 0.103 |
| C11orf67 | | | 0.227 |
| C11orf82 | | | 0.196 |
| C14orf49 | | | 0.217 |
| C16orf45 | Hs.738182 | NM_033201, NM_001142469 | 0.181 |
| C16orf74 | | NM_206967 | 0.197 |
| C17orf53 | Hs.437059 | NM_024032, NM_001171251 | 0.185 |
| C17orf66 | | | 0.229 |
| C1orf162 | Hs.288010 | NM_174896, NM_001300834 | 0.135 |
| C1orf54 | | NM_001301040, NM_001301039, NM_024579, NM_001301042 | 0.212 |
| C20orf111 | | | 0.0568 |
| C20orf112 | | | 0.102 |
| C2orf28 | | | 0.24 |
| C2orf89 | | | 0.159 |
| C5orf30 | Hs.482976 | NM_033211 | 0.207 |
| C5orf39 | | | 0.00226 |
| C7orf10 | | | 0.162 |
| C7orf59 | | | 0.0455 |
| C9orf23 | | | 0.0943 |
| CA6 | | NM_001215, NM_001270500, NM_001270501 | 0.0798 |
| CAMK1 | | NM_003656 | 0.215 |
| CAMK2G | | NM_001222, NM_172173, NM_172169, NM_172170, NM_001204492, NM_172171 | 0.0175 |
| CAMK4 | | NM_001744 | 0.0524 |
| CAPG | Hs.687978 | NM_001747, NM_001256140, NM_001256139 | 0.0735 |
| CAPS | | NM_080590, NM_004058 | 0.0524 |
| CARM1 | | NM_199141 | 0.162 |
| CBLB | Hs.430589 | NM_170662 | 0.061 |
| CCDC47 | Hs.202011 | NM_020198 | 0.104 |
| CCDC56 | | | 0.0674 |
| CCL20 | Hs.75498 | NM_001130046, NM_004591 | 0.249 |
| CCL4L1 | | | 0.0434 |
| CCL5 | | NM_002985, NM_001278736 | 0.015 |
| CCNB1 | Hs.23960 | NM_031966 | 0.195 |
| CCND3 | | NM_001760, NM_001287427, NM_001136126, NM_001136017, NM_001136125, NM_001287434 | 0.0618 |
| CCR6 | | NM_031409, NM_004367 | 0.0767 |
| CD109 | Hs.399891 | NM_133493, NM_001159588, NM_001159587 | 0.013 |
| CD200 | | NM_001004196, NM_005944 | 0.00952 |
| CD22 | Hs.579691, Hs.716252 | NM_001185099, NM_001771, NM_001185100, NM_001278417, NM_001185101 | 0.124 |
| CD244 | Hs.157872 | NM_016382, NM_001166663, NM_001166664 | 0.0605 |
| CD248 | Hs.195727 | NM_020404 | 0.0548 |
| CD3D | | NM_000732, NM_001040651 | 0.0455 |
| CD4 | | NM_000616 | 0.166 |
| CD5 | Hs.58685 | NM_014207 | 0.0926 |

TABLE 20-continued

Exemplary biomarkers for predicting patient response to CAR therapy

| Gene | Unigene | Accession No. | FDR |
|---|---|---|---|
| CD55 | | NM_000574, NM_001300903, NM_001300904, NM_001300902, NM_001114752 | 0.139 |
| CD68 | Hs.647419 | NM_001251, NM_001040059 | 0.144 |
| CD80 | Hs.838 | NM_005191 | 0.061 |
| CDC14A | Hs.127411 | NM_033312, NM_033313, NM_003672 | 0.149 |
| CDC25B | Hs.153752 | NM_001287519, NM_001287520, NM_021873, NM_004358, NM_001287522, NM_021872, NM_001287518, NM_001287516, NM_001287517 | 0.136 |
| CDC42BPB | Hs.654634 | NM_006035 | 0.0835 |
| CDC42EP3 | Hs.369574, Hs.689535 | NM_006449, NM_001270437, NM_001270438, NM_001270436 | 0.126 |
| CDC6 | | NM_001254 | 0.201 |
| CDKN1A | Hs.370771 | NM_000389, NM_001220778, NM_001220777, NM_078467 | 0.013 |
| CDKN2D | Hs.435051 | NM_079421, NM_001800 | 0.218 |
| CDT1 | | NM_030928 | 0.195 |
| CECR1 | Hs.170310 | NM_177405, NM_001282228, NM_001282227, NM_001282229, NM_001282226, NM_001282225 | 0.147 |
| CEMP1 | | NM_001048212 | 0.179 |
| CEP55 | Hs.14559 | NM_001127182, NM_018131 | 0.241 |
| CFH | Hs.363396 | NM_000186, NM_001014975 | 0.158 |
| CFHR2 | | NM_005666 | 0.074 |
| CGREF1 | Hs.159525 | NM_001166240, NM_006569, NM_001166239 | 0.201 |
| CHEK1 | Hs.24529 | NM_001114121, NM_001274, NM_001244846, NM_001114122 | 0.136 |
| CHL1 | Hs.148909, Hs.731409 | NM_006614, NM_001253387, NM_001253388 | 0.226 |
| CHMP7 | Hs.5019 | NM_152272 | 0.0594 |
| CHST11 | Hs.17569 | NM_001173982, NM_018413 | 0.149 |
| CHST12 | Hs.744987 | NM_001243794, NM_001243795, NM_018641 | 0.192 |
| CHST2 | Hs.8786 | NM_004267 | 0.00226 |
| CHSY1 | Hs.110488, Hs.734921 | NM_014918 | 0.11 |
| CLCA2 | Hs.241551 | NM_006536 | 0.172 |
| CMAHP | | | 0.0642 |
| CNPY3 | | NM_006586 | 0.0605 |
| COL18A1 | Hs.517356 | NM_130445, NM_030582, NM_130444 | 0.189 |
| COL6A1 | Hs.474053 | NM_001848 | 0.201 |
| CORO1C | Hs.330384 | NM_014325, NM_001276471, NM_001105237 | 0.0566 |
| COX4I1 | | NM_001861 | 0.222 |
| CRADD | Hs.591016, Hs.719191 | NM_003805 | 0.144 |
| CRKL | Hs.5613 | NM_005207 | 0.201 |
| CSGALNACT1 | Hs.613729 | NM_001130518, NM_018371 | 0.0589 |
| CSNK2A1 | | NM_001895, NM_177559, NM_177560 | 0.171 |
| CSTB | | NM_000100 | 0.0477 |
| CSTF2 | | NM_001325, NM_001306206 | 0.158 |
| CTDSP1 | Hs.444468 | NM_001206878, NM_182642, NM_021198 | 0.195 |
| CTNNA1 | Hs.445981, Hs.740112 | NM_001903, NM_001290310, NM_001290309, NM_001290307, NM_001290312 | 0.00562 |
| CTNNA2 | Hs.167368 | NM_004389, NM_001282598, NM_001164883, NM_001282597, NM_001282600, NM_001282599 | 0.145 |
| CTNNAL1 | | NM_001286974, NM_003798 | 0.124 |
| CTNNBIP1 | Hs.463759 | NM_020248, NM_001012329 | 0.091 |
| CTNND2 | Hs.314543 | NM_001332, NM_001288717, NM_001288715, NM_001288716 | 0.226 |
| CTSF | Hs.11590 | NM_003793 | 0.224 |
| CTSW | Hs.416848 | NM_001335 | 0.0929 |
| CTTN | Hs.596164 | NM_138565, NM_005231, NM_001184740 | 0.0642 |
| CUX1 | Hs.191482 | NM_181500, NM_001202546, NM_001202544, NM_001202543, NM_001202545, NM_181552, NM_001913 | 0.137 |
| CXCL13 | Hs.100431 | NM_006419 | 0.192 |
| CYB561 | Hs.355264 | NM_001017917, NM_001915, NM_001017916 | 0.208 |
| CYFIP1 | Hs.26704 | NM_014608, NM_001033028, NM_001287810 | 0.192 |
| D4S234E | | | 0.224 |
| DAB1 | Hs.477370 | NM_021080 | 0.0455 |
| DAXX | | NM_001141969, NM_001254717, NM_001141970, NM_001350 | 0.192 |
| DBN1 | | NM_004395, NM_080881 | 0.0127 |
| DENND2D | | NM_024901, NM_001271833 | 0.0882 |
| DENND3 | Hs.18166 | NM_014957 | 0.223 |
| DEPDC7 | Hs.280990 | NM_001077242, NM_139160 | 0.00865 |
| DGKD | Hs.471675 | NM_152879, NM_003648 | 0.0524 |
| DGKI | Hs.737768 | NM_004717 | 0.0596 |
| DHCR24 | Hs.498727 | NM_014762 | 0.0843 |

TABLE 20-continued

Exemplary biomarkers for predicting patient response to CAR therapy

| Gene | Unigene | Accession No. | FDR |
|---|---|---|---|
| DIXDC1 | Hs.655626 | NM_001278542, NM_001037954, NM_033425 | 0.224 |
| DLG2 | Hs.367656 | NM_001364, NM_001142702, NM_001142699, NM_001142700, NM_001300983, NM_001206769 | 0.00226 |
| DMRT1 | Hs.98586 | NM_021951 | 0.0589 |
| DNAJB5 | Hs.237506 | NM_001135004, NM_012266, NM_001135005 | 0.0843 |
| DNAJC6 | Hs.647643 | NM_014787, NM_001256864, NM_001256865 | 0.219 |
| DNM1 | Hs.522413 | NM_004408, NM_001005336, NM_001288737, NM_001288738, NM_001288739 | 0.244 |
| DOCK7 | Hs.744927 | NM_033407, NM_001272000, NM_001272002, NM_001271999, NM_001272001 | 0.061 |
| DONSON | | NM_017613 | 0.0754 |
| DPEP2 | Hs.372633 | NM_022355 | 0.11 |
| DPP7 | | NM_013379 | 0.236 |
| DPYD | Hs.335034 | NM_000110, NM_001160301 | 0.133 |
| DPYSL2 | Hs.593187 | NM_001197293, NM_001386, NM_001244604 | 0.106 |
| DSN1 | Hs.632268 | NM_001145318, NM_001145315, NM_001145317, NM_001145316, NM_024918 | 0.0767 |
| DTL | Hs.656473 | NM_016448, NM_001286229, NM_001286230 | 0.234 |
| DUSP10 | Hs.497822 | NM_007207 | 0.162 |
| DUSP16 | | NM_030640 | 0.238 |
| DUSP22 | | NM_020185, NM_001286555 | 0.0735 |
| DUSP4 | | NM_001394, NM_057158 | 0.00463 |
| DVL2 | Hs.118640 | NM_004422 | 0.0847 |
| DYNLL1 | Hs.5120 | NM_001037494, NM_001037495, NM_003746 | 0.195 |
| EAPP | Hs.433269 | NM_018453 | 0.246 |
| EBI3 | | NM_005755 | 0.00226 |
| EBI3 | | | 0.00226 |
| EED | | NM_003797, NM_152991, NM_001308007 | 0.0798 |
| EEF1D | | NM_001195203, NM_032378, NM_001130056, NM_001289950, NM_001960, NM_001130053, NM_001130055, NM_001130057 | 0.101 |
| EFS | Hs.24587 | NM_005864, NM_032459, NM_001277174 | 0.0594 |
| EGFL6 | Hs.12844 | NM_015507, NM_001167890 | 0.229 |
| EIF2C4 | | | 0.158 |
| ELL2 | Hs.192221 | NM_012081 | 0.0455 |
| EMB | Hs.561411 | NM_198449 | 0.24 |
| EMP1 | | NM_001423 | 0.0144 |
| ENPP2 | Hs.190977 | NM_006209, NM_001130863, NM_001040092 | 0.0275 |
| EPAS1 | Hs.468410 | NM_001430 | 0.00636 |
| EPB41L4B | Hs.591901 | NM_019114, NM_018424 | 0.172 |
| EPHA4 | Hs.371218 | NM_001304536, NM_001304537, NM_004438 | 0.157 |
| ERGIC3 | | NM_015966, NM_198398 | 0.207 |
| ERI2 | Hs.248437 | NM_080663, NM_001142725 | 0.0552 |
| ERP29 | | NM_006817, NM_001034025 | 0.0113 |
| ESPL1 | Hs.153479 | NM_012291 | 0.236 |
| ESR1 | Hs.208124 | NM_001291230, NM_001122741, NM_001291241, NM_000125, NM_001122742, NM_001122740 | 0.192 |
| ESRRG | | NM_001134285, NM_001243511, NM_001243518, NM_001438, NM_001243514, NM_001243513, NM_206595, NM_001243506, NM_001243510, NM_001243507, NM_001243512, NM_001243509, NM_001243515, NM_001243519, NM_206594 | 0.195 |
| ETV3 | | NM_001145312, NM_005240 | 0.208 |
| EVI5 | Hs.594434 | NM_005665, NM_001308248 | 0.0127 |
| FADS1 | Hs.503546, Hs.739285 | NM_013402 | 0.16 |
| FADS2 | | NM_001281501, NM_001281502, NM_004265 | 0.0243 |
| FAH | | NM_000137 | 0.131 |
| FAIM2 | Hs.567424 | NM_012306 | 0.215 |
| FAIM3 | | | 0.128 |
| FAM125B | | | 0.0735 |
| FAM134B | Hs.481704 | NM_019000, NM_001034850 | 0.0128 |
| FAM134C | Hs.632262 | NM_178126 | 0.107 |
| FAM40B | | | 0.00562 |
| FAM46C | Hs.356216 | NM_017709 | 0.241 |
| FAM65B | Hs.559459 | NM_014722, NM_015864, NM_001286447, NM_001286445, NM_001286446 | 0.0965 |
| FANCI | Hs.513126 | NM_018193, NM_001113378 | 0.133 |
| FAU | | NM_001997 | 0.137 |
| FDPS | | NM_001135822, NM_001242824, NM_002004, NM_001135821, NM_001242825 | 0.0852 |
| FGD3 | Hs.411081 | NM_001083536, NM_001286993, NM_033086 | 0.125 |
| FGF21 | Hs.283015 | NM_019113 | 0.249 |
| FHIT | Hs.655995 | NM_002012, NM_001166243 | 0.0505 |

TABLE 20-continued

Exemplary biomarkers for predicting patient response to CAR therapy

| Gene | Unigene | Accession No. | FDR |
|---|---|---|---|
| FKBP11 | | NM_001143781, NM_016594, NM_001143782 | 0.0128 |
| FLI1 | Hs.504281 | NM_002017, NM_001167681, NM_001271012, NM_001271010 | 0.0965 |
| FLT1 | Hs.594454 | NM_002019, NM_001160030, NM_001159920, NM_001160031 | 0.0243 |
| FLT3LG | | NM_001204502, NM_001459, NM_001278637, NM_001278638, NM_001204503 | 0.0124 |
| FLVCR2 | Hs.509966 | NM_017791, NM_001195283 | 0.149 |
| FMNL2 | Hs.654630 | NM_052905 | 0.171 |
| FNBP1 | | NM_015033 | 0.142 |
| FOXN3 | | NM_001085471, NM_005197 | 0.207 |
| FOXP1 | | NM_032682, NM_001244816, NM_001244815, NM_001244814, NM_001244808, NM_001244812, NM_001012505, NM_001244813, NM_001244810 | 0.015 |
| FXYD5 | | NM_014164, NM_144779, NM_001164605 | 0.0852 |
| FXYD7 | | NM_022006 | 0.189 |
| G0S2 | | NM_015714 | 0.0594 |
| GAB2 | Hs.429434 | NM_012296, NM_080491 | 0.0532 |
| GAB3 | Hs.496982 | NM_080612, NM_001282283, NM_001081573 | 0.136 |
| GABARAPL1 | Hs.524250 | NM_031412 | 0.162 |
| GAD2 | | NM_001134366, NM_000818 | 0.129 |
| GARS | Hs.404321 | NM_002047 | 0.109 |
| GATM | Hs.75335 | NM_001482 | 0.124 |
| GBP5 | Hs.513726 | NM_052942, NM_001134486 | 0.168 |
| GCET2 | | | 0.243 |
| GEM | Hs.654463 | NM_181702, NM_005261 | 0.00795 |
| GK | Hs.1466 | NM_203391, NM_001128127, NM_000167, NM_001205019 | 0.0432 |
| GLCCI1 | Hs.131673 | NM_138426 | 0.211 |
| GLIPR2 | Hs.493819 | NM_001287010, NM_001287013, NM_022343, NM_001287011, NM_001287014, NM_001287012 | 0.0466 |
| GMNN | | NM_001251990, NM_001251989, NM_015895, NM_001251991 | 0.215 |
| GNG4 | Hs.159711 | NM_004485, NM_001098722, NM_001098721 | 0.101 |
| GNLY | | NM_006433, NM_001302758, NM_012483 | 0.184 |
| GPC1 | | NM_002081 | 0.186 |
| GPD1L | Hs.82432 | NM_015141 | 0.099 |
| GPKOW | | NM_015698 | 0.167 |
| GPR114 | | | 0.17 |
| GPR56 | | | 0.00463 |
| GPRC5C | Hs.446438 | NM_022036, NM_018653 | 0.158 |
| GPRIN3 | | NM_198281 | 0.215 |
| GPSM3 | Hs.520046 | NM_001276501, NM_022107 | 0.122 |
| GRAMD3 | Hs.363558, Hs.664026 | NM_001146319, NM_023927, NM_001146322, NM_001146321, NM_001146320 | 0.0594 |
| GRAP | | NM_006613 | 0.158 |
| GTF3C4 | | NM_012204 | 0.231 |
| GTPBP1 | Hs.276925 | NM_004286 | 0.0665 |
| GYG1 | Hs.477892, Hs.727448 | NM_004130, NM_001184720, NM_001184721 | 0.124 |
| GZMA | | NM_006144 | 0.0211 |
| GZMH | | NM_001270780, NM_033423, NM_001270781 | 0.159 |
| H19 | Hs.533566 | | 0.151 |
| H1F0 | Hs.745024 | NM_005318 | 0.0432 |
| HAO2 | Hs.659767 | NM_001005783, NM_016527 | 0.17 |
| HBS1L | Hs.378532 | NM_006620, NM_001145158, NM_001145207 | 0.0528 |
| HERPUD2 | | NM_022373 | 0.236 |
| HKDC1 | Hs.522988 | NM_025130 | 0.236 |
| HLA-DPA1 | Hs.347270 | NM_033554, NM_001242524, NM_001242525 | 0.158 |
| HLA-DQA2 | | NM_020056, NM_002122 | 0.179 |
| HLA-DQB2 | Hs.731563 | NM_001198858, NM_001300790 | 0.226 |
| HLA-DRB5 | | NM_002125 | 0.0645 |
| HMGCR | Hs.628096 | NM_000859, NM_001130996 | 0.0466 |
| HMGCS1 | | NM_001098272, NM_002130 | 0.0666 |
| HNRPLL | | | 0.0566 |
| HOXC8 | | NM_022658 | 0.142 |
| HPGD | Hs.596913 | NM_000860, NM_001145816, NM_001256301, NM_001256306, NM_001256307, NM_001256305 | 0.0276 |
| HPS5 | Hs.437599 | NM_007216, NM_181507, NM_181508 | 0.167 |
| HSD11B1 | | NM_005525, NM_001206741, NM_181755 | 0.0502 |
| HSD17B11 | Hs.594923 | NM_016245 | 0.156 |
| HSD17B12 | Hs.132513 | NM_016142 | 0.143 |
| HSPA1L | Hs.690634 | NM_005527 | 0.193 |
| HSPD1 | | NM_002156, NM_199440 | 0.139 |

TABLE 20-continued

Exemplary biomarkers for predicting patient response to CAR therapy

| Gene | Unigene | Accession No. | FDR |
|---|---|---|---|
| ICAM1 | Hs.643447 | NM_000201 | 0.132 |
| ICAM2 | | NM_000873, NM_001099789, NM_001099788, NM_001099786, NM_001099787 | 0.0847 |
| ICAM3 | Hs.654563 | NM_002162 | 0.229 |
| IER2 | Hs.501629 | NM_004907 | 0.158 |
| IER3 | | NM_003897 | 0.206 |
| IFI44 | | NM_006417 | 0.223 |
| IFIH1 | Hs.163173 | NM_022168 | 0.0524 |
| IGBP1 | Hs.496267 | NM_001551 | 0.151 |
| IGSF3 | Hs.171057 | NM_001007237, NM_001542 | 0.0466 |
| IL17RA | Hs.48353 | NM_014339, NM_001289905 | 0.135 |
| IL1A | | NM_000575 | 0.00562 |
| IL1RAP | Hs.478673 | NM_001167929, NM_001167928, NM_002182, NM_134470, NM_001167930, NM_001167931 | 0.0524 |
| IL1RAPL1 | Hs.658912 | NM_014271 | 0.167 |
| IL1RN | | NM_173843, NM_173841, NM_000577, NM_173842 | 0.0168 |
| IL21 | | NM_021803, NM_001207006 | 0.167 |
| IL32 | | NM_001012718, NM_004221, NM_001012633, NM_001012631, NM_001012635, NM_001012634, NM_001012632, NM_001012636 | 0.177 |
| IL8 | | | 0.234 |
| INPP4B | | NM_003866, NM_001101669 | 0.0965 |
| IRF4 | | NM_002460, NM_001195286 | 0.142 |
| IRF6 | Hs.591415 | NM_006147, NM_001206696 | 0.0699 |
| IRF8 | | NM_002163 | 0.114 |
| ISG20 | Hs.459265 | NM_001303234, NM_001303233, NM_002201, NM_001303237 | 0.0354 |
| ITGA6 | Hs.133397 | NM_000210, NM_001079818 | 0.0441 |
| ITGAE | Hs.513867 | NM_002208 | 0.192 |
| ITPA | | NM_033453, NM_181493, NM_001267623 | 0.16 |
| ITPK1 | | NM_001142594, NM_001142593, NM_014216 | 0.12 |
| JUN | Hs.696684 | NM_002228 | 0.141 |
| JUNB | Hs.25292 | NM_002229 | 0.0455 |
| KAZALD1 | Hs.733496 | NM_030929 | 0.214 |
| KCNK1 | | NM_002245 | 0.104 |
| KCNK5 | Hs.444448 | NM_003740 | 0.246 |
| KCNQ1 | | NM_000218, NM_181798 | 0.205 |
| KIFC1 | Hs.436912 | NM_002263 | 0.234 |
| KIT | Hs.479754 | NM_001093772, NM_000222 | 0.0466 |
| KLF2 | Hs.744182 | NM_016270 | 0.166 |
| KLF3 | Hs.298658 | NM_016531 | 0.24 |
| KLF4 | Hs.376206 | NM_004235 | 0.136 |
| KLF7 | Hs.59908 | NM_003709, NM_001270943, NM_001270942, NM_001270944 | 0.203 |
| KLRB1 | Hs.169824 | NM_002258 | 0.00226 |
| KLRC1 | Hs.512576 | NM_001304448, NM_002259, NM_213657, NM_007328, NM_213658 | 0.0455 |
| KLRD1 | Hs.562457, Hs.668357 | NM_002262, NM_007334, NM_001114396 | 0.158 |
| KRT72 | Hs.662013 | NM_001146225, NM_001146226, NM_080747 | 0.212 |
| LAIR1 | | NM_001289026, NM_001289027, NM_002287, NM_021706, NM_001289025, NM_001289023 | 0.238 |
| LAMB3 | Hs.497636 | NM_000228, NM_001127641, NM_001017402 | 0.0642 |
| LCLAT1 | Hs.468048 | NM_001304445, NM_001002257, NM_182551 | 0.234 |
| LIF | Hs.2250 | NM_002309, NM_001257135 | 0.0837 |
| LIMA1 | Hs.525419 | NM_001243775, NM_001113546, NM_016357, NM_001113547 | 0.0774 |
| LITAF | Hs.459940 | NM_001136473, NM_004862, NM_001136472 | 0.0747 |
| LMCD1 | | NM_014583, NM_001278235, NM_001278233, NM_001278234 | 0.0127 |
| LMNA | Hs.594444 | NM_001282625, NM_005572, NM_170707, NM_001282626, NM_001257374, NM_001282624, NM_170708 | 0.0166 |
| LMNB2 | Hs.538286 | NM_032737 | 0.144 |
| LOC282997 | | | 0.198 |
| LOC728392 | | | 0.12 |
| LOC728855 | | | 0.0567 |
| LRRC16A | Hs.649550 | NM_001173977, NM_017640 | 0.0756 |
| LSAMP | Hs.26409 | NM_002338 | 0.223 |
| LTA | Hs.36 | NM_001159740, NM_000595 | 0.135 |
| LYAR | Hs.425427 | NM_017816, NM_001145725 | 0.0882 |
| MAP2K5 | | NM_145160, NM_002757, NM_001206804 | 0.107 |
| MAP2K6 | Hs.463978 | NM_002758 | 0.0594 |
| MATK | Hs.631845 | NM_139354, NM_139355, NM_002378 | 0.177 |
| MBP | Hs.551713 | NM_001025081, NM_001025090, NM_001025092, NM_002385, NM_001025100, NM_001025101 | 0.192 |

TABLE 20-continued

Exemplary biomarkers for predicting patient response to CAR therapy

| Gene | Unigene | Accession No. | FDR |
|---|---|---|---|
| MCAM | | NM_006500 | 0.245 |
| MCM10 | Hs.198363 | NM_018518, NM_182751 | 0.232 |
| MCM2 | Hs.477481 | NM_004526 | 0.119 |
| MCM4 | | NM_182746, NM_005914 | 0.144 |
| MCTP2 | Hs.33368 | NM_001159643, NM_018349, NM_001159644 | 0.147 |
| ME3 | Hs.199743 | NM_001014811, NM_001161586, NM_006680 | 0.136 |
| MEST | | NM_177524, NM_001253901, NM_001253902, NM_001253900, NM_002402, NM_177525 | 0.192 |
| METTL13 | Hs.494705 | NM_014955, NM_001007239, NM_015935 | 0.207 |
| METTL7A | Hs.744021 | NM_014033 | 0.0605 |
| MFNG | Hs.517603 | NM_002405, NM_001166343 | 0.061 |
| MGAT4C | Hs.589093, Hs.739389 | NM_013244 | 0.0544 |
| MICAL2 | Hs.501928, Hs.735627 | NM_014632, NM_001282663, NM_001282665, NM_001282666, NM_001282667, NM_001282664 | 0.158 |
| MID1IP1 | Hs.522605 | NM_001098790, NM_021242, NM_001098791 | 0.229 |
| MIR155HG | Hs.697120 | | 0.0386 |
| MIS18A | Hs.190518 | NM_018944 | 0.0906 |
| MLEC | Hs.701392, Hs.744910 | NM_001303627, NM_014730, NM_001303628 | 0.244 |
| MLH1 | Hs.195364 | NM_000249, NM_001258271, NM_001258274, NM_001167618, NM_001167617, NM_001167619, NM_001258273 | 0.159 |
| MMP19 | | NM_002429, NM_001272101 | 0.165 |
| MPP1 | Hs.496984 | NM_001166460, NM_002436, NM_001166461, NM_001166462 | 0.212 |
| MRC2 | Hs.7835 | NM_006039 | 0.215 |
| MRPL39 | | NM_017446, NM_080794 | 0.151 |
| MRPS17 | Hs.44298 | NM_015969 | 0.0524 |
| MT1G | | NM_005950, NM_001301267 | 0.214 |
| MTHFD1 | Hs.652308 | NM_005956 | 0.0524 |
| MTHFD2 | | NM_006636 | 0.0924 |
| MTMR4 | Hs.514373 | NM_004687 | 0.171 |
| MYB | Hs.606320, Hs.626299 | NM_001130173, NM_001130172, NM_005375, NM_001161657, NM_001161656, NM_001161658, NM_001161659, NM_001161660 | 0.0528 |
| MYL6 | | NM_021019, NM_079423 | 0.137 |
| MYO1C | Hs.286226 | NM_001080779, NM_001080950, NM_033375 | 0.128 |
| MYO1F | Hs.465818 | NM_012335 | 0.0965 |
| MYOF | Hs.602086 | NM_133337, NM_013451 | 0.0243 |
| NAB2 | Hs.159223 | NM_005967 | 0.0128 |
| NCAPD2 | Hs.5719 | NM_014865 | 0.233 |
| NCAPD3 | | NM_015261 | 0.236 |
| NCAPH | | NM_015341, NM_001281710, NM_001281711, NM_001281712 | 0.17 |
| NCKAP1 | Hs.603732 | NM_013436, NM_205842 | 0.0111 |
| NDFIP2 | Hs.525093 | NM_001161407, NM_019080 | 0.0528 |
| NELL2 | Hs.505326 | NM_001145108, NM_006159, NM_001145110, NM_001145107, NM_001145109 | 0.0558 |
| NFKBIZ | Hs.319171 | NM_001005474, NM_031419 | 0.181 |
| NHSL2 | Hs.397836, Hs.660859 | NM_001013627 | 0.192 |
| NINJ2 | | NM_016533, NM_001294345, NM_001294346 | 0.061 |
| NKG7 | | NM_005601 | 0.123 |
| NKIRAS1 | Hs.173202 | NM_020345 | 0.201 |
| NMT2 | | NM_004808, NM_001308295 | 0.0842 |
| NOG | Hs.248201 | NM_005450 | 0.171 |
| NOSIP | Hs.7236 | NM_001270960, NM_015953 | 3.65E−05 |
| NPC2 | Hs.433222 | NM_006432 | 0.156 |
| NPY | | NM_000905 | 0.0466 |
| NR1D2 | Hs.37288 | NM_001145425, NM_005126 | 0.139 |
| NR2E1 | Hs.157688 | NM_003269, NM_001286102 | 0.0871 |
| NR3C2 | Hs.163924 | NM_000901, NM_001166104 | 0.0645 |
| NR4A3 | Hs.279522 | NM_173199, NM_006981, NM_173200 | 0.171 |
| NSMCE1 | Hs.284295 | NM_145080 | 0.0711 |
| NUP205 | Hs.743250 | NM_015135 | 0.162 |
| OASL | | NM_003733, NM_198213, NM_001261825 | 0.192 |
| ODC1 | | NM_002539, NM_001287188, NM_001287190, NM_001287189 | 0.139 |
| OLFM2 | | NM_058164, NM_001304348, NM_001304347 | 0.229 |
| ORC6 | | NM_014321 | 0.0798 |
| OSBPL8 | Hs.430849 | NM_020841, NM_001003712 | 0.227 |
| OTUD7B | | NM_020205 | 0.0487 |
| P2RX4 | | NM_002560, NM_001256796, NM_001261397, NM_001261398 | 0.0671 |

TABLE 20-continued

Exemplary biomarkers for predicting patient response to CAR therapy

| Gene | Unigene | Accession No. | FDR |
|---|---|---|---|
| P4HA2 | Hs.519568 | NM_001142598, NM_001142599, NM_001017974, NM_001017973, NM_004199 | 0.107 |
| PACSIN3 | Hs.334639 | NM_016223, NM_001184974, NM_001184975 | 0.226 |
| PAICS | Hs.518774 | NM_001079525, NM_001079524, NM_006452 | 0.167 |
| PAM | Hs.369430, Hs.738567 | NM_001177306, NM_138822, NM_138821, NM_000919, NM_138766 | 0.218 |
| PANX2 | Hs.440092 | NM_001160300, NM_052839 | 0.0128 |
| PARP8 | Hs.369581 | NM_001178055, NM_024615, NM_001178056 | 0.122 |
| PBX4 | Hs.466257 | NM_025245 | 0.211 |
| PCSK5 | Hs.368542 | NM_006200, NM_001190482 | 0.0473 |
| PDCD1 | Hs.158297 | NM_005018 | 0.0747 |
| PDE10A | Hs.348762, Hs.638546 | NM_006661, NM_001130690 | 0.215 |
| PDGFRB | Hs.509067 | NM_002609 | 0.0628 |
| PECAM1 | Hs.376675 | NM_000442 | 0.0666 |
| PELP1 | Hs.744899 | NM_014389, NM_001278241 | 0.192 |
| PER1 | Hs.445534 | NM_002616 | 0.0674 |
| PEX16 |  | NM_057174, NM_004813 | 0.0666 |
| PFDN5 |  | NM_002624, NM_145897 | 0.135 |
| PFKM | Hs.75160 | NM_001166686, NM_000289, NM_001166688, NM_001166687 | 0.0961 |
| PGAP1 | Hs.229988 | NM_024989 | 0.158 |
| PGCP |  |  | 0.186 |
| PHEX |  | NM_001282754, NM_000444 | 0.149 |
| PHF6 | Hs.356501 | NM_032458, NM_001015877, NM_032335 | 0.202 |
| PHLPP1 | Hs.465337 | NM_194449 | 0.0853 |
| PIK3C2G | Hs.22500 | NM_001288772, NM_001288774, NM_004570 | 0.0629 |
| PINK1 | Hs.389171 | NM_032409 | 0.24 |
| PION |  |  | 0.187 |
| PITPNC1 | Hs.591185 | NM_181671, NM_012417 | 0.00827 |
| PKMYT1 | Hs.732385, Hs.734466 | NM_182687, NM_004203, NM_001258451, NM_001258450 | 0.246 |
| PLAC8 | Hs.546392 | NM_016619, NM_001130716, NM_001130715 | 0.0653 |
| PLAGL2 | Hs.154104 | NM_002657 | 0.174 |
| PLCG2 |  | NM_002661 | 0.118 |
| PLCL1 |  | NM_006226 | 0.107 |
| PLCL2 | Hs.202010, Hs.741267 | NM_001144382, NM_015184 | 0.141 |
| PLIN2 |  | NM_001122 | 0.0747 |
| PLK2 | Hs.398157 | NM_006622, NM_001252226 | 0.205 |
| PLXNB2 | Hs.3989 | NM_012401 | 0.0064 |
| PLXND1 | Hs.301685 | NM_015103 | 0.229 |
| PMAIP1 | Hs.96 | NM_021127 | 0.0316 |
| PMCH |  | NM_002674 | 0.0126 |
| PNLIPRP1 | Hs.73923 | NM_006229, NM_001303135 | 0.137 |
| PNMA1 | Hs.194709 | NM_006029 | 0.11 |
| POU2AF1 | Hs.654525, Hs.733573 | NM_006235 | 0.0127 |
| POU6F1 | Hs.555886 | NM_002702 | 0.229 |
| PPCDC | Hs.458922, Hs.640486 | NM_021823, NM_001301103, NM_001301101, NM_001301102, NM_001301104, NM_001301105 | 0.00748 |
| PPFIBP2 | Hs.655714, Hs.739217 | NM_003621, NM_001256568, NM_001256569 | 0.0544 |
| PPP1R15A | Hs.631593 | NM_014330 | 0.0645 |
| PPP2R2B | Hs.739387 | NM_181678, NM_181674, NM_181675, NM_181676, NM_001271899, NM_181677, NM_001271900, NM_001271948 | 0.061 |
| PPP2R3C | Hs.530712 | NM_017917, NM_001305156, NM_001305155 | 0.167 |
| PPP2R5C | Hs.368264, Hs.679341 | NM_001161726, NM_178586, NM_178587, NM_002719, NM_001161725 | 0.158 |
| PPP3CA | Hs.435512 | NM_000944, NM_001130692, NM_001130691 | 0.0679 |
| PQBP1 |  | NM_001167990, NM_005710, NM_001032384, NM_144495, NM_001032381, NM_001167989, NM_001032382, NM_001032383 | 0.141 |
| PRC1 | Hs.366401 | NM_003981, NM_199413, NM_001267580 | 0.0642 |
| PRDM1 | Hs.436023 | NM_001198, NM_182907 | 0.0127 |
| PRF1 | Hs.2200 | NM_001083116, NM_005041 | 0.192 |
| PRKAR1B | Hs.520851 | NM_001164761, NM_001164758, NM_002735, NM_001164760, NM_001164759, NM_001164762 | 0.167 |
| PRKCDBP |  | NM_145040 | 0.0181 |
| PRKCH | Hs.333907, Hs.630857 | NM_006255 | 0.0889 |
| PRKCQ | Hs.498570 | NM_006257, NM_001282644, NM_001242413, NM_001282645 | 0.115 |

TABLE 20-continued

Exemplary biomarkers for predicting patient response to CAR therapy

| Gene | Unigene | Accession No. | FDR |
|---|---|---|---|
| PRKD3 | Hs.660757 | NM_005813 | 0.195 |
| PRKG2 | Hs.570833 | NM_001282485, NM_006259, NM_001282483, NM_001282482, NM_001282481, NM_001282480 | 0.205 |
| PRNP | Hs.472010 | NM_001080121, NM_001271561, NM_001080122, NM_000311, NM_183079, NM_001080123 | 0.236 |
| PRR5 | | NM_015366, NM_001198721, NM_181333, NM_001017528, NM_001017530, NM_001017529 | 0.0135 |
| PRSS23 | Hs.25338, Hs.729257 | NM_001293180, NM_001293178, NM_007173, NM_001293179 | 0.158 |
| PSMA5 | Hs.485246 | NM_002790, NM_001199773, NM_001199774, NM_001199772 | 0.213 |
| PSMB9 | | NM_002800 | 0.234 |
| PSMC2 | Hs.437366 | NM_001204453, NM_002803 | 0.246 |
| PSMD11 | | NM_001270482, NM_002815 | 0.206 |
| PSMD14 | Hs.740477 | NM_005805 | 0.131 |
| PTGFRN | Hs.418093 | NM_020440 | 0.215 |
| PTPN12 | Hs.61812 | NM_002835, NM_001131008, NM_001131009 | 0.205 |
| PTPN14 | Hs.193557, Hs.688910 | NM_005401 | 0.124 |
| PTPN3 | Hs.436429, Hs.698275 | NM_001145368, NM_002829, NM_001145369, NM_001145370 | 0.135 |
| PTPN4 | Hs.469809 | NM_002830 | 0.187 |
| PTPN6 | Hs.63489 | NM_080548, NM_002831, NM_080549 | 0.0174 |
| PTTG1 | | NM_004219, NM_001282383, NM_001282382 | 0.235 |
| PUS7 | Hs.520619 | NM_019042 | 0.127 |
| PVR | | NM_006505, NM_001135769, NM_001135768, NM_001135770 | 0.0064 |
| PYCARD | | NM_013258, NM_145182 | 0.0843 |
| PYCR1 | | NM_006907, NM_153824, NM_001282279, NM_001282281, NM_001282280 | 0.235 |
| RAB37 | | NM_175738, NM_001163989, NM_001006638, NM_001163990 | 0.192 |
| RACGAP1 | Hs.505469 | NM_013277, NM_001126104, NM_001126103 | 0.167 |
| RAD51 | | NM_001164270, NM_002875, NM_133487, NM_001164269 | 0.246 |
| RAP1GAP2 | Hs.499659, Hs.685132 | NM_015085, NM_001100398 | 0.167 |
| RARRES3 | | NM_004585 | 0.116 |
| RASAL1 | Hs.528693 | NM_001193520, NM_004658, NM_001193521, NM_001301202 | 0.125 |
| RASGEF1A | Hs.125293 | NM_001282862, NM_145313 | 0.0831 |
| RASGRP2 | Hs.99491 | NM_001098671, NM_001098670, NM_153819 | 0.115 |
| RASGRP4 | Hs.130434 | NM_001146202, NM_001146204, NM_001146205, NM_170604, NM_001146207, NM_001146203, NM_001146206 | 0.129 |
| RBMS1 | Hs.470412, Hs.654231 | NM_016836, NM_002897 | 0.0466 |
| REEP2 | | NM_001271803, NM_016606 | 0.135 |
| REPIN1 | Hs.647086 | NM_001099695, NM_014374, NM_013400, NM_001099696 | 0.243 |
| RGS1 | Hs.75256 | NM_002922 | 0.149 |
| RGS12 | | NM_198229, NM_002926, NM_198227 | 0.192 |
| RGS9 | Hs.664380 | NM_001165933, NM_001081955, NM_003835 | 0.222 |
| RHOB | Hs.502876 | NM_004040 | 0.0842 |
| RNF125 | Hs.633703 | NM_017831 | 0.135 |
| RNF19A | Hs.292882, Hs.735657 | NM_015435, NM_183419, NM_001280539 | 0.0544 |
| RPLP2 | | NM_001004 | 0.111 |
| RPS20 | | NM_001146227, NM_001023 | 0.189 |
| RPS27 | | NM_001030 | 0.0505 |
| RPS28 | | NM_001031 | 0.0135 |
| RPS6KA3 | Hs.445387 | NM_004586 | 0.189 |
| RSAD2 | Hs.17518 | NM_080657 | 0.229 |
| RTF1 | Hs.511096 | NM_015138 | 0.219 |
| RYBP | | NM_012234 | 0.156 |
| S100A4 | | NM_019554, NM_002961 | 0.00133 |
| S1PR1 | Hs.154210 | NM_001400 | 0.151 |
| S1PR4 | Hs.662006, Hs.688059 | NM_003775 | 0.0505 |
| SALL2 | Hs.416358, Hs.745364 | NM_005407, NM_001291446, NM_001291447 | 0.0685 |
| SCD | Hs.558396 | NM_005063 | 0.0265 |
| SCGB1A1 | | NM_003357 | 0.152 |
| SCML4 | | NM_001286408, NM_001286409, NM_198081 | 0.0243 |
| SDC4 | Hs.632267 | NM_002999 | 0.156 |
| SDK2 | Hs.435719 | NM_001144952 | 0.0307 |

TABLE 20-continued

Exemplary biomarkers for predicting patient response to CAR therapy

| Gene | Unigene | Accession No. | FDR |
|---|---|---|---|
| SECTM1 | Hs.558009 | NM_003004 | 0.0735 |
| SELPLG | | NM_003006, NM_001206609 | 0.245 |
| SEMA3B | Hs.82222 | NM_001290060, NM_001005914, NM_001290061, NM_001290063, NM_001290062, NM_004636 | 0.0477 |
| SEPT3 | Hs.120483 | NM_145733, NM_019106 | 0.0175 |
| SERPINF1 | | NM_002615 | 0.11 |
| SERPINF2 | Hs.159509 | NM_001165921, NM_001165920, NM_000934 | 0.21 |
| SFMBT2 | Hs.407983 | NM_001018039, NM_001029880 | 0.0871 |
| SFXN1 | | NM_022754 | 0.174 |
| SGCB | Hs.438953 | NM_000232 | 0.12 |
| SGTB | Hs.482301 | NM_019072 | 0.246 |
| SH2B2 | Hs.489448 | NM_020979 | 0.0127 |
| SHF | Hs.310399 | NM_001301169, NM_001301168, NM_138356, NM_001301170, NM_001301171 | 0.0567 |
| SIGIRR | Hs.501624 | NM_001135054, NM_021805, NM_001135053 | 0.143 |
| SIGLEC9 | Hs.245828 | NM_014441, NM_001198558 | 0.246 |
| SIPA1L1 | Hs.654657 | NM_001284245, NM_015556, NM_001284247, NM_001284246 | 0.215 |
| SKAP1 | Hs.316931 | NM_003726, NM_001075099 | 0.0127 |
| SLA2 | Hs.713578 | NM_032214, NM_175077 | 0.227 |
| SLAMF1 | | NM_003037 | 0.246 |
| SLC11A1 | Hs.591607 | NM_000578 | 0.144 |
| SLC14A1 | | NM_001308278, NM_015865, NM_001146036, NM_001128588, NM_001308279, NM_001146037 | 0.243 |
| SLC16A1 | Hs.75231 | NM_003051, NM_001166496 | 0.18 |
| SLC1A4 | Hs.654352 | NM_001193493, NM_003038 | 0.246 |
| SLC1A5 | Hs.631582 | NM_005628, NM_001145145, NM_001145144 | 0.218 |
| SLC22A17 | Hs.373498 | NM_001289050, NM_016609, NM_020372 | 0.0366 |
| SLC25A20 | Hs.13845 | NM_000387 | 0.22 |
| SLC27A2 | Hs.11729 | NM_003645, NM_001159629 | 0.0274 |
| SLC29A1 | Hs.25450 | NM_001304463, NM_001078175, NM_001078177, NM_001304465, NM_001304466, NM_001304462 | 0.00562 |
| SLC2A1 | Hs.473721 | NM_006516 | 0.0507 |
| SLC2A3 | Hs.419240 | NM_006931 | 0.192 |
| SLC35F2 | Hs.524014 | NM_017515 | 0.0567 |
| SLC39A1 | Hs.7854 | NM_001271958, NM_001271957, NM_014437, NM_001271959, NM_001271960, NM_001271961 | 0.144 |
| SLC39A14 | Hs.491232 | NM_015359, NM_001135154, NM_001128431, NM_001135153 | 0.156 |
| SLC43A1 | Hs.591952 | NM_003627, NM_001198810 | 0.192 |
| SLC43A3 | Hs.99962 | NM_014096, NM_001278201, NM_199329, NM_017611, NM_001278206 | 0.015 |
| SLC46A3 | | NM_181785, NM_001135919 | 0.0767 |
| SLCO3A1 | Hs.311187 | NM_013272, NM_001145044 | 0.151 |
| SMAP2 | Hs.15200 | NM_022733, NM_001198978, NM_001198980, NM_001198979 | 0.164 |
| SMTN | | NM_134270, NM_006932, NM_134269, NM_001207018, NM_001207017 | 0.162 |
| SMYD5 | Hs.631882 | NM_006062 | 0.246 |
| SNAI2 | Hs.360174 | NM_003068 | 0.0502 |
| SNTB1 | Hs.46701 | NM_021021 | 0.162 |
| SNTG1 | | NM_001287813, NM_018967, NM_001287814 | 0.0585 |
| SORD | | NM_003104 | 0.0455 |
| SPATA7 | | NM_018418, NM_001040428 | 0.0965 |
| SPATS2L | Hs.120323, Hs.734045 | NM_001282735, NM_015535, NM_001100422, NM_001282743, NM_001100424, NM_001100423, NM_001282744 | 0.061 |
| SPINK2 | | NM_021114, NM_001271718, NM_001271720, NM_001271722, NM_001271721 | 0.0642 |
| SPINT1 | Hs.233950 | NM_003710, NM_001032367, NM_181642 | 0.246 |
| SPSB3 | Hs.592080 | NM_080861 | 0.122 |
| SQLE | Hs.71465 | NM_003129 | 0.0502 |
| SREK1IP1 | Hs.69504 | NM_173829 | 0.163 |
| SSBP3 | Hs.733025 | NM_145716, NM_001009955, NM_018070 | 0.0112 |
| SSH1 | | NM_018984, NM_001161330, NM_001161331 | 0.163 |
| SSR2 | | NM_003145 | 0.0544 |
| ST6GALNAC2 | Hs.592105 | NM_006456 | 0.224 |
| ST8SIA1 | Hs.408614 | NM_003034 | 0.0699 |
| STAMBP | Hs.469018, Hs.732857 | NM_213622, NM_006463, NM_201647 | 0.11 |
| STAP1 | Hs.435579 | NM_012108 | 0.0685 |
| STAT6 | Hs.524518 | NM_003153, NM_001178078, NM_001178081, NM_001178079, NM_001178080 | 0.158 |
| STIL | Hs.525198, Hs.673209 | NM_001282936, NM_003035, NM_001048166, NM_001282937, NM_001282939, NM_001282938 | 0.205 |

TABLE 20-continued

Exemplary biomarkers for predicting patient response to CAR therapy

| Gene | Unigene | Accession No. | FDR |
|---|---|---|---|
| STIP1 | Hs.337295, Hs.618350 | NM_001282652, NM_006819, NM_001282653 | 0.223 |
| STK38 | Hs.409578 | NM_001305102, NM_007271 | 0.0924 |
| STMN3 | | NM_015894, NM_001276310 | 0.0735 |
| STOM | | NM_004099, NM_001270526, NM_198194, NM_001270527 | 0.112 |
| STX1A | Hs.647024 | NM_004603, NM_001165903 | 0.222 |
| STX6 | Hs.518417 | NM_005819, NM_001286210 | 0.236 |
| SV2A | Hs.516153 | NM_014849 | 0.216 |
| SVIL | Hs.499209 | NM_003174, NM_021738 | 0.243 |
| SYT1 | Hs.310545 | NM_001135805, NM_005639, NM_001291901, NM_001135806 | 0.0645 |
| SYTL1 | | NM_032872, NM_001193308 | 0.23 |
| SYTL2 | Hs.369520 | NM_206929, NM_206930, NM_001162951, NM_001162952, NM_001289610, NM_001289608, NM_032943, NM_001162953 | 0.0502 |
| SYTL3 | | NM_001242395, NM_001009991, NM_001242384, NM_001242394 | 0.129 |
| TAF7 | Hs.438838 | NM_005642 | 0.0836 |
| TARP | | | 0.22 |
| TARS | | NM_001258437, NM_152295, NM_001258438 | 0.158 |
| TBCC | | NM_003192 | 0.246 |
| TBX15 | Hs.146196 | NM_152380 | 0.00865 |
| TCEAL4 | | NM_001300901, NM_024863, NM_001006935, NM_001006937 | 0.0594 |
| TCF7 | | NM_003202, NM_201634, NM_001134851, NM_213648, NM_201632 | 0.114 |
| TERT | Hs.492203 | NM_198253, NM_001193376 | 0.0311 |
| TGFB1 | Hs.645227 | NM_000660 | 0.12 |
| TGFBR3 | | NM_001195684, NM_001195683, NM_003243 | 0.188 |
| TIGIT | Hs.421750 | NM_173799 | 0.234 |
| TJP3 | Hs.25527 | NM_001267560, NM_001267561 | 0.248 |
| TLE4 | | NM_007005, NM_001282760, NM_001282748, NM_001282749, NM_001282753 | 0.0302 |
| TMEM194A | | | 0.106 |
| TMEM212 | Hs.642307 | NM_001164436 | 0.102 |
| TMEM48 | | | 0.171 |
| TMEM5 | Hs.216386 | NM_014254, NM_001278237 | 0.178 |
| TMEM71 | Hs.293842 | NM_144649, NM_001145153 | 0.234 |
| TMEM80 | | NM_001042463, NM_174940, NM_001276274, NM_001276253 | 0.246 |
| TMEM9B | | NM_001286094, NM_020644, NM_001286095 | 0.192 |
| TMPRSS6 | Hs.370885 | NM_153609, NM_001289001, NM_001289000 | 0.0585 |
| TNFAIP1 | Hs.76090 | NM_021137 | 0.167 |
| TNFRSF11A | | NM_001270951, NM_003839, NM_001278268, NM_001270949, NM_001270950 | 0.0605 |
| TNFRSF18 | Hs.212680 | NM_148901, NM_004195, NM_148902 | 0.0366 |
| TNFRSF25 | Hs.462529 | NM_148967, NM_148970, NM_148966, NM_003790, NM_148965 | 0.163 |
| TNFRSF4 | Hs.129780 | NM_003327 | 0.0337 |
| TNFRSF8 | Hs.1314 | NM_001243, NM_001281430 | 0.106 |
| TNFRSF9 | Hs.86447 | NM_001561 | 0.0524 |
| TOX2 | Hs.26608 | NM_001098797, NM_001098796, NM_032883, NM_001098798 | 0.0107 |
| TP53INP2 | Hs.516994 | NM_021202 | 0.139 |
| TPCN1 | Hs.524763 | NM_017901, NM_001143819, NM_001301214 | 0.181 |
| TPK1 | Hs.660232 | NM_022445, NM_001042482 | 0.24 |
| TPMT | Hs.444319 | NM_000367 | 0.232 |
| TRAPPC6A | | NM_024108, NM_001270893, NM_001270891, NM_001270892 | 0.0638 |
| TRIB1 | Hs.444947 | NM_025195, NM_001282985 | 0.074 |
| TRIB2 | Hs.467751 | NM_021643 | 0.0181 |
| TRIM25 | Hs.528952 | NM_005082 | 0.143 |
| TRIP10 | Hs.515094 | NM_004240, NM_001288962, NM_001288963 | 0.149 |
| TRPM3 | | NM_001007471, NM_020952, NM_206946, NM_206945, NM_001007470, NM_206948, NM_024971, NM_206944, NM_206947 | 0.195 |
| TSPAN18 | Hs.385634 | NM_130783 | 0.129 |
| TSPAN32 | | NM_139022 | 0.0502 |
| TTC21B | Hs.310672 | NM_024753 | 0.243 |
| TTC39C | Hs.733420 | NM_153211, NM_001243425, NM_001135993, NM_001292030 | 0.00494 |
| TTLL4 | Hs.471405 | NM_014640 | 0.158 |
| TUBB | Hs.636480 | NM_001293213, NM_178014, NM_001293215, NM_001293216, NM_001293212 | 0.236 |
| TUBB2B | Hs.300701 | NM_178012 | 0.0386 |

TABLE 20-continued

Exemplary biomarkers for predicting patient response to CAR therapy

| Gene | Unigene | Accession No. | FDR |
|---|---|---|---|
| TUBB6 | Hs.193491, Hs.744066 | NM_001303524, NM_032525, NM_001303529, NM_001303526, NM_001303525 | 0.00952 |
| UBA52 | Hs.5308 | NM_003333, NM_001033930 | 0.0902 |
| UBASH3B | Hs.444075 | NM_032873 | 0.0666 |
| UBL3 | Hs.145575 | NM_007106 | 0.0929 |
| UHRF1BP1L | Hs.620701 | NM_015054, NM_001006947 | 0.0666 |
| UNC119 | Hs.410455 | NM_005148, NM_054035 | 0.168 |
| URGCP | Hs.663312 | NM_017920, NM_001077664, NM_001290075, NM_001290076, NM_001077663 | 0.141 |
| USP22 | Hs.462492 | NM_015276 | 0.0745 |
| USP25 | | NM_013396, NM_001283042, NM_001283041 | 0.232 |
| USP51 | Hs.40061 | NM_201286 | 0.186 |
| UXS1 | Hs.730756 | NM_001253875, NM_025076, NM_001253876 | 0.167 |
| UXT | | NM_004182, NM_153477 | 0.0826 |
| VDAC3 | | NM_001135694, NM_005662 | 0.158 |
| VDR | Hs.524368 | NM_001017535, NM_001017536, NM_000376 | 0.124 |
| VIPR1 | Hs.348500, Hs.683175 | NM_001251882, NM_001251885, NM_004624, NM_001251883, NM_001251884 | 0.0642 |
| VNN2 | Hs.293130, Hs.740120 | NM_004665, NM_078488, NM_001242350 | 0.129 |
| VSIG1 | Hs.177164 | NM_182607, NM_001170553 | 0.0709 |
| WASF2 | Hs.469244 | NM_006990, NM_001201404 | 0.137 |
| WEE1 | | NM_003390, NM_001143976 | 0.0594 |
| WIPI1 | Hs.463964 | NM_017983 | 0.171 |
| WNT10A | Hs.121540 | NM_025216 | 0.0502 |
| XYLT1 | Hs.22907 | NM_022166 | 0.0278 |
| YPEL1 | | NM_013313 | 0.195 |
| YWHAG | Hs.744840 | NM_012479 | 0.0783 |
| ZBP1 | Hs.302123 | NM_001160417, NM_030776, NM_001160418, NM_001160419 | 0.218 |
| ZBTB20 | | NM_001164343, NM_001164347, NM_001164345, NM_001164342, NM_015642, NM_001164344, NM_001164346 | 0.00562 |
| ZBTB32 | Hs.99430, Hs.736841 | NM_014383 | 0.0128 |
| ZC3H12A | Hs.656294 | NM_025079 | 0.198 |
| ZC3H12C | Hs.376289 | NM_033390 | 0.0628 |
| ZC3H12D | | NM_207360 | 0.0709 |
| ZEB2 | Hs.34871 | NM_014795, NM_001171653 | 0.0594 |
| ZFP161 | | | 0.0965 |
| ZFP36L2 | Hs.503093 | NM_006887 | 0.218 |
| ZHX2 | Hs.377090 | NM_014943 | 0.144 |
| ZNF267 | | NM_003414 | 0.127 |
| ZNF282 | Hs.729056 | NM_003575, NM_001303481 | 0.121 |
| ZNF506 | | NM_001099269, NM_001145404 | 0.195 |
| ZNF587 | Hs.744891 | NM_032828, NM_001204817 | 0.236 |
| ZNF652 | | NM_014897, NM_001145365 | 0.0429 |
| ZNF688 | | NM_145271, NM_001024683 | 0.229 |
| ZNF704 | Hs.434957, Hs.730558 | NM_001033723 | 0.215 |
| ZNRF1 | Hs.427284 | NM_032268 | 0.164 |

Example 3: Prognostic Flow Cytometry-Based Assays

Prognostic flow cytometry-based assays are developed to screen subjects with cancer (e.g., patients with a hematological cancer such as ALL and CLL) for CAR-expressing cell (e.g., T cell, NK cell) therapy, e.g., CD19 CAR-expressing cell therapy as described herein such as, e.g., CTL019 therapy. In some embodiments, subjects are participating in clinical trials.

A sample (e.g., a blood sample) is isolated from a patient and a fluorescent flow cytometry-based assay is performed screening for one or more cell surface or secreted biomarkers described in Examples 1 and 2. An exemplary list of markers that are measured, e.g., by flow cytometry if cell surface-expressed, or by ELISA if secreted, and whose expression values predict patient response to CAR-expressing cell (e.g., T cell, NK cell) therapy, e.g., CD19 CAR-expressing cell therapy as described herein such as, e.g., CTL019 therapy includes, but is not limited to, genes listed in Table 8.

TABLE 8

Exemplary markers measured that predict patient response to CAR-expressing cell therapy

| Gene | Unigene | Accession No. |
|---|---|---|
| ATP1B3 | Hs.477789 | NM_001679 |
| CCL17 | Hs.546294 | NM_002987 |

TABLE 8-continued

Exemplary markers measured that predict patient response to CAR-expressing cell therapy

| Gene | Unigene | Accession No. |
|---|---|---|
| CCL3 | Hs.514107 | NM_002983 |
| CCL4 | Hs.75703 | NM_002984 |
| CCR1 | Hs.301921 | NM_001295 |
| CD40LG | Hs.592244 | NM_000074 |
| CD58 | Hs.34341 | NM_001144822, NM_001779 |
| CD70 | Hs.715224, Hs.501497 | NM_001252 |
| CD80 | Hs.838 | NM_005191 |
| CSF1 | Hs.591402 | NM_000757, NM_172212, NM_172211, NM_172210 |
| FCER2 | Hs.465778 | NM_002002 |
| GPR56 | Hs.513633 | NM_001145773, NM_001145774, NM_001145771, NM_001145772, NM_005682, NM_201525, NM_001145770 |
| HAVCR1 | Hs.129711 | NM_001099414, NM_012206 |
| HLA-DMA | Hs.351279 | NM_006120 |
| HLA-DPA1 | Hs.347270 | NM_033554 |
| HLA-DRA | Hs.520048 | NM_019111 |
| HLA-DRB1 | Hs.716081, Hs.696211, Hs.723344, Hs.534322 | NM_002124, NM_021983, XM_002346251 |
| HLA-DRB5 | Hs.534322 | NM_002125 |
| ICAM3 | Hs.654563 | NM_002162 |
| IFNAR2 | Hs.708195 | NM_207584, NM_207585, NM_000874 |
| IFNG | Hs.856 | NM_207585 |
| IGF1R | Hs.643120, Hs.714012 | NM_000875 |
| IL10 | Hs.193717 | NM_000572 |
| IL13 | Hs.845 | NM_002188 |
| IL15RA | Hs.524117 | NM_002189, NM_172200 |
| IL21 | Hs.567559 | NM_021803 |
| IL2RA | Hs.231367 | NM_000417 |
| IL2RB | Hs.474787 | NM_000878 |
| IL3 | Hs.694 | NM_000588 |
| IL4 | Hs.73917 | NM_000589, NM_172348 |
| IL5 | Hs.2247 | NM_000879 |
| IL6ST | Hs.532082 | NM_002184, NM_175767 |
| IL9 | Hs.960 | NM_000590 |
| ITGA6 | Hs.133397 | NM_000210, NM_001079818 |
| KIT | Hs.479754 | NM_000222, NM_001093772 |
| LAIR1 | Hs.572535 | NM_001289023, NM_001289025, NM_001289026, NM_001289027, NM_002287, NM_021706 |
| NFATC1 | Hs.534074, Hs.701518 | NM_001278669, NM_001278670, NM_001278672, NM_001278673, NM_001278675, NM_006162, NM_172387, NM_172388, NM_172389, NM_172390 |
| SELL | Hs.728756 | NM_000655 |
| SELP | Hs.73800 | NM_003005 |
| SIRPG | Hs.590883 | NM_001039508, NM_018556, NM_080816 |
| STAT6 | Hs.524518 | NM_001178078, NM_001178079, NM_001178080, NM_001178081, NM_003153 |
| TFRC | Hs.529618 | NM_001128148, NM_003234 |
| TIMD4 | Hs.334907 | NM_001146726, NM_138379 |
| TNFRSF1B | Hs.256278 | NM_001066 |
| TNFRSF9 | Hs.86447, Hs.738942 | NM_001561 |

Example 4: Classifiers to Predict Class Membership

Based on the biological understanding, combinations of genes from unbiased feature selection, gene sets, and selected genes of interest are used to further differentiate complete responders from partial responders and non-responders. In an embodiment, combinations of genes from unbiased feature selection, gene sets, and selected genes of interest are used to further differentiate relapsers from non-relapsers. In an embodiment, classifiers are built based on all genes to predict class membership. In an embodiment, predictions of class membership further differentiate NR's, PR's, and CR's. In an embodiment, predictions of class membership further differentiate relapsers from non-relapsers. Alternatively or additionally, a classifier is built which uses a subset of predetermined significant features. Significant features include, but are not limited to, enriched meta-gene, a subset of significantly differentially expressed genes in the meta-genes, and combinations thereof.

Example 5: Cytokine Expression Signatures Predictive of CAR-Expressing Cell Potency The present example describes the identification of exemplary cytokine expression signatures that predict patient response to CAR-expressing cell (e.g., T cell, NK cell) therapy (e.g., a CD19 CAR-expressing cell (e.g., T cell, NK cell) therapy, e.g., a CTL019 therapy) in Chronic Lymphoid Leukemia (CLL) and Acute Lymphoblastic Leukemia (ALL), for use in accordance with the present invention.

Among other things, the present Example describes novel cytokine expression signatures that predict the potency of manufactured CAR-expressing cell (e.g., T cell, NK cell) cell products based on secreted cytokine profiles following activation in vitro.

In an embodiment, novel cytokine expression signatures described herein predict the potency of manufactured CAR-expressing cell (e.g., T cell, NK cell) products to kill target tumor cells.

In an embodiment, novel cytokine expression signatures described herein are correlated with patient response to CAR-expressing cell (e.g., T cell, NK cell) therapy (e.g. CD19 CAR-expressing cell (e.g., T cell, NK cell) therapy, e.g., a CTL019 CAR-expressing cell therapy) in CLL to improve the CAR-expressing cell product prior to infusion in patients.

In an embodiment, novel cytokine expression signatures described herein are used to assess manufactured CAR-expressing cell (e.g., T cell, NK cell) products (e.g., CD19 CAR-expressing cell products, e.g., CTL019 product). In an embodiment, novel cytokine expression signatures described herein provide an endpoint in manufacturing process optimization.

Novel cytokine expression signatures based on cytokine protein expression levels in manufactured CD19 CAR-expressing cell (e.g., T cell, NK cell) product samples prior to re-infusion have been identified that predict patient response to CD19 CAR-expressing cell (e.g., T cell, NK cell) therapy in Chronic Lymphoid Leukemia (CLL). The identified signatures were discovered in a cytokine protein expression study of manufactured product samples prepared from 21 CLL subject samples. CLL subject samples (21 total) were stratified as follows: CTL019 manufactured product was derived from 6 patients that were complete responders (CRs) to CTL019 therapy, 5 patients that were partial responders (PRs), and 10 non-responders (NRs). Several cytokine expression signatures discriminating responders from non-responders in manufactured product were discovered using a Luminex® panel of 13 cytokines.

The potency of CTL019 manufactured products from 21 CLL patients were assessed in a tumor cell killing assay. Briefly, manufactured CTL019 products were "activated" in vitro by CD19-expressing K562 (K562-19 cells). Without wishing to be bound by a particular theory, CD19 expressing K562 cells (e.g., K562-19 cells) mimic leukemic CD19 expressing B-cells in CLL patients. CTL019 cells are engineered to identify and kill cells that express CD19 antigen on their cell surface and CTL019-mediated killing of K562-19 cells serves as a proxy for assessing potency of CTL019-mediated killing of tumor cells.

Following CTL019 product activation, cytokine protein expression profiles were measured in the co-cultured media using a Luminex® panel of cytokines. The expression profiles of exemplary cytokines were measured and the potency of CTL019 cell products was correlated with the expression of different cytokines. Exemplary cytokines considered in this analysis are provided in Table 14.

TABLE 14

Exemplary cytokines

| Cytokine | Entrez ID | Official Gene Symbol |
| --- | --- | --- |
| CCL-20/MIP-3a | 6364 | CCL20 |
| GM-CSF | 1437 | CSF2 |
| IFNγ | 3458 | IFNG |
| IL-10 | 3586 | IL10 |
| IL-13 | 3596 | IL13 |
| IL-17a | 3605 | IL17A |
| IL-2 | 3558 | IL2 |
| IL-21 | 59067 | IL21 |
| IL-4 | 3565 | IL4 |
| IL-5 | 3567 | IL5 |
| IL-6 | 3569 | IL6 |
| IL-9 | 3578 | IL9 |
| TNFα | 7124 | TNF |

Novel cytokine expression profiles were then discovered using various data analytical approaches including 1) bi-clustering analysis; and 2) univariate analysis.

Figure 17:
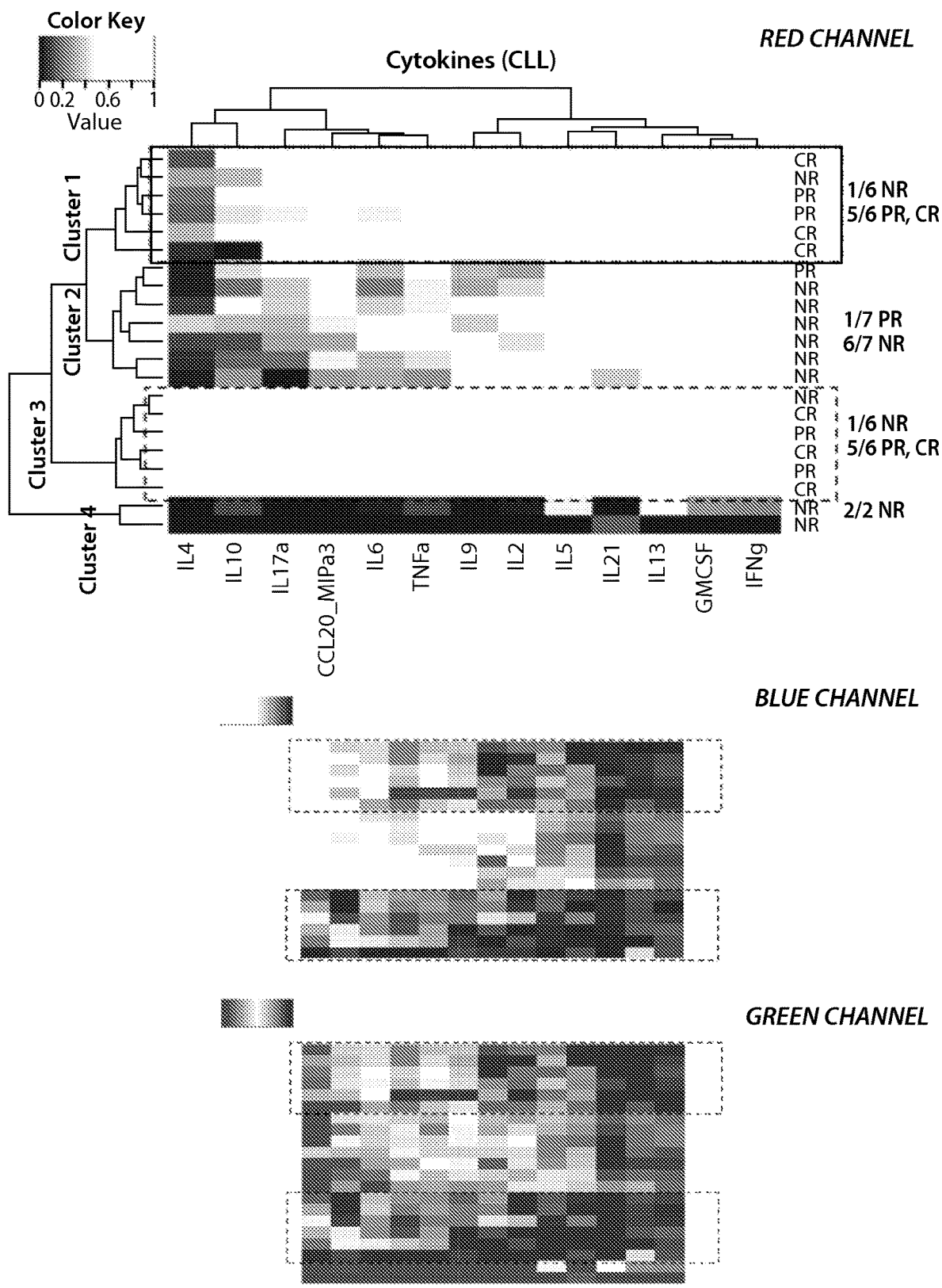
FIG. 17 depicts an exemplary heatmap showing bi-clustering of cytokine expression in stimulated CTL019 products and CLL patients. Two clusters (Cluster 1 and Cluster 3) were almost exclusively comprised of CRs and PRs, whereas the other two clusters (Cluster 2 and Cluster 4) contained predominantly NRs. On average, cytokine expression levels were higher in CRs/PRs versus NRs. The top panel shows the red channel of the heatmap image, the center panel shows the blue channel, and the bottom panel shows the green channel.

Cytokine expression data derived from the Luminex® assay were log-normalized and subjected to bi-clustering analyses (hierarchical clustering was performed using the complete linkage method). Bi-clustering analyses of cytokine expression in stimulated CTL019 products and CLL patients yield four major clusters (a cut-off distance≤1.0, resulted in 4 clusters as shown in FIG. 17) and distinct subgroups of CRs/PRs and NRs were identified. An exemplary heatmap of bi-clustering of cytokine expression in stimulated CTL019 products and CLL patients is shown in FIG. 17. Surprisingly, two clusters (Cluster 1 and Cluster 3) were almost exclusively comprised of CRs and PRs, whereas the other two clusters (Cluster 2 and Cluster 4) contained predominantly NRs. On average, cytokine expression levels were higher in CRs/PRs versus NRs (FIG. 17).

Next, a 3-group univariate analysis using ANOVA (analysis of variance) was performed that compared CRs versus PRs versus NRs. Statistical significance was determined using a p-value cut-off of 0.05. Statistical significance (e.g., p-values) of different cytokines to distinguish CRs, PRs and NRs are listed in Table 15.

TABLE 15

Statistical significance of different cytokines to distinguish
CRs, PRs and NRs in a 3-group univariate analysis using ANOVA

| Cytokine | p-value |
| --- | --- |
| CCL20/MIP3a | 0.001838 |
| IL-17a | 0.001857 |
| IL-6 | 0.006017 |
| TNFα | 0.013499 |
| IL-2 | 0.034397 |
| IL-21 | 0.055684 |
| IL-5 | 0.075396 |
| IL-10 | 0.08935 |
| IL-9 | 0.098761 |
| IFNγ | 0.137263 |
| GM-CSF | 0.191839 |
| IL-4 | 0.197774 |
| IL-13 | 0.222134 |

Figure 18:
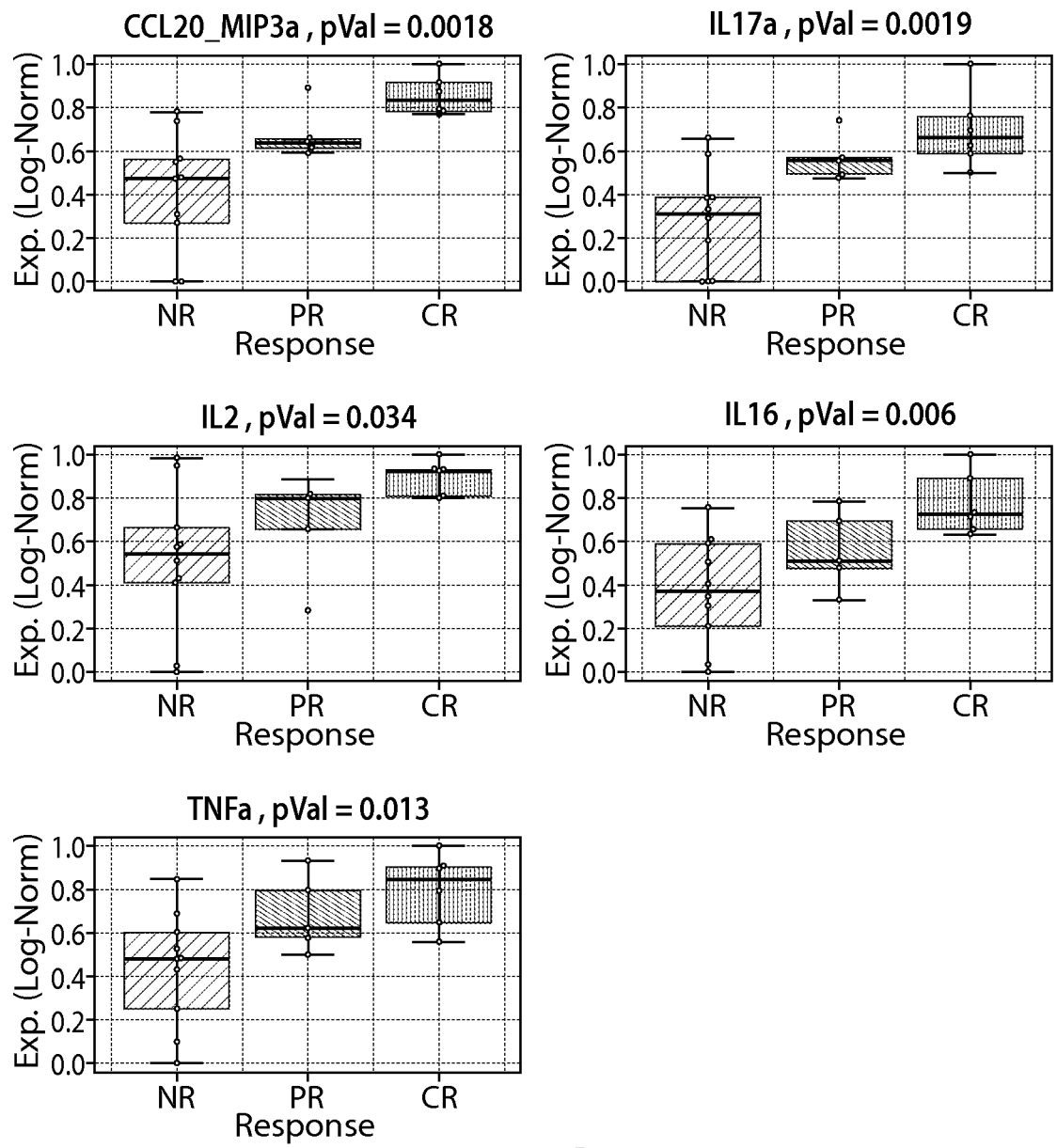
FIG. 18 depicts exemplary results of log-normalized expressions of statistically significant cytokines (e.g., CCL20/MIP3a, IL2, TNFα, IL17a and IL6) to distinguish CRs, PRs and NRs in CLL patients.

The 3-group model of univariate analysis identified 5 cytokines, e.g., IL-17a, CCL-20/MIP3a, IL-6, IL-2, and TNFα, as statistically significant markers of response to CTL019 therapy in CLL patients (FIG. 18 and Table 15). Exemplary results of log-normalized expressions of statistically significant cytokines that distinguish CRs, PRs and NRs in CLL patients are shown in FIG. 18.

Manufactured CTL019 product was evaluated by flow cytometry to determine percentages of CAR+ cells. The 5 cytokines identified in the 3-group model of univariate analysis were further correlated to the percentage of CAR+ cells in each of the manufactured CTL019 products. Exemplary correlation coefficients and corresponding p-values of cytokine expression (derived from Luminex® panel discussed above) and percentages of CAR+ cells (determined by flow cytometery) are provided in Table 16.

TABLE 16

Correlation coefficients and corresponding p-values
of cytokine expression and percentage of CAR+ cells

| Cytokine | Correlation coefficient | p. value |
| --- | --- | --- |
| IL-17a | 0.278349 | 0.221794 |
| IL-10 | 0.390318 | 0.08024 |

TABLE 16-continued

Correlation coefficients and corresponding p-values of cytokine expression and percentage of CAR+ cells

| Cytokine | Correlation coefficient | p. value |
|---|---|---|
| CCL20/MIP3a | 0.395273 | 0.076147 |
| IL-5 | 0.494758 | 0.022598 |
| IL-4 | 0.525982 | 0.014321 |
| TNFα | 0.539276 | 0.011642 |
| GM-CSF | 0.588262 | 0.005032 |
| IL-6 | 0.631841 | 0.002122 |
| IFNγ | 0.660738 | 0.001112 |
| IL-2 | 0.661608 | 0.001089 |
| IL-21 | 0.674378 | 0.0008 |
| IL-9 | 0.70858 | 0.000324 |
| IL-13 | 7.53E−01 | 8.19E−05 |

Figure 21:
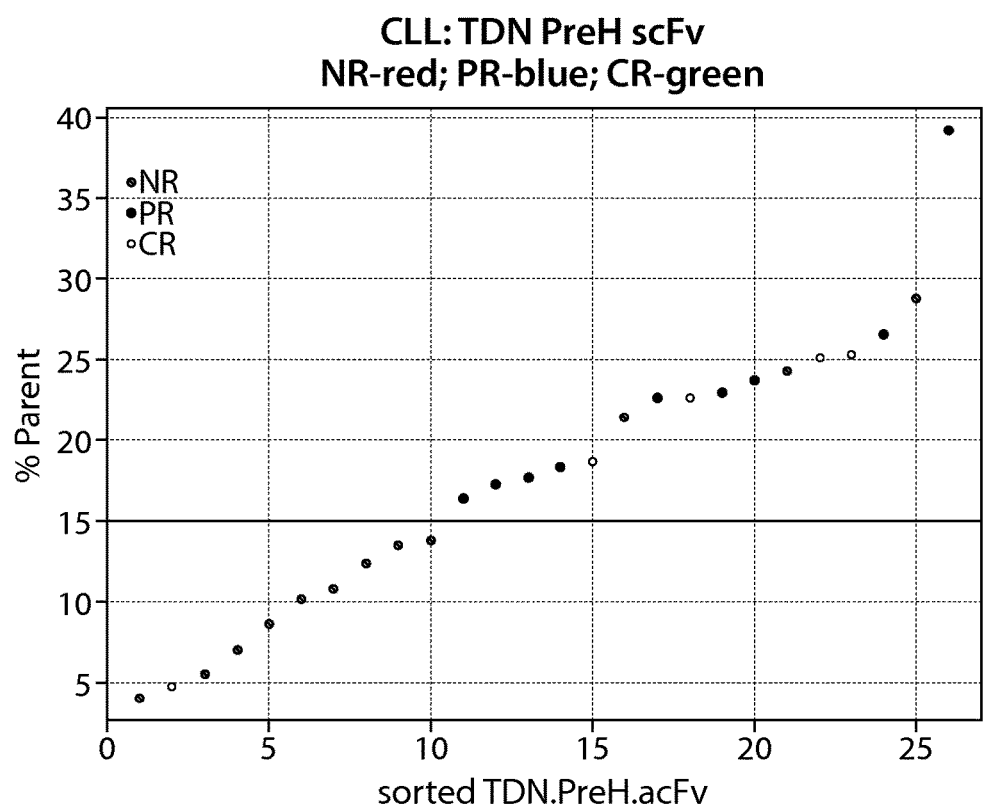
FIG. 21 depicts an exemplary scatter plot showing percent of CAR+ cells (i.e., transduction rate) at pre-harvest for complete responders (CR) in white, partial responders (PR) in black and non-responders (NR) in hatching. Transduction efficiencies were measured pre-harvest and correlated with subject response (e.g., CR, PR, or NR). The solid line represents a 15% transduction efficiency that separates the majority of non-responders from responders. Without wishing to be bound to a particular theory, these data indicate that pre-harvest CAR transduction rate is a marker of response to CAR-expressing cell (e.g., T cell, NK cell) therapy in CLL.

The percentage of CAR+ cells in CTL019 product represents transduction efficiency. In CLL, the percent of CAR+ cells at pre-harvest levels distinguish responders (e.g., complete responders and partial responders) from non-responders (NR). FIG. 21 depicts an exemplary scatter plot showing percent of CAR+ cells (i.e., transduction rate) at pre-harvest for complete responders (CR) in red, partial responders (PR) in blue and non-responders (NR) in red. Transduction efficiencies were measured pre-harvest and correlated with subject response (e.g., CR, PR, or NR). The solid line represents a 15% transduction efficiency that separates the majority of non-responders from responders. Without wishing to be bound to a particular theory, these data indicate that pre-harvest CAR transduction efficiency is a marker of response to CAR-expressing cell (e.g., T cell, NK cell) therapy in CLL.

Figure 19B:
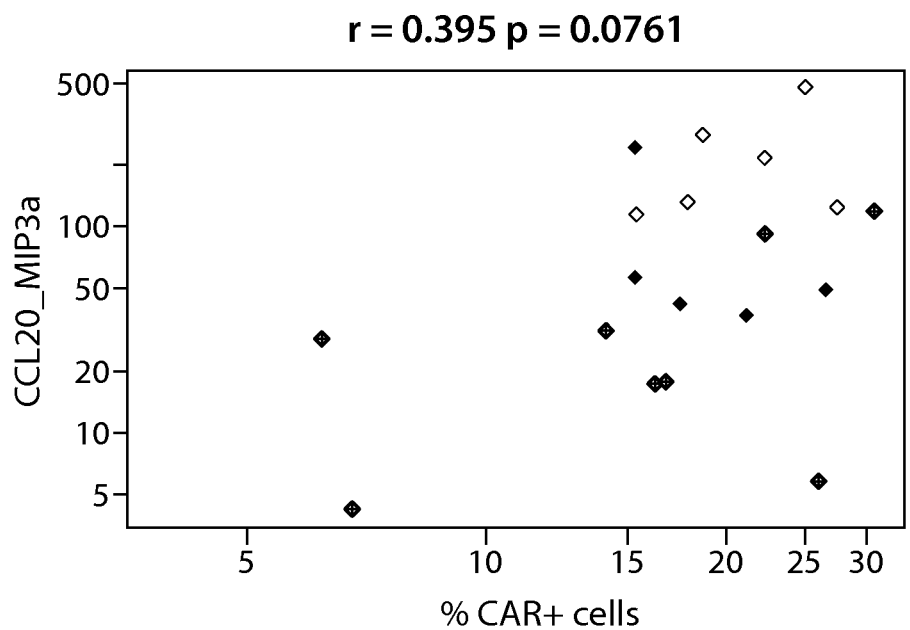
FIG. 19B depicts an exemplary scatter plot showing correlation of CCL20 with percentage of CAR+ cells with a correlation coefficient of 0.395 and corresponding p-value of 0.0761. Each dot represents a CLL patient, and the cross-hatch (NR), black (PR) and white (CR) represent the clinical response. The correlation coefficient is represented by "r" and corresponding p-value for correlation using "p.value".
Figure 19C:
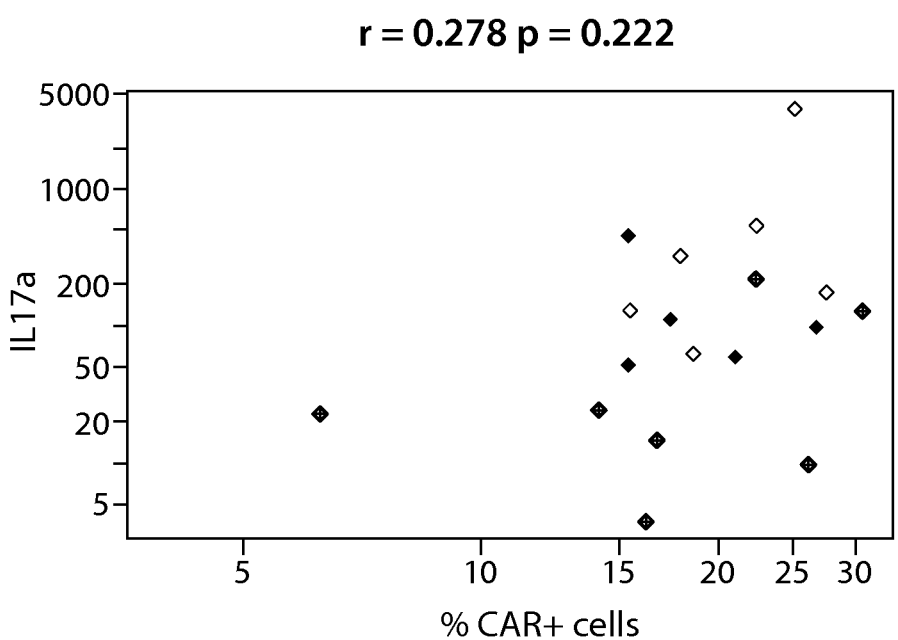
FIG. 19C depicts an exemplary scatter plot showing correlation of IL17a with percentage of CAR+ cells with a correlation coefficient of 0.278 and corresponding p-value of 0.222. Each dot represents a CLL patient, and the cross-hatch (NR), black (PR) and white (CR) represent the clinical response. The correlation coefficient is represented by "r" and corresponding p-value for correlation using "p.value".

Correlation analysis of IL17a with CCL20 cytokine expression was performed, and their association with clinical response was evaluated by scatter plot analyses. FIG. 19A depicts an exemplary scatter plot showing log-normalized correlation of IL17A (y-axis) and CCL20 (x-axis) expression with a correlation coefficient of 0.928 and corresponding p-value of 1.36e-09. Dashed lines represent the classification boundary for separating NRs from CRs/PRs. Each dot in FIG. 19A represents a CLL patient, and the cross-hatch (NR), black (PR) and white (CR) represent the clinical response. Classification boundary in FIG. 19A demonstrates that the combination of IL-17a and CCL20 separates almost all NRs from CRs/PRs, and PRs in turn are clustered separately from CRs. Among other things, these data demonstrate CAR+ cell expression of one or more cytokines listed in Table 16 predict clinical response.

Surprisingly, IL-17a and CCL-20 expression levels were not correlated with the percentage of CAR+ cells in the CTL019 product (representing transduction efficiency). Without wishing to be bound by a particular theory, these data indicate IL-17a and CCL-20 cytokine expression levels are informative (e.g., predictive of response) with regard to potency of a manufactured CAR-expressing cell (e.g., T cell, NK cell) product, e.g., a manufactured CD19 CAR-expressing cell product, in several ways. First, cytokine signatures are correlated with patient response to CTL019 CAR-expressing cell therapy in CLL. Therefore, cytokine signatures described herein can be used to improve and/or modify CAR-expressing cell (e.g., T cell, NK cell) product (e.g., a CD19 CAR-expressing cell product such as, e.g., CTL019) prior to infusion in patients, for greater clinical efficacy. Second, cytokine signatures described herein can be used to assess manufactured CAR-expressing cell (e.g., T cell, NK cell) products thereby providing, among other things, an end point in manufacturing process optimization.

In an embodiment, cytokine signatures described herein define the potency of a CAR-expressing cell (e.g., T cell, NK cell) product. In an embodiment, cytokine signatures described herein are markers of response to a CAR-expressing cell (e.g., T cell, NK cell) product in a hematological cancer (e.g., CLL or ALL).

In an embodiment, cytokine signatures described herein predict subject response to a CAR-expressing cell (e.g., T cell, NK cell) product.

In an embodiment, cytokine signatures described in Table 16 predict subject response to a CAR-expressing cell (e.g., T cell, NK cell) product.

In an embodiment, IL-17a and CCL-20 expression levels predict subject response to a CAR-expressing cell (e.g., T cell, NK cell) product.

Example 6: Identification of Factors that Predict Subject Relapse to CD19 CAR-Expressing Cell Therapy in B-Cell Acute Lymphocytic Leukemia (B-ALL)

The present Example describes, among other things, the identification of novel transcriptional gene signatures that predict patient relapse to CD19 CAR-expressing cell (e.g., T cell, NK cell) therapy (e.g., CTL019 therapy) in B cell Acute Lymphocytic Leukemia (B-ALL), for use in accordance with the present invention.

Among other things, the present Example describes novel gene signatures based on mRNA expression levels of selected genes in the patient prior to CD19 CAR-expressing cell (e.g., T cell, NK cell) treatment (e.g., CTL019) (apheresis or bone marrow) or in manufactured CD19 CAR-expressing cell (e.g., T cell, NK cell) product samples (e.g., CTL019) prior to re-infusion. In an embodiment, the present example describes novel gene signatures that discriminate relapsers to CTL019 therapy in B-ALL from non-relapsers to CTL019 therapy in B-ALL.

The present Example describes methods of unbiased feature selection to discover novel gene signatures that predict subject relapse to CD19 CAR-expressing cell (e.g., T cell, NK cell) therapy (e.g., CTL019) in B-ALL, for use in accordance with the present invention.

The present Example also describes methods of Gene Set Analysis to discover novel gene signatures, for use in accordance with the present invention.

Novel gene signatures based on mRNA expression levels in manufactured CD19 CAR-expressing cell (e.g., T cell, NK cell) product samples prior to re-infusion were identified that predict subject relapse to CD19 CAR-expressing cell (e.g., T cell, NK cell) therapy in B cell Acute Lymphocytic Leukemia (B-ALL). The identified signatures were discovered in a whole genome RNAseq study of manufactured product samples which included 7 B-ALL subject samples. B-ALL subject samples (7 total) were stratified as follows: biological samples were taken from 4 subjects who did not relapse ("non-relapsers") following CTL019 therapy, and 3 subjects who did relapse ("relapsers") following CTL019 therapy. Several gene signatures discriminating responders from non-responders, and relapsers from non-relapsers, in manufactured product samples were discovered and are described further in detail below.

Novel gene signatures were then discovered using various data analytical approaches: 1) unbiased feature selection; 2) gene set analysis; and 3) differential expression analysis of selected genes of interest.

Figure 2B:
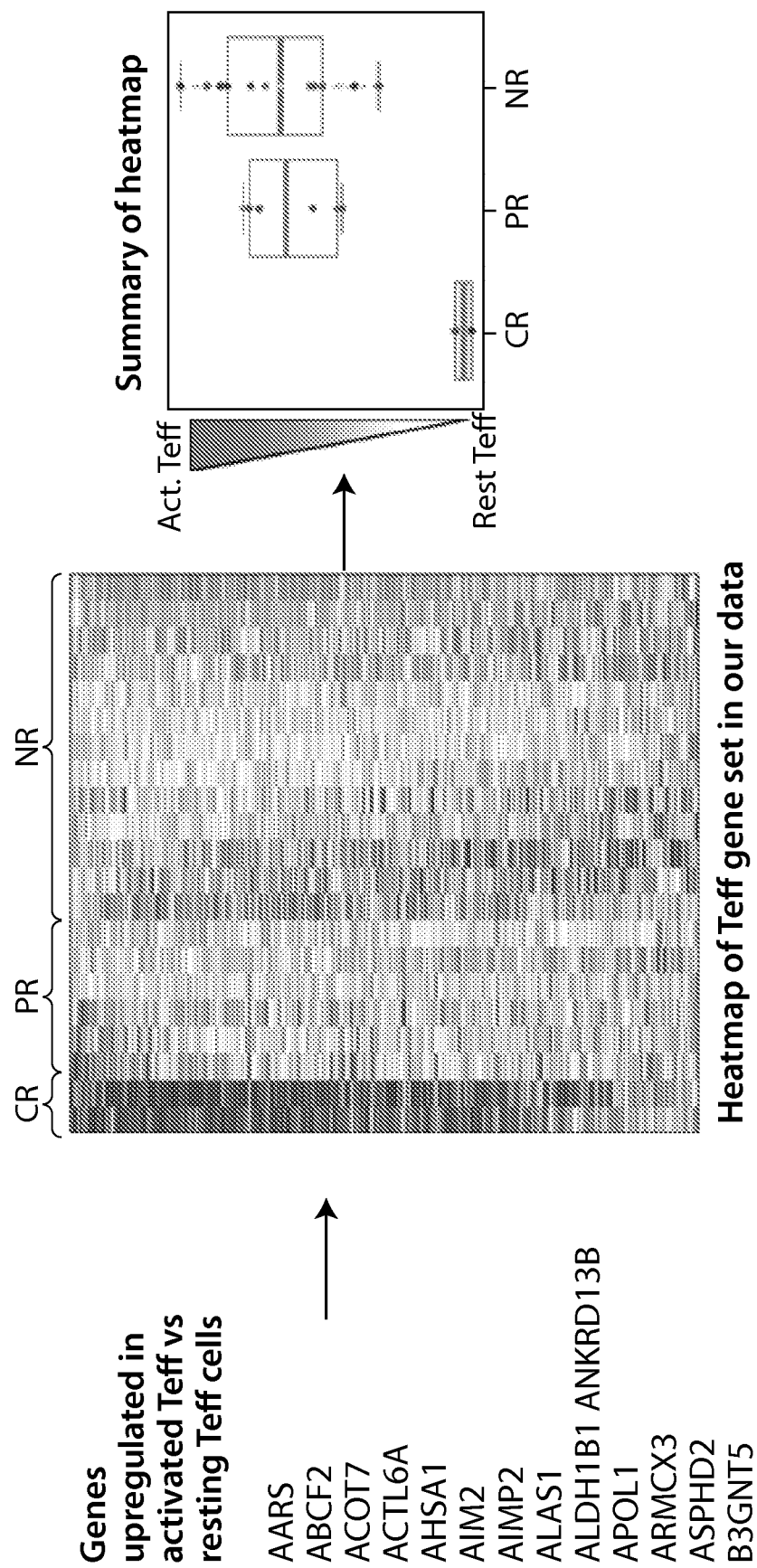
FIG. 2B is an exemplary schematic illustrating an overview of the analysis. Briefly, for each gene set, a 3-group statistical model was applied to determine whether the meta-gene was statistically different between the CLL product CRs, PRs, and NRs. CRs are more like resting $T_{EFF}$ cells, whereas NR are more like activated $T_{EFF}$ cells. CTL019 NR samples are in a more activated state than CR samples.

Novel gene signatures derived from unbiased feature selection were discovered by determining which genes were differentially expressed between the 2-group comparison of relapsers and non-relapsers which compared the 3 relapsers to the 4 non-relapsers. Genes were defined as differentially expressed if their differential expression was statistically significant in the 2-group comparison with a FDR p-value cutoff of 0.25. The gene list for the relapser versus non-relapser comparison (N=17) is tabulated in Table 17. 2-group statistical models were applied to determine whether the meta-gene was statistically different between the groups, similar to the approach illustrated in FIG. 2B. FIG. 2B depicts an exemplary heat map of genes upregulated in activated $T_{EFF}$ versus resting $T_{EFF}$ cells for complete responders (CR), partial responders (PR), and non-responders (NR).

Without wishing to be bound by a particular theory, these data indicate that the differentiation state of T cells in CD19 CAR-expressing cell (e.g., T cell, NK cell) product (e.g., CTL019) correlate with subject response (i.e., CR, PR, or NR) and predict subject relapse to CD19 CAR-expressing cell (e.g., T cell, NK cell) therapy (e.g., CTL019 therapy) in B-ALL. As described in Example 1, complete responders gene signatures are more like resting $T_{REG}$ and $T_{EFF}$ cells. Among other things, gene signatures for relapsers (e.g., a complete responder that relapses to CTL019 therapy) contain genes upregulated in $T_{REG}$ versus $T_{EFF}$ cells at resting. Without wishing to be bound by a particular theory, these data indicate that relapsers to CAR-expressing cell (e.g., T cell, NK cell) therapy (e.g., CTL019) in B-ALL have higher levels of $T_{REG}$ compared to non-relapsers to CAR-expressing cell (e.g., T cell, NK cell) therapy (e.g., CTL019). FIG. 21 depicts exemplary results illustrating that $T_{REG}$ are differentially enriched in relapsers (R) versus non-relapsers, e.g., relapsers express high levels of $T_{REG}$ genes compared to complete responders (CR) (e.g., non-relapsers). An exemplary publication or sequence number disclosing the sequence of each gene is also given in Table 17, and each publication is incorporated by reference in its entirety, including all nucleic acid and protein sequences therein.

TABLE 17

Exemplary Genes that Predict Patient Relapse to CTL019 Therapy
Table 17

| Gene | miRBase | Unigene | Accession No. | FDR | Exemplary Publication |
|---|---|---|---|---|---|
| MIR199A1 | MI0000242 | | NR_029586.1 | 2.11E−05 | Landgraf et al., Cell 129 (7), 1401-1414 (2007) |
| PPIAL4D | | Hs.730589 | NM_001164261.1 | 3.94E−05 | SEQ ID NO: 102 |
| MIR1203 | MI0006335 | | NR_031607.1 | 4.63E−03 | Marton et al., Leukemia 22 (2), 330-338 (2008) |
| uc021ovp | | | | 6.73E−03 | SEQ ID NO: 103 |
| ITM2C | | Hs.111577 | NM_001012514.2 NM_001012516.2 NM_001287240.1 NM_001287241.1 NM_030926.5 | 1.17E−01 | Yoshida et al., Int. J. Mol. Med. 25 (4), 649-656 (2010) |
| HLA-DQB1 | | Hs.409934 Hs.534322 | NM_001243961.1 NM_001243962.1 NM_002123.4 | 1.17E−01 | Pankuweit et al., Gene 531 (2), 180-183 (2013) |
| TTTY10 | | Hs.461175 | NR_001542.1 | 1.25E−01 | Derrien et al., Genome Res. 22 (9), 1775-1789 (2012) |
| TXLNG2P | | Hs.522863 | NR_045128.1 NR_045129.1 | 2.27E−01 | Prakash et al., PLoS ONE 5 (10), E13284 (2010) |
| MIR4650-1 | MI0017277 | | NR_039793.1 | 2.27E−01 | Persson et al., Cancer Res. 71 (1), 78-86 (2011) |
| KDM5D | | Hs.80358 | NM_001146705.1 NM_001146706.1 NM_004653.4 | 2.27E−01 | Kim et al., J. Am. Soc. Nephrol. 20 (9), 2025-2033 (2009) |
| USP9Y | | Hs.598540 | NM_004654.3 | 2.27E−01 | Luddi et al., N. Engl. J. Med. 360 (9), 881-885 (2009) |
| PRKY | | Hs.584730 | NR_028062.1 | 2.27E−01 | Hogan et al., Clin Med Res 7 (3), 69-84 (2009) |
| RPS4Y2 | | Hs.367761 | NM_001039567.2 | 2.27E−01 | Ye et al., BMC Bioinformatics 13, 134 (2012) |
| RPS4Y1 | | Hs.282376 | NM_001008.3 | 2.27E−01 | Eljaafari et al., J. Immunol. 190 (1), 184-194 (2013) |
| NCRNA00185 | | Hs.138453 Hs.729534 Hs.734681 | NR_001543.3 NR_125733.1 NR_125734.1 NR_125735.1 NR_125736.1 NR_125737.1 | 2.28E−01 | Prakash et al., PLoS ONE 5 (10), E13284 (2010) |

TABLE 17-continued

Exemplary Genes that Predict Patient Relapse to CTL019 Therapy
Table 17

| Gene | miRBase | Unigene | Accession No. | FDR | Exemplary Publication |
|---|---|---|---|---|---|
| SULT1E1 | | Hs.479898 | NM_005420.2 | 2.33E−01 | Xu et al., Mol. Cell. Endocrinol. 369 (1-2), 140-149 (2013) |
| EIF1AY | | Hs.461178 | NM_001278612.1 NM_004681.3 | 2.38E−01 | Luna et al., Biochemistry 52 (52), 9510-9518 (2013) |

Gene set analysis yielded a number of gene signatures predictive of subject relapse to CTL019 therapy in B-ALL. The following genes showed increased levels in relapsers and decreased levels in non relapsers: MIR199A1, MIR1203, uc021ovp, ITM2C, and HLA-DQB1. The following genes showed decreased levels in relapsers and increased levels in non relapsers: PPIAL4D, TTTY10, TXLNG2P, MIR4650-1, KDM5D, USP9Y, PRKY, RPS4Y2, RPS4Y1, NCRNA00185, SULT1E1, and EIF1AY.

In particular, the present Example describes methods of Gene Set Analysis to discover novel gene signatures, for use in accordance with the present invention.

Among other things, the present Example describes novel gene signatures based on Gene Set Analysis, that are predictive of patent relapse to CD19 CAR-expressing cell (e.g., T cell, NK cell) therapy (e.g., CTL019) in B-ALL. Gene set analysis was performed on gene sets described in Table 17, and with gene sets described in Example 2, e.g., gene sets were sourced from (1) additional experiments were based on gene sets by Szabo et al., (disclosed herein); (2) gene sets published by Abbas et al. in Genome Research 2005; and (3) gene sets published by Gattinoni et al. in Nature Medicine 2011. Each of Szabo, Abbas and Gattinoni gene sets are described in detail in Example 2. The gene sets defined by Szabo and considered in this analysis are tabulated in Table 2 of Example 2. The gene sets defined by Abbas and considered in this analysis are tabulated in Table 3 of Example 2. The gene sets defined by Gattinoni and considered in this analysis are tabulated in Table 4 of Example 2.

Each gene set (e.g., B-ALL RNAseq gene sets, Szabo gene sets, Abbas gene sets, and Gattinoni gene sets) was evaluated to determine its association with subject response (i.e., relapser or non-relapser) in the following manner: a meta-gene was calculated for each subject, where the meta-gene score for subject j was defined as $$m_j = \sum_{i=G}^{1} x_{ij} - \mu(x_{.j})/\sigma(x_{.j})$$

where $x_{ij}$ is the expression value of gene i in subject j for a given gene set n=1, ..., G; $\mu(x_{.j})$ is the mean of genes 1, ..., G in subject j; and $\sigma(x_{.j})$ is the standard deviation of genes 1, ..., G in subject j.

Figure 20:
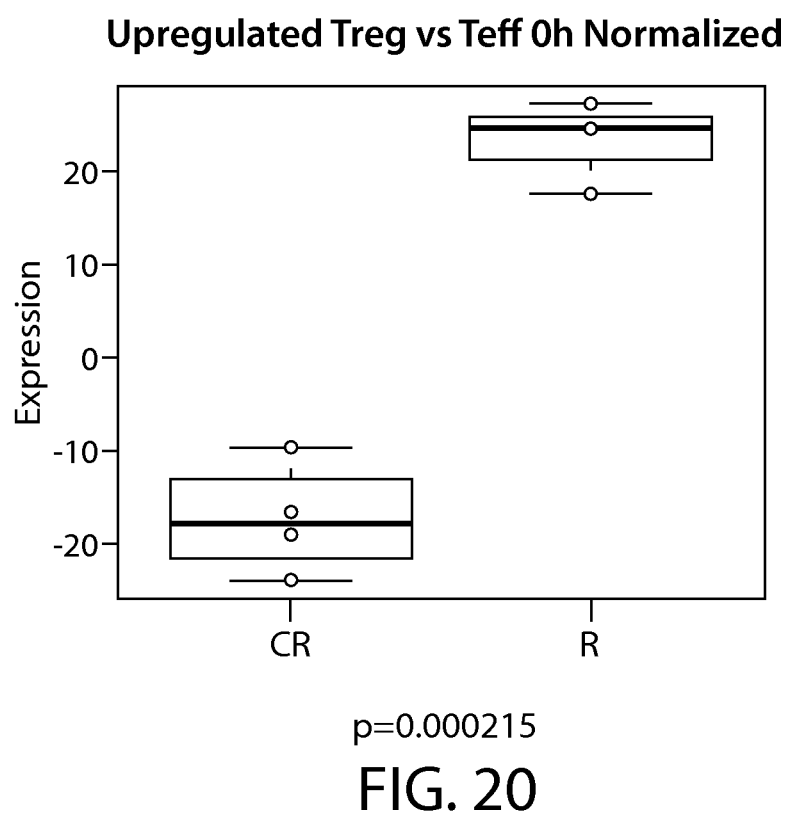
FIG. 20 depicts exemplary results (p=0.000215) illustrating that $T_{REG}$ genes have high expression levels in relapsers (R) compared to non-relapser, complete responders (CR). The x-axis is samples by response group where CR=complete responder and R=relapser. The y-axis is normalized meta-gene expression scores.

A 2-group statistical model was applied to each gene set to determine whether the meta-gene was statistically different between the manufactured CTL019 product of relapsers and non-relapsers. A schematic illustrating this approach is given in FIG. 2B. Of the Szabo, Abbas, and Gattinoni gene sets, there was one gene set that was significantly differentially enriched between relapsers and non-relapsers. This gene set was from the Szabo collection and contains genes upregulated in $T_{REG}$ versus $T_{EFF}$ cells at resting, and correlated with patient relapse to CTL019 therapy. Specifically, this gene set was found to be enriched in relapsers, indicating that relapsers have higher levels of $T_{REGS}$ compared to non-relapsers. For example, the meta-gene score for the gene set comprised of genes upregulated in $T_{REG}$ in comparison to $T_{EFF}$ cells is found to be correlated with patient relapse in product samples (see FIG. 20). FIG. 20 depicts exemplary results (p=0.000215) illustrating that $T_{REG}$ genes have high expression levels in relapsers (R) compared to non-relapser, complete responders (CR). The x-axis is samples by response group where CR=complete responder and R=relapser. The y-axis is normalized meta-gene expression scores.

In an embodiment, gene signatures described herein are used to enable manufactured product improvements, thereby reducing the likelihood of patient relapse. In an embodiment, gene signatures described herein are used to modify therapeutic application of manufactured product, thereby reducing the likelihood of patient relapse.

In an embodiment, gene signatures described herein are identified in a subject prior to CAR-expressing cell (e.g., T cell, NK cell) treatment (e.g., a CD19 CAR-expressing cell treatment, e.g., CTL019 therapy) that predict relapse to CAR-expressing cell (e.g., T cell, NK cell) treatment. In an embodiment, gene signatures described herein are identified in an apheresis sample. In an embodiment, gene signatures described herein are identified in a bone marrow sample. In an embodiment, gene signatures described herein are identified in a manufactured CAR-expressing cell (e.g., T cell, NK cell) product (e.g., a CD19 CAR-expressing cell product, e.g., CTL019) prior to infusion.

Without wishing to be bound by a particular theory, these data indicate that decreasing the $T_{REG}$ signature in the patient prior to apheresis or during manufacturing of the CAR-expressing cell (e.g., T cell, NK cell) product significantly reduces the risk of patient relapse.

Figure 22:
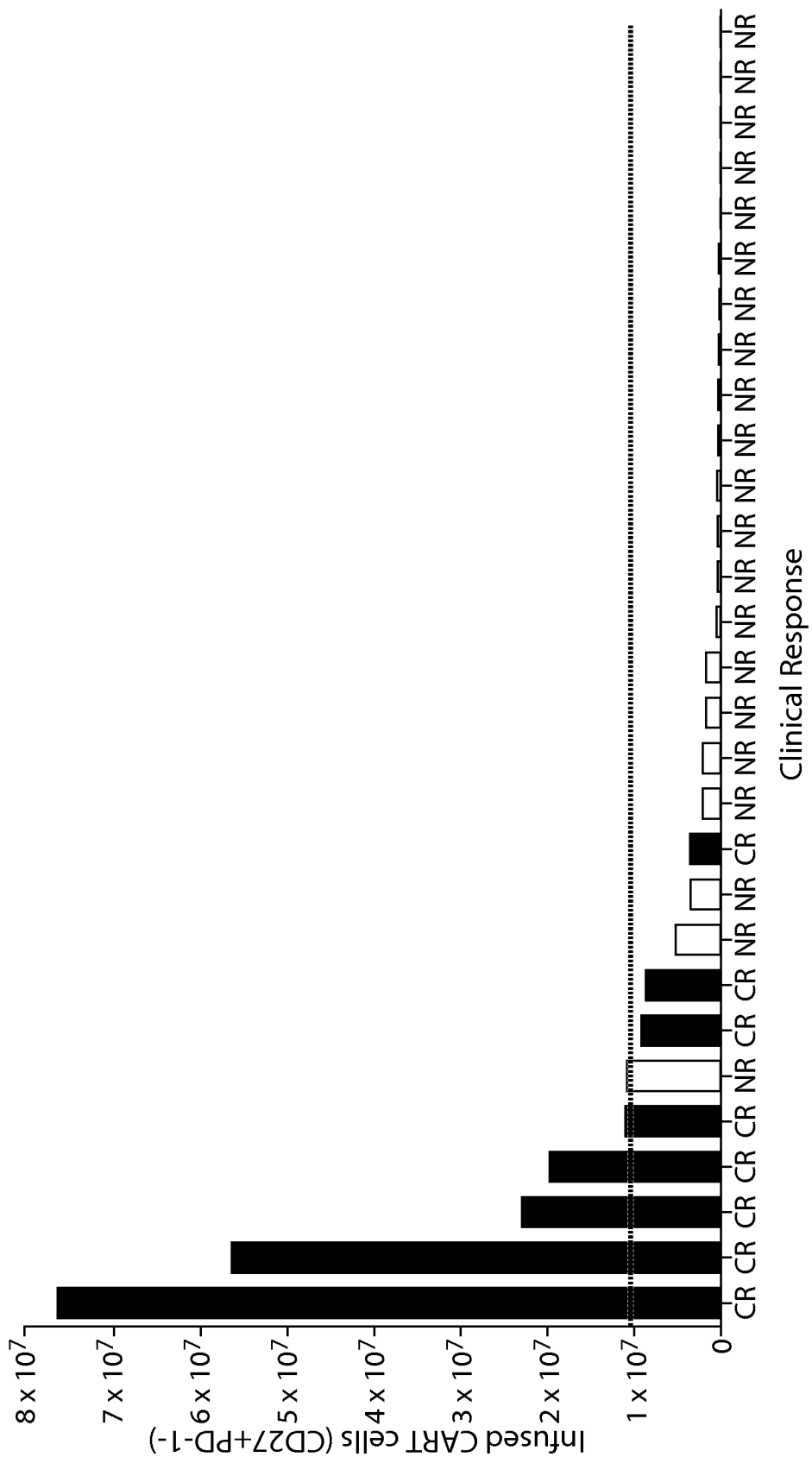
FIG. 22 is a bar graph depicting the relationship between number of CD27+ PD1− CART cells infused and response to therapy.
Figure 23:
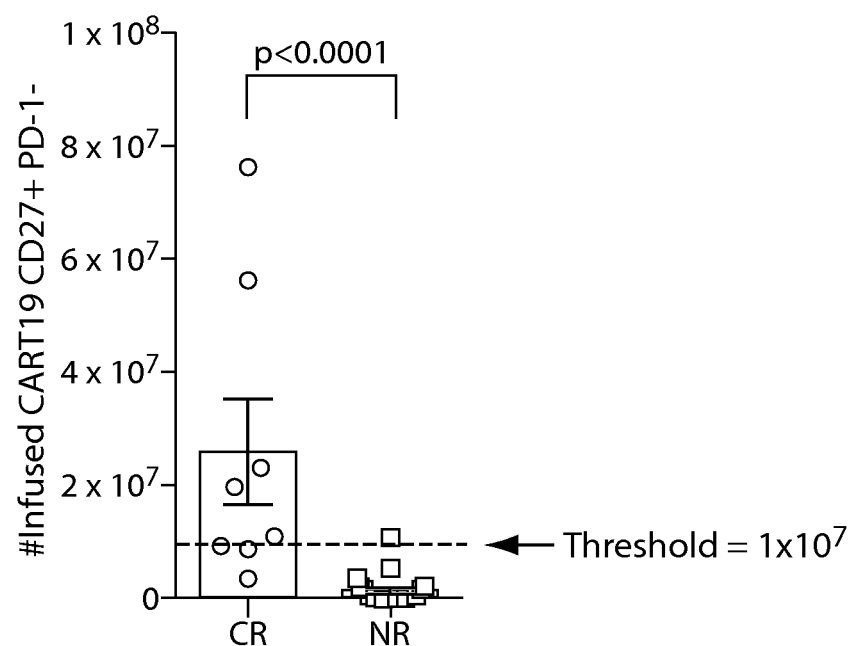
FIG. 23 is a scatter plot depicting the relationship between number of CD27+ PD1− CART cells infused and response to therapy.

Example 7: Quantity of CD27+PD1− CART Cells Infused into Patient Predicts Response to Therapy The number of CD27+PD1− cells in the CTL019 infusion product was determined for 29 CLL patients (8 complete responders and 21 non-responders). The relationship between number of CD27+ PD1− CART cells infused and response to therapy is shown as a bar graph in FIG. 22. and as a scatter plot in FIG. 23. A threshold was set at 1×10$^7$ CART cells per patient. A statistically significant difference (p<0.0001) was observed between the complete responders and non-responders. This experiment shows that complete remission of CLL patients to CART19 immunotherapy is associated with higher numbers of infused CD27+PD1− CART cells.

EQUIVALENTS

Other embodiments of the invention will be apparent to those skilled in the art from a consideration of the specification or practice of the invention disclosed herein. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A method for treating a subject having a cancer with a CD19 chimeric antigen receptor (CAR19)-expressing cell therapy, the method comprising:
   acquiring a value for the level of CD27+ CD45RO− in CD8+ T cells in a sample comprising an immune effector cell population from the subject, wherein an increased level of CD27+ CD45RO− in CD8+ T cells in the sample indicates that the subject is responsive to the CAR19-expressing cell therapy, thereby determining that the subject is responsive to the CAR19-expressing cell therapy; and
   administering to the subject determined to be responsive, a therapeutically effective dose of said CAR19-expressing cell therapy,
   thereby treating the subject.

2. A method for optimizing manufacturing of a CD19 chimeric antigen receptor (CAR19)-expressing cell product comprising:
   acquiring a value for the level of CD27+ CD45RO− in CD8+ T cells in a sample comprising an immune effector cell population from a subject, wherein an increased level of CD27+ CD45RO− in CD8+ T cells in the sample indicates that the immune effector cell population results in a CAR19-expressing cell product having increased potency, thereby determining that the immune effector cell population has increased potency; and
   introducing a nucleic acid encoding CAR19 into the immune effector cell population determined to have increased potency,
   thereby optimizing the manufacture of the CAR19-expressing cell product.

3. The method of claim 1, further comprising identifying the subject as: a responder, a partial responder, a complete responder, a non-responder, a relapser or a non-relapser, based on the level of CD27+ CD45RO− immune effector cells in the sample.

4. The method of claim 1, wherein the level of CD27+ CD45RO− in CD8+ T cells is evaluated using a profile of one or more of gene expression, flow cytometry or protein expression.

5. The method of claim 1, wherein the level of CD27+ CD45RO− in CD8+ T cells is evaluated using a profile or signature indicative of the percentage of CD27+ CD45RO− in CD8+ T cells in the sample.

6. The method of claim 3, wherein the subject identified as being responsive to the therapy is a responder or a complete responder.

7. The method of claim 1, wherein the subject identified as being responsive to the therapy has a greater percentage of CD27+ CD45RO− in CD8+ T cells compared to a reference value.

8. The method of claim 7, wherein the reference value is a value of a non-responder number of CD27+ CD45RO− in CD8+ T cells.

9. The method of claim 1, wherein the CAR19-expressing cell therapy comprises a plurality of CAR19-expressing immune effector cells.

10. The method of claim 1, wherein the CAR19-expressing cell therapy comprises CTL019.

11. The method of claim 1, wherein the value for the level of CD27+ CD45RO− in CD8+ T cells is determined from an apheresis sample acquired from the subject.

12. The method of claim 1, wherein the value for the level of CD27+ CD45RO− in CD8+ T cells is determined from a manufactured CAR19-expressing cell product sample.

13. The method of claim 1, wherein the subject is evaluated prior to, during, or after receiving the CAR19-expressing cell therapy.

14. The method of claim 1, wherein the cancer is associated with CD19 expression.

15. The method of claim 1, wherein the cancer is a hematological cancer.

16. The method of claim 15, wherein the hematological cancer is selected from the group consisting of B-cell acute lymphocytic leukemia (B-ALL), T-cell acute lymphocytic leukemia (T-ALL), acute lymphocytic leukemia (ALL), chronic myelogenous leukemia (CML), chronic lymphocytic leukemia (CLL), B cell promyelocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, and Waldenstrom macroglobulinemia.

17. The method of claim 1, wherein the subject is a human patient.

18. The method of claim 1, wherein the subject receives a treatment prior to the initiation of a CAR19-expressing cell therapy or a treatment post-CAR19-expressing cell therapy.

19. The method of claim 1, wherein the sample comprises a CD4+ or a CD8+ T cell population.

20. The method of claim 11, wherein the apheresis sample is evaluated prior to infusion or re-infusion.

21. The method of claim 2, further comprising a step of enriching for cells having an increased level of $CD27^+$ $CD45RO-$.

22. The method of claim 2, which further comprises a step of depleting $T_{REG}$ cells.

23. The method of claim 2, wherein the level of $CD27_+$ CD45RO− in CD8+ T cells in the CAR-expressing cell product is evaluated following activation in vitro.

24. The method of claim 2, wherein the CAR19-expressing cell product comprises CTL019.

25. The method of claim 2, wherein the manufactured CAR19-expressing cell product is evaluated prior to infusion or re-infusion into the subject.

26. The method of claim 15, wherein the hematological cancer is CLL.

27. The method of claim 1, wherein the sample is from a subject having CLL.

28. The method of claim 7, wherein the subject has 7% or a greater percentage of CD27+ CD45RO− in CD8+ T cells compared to a reference value.

29. The method of claim 2, wherein the immune effector cell population which is determined to result in a CAR19-expressing cell product having increased potency has a greater percentage of CD27+ CD45RO− in CD8+ T cells compared to a reference value.

30. The method of claim 29, wherein the immune effector cell population has 7% or a greater percentage of CD27+ CD45RO− in CD8+ T cells compared to a reference value.

31. The method of claim 29, wherein the reference value is a value of a non-responder number of CD27+ CD45RO− in CD8+ T cells.

* * * * *

UNITED STATES PATENT AND TRADEMARK OFFICE
CERTIFICATE OF CORRECTION

| | |
|---|---|
| PATENT NO. | : 10,774,388 B2 |
| APPLICATION NO. | : 15/517597 |
| DATED | : September 15, 2020 |
| INVENTOR(S) | : Felipe Bedoya et al. |

It is certified that error appears in the above-identified patent and that said Letters Patent is hereby corrected as shown below:

In the Claims

At Column 391, Claim number 21, Line 29, delete "enriching for cells having an increased level $CD27^+$" and insert -- enriching for cells having an increased level CD27+ --.

At Column 392, Claim number 22, Line number 1, delete "The method of claim 2, which further comprises a step of depleting $T_{REG}$ cells" and insert -- The method of claim 2, which further comprises a step of depleting $T_{REG}$ cells --.

Signed and Sealed this
Second Day of April, 2024

Katherine Kelly Vidal
*Director of the United States Patent and Trademark Office*

SEQUENCE LISTING

<160> NUMBER OF SEQ ID NOS: 103

<210> SEQ ID NO 1
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1

```
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt ttcccgaggg tggggagaa ccgtatataa      180
gtgcagtagt cgccgtgaac gttcttttc gcaacgggtt tgccgccaga acacaggtaa     240
gtgccgtgtg tggttcccgc gggcctggcc tctttacggg ttatggccct tgcgtgcctt    300
gaattacttc cacctggctg cagtacgtga ttcttgatcc cgagcttcgg gttggaagtg    360
ggtgggagag ttcgaggcct tgcgcttaag gagccccttc gcctcgtgct tgagttgagg    420
cctggcctgg gcgctgggc cgccgcgtgc gaatctggtg gcaccttcgc gcctgtctcg     480
ctgctttcga taagtctcta gccatttaaa attttgatg acctgctgcg acgcttttt      540
tctggcaaga tagtcttgta aatgcgggcc aagatctgca cactggtatt tcggttttg     600
gggccgcggg cggcgacggg gcccgtgcgt cccagcgcac atgttcggcg aggcggggcc    660
tgcgagcgcg gccaccgaga atcggacggg ggtagtctca agctggccgg cctgctctgg    720
tgcctggcct cgcgccgccg tgtatcgccc cgccctgggc ggcaaggctg gcccggtcgg    780
caccagttgc gtgagcggaa agatggccgc ttcccggccc tgctgcaggg agctcaaaat    840
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttgggggag gggttttatg   1020
cgatggagtt tccccacact gagtgggtgg agactgaagt taggccagct tggcacttga   1080
tgtaattctc cttggaattt gcccttttg agtttggatc ttggttcatt ctcaagcctc   1140
agacagtggt tcaaagtttt tttcttccat ttcaggtgtc gtga                   1184
```

<210> SEQ ID NO 2
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
atggccctgc ctgtgacagc cctgctgctg cctctggctc tgctgctgca tgccgctaga    60
ccc                                                                 63

<210> SEQ ID NO 4
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                   135

<210> SEQ ID NO 6
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

| | | | | | | | | | | | | | | |
|---|---|---|---|---|---|---|---|---|---|---|---|---|---|---|
|Glu|Val|His|Asn|Ala|Lys|Thr|Lys|Pro|Arg|Glu|Gln|Phe|Asn|Ser|
|65| | | |70| | | |75| | | |80| | |

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
              100                 105                 110

Ser Ile Glu Lys Thr Ile Ser Lys Ala Lys Gly Gln Pro Arg Glu Pro
          115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230

<210> SEQ ID NO 7
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
gagagcaagt acggccctcc ctgcccccct tgccctgccc ccgagttcct gggcggaccc      60
agcgtgttcc tgttcccccc caagcccaag gacacccctga tgatcagccg gacccccgag    120
gtgacctgtg tggtggtgga cgtgtcccag gaggaccccg aggtccagtt caactggtac    180
gtggacggcg tggaggtgca caacgccaag accaagcccc gggaggagca gttcaatagc    240
acctaccggg tggtgtccgt gctgaccgtg ctgcaccagg actggctgaa cggcaaggaa    300
tacaagtgta aggtgtccaa caagggcctg cccagcagca tcgagaaaac catcagcaag    360
gccaagggcc agcctcggga gccccaggtg tacaccctgc cccctagcca agaggagatg    420
accaagaacc aggtgtccct gacctgcctg gtgaagggct tctacccag cgacatcgcc     480 gtggagtggg agagcaacgg ccagcccgag aacaactaca agaccacccc ccctgtgctg    540
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                     690

<210> SEQ ID NO 8
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Arg Trp Pro Glu Ser Pro Lys Ala Gln Ala Ser Ser Val Pro Thr Ala
1               5                   10                  15
Gln Pro Gln Ala Glu Gly Ser Leu Ala Lys Ala Thr Thr Ala Pro Ala
            20                  25                  30
Thr Thr Arg Asn Thr Gly Arg Gly Glu Glu Lys Lys Lys Glu Lys
        35                  40                  45
Glu Lys Glu Glu Gln Glu Arg Glu Thr Lys Thr Pro Glu Cys Pro
    50                  55                  60
Ser His Thr Gln Pro Leu Gly Val Tyr Leu Leu Thr Pro Ala Val Gln
65                  70                  75                  80
Asp Leu Trp Leu Arg Asp Lys Ala Thr Phe Thr Cys Phe Val Val Gly
                85                  90                  95
Ser Asp Leu Lys Asp Ala His Leu Thr Trp Glu Val Ala Gly Lys Val
            100                 105                 110
Pro Thr Gly Gly Val Glu Glu Gly Leu Leu Glu Arg His Ser Asn Gly
        115                 120                 125
Ser Gln Ser Gln His Ser Arg Leu Thr Leu Pro Arg Ser Leu Trp Asn
130                 135                 140
Ala Gly Thr Ser Val Thr Cys Thr Leu Asn His Pro Ser Leu Pro Pro
145                 150                 155                 160
Gln Arg Leu Met Ala Leu Arg Glu Pro Ala Ala Gln Ala Pro Val Lys
                165                 170                 175
Leu Ser Leu Asn Leu Leu Ala Ser Ser Asp Pro Pro Glu Ala Ala Ser
            180                 185                 190
Trp Leu Leu Cys Glu Val Ser Gly Phe Ser Pro Pro Asn Ile Leu Leu
        195                 200                 205
Met Trp Leu Glu Asp Gln Arg Glu Val Asn Thr Ser Gly Phe Ala Pro
    210                 215                 220
Ala Arg Pro Pro Pro Gln Pro Gly Ser Thr Thr Phe Trp Ala Trp Ser
225                 230                 235                 240
Val Leu Arg Val Pro Ala Pro Pro Ser Pro Gln Pro Ala Thr Tyr Thr
                245                 250                 255
Cys Val Val Ser His Glu Asp Ser Arg Thr Leu Leu Asn Ala Ser Arg
            260                 265                 270
Ser Leu Glu Val Ser Tyr Val Thr Asp His
        275                 280
```

<210> SEQ ID NO 9
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
aggtggcccg aaagtcccaa ggcccaggca tctagtgttc ctactgcaca gccccaggca    60
gaaggcagcc tagccaaagc tactactgca cctgccacta cgcgcaatac tggccgtggc   120
ggggaggaga agaaaaagga gaaagagaaa gaagaacagg aagagaggga gaccaagacc   180
cctgaatgtc catcccatac ccagccgctg ggcgtctatc tcttgactcc cgcagtacag   240
gacttgtggc ttagagataa ggccaccttt acatgtttcg tcgtgggctc tgacctgaag   300
```

```
gatgcccatt tgacttggga ggttgccgga aaggtaccca caggggggt tgaggaaggg       360 ttgctggagc gccattccaa tggctctcag agccagcact caagactcac ccttccgaga       420
tccctgtgga acgccgggac ctctgtcaca tgtactctaa atcatcctag cctgccccca       480
cagcgtctga tggcccttag agagccagcc gcccaggcac cagttaagct tagcctgaat       540
ctgctcgcca gtagtgatcc cccagaggcc gccagctggc tcttatgcga agtgtccggc       600
tttagcccgc caacatctt gctcatgtgg ctggaggacc agcgagaagt gaacaccagc       660
ggcttcgctc cagcccggcc cccacccccag ccgggttcta ccacattctg ggcctggagt       720
gtcttaaggg tcccagcacc acctagcccc cagccagcca catacacctg tgttgtgtcc       780
catgaagata gcaggaccct gctaaatgct tctaggagtc tggaggtttc ctacgtgact       840
gaccatt                                                                 847
```

```
<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Ser Gly Gly Gly Gly Ser
1               5                   10

<210> SEQ ID NO 11
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ggtggcggag gttctggagg tggaggttcc                                        30

<210> SEQ ID NO 12
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 13
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
```

```
atctacatct gggcgcccct tggccgggact tgtggggtcc ttctcctgtc actggttatc    60 acccttact  gc                                                         72
```

<210> SEQ ID NO 14
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 15
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 16
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 17
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
``` tcc                                                                          123

<210> SEQ ID NO 18
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat     180
gaactgcaga aagataagat ggcggaggcc tacagtgaga ttgggatgaa aggcgagcgc     240 cggagggggca aggggcacga tggcctttac cagggtctca gtacagccac caaggacacc     300
tacgacgccc ttcacatgca ggccctgccc cctcgc                                336

<210> SEQ ID NO 20
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys

```
                35                  40                  45
Pro Arg Arg Lys Asn Pro Gln Glu Gly Leu Tyr Asn Glu Leu Gln Lys
            50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Gly Gly Gly Ser
1               5

<210> SEQ ID NO 23
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ggtggcggag gttctggagg tggaggttcc                                       30

<210> SEQ ID NO 24
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24
```

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
                180                 185                 190

Lys Asp Asn Ser Lys Asn Gln Val Ser Leu Lys Leu Ser Ser Val Thr
            195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 25
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
                100                 105                 110

```
Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
        130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
                180                 185                 190

Lys Asp Asn Ser Lys Asn Gln Val Ser Leu Lys Leu Ser Ser Val Thr
            195                 200                 205

Ala Ala Asp Thr Ala Val Tyr Tyr Cys Ala Lys His Tyr Tyr Tyr Gly
        210                 215                 220

Gly Ser Tyr Ala Met Asp Tyr Trp Gly Gln Gly Thr Leu Val Thr Val
225                 230                 235                 240

Ser Ser
```

<210> SEQ ID NO 26
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
```

```
                210                 215                 220

Gln Gly Asn Thr Leu Pro Tyr Thr Phe Gly Gln Gly Thr Lys Leu Glu
225                 230                 235                 240

Ile Lys

<210> SEQ ID NO 27
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 28
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(40)
<223> OTHER INFORMATION: /note="This sequence may encompass 1-10
``` repeating "Gly Gly Gly Ser" units"

<400> SEQUENCE: 28

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 29
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Gly Gly Gly Ser Gly Gly Gly Gly Ser Gly Gly Gly Gly Ser Gly
1               5                   10                  15

Gly Gly Gly Ser
            20

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Gly Gly Ser
1

<210> SEQ ID NO 32
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180

| aaaaaaaaaa aaaaaaaaaa aaaaaaaaaa aaaaaaaaaa aaaaaaaaaa aaaaaaaaaa | 240 |
| aaaaaaaaaa aaaaaaaaaa aaaaaaaaaa aaaaaaaaaa aaaaaaaaaa aaaaaaaaaa | 300 |
| aaaaaaaaaa aaaaaaaaaa aaaaaaaaaa aaaaaaaaaa aaaaaaaaaa aaaaaaaaaa | 360 |
| aaaaaaaaaa aaaaaaaaaa aaaaaaaaaa aaaaaaaaaa aaaaaaaaaa aaaaaaaaaa | 420 |
| aaaaaaaaaa aaaaaaaaaa aaaaaaaaaa aaaaaaaaaa aaaaaaaaaa aaaaaaaaaa | 480 |
| aaaaaaaaaa aaaaaaaaaa aaaaaaaaaa aaaaaaaaaa aaaaaaaaaa aaaaaaaaaa | 540 |
| aaaaaaaaaa aaaaaaaaaa aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaaaa aaaaaaaaaa aaaaaaaaaa aaaaaaaaaa aaaaaaaaaa aaaaaaaaaa | 720 |
| aaaaaaaaaa aaaaaaaaaa aaaaaaaaaa aaaaaaaaaa aaaaaaaaaa aaaaaaaaaa | 780 |
| aaaaaaaaaa aaaaaaaaaa aaaaaaaaaa aaaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaaaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaaaaa aaaaaaaaaa aaaaaaaaaa aaaaaaaaaa | 1200 |
| aaaaaaaaaa aaaaaaaaaa aaaaaaaaaa aaaaaaaaaa aaaaaaaaaa aaaaaaaaaa | 1260 |
| aaaaaaaaaa aaaaaaaaaa aaaaaaaaaa aaaaaaaaaa aaaaaaaaaa aaaaaaaaaa | 1320 |
| aaaaaaaaaa aaaaaaaaaa aaaaaaaaaa aaaaaaaaaa aaaaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaaaaaaaaa aaaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa aaaaaaaaaa aaaaaaaaaa aaaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aaaaaaaaaa aaaaaaaaaa | 1980 |
| aaaaaaaaaa aaaaaaaaaa | 2000 |

<210> SEQ ID NO 33
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33

| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa | 150 |

<210> SEQ ID NO 34
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: MISC_FEATURE
<222> LOCATION: (1)..(40)
<223> OTHER INFORMATION: /note="This sequence may encompass 50-5000 nucleotides"
<220> FEATURE:
<221> NAME/KEY: source
<223> OTHER INFORMATION: /note="See specification as filed for detailed description of substitutions and preferred embodiments"

<400> SEQUENCE: 34

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
```

```
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
```

| | |
|---|---|
| aaaaaaaaaa aaaaaaaaaa aaaaaaaaaa aaaaaaaaaa aaaaaaaaaa aaaaaaaaaa | 4140 |
| aaaaaaaaaa aaaaaaaaaa aaaaaaaaaa aaaaaaaaaa aaaaaaaaaa aaaaaaaaaa | 4200 |
| aaaaaaaaaa aaaaaaaaaa aaaaaaaaaa aaaaaaaaaa aaaaaaaaaa aaaaaaaaaa | 4260 |
| aaaaaaaaaa aaaaaaaaaa aaaaaaaaaa aaaaaaaaaa aaaaaaaaaa aaaaaaaaaa | 4320 |
| aaaaaaaaaa aaaaaaaaaa aaaaaaaaaa aaaaaaaaaa aaaaaaaaaa aaaaaaaaaa | 4380 |
| aaaaaaaaaa aaaaaaaaaa aaaaaaaaaa aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaaaaaa aaaaaaaaaa aaaaaaaaaa aaaaaaaaaa aaaaaaaaaa aaaaaaaaaa | 4560 |
| aaaaaaaaaa aaaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaaa aaaaaaaaaa aaaaaaaaaa aaaaaaaaaa aaaaaaaaaa aaaaaaaaaa | 4740 |
| aaaaaaaaaa aaaaaaaaaa aaaaaaaaaa aaaaaaaaaa aaaaaaaaaa aaaaaaaaaa | 4800 |
| aaaaaaaaaa aaaaaaaaaa aaaaaaaaaa aaaaaaaaaa aaaaaaaaaa aaaaaaaaaa | 4860 |
| aaaaaaaaaa aaaaaaaaaa aaaaaaaaaa aaaaaaaaaa aaaaaaaaaa aaaaaaaaaa | 4920 |
| aaaaaaaaaa aaaaaaaaaa aaaaaaaaaa aaaaaaaaaa aaaaaaaaaa aaaaaaaaaa | 4980 |
| aaaaaaaaaa aaaaaaaaaa | 5000 |

<210> SEQ ID NO 35
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 35

| | |
|---|---|
| tttttttttt tttttttttt tttttttttt tttttttttt tttttttttt tttttttttt | 60 |
| tttttttttt tttttttttt tttttttttt tttttttttt | 100 |

<210> SEQ ID NO 36
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

| | |
|---|---|
| tttttttttt tttttttttt tttttttttt tttttttttt tttttttttt tttttttttt | 60 |
| tttttttttt tttttttttt tttttttttt tttttttttt tttttttttt tttttttttt | 120 |
| tttttttttt tttttttttt tttttttttt tttttttttt tttttttttt tttttttttt | 180 |
| tttttttttt tttttttttt tttttttttt tttttttttt tttttttttt tttttttttt | 240 |
| tttttttttt tttttttttt tttttttttt tttttttttt tttttttttt tttttttttt | 300 |
| tttttttttt tttttttttt tttttttttt tttttttttt tttttttttt tttttttttt | 360 |
| tttttttttt tttttttttt tttttttttt tttttttttt tttttttttt tttttttttt | 420 |
| tttttttttt tttttttttt tttttttttt tttttttttt tttttttttt tttttttttt | 480 |
| tttttttttt tttttttttt tttttttttt tttttttttt tttttttttt tttttttttt | 540 |
| tttttttttt tttttttttt tttttttttt tttttttttt tttttttttt tttttttttt | 600 |

| | | | | | | |
|---|---|---|---|---|---|---|
| tttttttttt | tttttttttt | tttttttttt | tttttttttt | tttttttttt | tttttttttt | 660 |
| tttttttttt | tttttttttt | tttttttttt | tttttttttt | tttttttttt | tttttttttt | 720 |
| tttttttttt | tttttttttt | tttttttttt | tttttttttt | tttttttttt | tttttttttt | 780 |
| tttttttttt | tttttttttt | tttttttttt | tttttttttt | tttttttttt | tttttttttt | 840 |
| tttttttttt | tttttttttt | tttttttttt | tttttttttt | tttttttttt | tttttttttt | 900 |
| tttttttttt | tttttttttt | tttttttttt | tttttttttt | tttttttttt | tttttttttt | 960 |
| tttttttttt | tttttttttt | tttttttttt | tttttttttt | tttttttttt | tttttttttt | 1020 |
| tttttttttt | tttttttttt | tttttttttt | tttttttttt | tttttttttt | tttttttttt | 1080 |
| tttttttttt | tttttttttt | tttttttttt | tttttttttt | tttttttttt | tttttttttt | 1140 |
| tttttttttt | tttttttttt | tttttttttt | tttttttttt | tttttttttt | tttttttttt | 1200 |
| tttttttttt | tttttttttt | tttttttttt | tttttttttt | tttttttttt | tttttttttt | 1260 |
| tttttttttt | tttttttttt | tttttttttt | tttttttttt | tttttttttt | tttttttttt | 1320 |
| tttttttttt | tttttttttt | tttttttttt | tttttttttt | tttttttttt | tttttttttt | 1380 |
| tttttttttt | tttttttttt | tttttttttt | tttttttttt | tttttttttt | tttttttttt | 1440 |
| tttttttttt | tttttttttt | tttttttttt | tttttttttt | tttttttttt | tttttttttt | 1500 |
| tttttttttt | tttttttttt | tttttttttt | tttttttttt | tttttttttt | tttttttttt | 1560 |
| tttttttttt | tttttttttt | tttttttttt | tttttttttt | tttttttttt | tttttttttt | 1620 |
| tttttttttt | tttttttttt | tttttttttt | tttttttttt | tttttttttt | tttttttttt | 1680 |
| tttttttttt | tttttttttt | tttttttttt | tttttttttt | tttttttttt | tttttttttt | 1740 |
| tttttttttt | tttttttttt | tttttttttt | tttttttttt | tttttttttt | tttttttttt | 1800 |
| tttttttttt | tttttttttt | tttttttttt | tttttttttt | tttttttttt | tttttttttt | 1860 |
| tttttttttt | tttttttttt | tttttttttt | tttttttttt | tttttttttt | tttttttttt | 1920 |
| tttttttttt | tttttttttt | tttttttttt | tttttttttt | tttttttttt | tttttttttt | 1980 |
| tttttttttt | tttttttttt | tttttttttt | tttttttttt | tttttttttt | tttttttttt | 2040 |
| tttttttttt | tttttttttt | tttttttttt | tttttttttt | tttttttttt | tttttttttt | 2100 |
| tttttttttt | tttttttttt | tttttttttt | tttttttttt | tttttttttt | tttttttttt | 2160 |
| tttttttttt | tttttttttt | tttttttttt | tttttttttt | tttttttttt | tttttttttt | 2220 |
| tttttttttt | tttttttttt | tttttttttt | tttttttttt | tttttttttt | tttttttttt | 2280 |
| tttttttttt | tttttttttt | tttttttttt | tttttttttt | tttttttttt | tttttttttt | 2340 |
| tttttttttt | tttttttttt | tttttttttt | tttttttttt | tttttttttt | tttttttttt | 2400 |
| tttttttttt | tttttttttt | tttttttttt | tttttttttt | tttttttttt | tttttttttt | 2460 |
| tttttttttt | tttttttttt | tttttttttt | tttttttttt | tttttttttt | tttttttttt | 2520 |
| tttttttttt | tttttttttt | tttttttttt | tttttttttt | tttttttttt | tttttttttt | 2580 |
| tttttttttt | tttttttttt | tttttttttt | tttttttttt | tttttttttt | tttttttttt | 2640 |
| tttttttttt | tttttttttt | tttttttttt | tttttttttt | tttttttttt | tttttttttt | 2700 |
| tttttttttt | tttttttttt | tttttttttt | tttttttttt | tttttttttt | tttttttttt | 2760 |
| tttttttttt | tttttttttt | tttttttttt | tttttttttt | tttttttttt | tttttttttt | 2820 |
| tttttttttt | tttttttttt | tttttttttt | tttttttttt | tttttttttt | tttttttttt | 2880 |
| tttttttttt | tttttttttt | tttttttttt | tttttttttt | tttttttttt | tttttttttt | 2940 |

| | | |
|---|---|---|
| tttttttttt tttttttttt tttttttttt tttttttttt tttttttttt tttttttttt | 3000 | |
| tttttttttt tttttttttt tttttttttt tttttttttt tttttttttt tttttttttt | 3060 | |
| tttttttttt tttttttttt tttttttttt tttttttttt tttttttttt tttttttttt | 3120 | |
| tttttttttt tttttttttt tttttttttt tttttttttt tttttttttt tttttttttt | 3180 | |
| tttttttttt tttttttttt tttttttttt tttttttttt tttttttttt tttttttttt | 3240 | |
| tttttttttt tttttttttt tttttttttt tttttttttt tttttttttt tttttttttt | 3300 | |
| tttttttttt tttttttttt tttttttttt tttttttttt tttttttttt tttttttttt | 3360 | |
| tttttttttt tttttttttt tttttttttt tttttttttt tttttttttt tttttttttt | 3420 | |
| tttttttttt tttttttttt tttttttttt tttttttttt tttttttttt tttttttttt | 3480 | |
| tttttttttt tttttttttt tttttttttt tttttttttt tttttttttt tttttttttt | 3540 | |
| tttttttttt tttttttttt tttttttttt tttttttttt tttttttttt tttttttttt | 3600 | |
| tttttttttt tttttttttt tttttttttt tttttttttt tttttttttt tttttttttt | 3660 | |
| tttttttttt tttttttttt tttttttttt tttttttttt tttttttttt tttttttttt | 3720 | |
| tttttttttt tttttttttt tttttttttt tttttttttt tttttttttt tttttttttt | 3780 | |
| tttttttttt tttttttttt tttttttttt tttttttttt tttttttttt tttttttttt | 3840 | |
| tttttttttt tttttttttt tttttttttt tttttttttt tttttttttt tttttttttt | 3900 | |
| tttttttttt tttttttttt tttttttttt tttttttttt tttttttttt tttttttttt | 3960 | |
| tttttttttt tttttttttt tttttttttt tttttttttt tttttttttt tttttttttt | 4020 | |
| tttttttttt tttttttttt tttttttttt tttttttttt tttttttttt tttttttttt | 4080 | |
| tttttttttt tttttttttt tttttttttt tttttttttt tttttttttt tttttttttt | 4140 | |
| tttttttttt tttttttttt tttttttttt tttttttttt tttttttttt tttttttttt | 4200 | |
| tttttttttt tttttttttt tttttttttt tttttttttt tttttttttt tttttttttt | 4260 | |
| tttttttttt tttttttttt tttttttttt tttttttttt tttttttttt tttttttttt | 4320 | |
| tttttttttt tttttttttt tttttttttt tttttttttt tttttttttt tttttttttt | 4380 | |
| tttttttttt tttttttttt tttttttttt tttttttttt tttttttttt tttttttttt | 4440 | |
| tttttttttt tttttttttt tttttttttt tttttttttt tttttttttt tttttttttt | 4500 | |
| tttttttttt tttttttttt tttttttttt tttttttttt tttttttttt tttttttttt | 4560 | |
| tttttttttt tttttttttt tttttttttt tttttttttt tttttttttt tttttttttt | 4620 | |
| tttttttttt tttttttttt tttttttttt tttttttttt tttttttttt tttttttttt | 4680 | |
| tttttttttt tttttttttt tttttttttt tttttttttt tttttttttt tttttttttt | 4740 | |
| tttttttttt tttttttttt tttttttttt tttttttttt tttttttttt tttttttttt | 4800 | |
| tttttttttt tttttttttt tttttttttt tttttttttt tttttttttt tttttttttt | 4860 | |
| tttttttttt tttttttttt tttttttttt tttttttttt tttttttttt tttttttttt | 4920 | |
| tttttttttt tttttttttt tttttttttt tttttttttt tttttttttt tttttttttt | 4980 | |
| tttttttttt tttttttttt | 5000 | |

```
<210> SEQ ID NO 37
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 37
aaaaaaaaaa aaaaaaaaaa aaaaaaaaaa aaaaaaaaaa aaaaaaaaaa aaaaaaaaaa    60
aaaa    64

<210> SEQ ID NO 38
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa aaaaaaaaaa aaaaaaaaaa aaaaaaaaaa aaaaaaaaaa   240
aaaaaaaaaa aaaaaaaaaa aaaaaaaaaa aaaaaaaaaa aaaaaaaaaa aaaaaaaaaa   300
aaaaaaaaaa aaaaaaaaaa aaaaaaaaaa aaaaaaaaaa aaaaaaaaaa aaaaaaaaaa   360
aaaaaaaaaa aaaaaaaaaa aaaaaaaaaa aaaaaaaaaa    400

<210> SEQ ID NO 39
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser

```
                    180                 185                 190
Arg Val Thr Ile Ser Lys Asp Asn Ser Lys Asn Gln Val Ser Leu Lys
                195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 40
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
                20                  25                  30

Trp Asn Pro Pro Thr Phe Ser Pro Ala Leu Leu Val Val Thr Glu Gly
            35                  40                  45

Asp Asn Ala Thr Phe Thr Cys Ser Phe Ser Asn Thr Ser Glu Ser Phe
50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
                100                 105                 110

Arg Ala Arg Arg Asn Asp Ser Gly Thr Tyr Leu Cys Gly Ala Ile Ser
            115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
    195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
                260                 265                 270

Pro Glu Glu Glu Glu Gly Gly Cys Glu Leu Arg Val Lys Phe Ser Arg
            275                 280                 285
```

```
Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390

<210> SEQ ID NO 41
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240
```

```
Thr Gln Glu Glu Asp Gly Cys Ser Cys Arg Phe Pro Glu Glu Glu
                245                 250                 255
Gly Gly Cys Glu Leu Arg Val Lys Phe Ser Arg Ser Ala Asp Ala Pro
            260                 265                 270
Ala Tyr Lys Gln Gly Gln Asn Gln Leu Tyr Asn Glu Leu Asn Leu Gly
        275                 280                 285
Arg Arg Glu Glu Tyr Asp Val Leu Asp Lys Arg Arg Gly Arg Asp Pro
    290                 295                 300
Glu Met Gly Gly Lys Pro Arg Arg Lys Asn Pro Gln Glu Gly Leu Tyr
305                 310                 315                 320
Asn Glu Leu Gln Lys Asp Lys Met Ala Glu Ala Tyr Ser Glu Ile Gly
                325                 330                 335
Met Lys Gly Glu Arg Arg Arg Gly Lys Gly His Asp Gly Leu Tyr Gln
            340                 345                 350
Gly Leu Ser Thr Ala Thr Lys Asp Thr Tyr Asp Ala Leu His Met Gln
        355                 360                 365
Ala Leu Pro Pro Arg
    370
```

<210> SEQ ID NO 42
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42

```
atggccctcc ctgtcactgc cctgcttctc cccctcgcac tcctgctcca cgccgctaga      60
ccacccggat ggtttctgga ctctccggat cgcccgtgga atccccccaac cttctcaccg    120
gcactcttgg ttgtgactga gggcgataat gcgaccttca cgtgctcgtt ctccaacacc    180
tccgaatcat tcgtgctgaa ctggtaccgc atgagcccgt caaaccagac cgacaagctc    240
gccgcgtttc cggaagatcg gtcgcaaccg ggacaggatt gtcggttccg cgtgactcaa    300
ctgccgaatg gcagagactt ccacatgagc gtggtccgcg ctaggcgaaa cgactccggg    360
acctacctgt gcggagccat ctcgctggcg cctaaggccc aaatcaaaga gagcttgagg    420
gccgaactga gagtgaccga cgcagagct gaggtgccaa ctgcacatcc atccccatcg    480
cctcggcctg cggggcagtt tcagaccctg gtcacgacca ctccggcgcc cgcccaccg    540
actccggccc caactatcgc gagccagccc tgtcgctga ggccggaagc atgccgccct    600
gccgccggag gtgctgtgca tacccgggga ttggacttcg catgcgacat ctacatttgg    660
gctcctctcg ccggaacttg tggcgtgctc cttctgtccc tggtcatcac cctgtactgc    720
aagcggggtc ggaaaaagct tctgtacatt ttcaagcagc ccttcatgag gcccgtgcaa    780
accacccagg aggaggacgg ttgctcctgc cggttccccg aagaggaaga aggaggttgc    840
gagctgcgcg tgaagttctc ccggagcgcc gacgccccg cctataagca gggccagaac    900
cagctgtaca cgaactgaa cctgggacgg cgggaagagt acgatgtgct ggacaagcgg    960
cgcggccggg accccgaaat gggcgggaag cctagaagaa gaaccctca ggaaggcctg   1020
tataacgagc tgcagaagga caagatggcc gaggcctact ccgaaattgg gatgaaggga   1080
gagcggcgga ggggaaaggg gcacgacggc ctgtaccaag gactgtccac cgccaccaag   1140
gacacatacg atgccctgca catgcaggcc cttccccctc gc                      1182
```

<210> SEQ ID NO 43
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 44
<211> LENGTH: 150
<212> TYPE: PRT
<213> ORGANISM: Homo sapiens

<400> SEQUENCE: 44

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

```
Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 45
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Ser Thr Ser Gly Ser Gly Lys Pro Gly Ser Gly Glu Gly Ser Thr
1               5                   10                  15

Lys Gly

<210> SEQ ID NO 46
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
```

165                 170                 175
Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 47
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 48

```
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 49
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45
```

```
Gly Val Ile Trp Gly Ser Glu Thr Thr Tyr Tyr Asn Ser Ser Leu Lys
 50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Glu Ile Val Met
130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 50
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
```

```
145                 150                 155                 160
Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
                180                 185                 190

Lys Asp Asn Ser Lys Asn Gln Val Ser Leu Lys Leu Ser Ser Val Thr
                195                 200                 205

Ala Ala Asp Thr Ala Val Tyr Tyr Cys Ala Lys His Tyr Tyr Tyr Gly
210                 215                 220

Gly Ser Tyr Ala Met Asp Tyr Trp Gly Gln Gly Thr Leu Val Thr Val
225                 230                 235                 240

Ser Ser

<210> SEQ ID NO 51
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
                20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Asn Ser Ser Leu Lys
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
210                 215                 220

Gln Gly Asn Thr Leu Pro Tyr Thr Phe Gly Gln Gly Thr Lys Leu Glu
225                 230                 235                 240

Ile Lys
```

```
<210> SEQ ID NO 52
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 53
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45
```

```
Gly Gln Ile Tyr Pro Gly Asp Gly Asp Thr Asn Tyr Asn Gly Lys Phe
 50                  55                  60

Lys Gly Gln Ala Thr Leu Thr Ala Asp Lys Ser Ser Thr Ala Tyr
 65                  70                  75                  80

Met Gln Leu Ser Gly Leu Thr Ser Glu Asp Ser Ala Val Tyr Ser Cys
             85                  90                  95

Ala Arg Lys Thr Ile Ser Ser Val Val Asp Phe Tyr Phe Asp Tyr Trp
            100                 105                 110

Gly Gln Gly Thr Thr Val Thr
            115
```

<210> SEQ ID NO 54
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

```
Glu Leu Val Leu Thr Gln Ser Pro Lys Phe Met Ser Thr Ser Val Gly
 1               5                  10                  15

Asp Arg Val Ser Val Thr Cys Lys Ala Ser Gln Asn Val Gly Thr Asn
                 20                  25                  30

Val Ala Trp Tyr Gln Gln Lys Pro Gly Gln Ser Pro Lys Pro Leu Ile
             35                  40                  45

Tyr Ser Ala Thr Tyr Arg Asn Ser Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Lys Asp Leu Ala Asp Tyr Phe Tyr Phe Cys Gln Tyr Asn Arg Tyr Pro
             85                  90                  95

Tyr Thr Ser Gly Gly Gly Thr Lys Leu Glu Ile Lys Arg Arg Ser
            100                 105                 110
```

<210> SEQ ID NO 55
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55

```
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaaatacc ttaattggta tcaacagaag     180
cccggacagg ctcctcgcct tctgatctac acaccagcc ggctccattc tggaatccct      240
gccaggttca gcggtagcgg atctgggacc gactacaccc tcactatcag ctcactgcag     300
ccagaggact cgctgtcta tttctgtcag caagggaaca ccctgcccta cacctttgga     360
cagggcacca agctcgagat aaaggtgga ggtggcagcg aggaggtgg gtccggcggt      420
ggaggaagcc aggtccaact ccaagaaagc ggaccgggtc ttgtgaagcc atcagaaact     480
ctttcactga cttgtactgt gagcggagtg tctctccccg attacggggt gtcttggatc     540
agacagccac cggggaaggg tctggaatgg attggagtga tttggggctc tgagactact     600
```

```
tactactctt catccctcaa gtcacgcgtc accatctcaa aggacaactc taagaatcag    660
gtgtcactga aactgtcatc tgtgaccgca gccgacaccg ccgtgtacta ttgcgctaag    720
cattactatt atggcgggag ctacgcaatg gattactggg gacagggtac tctggtcacc    780
gtgtccagca ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta gcaacccctt catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggacccc agaaatgggc   1260
gggaagccgc gcagaaagaa tccccaagag ggcctgtaca acgagctcca aaaggataag   1320
atggcagaag cctatagcga gattggtatg aaaggggaac gcagaagagg caaaggccac   1380
gacggactgt accagggact cagcaccgcc accaaggaca cctatgacgc tcttcacatg   1440
caggccctgc cgcctcgg                                                 1458
```

<210> SEQ ID NO 56
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Leu Lys Ser
            195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
    275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
    355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
    435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 57
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaatacc ttaattggta tcaacagaag     180
cccggacagg ctcctcgcct tctgatctac cacaccagcc ggctccattc tggaatccct     240
gccaggttca gcggtagcgg atctgggacc gactacaccc tcactatcag ctcactgcag     300

```
ccagaggact tcgctgtcta tttctgtcag caagggaaca ccctgcccta cacctttgga    360
cagggcacca agctcgagat taaaggtgga ggtggcagcg gaggaggtgg gtccggcggt    420
ggaggaagcc aggtccaact ccaagaaagc ggaccgggtc ttgtgaagcc atcagaaact    480
ctttcactga cttgtactgt gagcggagtg tctctccccg attacggggt gtcttggatc    540
agacagccac cggggaaggg tctggaatgg attggagtga tttggggctc tgagactact    600
tactaccaat catccctcaa gtcacgcgtc accatctcaa aggacaactc taagaatcag    660
gtgtcactga aactgtcatc tgtgaccgca gccgacaccg ccgtgtacta ttgcgctaag    720
cattactatt atggcgggag ctacgcaatg gattactggg gacagggtac tctggtcacc    780
gtgtccagca ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta gcaaccctt catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggaccc agaaatgggc   1260 gggaagccgc gcagaaagaa tccccaagag gcctgtaca cgagctcca aaaggataag   1320 atggcagaag cctatagcga gattggtatg aaagggaac gcagaagagg caaaggccac   1380
gacggactgt accagggact cagcaccgcc accaaggaca cctatgacgc tcttcacatg   1440
caggccctgc cgcctcgg                                                 1458
```

<210> SEQ ID NO 58
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
    130                 135                 140
```

```
Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
            165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
            195                 200                 205

Arg Val Thr Ile Ser Lys Asp Asn Ser Lys Asn Gln Val Ser Leu Lys
210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 59
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
atggctctgc ccgtgaccgc actcctcctg ccactggctc tgctgcttca cgccgctcgc      60
```

```
ccacaagtcc agcttcaaga atcagggcct ggtctggtga agccatctga gactctgtcc    120
ctcacttgca ccgtgagcgg agtgtccctc ccagactacg gagtgagctg gattagacag    180
cctcccggaa agggactgga gtggatcgga gtgatttggg gtagcgaaac cacttactat    240
tcatcttccc tgaagtcacg ggtcaccatt tcaaaggata actcaaagaa tcaagtgagc    300
ctcaagctct catcagtcac cgccgctgac accgccgtgt attactgtgc caagcattac    360
tactatggag ggtcctacgc catggactac tggggccagg gaactctggt cactgtgtca    420
tctggtggag gaggtagcgg aggaggcggg agcggtggag gtggctccga aatcgtgatg    480
acccagagcc ctgcaaccct gtcccttcct cccggggaac gggctaccct ttcttgtcgg    540
gcatcacaag atatctcaaa atacctcaat tggtatcaac agaagccggg acaggcccct    600
aggcttctta tctaccacac ctctcgcctg catagcggga ttcccgcacg ctttagcggg    660
tctggaagcg ggaccgacta cactctgacc atctcatctc tccagcccga ggacttcgcc    720
gtctacttct gccagcaggg taacaccctg ccgtacacct tcggccaggg caccaagctt    780
gagatcaaaa ccactactcc cgctccaagg ccacccaccc ctgccccgac catcgcctct    840
cagccgcttt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta agcaaccctt catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggaccc agaaatgggc   1260
gggaagccgc gcagaaagaa tccccaagag ggcctgtaca cgagctcca aaaggataag   1320
atggcagaag cctatagcga gattggtatg aaagggaac gcagaagagg caaaggccac   1380
gacggactgt accagggact cagcaccgcc accaaggaca cctatgacgc tcttcacatg   1440
caggccctgc cgcctcgg                                                 1458
```

<210> SEQ ID NO 60
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Val
            35                  40                  45

Ser Leu Pro Asp Tyr Gly Val Ser Trp Ile Arg Gln Pro Pro Gly Lys
        50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95
```

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
115                 120                 125

Asp Tyr Trp Gly Gln Gly Thr Leu Val Thr Val Ser Ser Gly Gly Gly
130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 61
<211> LENGTH: 1458
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

```
atggctctgc ccgtgaccgc actcctcctg ccactggctc tgctgcttca cgccgctcgc      60
ccacaagtcc agcttcaaga atcagggcct ggtctggtga agccatctga gactctgtcc     120
ctcacttgca ccgtgagcgg agtgtccctc ccagactacg gagtgagctg gattagacag     180
cctcccggaa agggactgga gtggatcgga gtgatttggg gtagcgaaac cacttactat     240
caatcttccc tgaagtcacg ggtcaccatt tcaaaggata actcaaagaa tcaagtgagc     300
ctcaagctct catcagtcac cgccgctgac accgccgtgt attactgtgc caagcattac     360
tactatggag ggtcctacgc catggactac tggggccagg gaactctggt cactgtgtca     420
tctggtggag gaggtagcgg aggaggcggg agcggtggag gtggctccga aatcgtgatg     480
acccagagcc ctgcaaccct gtcccttcct cccggggaac gggctaccct ttcttgtcgg     540
gcatcacaag atatctcaaa ataccctaat tggtatcaac agaagccggg acaggcccct     600
aggcttctta tctaccacac ctctcgcctg catagcggga ttcccgcacg ctttagcggg     660
tctggaagcg ggaccgacta cactctgacc atctcatctc tccagcccga ggacttcgcc     720
gtctacttct gccagcaggg taacaccctg ccgtacacct cggcccaggg caccaagctt     780
gagatcaaaa ccactactcc cgctccaagg ccacccaccc ctgccccgac catcgcctct     840
cagccgcttt ccctgcgtcc ggaggcatgt agacccgcag ctggtgggc cgtgcatacc     900
cggggtcttg acttcgcctg cgatatctac atttgggccc ctctggctgg tacttgcggg     960
gtcctgctgc tttcactcgt gatcactctt tactgtaagc gcggtcggaa gaagctgctg    1020
tacatcttta gcaacccctt catgaggcct gtgcagacta ctcaagagga ggacggctgt    1080
tcatgccggt tcccagagga ggaggaaggc ggctgcgaac tgcgcgtgaa attcagccgc    1140
agcgcagatg ctccagccta caagcagggg cagaaccagc tctacaacga actcaatctt    1200
ggtcggagag aggagtacga cgtgctggac aagcggagag acgggaccc agaaatgggc    1260
gggaagccgc gcagaaagaa tccccaagag gcctgtaca cgagctcca aaaggataag    1320
atggcagaag cctatagcga gattggtatg aaagggaac gcagaagagg caaaggccac    1380
gacggactgt accagggact cagcaccgcc accaaggaca cctatgacgc tcttcacatg    1440
caggccctgc cgcctcgg                                                  1458
```

<210> SEQ ID NO 62
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45
```

-continued

```
Ser Leu Pro Asp Tyr Gly Val Ser Trp Ile Arg Gln Pro Pro Gly Lys
    50                  55                  60
Gly Leu Glu Trp Ile Gly Val Ile Trp Gly Ser Glu Thr Thr Tyr Tyr
 65                  70                  75                  80
Gln Ser Ser Leu Lys Ser Arg Val Thr Ile Ser Lys Asp Asn Ser Lys
                 85                  90                  95
Asn Gln Val Ser Leu Lys Leu Ser Ser Val Thr Ala Ala Asp Thr Ala
            100                 105                 110
Val Tyr Tyr Cys Ala Lys His Tyr Tyr Gly Gly Ser Tyr Ala Met
        115                 120                 125
Asp Tyr Trp Gly Gln Gly Thr Leu Val Thr Val Ser Ser Gly Gly Gly
    130                 135                 140
Gly Ser Gly Gly Gly Gly Ser Gly Gly Gly Gly Ser Glu Ile Val Met
145                 150                 155                 160
Thr Gln Ser Pro Ala Thr Leu Ser Leu Ser Pro Gly Glu Arg Ala Thr
                165                 170                 175
Leu Ser Cys Arg Ala Ser Gln Asp Ile Ser Lys Tyr Leu Asn Trp Tyr
            180                 185                 190
Gln Gln Lys Pro Gly Gln Ala Pro Arg Leu Leu Ile Tyr His Thr Ser
        195                 200                 205
Arg Leu His Ser Gly Ile Pro Ala Arg Phe Ser Gly Ser Gly Ser Gly
    210                 215                 220
Thr Asp Tyr Thr Leu Thr Ile Ser Ser Leu Gln Pro Glu Asp Phe Ala
225                 230                 235                 240
Val Tyr Phe Cys Gln Gln Gly Asn Thr Leu Pro Tyr Thr Phe Gly Gln
                245                 250                 255
Gly Thr Lys Leu Glu Ile Lys Thr Thr Thr Pro Ala Pro Arg Pro Pro
            260                 265                 270
Thr Pro Ala Pro Thr Ile Ala Ser Gln Pro Leu Ser Leu Arg Pro Glu
        275                 280                 285
Ala Cys Arg Pro Ala Ala Gly Gly Ala Val His Thr Arg Gly Leu Asp
    290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                325                 330                 335
Lys Lys Leu Leu Tyr Ile Phe Lys Gln Pro Phe Met Arg Pro Val Gln
            340                 345                 350
Thr Thr Gln Glu Glu Asp Gly Cys Ser Cys Arg Phe Pro Glu Glu Glu
        355                 360                 365
Glu Gly Gly Cys Glu Leu Arg Val Lys Phe Ser Arg Ser Ala Asp Ala
    370                 375                 380
Pro Ala Tyr Lys Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                405                 410                 415
Pro Glu Met Gly Gly Lys Pro Arg Arg Lys Asn Pro Gln Glu Gly Leu
            420                 425                 430
Tyr Asn Glu Leu Gln Lys Asp Lys Met Ala Glu Ala Tyr Ser Glu Ile
        435                 440                 445
Gly Met Lys Gly Glu Arg Arg Arg Gly Lys Gly His Asp Gly Leu Tyr
    450                 455                 460
Gln Gly Leu Ser Thr Ala Thr Lys Asp Thr Tyr Asp Ala Leu His Met
```

Gln Ala Leu Pro Pro Arg
            485

<210> SEQ ID NO 63
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 64
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
atggccctcc ctgtcaccgc cctgctgctt ccgctggctc ttctgctcca cgccgctcgg    60

```
cccgaaattg tgatgaccca gtcacccgcc actcttagcc tttcacccgg tgagcgcgca    120
accctgtctt gcagagcctc ccaagacatc tcaaaatacc ttaattggta tcaacagaag    180
cccggacagg ctcctcgcct tctgatctac cacaccagcc ggctccattc tggaatccct    240
gccaggttca gcgtagcgg atctgggacc gactacaccc tcactatcag ctcactgcag    300
ccagaggact cgctgtctca tttctgtcag caagggaaca ccctgcccta ccctttgga    360
cagggcacca agctcgagat taaaggtgga ggtggcagcg gaggaggtgg gtccggcggt    420
ggaggaagcg gcggaggcgg gagccaggtc caactccaag aaagcggacc gggtcttgtg    480
aagccatcag aaactctttc actgacttgt actgtgagcg gagtgtctct ccccgattac    540
ggggtgtctt ggatcagaca gccaccgggg aagggtctgg aatggattgg agtgatttgg    600
ggctctgaga ctacttacta ctcttcatcc ctcaagtcac gcgtcaccat ctcaaaggac    660
aactctaaga tcaggtgtc actgaaactg tcatctgtga ccgcagccga caccgccgtg    720
tactattgcg ctaagcatta ctattatggc gggagctacg caatggatta ctggggacag    780
ggtactctgg tcaccgtgtc cagcaccact accccagcac cgaggccacc caccccggct    840
cctaccatcg cctcccagcc tctgtccctg cgtccggagg catgtagacc cgcagctggt    900
ggggccgtgc atacccgggg tcttgacttc gcctgcgata tctacatttg gcccctctg    960
gctggtactt gcggggtcct gctgctttca ctcgtgatca ctctttactg taagcgcggt   1020
cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
aacgaactca atcttggtcg gagagaggag tacgacgtgc tggacaagcg gagaggacgg   1260
gacccagaaa tgggcgggaa gccgcgcaga aagaatcccc aagagggcct gtacaacgag   1320
ctccaaaagg ataagatggc agaagcctat agcgagattg gtatgaaagg ggaacgcaga   1380
agaggcaaag gccacgacgg actgtaccag ggactcagca ccgccaccaa ggacacctat   1440
gacgctcttc acatgcaggc cctgccgcct cgg                                1473
```

<210> SEQ ID NO 65
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
```

```
            100                 105                 110
Asn Thr Leu Pro Tyr Thr Phe Gly Gln Gly Thr Lys Leu Glu Ile Lys
        115                 120                 125
Gly Gly Gly Gly Ser Gly Gly Gly Gly Ser Gly Gly Gly Ser Gly
130                 135                 140
Gly Gly Gly Ser Gln Val Gln Leu Gln Glu Ser Gly Pro Gly Leu Val
145                 150                 155                 160
Lys Pro Ser Glu Thr Leu Ser Leu Thr Cys Thr Val Ser Gly Val Ser
                165                 170                 175
Leu Pro Asp Tyr Gly Val Ser Trp Ile Arg Gln Pro Pro Gly Lys Gly
            180                 185                 190
Leu Glu Trp Ile Gly Val Ile Trp Gly Ser Glu Thr Thr Tyr Tyr Ser
        195                 200                 205
Ser Ser Leu Lys Ser Arg Val Thr Ile Ser Lys Asp Asn Ser Lys Asn
    210                 215                 220
Gln Val Ser Leu Lys Leu Ser Ser Val Thr Ala Ala Asp Thr Ala Val
225                 230                 235                 240
Tyr Tyr Cys Ala Lys His Tyr Tyr Gly Gly Ser Tyr Ala Met Asp
                245                 250                 255
Tyr Trp Gly Gln Gly Thr Leu Val Thr Val Ser Ser Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Lys Arg Gly Arg Lys Lys Leu Leu Tyr Ile Phe Lys Gln Pro Phe
            340                 345                 350
Met Arg Pro Val Gln Thr Thr Gln Glu Glu Asp Gly Cys Ser Cys Arg
        355                 360                 365
Phe Pro Glu Glu Glu Glu Gly Gly Cys Glu Leu Arg Val Lys Phe Ser
    370                 375                 380
Arg Ser Ala Asp Ala Pro Ala Tyr Lys Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
            420                 425                 430
Pro Gln Glu Gly Leu Tyr Asn Glu Leu Gln Lys Asp Lys Met Ala Glu
        435                 440                 445
Ala Tyr Ser Glu Ile Gly Met Lys Gly Glu Arg Arg Arg Gly Lys Gly
    450                 455                 460
His Asp Gly Leu Tyr Gln Gly Leu Ser Thr Ala Thr Lys Asp Thr Tyr
465                 470                 475                 480
Asp Ala Leu His Met Gln Ala Leu Pro Pro Arg
                485                 490

<210> SEQ ID NO 66
<211> LENGTH: 1473
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 66

| | | | | | |
|---|---|---|---|---|---|
| atggccctcc | ctgtcaccgc | cctgctgctt | ccgctggctc | ttctgctcca | cgccgctcgg | 60 |
| cccgaaattg | tgatgaccca | gtcacccgcc | actcttagcc | tttcacccgg | tgagcgcgca | 120 |
| accctgtctt | gcagagcctc | ccaagacatc | tcaaaatacc | ttaattggta | tcaacagaag | 180 |
| cccggacagg | ctcctcgcct | tctgatctac | cacaccagcc | ggctccattc | tggaatccct | 240 |
| gccaggttca | gcgtagcgg | atctgggacc | gactacaccc | tcactatcag | ctcactgcag | 300 |
| ccagaggact | tcgctgtcta | tttctgtcag | caagggaaca | ccctgcccta | cacctttgga | 360 |
| cagggcacca | agctcgagat | taaaggtgga | ggtggcagcg | gaggaggtgg | gtccggcggt | 420 |
| ggaggaagcg | gaggcggagg | gagccaggtc | caactccaag | aaagcggacc | gggtcttgtg | 480 |
| aagccatcag | aaactctttc | actgacttgt | actgtgagcg | gagtgtctct | ccccgattac | 540 |
| ggggtgtctt | ggatcagaca | gccaccgggg | aagggtctgg | aatggattgg | agtgatttgg | 600 |
| ggctctgaga | ctacttacta | ccaatcatcc | ctcaagtcac | gcgtcaccat | ctcaaaggac | 660 |
| aactctaaga | tcaggtgtc | actgaaactg | tcatctgtga | ccgcagccga | caccgccgtg | 720 |
| tactattgcg | ctaagcatta | ctattatggc | gggagctacg | caatggatta | ctggggacag | 780 |
| ggtactctgg | tcaccgtgtc | cagcaccact | accccagcac | cgaggccacc | caccccggct | 840 |
| cctaccatcg | cctcccagcc | tctgtccctg | cgtccggagg | catgtagacc | cgcagctggt | 900 |
| ggggccgtgc | atacccgggg | tcttgacttc | gcctgcgata | tctacatttg | gcccctctg | 960 |
| gctggtactt | gcggggtcct | gctgctttca | ctcgtgatca | ctctttactg | taagcgcggt | 1020 |
| cggaagaagc | tgctgtacat | cttaagcaa | cccttcatga | ggcctgtgca | gactactcaa | 1080 |
| gaggaggacg | gctgttcatg | ccggttccca | gaggaggagg | aaggcggctg | cgaactgcgc | 1140 |
| gtgaaattca | gccgcagcgc | agatgctcca | gcctacaagc | aggggcagaa | ccagctctac | 1200 |
| aacgaactca | atcttggtcg | agagaggag | tacgacgtgc | tggacaagcg | agaggacgg | 1260 |
| gacccagaaa | tgggcgggaa | gccgcgcaga | aagaatcccc | aagagggcct | gtacaacgag | 1320 |
| ctccaaaagg | ataagatggc | agaagcctat | agcgagattg | gtatgaaagg | ggaacgcaga | 1380 |
| agaggcaaag | gccacgacgg | actgtaccag | ggactcagca | ccgccaccaa | ggacacctat | 1440 |
| gacgctcttc | acatgcaggc | cctgccgcct | cgg | | | 1473 |

<210> SEQ ID NO 67
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Met Ala Leu Pro Val Thr Ala Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala

```
            50                  55                  60
Pro Arg Leu Leu Ile Tyr His Thr Ser Arg Leu His Ser Gly Ile Pro
 65                  70                  75                  80

Ala Arg Phe Ser Gly Ser Gly Ser Gly Thr Asp Tyr Thr Leu Thr Ile
                 85                  90                  95

Ser Ser Leu Gln Pro Glu Asp Phe Ala Val Tyr Phe Cys Gln Gln Gly
                100                 105                 110

Asn Thr Leu Pro Tyr Thr Phe Gly Gln Gly Thr Lys Leu Glu Ile Lys
                115                 120                 125

Gly Gly Gly Gly Ser Gly Gly Gly Ser Gly Gly Gly Ser Gly
                130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
                180                 185                 190

Leu Glu Trp Ile Gly Val Ile Trp Gly Ser Glu Thr Thr Tyr Tyr Gln
                195                 200                 205

Ser Ser Leu Lys Ser Arg Val Thr Ile Ser Lys Asp Asn Ser Lys Asn
                210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
                260                 265                 270

Ala Pro Arg Pro Pro Thr Pro Ala Pro Thr Ile Ala Ser Gln Pro Leu
                275                 280                 285

Ser Leu Arg Pro Glu Ala Cys Arg Pro Ala Ala Gly Gly Ala Val His
                290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
                355                 360                 365

Phe Pro Glu Glu Glu Glu Gly Gly Cys Glu Leu Arg Val Lys Phe Ser
                370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480
```

Asp Ala Leu His Met Gln Ala Leu Pro Pro Arg
                485                 490

<210> SEQ ID NO 68
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

| | | | | | |
|---|---|---|---|---|---|
| atggctctgc | ccgtgaccgc | actcctcctg | ccactggctc | tgctgcttca | cgccgctcgc | 60 |
| ccacaagtcc | agcttcaaga | tcagggcct | ggtctggtga | agccatctga | gactctgtcc | 120 |
| ctcacttgca | ccgtgagcgg | agtgtccctc | ccagactacg | gagtgagctg | gattagacag | 180 |
| cctcccggaa | agggactgga | gtggatcgga | gtgatttggg | gtagcgaaac | cacttactat | 240 |
| tcatcttccc | tgaagtcacg | ggtcaccatt | tcaaaggata | actcaaagaa | tcaagtgagc | 300 |
| ctcaagctct | catcagtcac | cgccgctgac | accgccgtgt | attactgtgc | caagcattac | 360 |
| tactatggag | gtcctacgc | catggactac | tggggccagg | gaactctggt | cactgtgtca | 420 |
| tctggtggag | gaggtagcgg | aggaggcggg | agcggtggag | gtggctccgg | aggtggcgga | 480 |
| agcgaaatcg | tgatgaccca | gagccctgca | acctgtccc | tttctcccgg | ggaacgggct | 540 |
| acccttttctt | gtcgggcatc | acaagatatc | tcaaaatacc | tcaattggta | tcaacagaag | 600 |
| ccgggacagg | cccctaggct | tcttatctac | cacacctctc | gcctgcatag | cgggattccc | 660 |
| gcacgcttta | gcgggtctgg | aagcgggacc | gactacactc | tgaccatctc | atctctccag | 720 |
| cccgaggact | tcgccgtcta | cttctgccag | cagggtaaca | ccctgccgta | cacctttcggc | 780 |
| cagggcacca | agcttgagat | caaaaccact | actcccgctc | aaggccacc | caccccctgcc | 840 |
| ccgaccatcg | cctctcagcc | gctttccctg | cgtccggagg | catgtagacc | cgcagctggt | 900 |
| gggggccgtgc | ataccccgggg | tcttgacttc | gcctgcgata | tctacatttg | ggcccctctg | 960 |
| gctggtactt | gcggggtcct | gctgctttca | ctcgtgatca | ctctttactg | taagcgcggt | 1020 |
| cggaagaagc | tgctgtacat | ctttaagcaa | cccttcatga | ggcctgtgca | gactactcaa | 1080 |
| gaggaggacg | gctgttcatg | ccggttccca | gaggaggagg | aaggcggctg | cgaactgcgc | 1140 |
| gtgaaattca | gccgcagcgc | agatgctcca | gcctacaagc | aggggcagaa | ccagctctac | 1200 |
| aacgaactca | atcttggtcg | gagagaggag | tacgacgtgc | tggacaagcg | gagaggacgg | 1260 |
| gacccagaaa | tgggcgggaa | gccgcgcaga | aagaatcccc | aagagggcct | gtacaacgag | 1320 |
| ctccaaaagg | ataagatggc | agaagcctat | agcgagattg | gtatgaaagg | ggaacgcaga | 1380 |
| agaggcaaag | gccacgacgg | actgtaccag | ggactcagca | ccgccaccaa | ggacacctat | 1440 |
| gacgctcttc | acatgcaggc | cctgccgcct | cgg | | | 1473 |

<210> SEQ ID NO 69
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Met Ala Leu Pro Val Thr Ala Leu Leu Leu Pro Leu Ala Leu Leu Leu

-continued

```
1               5                   10                  15
His Ala Ala Arg Pro Gln Val Gln Leu Gln Glu Ser Gly Pro Gly Leu
            20                  25                  30
Val Lys Pro Ser Glu Thr Leu Ser Leu Thr Cys Thr Val Ser Gly Val
            35                  40                  45
Ser Leu Pro Asp Tyr Gly Val Ser Trp Ile Arg Gln Pro Pro Gly Lys
            50                  55                  60
Gly Leu Glu Trp Ile Gly Val Ile Trp Gly Ser Glu Thr Thr Tyr Tyr
65                  70                  75                  80
Ser Ser Ser Leu Lys Ser Arg Val Thr Ile Ser Lys Asp Asn Ser Lys
            85                  90                  95
Asn Gln Val Ser Leu Lys Leu Ser Ser Val Thr Ala Ala Asp Thr Ala
            100                 105                 110
Val Tyr Tyr Cys Ala Lys His Tyr Tyr Gly Gly Ser Tyr Ala Met
            115                 120                 125
Asp Tyr Trp Gly Gln Gly Thr Leu Val Thr Val Ser Ser Gly Gly Gly
            130                 135                 140
Gly Ser Gly Gly Gly Gly Ser Gly Gly Gly Gly Ser Gly Gly Gly Gly
145                 150                 155                 160
Ser Glu Ile Val Met Thr Gln Ser Pro Ala Thr Leu Ser Leu Ser Pro
            165                 170                 175
Gly Glu Arg Ala Thr Leu Ser Cys Arg Ala Ser Gln Asp Ile Ser Lys
            180                 185                 190
Tyr Leu Asn Trp Tyr Gln Gln Lys Pro Gly Gln Ala Pro Arg Leu Leu
            195                 200                 205
Ile Tyr His Thr Ser Arg Leu His Ser Gly Ile Pro Ala Arg Phe Ser
            210                 215                 220
Gly Ser Gly Ser Gly Thr Asp Tyr Thr Leu Thr Ile Ser Ser Leu Gln
225                 230                 235                 240
Pro Glu Asp Phe Ala Val Tyr Phe Cys Gln Gln Gly Asn Thr Leu Pro
            245                 250                 255
Tyr Thr Phe Gly Gln Gly Thr Lys Leu Glu Ile Lys Thr Thr Thr Pro
            260                 265                 270
Ala Pro Arg Pro Pro Thr Pro Ala Pro Thr Ile Ala Ser Gln Pro Leu
            275                 280                 285
Ser Leu Arg Pro Glu Ala Cys Arg Pro Ala Ala Gly Gly Ala Val His
            290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
            325                 330                 335
Cys Lys Arg Gly Arg Lys Lys Leu Leu Tyr Ile Phe Lys Gln Pro Phe
            340                 345                 350
Met Arg Pro Val Gln Thr Thr Gln Glu Glu Asp Gly Cys Ser Cys Arg
            355                 360                 365
Phe Pro Glu Glu Glu Glu Gly Gly Cys Glu Leu Arg Val Lys Phe Ser
            370                 375                 380
Arg Ser Ala Asp Ala Pro Ala Tyr Lys Gln Gly Gln Asn Gln Leu Tyr
385                 390                 395                 400
Asn Glu Leu Asn Leu Gly Arg Arg Glu Glu Tyr Asp Val Leu Asp Lys
            405                 410                 415
Arg Arg Gly Arg Asp Pro Glu Met Gly Gly Lys Pro Arg Arg Lys Asn
            420                 425                 430
```

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 70
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

```
atggctctgc ccgtgaccgc actcctcctg ccactggctc tgctgcttca cgccgctcgc      60
ccacaagtcc agcttcaaga tcagggcct ggtctggtga agccatctga gactctgtcc      120
ctcacttgca ccgtgagcgg agtgtccctc ccagactacg gagtgagctg gattagacag      180
cctcccggaa agggactgga gtggatcgga gtgatttggg gtagcgaaac cacttactat      240
caatcttccc tgaagtcacg ggtcaccatt tcaaaggata actcaaagaa tcaagtgagc      300
ctcaagctct catcagtcac cgccgctgac accgccgtgt attactgtgc caagcattac      360
tactatggag gtcctacgc catggactac tggggccagg gaactctggt cactgtgtca      420
tctggtggag gaggtagcgg aggaggcggg agcggtggag gtggctccgg aggcggtggg      480
tcagaaatcg tgatgaccca gagccctgca accctgtccc tttctccgg ggaacgggct      540 accctttctt gtcgggcatc acaagatatc tcaaaatacc tcaattggta tcaacagaag      600
ccgggacagg cccctaggct tcttatctac cacacctctc gcctgcatag cgggattccc      660
gcacgcttta gcgggtctgg aagcgggacc gactacactc tgaccatctc atctctccag      720
cccgaggact cgccgtcta cttctgccag cagggtaaca ccctgccgta caccttcggc      780
cagggcacca agcttgagat caaaaccact actcccgctc aaggccacc cacccctgcc      840 ccgaccatcg cctctcagcc gctttccctg cgtccggagg catgtagacc cgcagctggt      900
ggggccgtgc atacccgggg tcttgacttc gcctgcgata tctacatttg gcccctctg      960 gctggtactt gcgggtcct gctgctttca ctcgtgatca ctctttactg taagcgcggt     1020
cggaagaagc tgctgtacat ctttaagcaa cccttcatga ggcctgtgca gactactcaa     1080
gaggaggacg ctgttcatg ccggttccca gaggaggag aaggcggctg cgaactgcgc     1140
gtgaaattca gccgcagcgc agatgctcca gcctacaagc aggggcagaa ccagctctac     1200
aacgaactca atcttggtcg gagagaggag tacgacgtgc tggacaagcg agaggacgg     1260 gacccagaaa tgggcgggaa gccgcgcaga aagaatcccc aagagggcct gtacaacgag     1320
ctccaaaagg ataagatggc agaagcctat agcgagattg gtatgaaagg ggaacgcaga     1380
agaggcaaag gccacgacgg actgtaccag ggactcagca ccgccaccaa ggacacctat     1440
gacgctcttc acatgcaggc cctgccgcct cgg                                  1473
```

<210> SEQ ID NO 71
<211> LENGTH: 491
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met Asp
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380
```

```
Arg Ser Ala Asp Ala Pro Ala Tyr Lys Gln Gly Gln Asn Gln Leu Tyr
            385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Lys Asn
        420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 72
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72

```
atggccctcc ctgtcaccgc cctgctgctt ccgctggctc ttctgctcca cgccgctcgg    60
cccgaaattg tgatgaccca gtcacccgcc actcttagcc tttcacccgg tgagcgcgca   120
accctgtctt gcagagcctc ccaagacatc tcaaatacc ttaattggta tcaacagaag   180
cccggacagc tcctcgcct tctgatctac cacaccagcc ggctccattc tggaatccct   240
gccaggttca gcggtagcgg atctgggacc gactacaccc tcactatcag ctcactgcag   300
ccagaggact cgctgtcta tttctgtcag caagggaaca ccctgcccta ccctttgga   360
cagggcacca agctcgagat taaggtgga ggtggcagcg gaggaggtgg gtccggcggt   420
ggaggaagcg gaggcggtgg gagccaggtc caactccaag aaagcggacc gggtcttgtg   480
aagccatcag aaactctttc actgacttgt actgtgagcg gagtgtctct ccccgattac   540
ggggtgtctt ggatcagaca gccaccgggg aagggtctgg aatggattgg agtgatttgg   600
ggctctgaga ctacttacta caactcatcc ctcaagtcac gcgtcaccat ctcaaaggac   660
aactctaaga tcaggtgtc actgaaactg tcatctgtga ccgcagccga caccgccgtg   720
tactattgcg ctaagcatta ctattatggc gggagctacg caatggatta ctggggacag   780
ggtactctgg tcaccgtgtc cagcaccact accccagcac cgaggccacc caccccggct   840
cctaccatcg cctcccagcc tctgtccctg cgtccggagg catgtagacc cgcagctggt   900
ggggccgtgc ataccgggg tcttgacttc gcctgcgata tctacatttg gcccctctg   960
gctggtactt gcgggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg agaggacgg  1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
```

-continued

```
agaggcaaag gccacgacgg actgtaccag ggactcagca ccgccaccaa ggacacctat    1440
gacgctcttc acatgcaggc cctgccgcct cgg                                 1473
```

<210> SEQ ID NO 73
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 73

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335
```

```
Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
            355                 360                 365

Phe Pro Glu Glu Glu Gly Gly Cys Glu Leu Arg Val Lys Phe Ser
        370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 74
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaaatacc ttaattggta tcaacagaag     180
cccggacagg ctcctcgcct tctgatctac cacaccagcc ggctccattc tggaatccct     240
gccaggttca gcggtagcgg atctgggacc gactacaccc tcactatcag ctcactgcag     300
ccagaggact cgctgtgtcta tttctgtcag caagggaaca ccctgcccta caccttggc      360 cagggcacca agctcgagat taaaggtgga ggtggcagcg gaggaggtgg gtccggcggt     420
ggaggaagcg gaggcggtgg gagccaggtc caactccaag aaagcggacc gggtcttgtg     480
aagccatcag aaactctttc actgacttgt actgtgagcg gagtgtctct ccccgattac     540
ggggtgtctt ggatcagaca gccaccgggg aagggtctgg aatggattgg agtgatttgg     600
ggctctgaga ctacttacta caactcatcc ctcaagtcac gcgtcaccat ctcaaaggac     660
aactctaaga tcaggtgtc actgaaactg tcatctgtga ccgcagccga caccgccgtg     720
tactattgcg ctaagcatta ctattatggc gggagctacg caatggatta ctggggacag     780
ggtactctgg tcaccgtgtc cagcaccact accccagcac cgaggccacc cacccccggct     840 cctaccatcg cctcccagcc tctgtccctg cgtccgagg catgtagacc cgcagctggt     900
ggggccgtgc ataccggggg tcttgacttc gcctgcgata tctacatttg ggcccctctg     960
gctggtactt gcggggtcct gctgcttttca ctcgtgatca ctctttactg taagcgcggt    1020
cggaagaagc tgctgtacat ctttaagcaa cccttcatga ggcctgtgca gactactcaa    1080
```

```
gaggaggacg gctgttcatg ccggttccca gaggaggagg aaggcggctg cgaactgcgc    1140
gtgaaattca gccgcagcgc agatgctcca gcctacaagc aggggcagaa ccagctctac    1200
aacgaactca atcttggtcg gagagaggag tacgacgtgc tggacaagcg agaggacgg     1260 gacccagaaa tgggcgggaa gccgcgcaga aagaatcccc aagagggcct gtacaacgag    1320
ctccaaaagg ataagatggc agaagcctat agcgagattg gtatgaaagg ggaacgcaga    1380
agaggcaaag ccacgacgg actgtaccag ggactcagca ccgccaccaa ggacacctat     1440
gacgctcttc acatgcaggc cctgccgcct cgg                                 1473
```

<210> SEQ ID NO 75
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285
```

```
Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
        370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 76
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
atggctctgc ccgtgaccgc actcctcctg ccactggctc tgctgcttca cgccgctcgc      60
ccacaagtcc agcttcaaga atcagggcct ggtctggtga agccatctga gactctgtcc     120
ctcacttgca ccgtgagcgg agtgtccctc ccagactacg gagtgagctg gattagacag     180
cctcccggaa agggactgga gtggatcgga gtgatttggg gtagcgaaac cacttactat     240
aactcttccc tgaagtcacg ggtcaccatt tcaaaggata ctcaaagaa tcaagtgagc      300 ctcaagctct catcagtcac cgccgctgac accgccgtgt attactgtgc caagcattac     360
tactatggag gtcctacgc catggactac tggggccagg gaactctggt cactgtgtca     420
tctggtggag gaggtagcgg aggaggcggg agcggtggag gtggctccgg aggtggcgga     480
agcgaaatcg tgatgaccca gagccctgca accctgtccc tttctcccgg ggaacgggct     540
accctttctt gtcgggcatc acaagatatc tcaaaatacc tcaattggta tcaacagaag     600
ccgggacagg cccctaggct tcttatctac cacacctctc gcctgcatag cgggattccc     660
gcacgcttta gcgggtctgg aagcgggacc gactacactc tgaccatctc atctctccag     720
cccgaggact cgccgtcta cttctgccag cagggtaaca ccctgccgta cccttcggc      780 cagggcacca agcttgagat caaaaccact actcccgctc aaggccacc caccctgcc      840
```

```
ccgaccatcg cctctcagcc gctttccctg cgtccggagg catgtagacc cgcagctggt    900
ggggccgtgc atacccgggg tcttgacttc gcctgcgata tctacatttg ggcccctctg    960
gctggtactt gcggggtcct gctgctttca ctcgtgatca ctctttactg taagcgcggt   1020
cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
aacgaactca atcttggtcg gagagaggag tacgacgtgc tggacaagcg gagaggacgg   1260
gacccagaaa tgggcgggaa gccgcgcaga aagaatcccc aagagggcct gtacaacgag   1320
ctccaaaagg ataagatggc agaagcctat agcgagattg gtatgaaagg ggaacgcaga   1380
agaggcaaag gccacgacgg actgtaccag ggactcagca ccgccaccaa ggacacctat   1440
gacgctcttc acatgcaggc cctgccgcct cgg                                1473
```

<210> SEQ ID NO 77
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240
```

```
Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 78
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
atggccctcc ctgtcaccgc cctgctgctt ccgctggctc ttctgctcca cgccgctcgg     60
cccgaaattg tgatgaccca gtcacccgcc actcttagcc tttcacccgg tgagcgcgca    120
accctgtctt gcagagcctc ccaagacatc tcaaatacc ttaattggta tcaacagaag    180
cccggacagg ctcctcgcct tctgatctac cacaccagcc ggctccattc tggaatccct    240
gccaggttca gcggtagcgg atctgggacc gactacaccc tcactatcag ctcactgcag    300
ccagaggact cgctgtctca tttctgtcag caagggaaca ccctgcccta cacctttgga    360
cagggcacca agctcgagat taaggtgga ggtggcagcg aggaggtgg gtccggcggt    420 ggaggaagcc aggtccaact ccaagaaagc ggaccgggtc ttgtgaagcc atcagaaact    480
ctttcactga cttgtactgt gagcggagtg tctctccccg attacggggt gtcttggatc    540
```

```
agacagccac cggggaaggg tctggaatgg attggagtga tttggggctc tgagactact    600
tactacaact catccctcaa gtcacgcgtc accatctcaa aggacaactc taagaatcag    660
gtgtcactga aactgtcatc tgtgaccgca gccgacaccg ccgtgtacta ttgcgctaag    720
cattactatt atggcgggag ctacgcaatg gattactggg gacagggtac tctggtcacc    780
gtgtccagca ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta agcaaccctt catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggaccc agaaatgggc    1260 gggaagccgc gcagaaagaa tccccaagag ggcctgtaca cgagctcca aaaggataag   1320 atggcagaag cctatagcga gattggtatg aaagggggaac gcagaagagg caaaggccac   1380
gacggactgt accagggact cagcaccgcc accaaggaca cctatgacgc tcttcacatg   1440
caggccctgc cgcctcgg                                                 1458
```

<210> SEQ ID NO 79
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

Met Ala Leu Pro Val Thr Ala Leu Leu Pro Leu Ala Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
        50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
                130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ser Leu Lys Ser
            195                 200                 205

Arg Val Thr Ile Ser Lys Asp Asn Ser Lys Asn Gln Val Ser Leu Lys
        210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Leu Val Thr Val Ser Ser Thr Thr Pro Ala Pro Arg Pro Pro
        260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
        340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
        370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
        420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 80
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80 atggcttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300

```
caagaagata ttgccactta cttttgccaa cagggtaata cgcttccgta cacgttcgga    360
gggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcagggtc tcattaccg actatggtgt aagctggatt      540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cgggggggcgc agtgcacacg    900
aggggggctgg acttcgcctg tgatatctac atctgggcgc ccttggccgg gacttgtggg    960
gtccttctcc tgtcactggt tatcaccctt tactgcaaac ggggcagaaa gaaactcctg   1020
tatatattca acaaccatt tatgagacca gtacaaacta ctcaagagga gatggctgt     1080
agctgccgat ttccagaaga agaagaagga ggatgtgaac tgagagtgaa gttcagcagg   1140
agcgcagacg ccccccgcgta caagcagggc cagaaccagc tctataacga gctcaatcta   1200
ggacgaagag aggagtacga tgttttggac aagagacgtg gccgggaccc tgagatgggg   1260
ggaaagccga aaggaagaa ccctcaggaa ggcctgtaca atgaactgca gaaagataag   1320
atggcggagg cctacagtga gattgggatg aaaggcgagc gccggagggg caagggggcac   1380
gatggccttt accagggtct cagtacagcc accaaggaca cctacgacgc ccttcacatg   1440
caggccctgc cccctcgc                                                  1458
```

<210> SEQ ID NO 81
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Glu
        130                 135                 140

```
Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 82
<211> LENGTH: 1132
<212> TYPE: PRT
<213> ORGANISM: Homo sapiens

<400> SEQUENCE: 82

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
```

-continued

```
                20                  25                  30
Pro Gln Gly Trp Arg Leu Val Gln Arg Gly Asp Pro Ala Ala Phe Arg
            35                  40                  45
Ala Leu Val Ala Gln Cys Leu Val Cys Val Pro Trp Asp Ala Arg Pro
         50                  55                  60
Pro Pro Ala Ala Pro Ser Phe Arg Gln Val Ser Cys Leu Lys Glu Leu
 65                  70                  75                  80
Val Ala Arg Val Leu Gln Arg Leu Cys Glu Arg Gly Ala Lys Asn Val
                 85                  90                  95
Leu Ala Phe Gly Phe Ala Leu Leu Asp Gly Ala Arg Gly Gly Pro Pro
            100                 105                 110
Glu Ala Phe Thr Thr Ser Val Arg Ser Tyr Leu Pro Asn Thr Val Thr
            115                 120                 125
Asp Ala Leu Arg Gly Ser Gly Ala Trp Gly Leu Leu Arg Arg Val
        130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro Pro His Ala Ser Gly
            180                 185                 190
Pro Arg Arg Arg Leu Gly Cys Glu Arg Ala Trp Asn His Ser Val Arg
            195                 200                 205
Glu Ala Gly Val Pro Leu Gly Leu Pro Ala Pro Gly Ala Arg Arg Arg
            210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
            260                 265                 270
Val Ser Pro Ala Arg Pro Ala Glu Glu Ala Thr Ser Leu Glu Gly Ala
            275                 280                 285
Leu Ser Gly Thr Arg His Ser His Pro Ser Val Gly Arg Gln His His
         290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
            355                 360                 365
Arg Pro Trp Met Pro Gly Thr Pro Arg Arg Leu Pro Arg Leu Pro Gln
         370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Glu Asp Thr Asp Pro Arg Arg Leu
            435                 440                 445
```

```
Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Gly Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
    850                 855                 860
```

```
Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Asn Phe Pro Val Glu Asp Glu
        900                 905                 910

Ala Leu Gly Gly Thr Ala Phe Val Gln Met Pro Ala His Gly Leu Phe
            915                 920                 925

Pro Trp Cys Gly Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 83
<211> LENGTH: 4027
<212> TYPE: DNA
<213> ORGANISM: Homo sapiens

<400> SEQUENCE: 83
caggcagcgt ggtcctgctg cgcacgtggg aagccctggc cccggccacc cccgcgatgc      60
cgcgcgctcc ccgctgccga gccgtgcgct ccctgctgcg cagccactac cgcgaggtgc     120
tgccgctggc cacgttcgtg cggcgcctgg ggccccaggg ctggcggctg gtgcagcgcg     180
gggacccggc ggcttttccgc gcgctggtgg cccagtgcct ggtgtgcgtg ccctgggacg     240 cacgccgcc cccgccgcc cctccttcc gccaggtgtc ctgcctgaag gagctggtgg        300
cccgagtgct gcagaggctg tgcgagcgcg gcgcgaagaa cgtgctggcc ttcggcttcg     360
cgctgctgga cggggcccgc gggggccccc ccgaggcctt caccaccagc gtgcgcagct     420
acctgcccaa cacggtgacc gacgcactgc ggggagcgg ggcgtggggg ctgctgtttgc     480 gccgcgtggg cgacgacgtg ctggttcacc tgctggcacg ctgcgcgctc tttgtgctgg     540
```

-continued

```
tggctcccag ctgcgcctac caggtgtgcg ggccgccgct gtaccagctc ggcgctgcca      600
ctcaggcccg gcccccgcca cacgctagtg gaccccgaag gcgtctggga tgcgaacggg      660
cctggaacca tagcgtcagg gaggccgggg tcccctggg cctgccagcc ccgggtgcga       720
ggaggcgcgg gggcagtgcc agccgaagtc tgccgttgcc caagaggccc aggcgtggcg      780
ctgcccctga gccggagcgg acgcccgttg ggcagggtc ctgggcccac ccgggcagga      840
cgcgtggacc gagtgaccgt ggtttctgtg tggtgtcacc tgccagaccc gccgaagaag      900
ccacctcttt ggagggtgcg ctctctggca cgcgccactc ccacccatcc gtgggccgcc      960
agcaccacgc gggcccccca tccacatcgc ggccaccacg tccctgggac acgccttgtc     1020
ccccggtgta cgccgagacc aagcacttcc tctactcctc aggcgacaag gagcagctgc     1080
ggccctcctt cctactcagc tctctgaggc ccagcctgac tggcgctcgg aggctcgtgg     1140
agaccatctt tctgggttcc aggccctgga tgccagggac tccccgcagg ttgccccgcc     1200
tgccccagcg ctactggcaa atgcggcccc tgtttctgga gctgcttggg aaccacgcgc     1260
agtgccccta cggggtgctc ctcaagacgc actgcccgct gcgagctgcg gtcacccag      1320 cagccggtgt ctgtgcccgg gagaagcccc agggctctgt ggcggccccc gaggaggag      1380 acacagaccc ccgtcgcctg gtgcagctgc tccgccagca cagcagcccc tggcaggtgt     1440
acggcttcgt gcgggcctgc ctgcgccggc tggtgccccc aggcctctgg ggctccaggc     1500
acaacgaacg ccgcttcctc aggaacacca agaagttcat ctccctgggg aagcatgcca     1560
agctctcgct gcaggagctg acgtggaaga tgagcgtgcg gggctgcgct tggctgcgca     1620
ggagcccagg ggttggctgt gttccggccg cagagcaccg tctgcgtgag gagatcctgg     1680
ccaagttcct gcactggctg atgagtgtgt acgtcgtcga gctgctcagg tctttctttt     1740
atgtcacgga gaccacgttt caaaagaaca ggctcttttt ctaccggaag agtgtctgga     1800
gcaagttgca aagcattgga atcagacagc acttgaagag ggtgcagctg cgggagctgt     1860
cggaagcaga ggtcaggcag catcgggaag ccaggcccgc cctgctgacg tccagactcc     1920
gcttcatccc caagcctgac gggctgcgg cgattgtgaa catggactac gtcgtgggag     1980
ccagaacgtt ccgcagagaa agagggccg agcgtctcac ctcgagggtg aaggcactgt     2040
tcagcgtgct caactacgag cgggcgcggc gccccggcct cctgggcgcc tctgtgctgg     2100
gcctggacga tatccacagg gcctggcgca ccttcgtgct gcgtgtgcgg gcccaggacc     2160
cgccgcctga gctgtacttt gtcaaggtgg atgtgacggg cgcgtacgac accatccccc     2220
aggacaggct cacggaggtc atcgccagca tcatcaaacc ccagaacacg tactgcgtgc     2280
gtcggtatgc cgtggtccag aaggccgccc atgggcacgt ccgcaaggcc ttcaagagcc     2340
acgtctctac cttgacagac ctccagccgt acatgcgaca gttcgtggct cacctgcagg     2400
agaccagccc gctgagggat gccgtcgtca tcgagcagag ctcctccctg aatgaggcca     2460
gcagtggcct cttcgacgtc ttcctacgct tcatgtgcca ccacgccgtg cgcatcaggg     2520
gcaagtccta cgtccagtgc caggggatcc cgcagggctc catcctctcc acgctgctct     2580
gcagcctgtg ctacggcgac atggagaaca agctgtttgc ggggattcgg cgggacgggc     2640
tgctcctgcg tttggtggat gatttcttgt tggtgacacc tcacctcacc cacgcgaaaa     2700
ccttcctcag gaccctggtc cgaggtgtcc ctgagtatgg ctgcgtggtg aacttgcgga     2760
agacagtggt gaacttccct gtagaagacg aggccctggg tggcacggct tttgttcaga     2820
tgccggccca cggcctattc ccctggtgcg gcctgctgct ggataccggg accctggagg     2880
```

```
tgcagagcga ctactccagc tatgcccgga cctccatcag agccagtctc accttcaacc    2940
gcggcttcaa ggctgggagg aacatgcgtc gcaaactctt tggggtcttg cggctgaagt    3000
gtcacagcct gtttctggat ttgcaggtga acagcctcca gacggtgtgc accaacatct    3060
acaagatcct cctgctgcag gcgtacaggt tcacgcatg tgtgctgcag ctcccatttc     3120
atcagcaagt ttggaagaac cccacatttt tcctgcgcgt catctctgac acggcctccc    3180
tctgctactc catcctgaaa gccaagaacg cagggatgtc gctgggggcc aagggcgccg    3240
ccggccctct gccctccgag gccgtgcagt ggctgtgcca ccaagcattc ctgctcaagc    3300
tgactcgaca ccgtgtcacc tacgtgccac tcctggggtc actcaggaca gcccagacgc    3360
agctgagtcg gaagctcccg gggacgacgc tgactgccct ggaggccgca gccaacccgg    3420
cactgccctc agacttcaag accatcctgg actgatggcc accgcccac agccaggccg     3480 agagcagaca ccagcagccc tgtcacgccg ggctctacgt cccagggagg gaggggcggc    3540
ccacacccag gcccgcaccg ctgggagtct gaggcctgag tgagtgtttg gccgaggcct    3600
gcatgtccgg ctgaaggctg agtgtccggc tgaggcctga gcgagtgtcc agccaagggc    3660
tgagtgtcca gcacacctgc cgtcttcact tccccacagg ctggcgctcg gctccacccc    3720
agggccagct tttcctcacc aggagcccgg cttccactcc ccacatagga atagtccatc    3780
cccagattcg ccattgttca cccctcgccc tgccctcctt tgccttccac ccccaccatc    3840
caggtggaga ccctgagaag gaccctggga gctctgggaa tttggagtga ccaaaggtgt    3900
gccctgtaca caggcgagga ccctgcacct ggatgggggt ccctgtgggt caaattgggg    3960
ggaggtgctg tgggagtaaa atactgaata tatgagtttt tcagtttga aaaaaaaaa     4020 aaaaaaa                                                              4027
```

<210> SEQ ID NO 84
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

```
Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Ser Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Gly Gly Gly Ser Gly Gly Gly Ser Gly
        115                 120                 125

Gly Gly Ser Gly Gly Gly Ser Glu Leu Val Leu Thr Gln Ser Pro Lys
    130                 135                 140
```

```
Phe Met Ser Thr Ser Val Gly Asp Arg Val Ser Val Thr Cys Lys Ala
145                 150                 155                 160

Ser Gln Asn Val Gly Thr Asn Val Ala Trp Tyr Gln Gln Lys Pro Gly
                165                 170                 175

Gln Ser Pro Lys Pro Leu Ile Tyr Ser Ala Thr Tyr Arg Asn Ser Gly
            180                 185                 190

Val Pro Asp Arg Phe Thr Gly Ser Gly Ser Gly Thr Asp Phe Thr Leu
        195                 200                 205

Thr Ile Thr Asn Val Gln Ser Lys Asp Leu Ala Asp Tyr Phe Cys Gln
    210                 215                 220

Tyr Asn Arg Tyr Pro Tyr Thr Ser Phe Phe Thr Lys Leu Glu Ile
225                 230                 235                 240

Lys Arg Arg Ser
```

<210> SEQ ID NO 85
<211> LENGTH: 464
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 85

```
Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Ser Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Gly Gly Gly Ser Gly Gly Gly Ser Gly
        115                 120                 125

Gly Gly Ser Gly Gly Gly Ser Glu Leu Val Leu Thr Gln Ser Pro Lys
    130                 135                 140

Phe Met Ser Thr Ser Val Gly Asp Arg Val Ser Val Thr Cys Lys Ala
145                 150                 155                 160

Ser Gln Asn Val Gly Thr Asn Val Ala Trp Tyr Gln Gln Lys Pro Gly
                165                 170                 175

Gln Ser Pro Lys Pro Leu Ile Tyr Ser Ala Thr Tyr Arg Asn Ser Gly
            180                 185                 190

Val Pro Asp Arg Phe Thr Gly Ser Gly Ser Gly Thr Asp Phe Thr Leu
        195                 200                 205

Thr Ile Thr Asn Val Gln Ser Lys Asp Leu Ala Asp Tyr Phe Cys Gln
    210                 215                 220

Tyr Asn Arg Tyr Pro Tyr Thr Ser Phe Phe Thr Lys Leu Glu Ile
225                 230                 235                 240

Lys Arg Arg Ser Lys Ile Glu Val Met Tyr Pro Pro Pro Tyr Leu Asp
                245                 250                 255
```

```
Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
            275                 280                 285

Val Val Val Gly Gly Val Leu Ala Cys Tyr Ser Leu Leu Val Thr Val
            290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Arg Val Lys Phe Ser Arg Ser Ala Asp Ala Pro Ala Tyr Gln Gln Gly
            355                 360                 365

Gln Asn Gln Leu Tyr Asn Glu Leu Asn Leu Gly Arg Arg Glu Glu Tyr
            370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
            435                 440                 445

Thr Lys Asp Thr Tyr Asp Ala Leu His Met Gln Ala Leu Pro Pro Arg
            450                 455                 460

<210> SEQ ID NO 86
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
            130                 135                 140
```

```
Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Glu
                245
```

<210> SEQ ID NO 87
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Glu Ser Lys Tyr Gly Pro Pro Cys Pro Pro Cys
```

```
                        245                 250                 255
Pro Met Phe Trp Val Leu Val Val Gly Val Leu Ala Cys Tyr
            260                 265                 270

Ser Leu Leu Val Thr Val Ala Phe Ile Ile Phe Trp Val Lys Arg Gly
            275                 280                 285

Arg Lys Lys Leu Leu Tyr Ile Phe Lys Gln Pro Phe Met Arg Pro Val
            290                 295                 300

Gln Thr Thr Gln Glu Glu Asp Gly Cys Ser Cys Arg Phe Glu Glu
305                 310                 315                 320

Glu Gly Gly Cys Glu Leu Arg Val Lys Phe Ser Arg Ser Ala Asp Ala
            325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Arg Gly Arg Asp
            355                 360                 365

Pro Glu Met Gly Gly Lys Pro Arg Arg Lys Asn Pro Gln Glu Gly Leu
            370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
            405                 410                 415

Gln Gly Leu Ser Thr Ala Thr Lys Asp Thr Tyr Asp Ala Leu His Met
            420                 425                 430

Gln Ala Leu Pro Pro Arg Leu
            435

<210> SEQ ID NO 88
<211> LENGTH: 819
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
            85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
        130                 135                 140

Val Thr Cys Thr Val Ser Gly Val Ser Leu Pro Asp Tyr Gly Val Ser
145                 150                 155                 160
```

-continued

```
Trp Ile Arg Gln Pro Pro Arg Lys Gly Leu Glu Trp Leu Gly Val Ile
            165                 170                 175
Trp Gly Ser Glu Thr Thr Tyr Tyr Asn Ser Ala Leu Lys Ser Arg Leu
        180                 185                 190
Thr Ile Ile Lys Asp Asn Ser Lys Ser Gln Val Phe Leu Lys Met Asn
    195                 200                 205
Ser Leu Gln Thr Asp Asp Thr Ala Ile Tyr Tyr Cys Ala Lys His Tyr
210                 215                 220
Tyr Tyr Gly Gly Ser Tyr Ala Met Asp Tyr Trp Gly Gln Gly Thr Ser
225                 230                 235                 240
Val Thr Val Ser Ser Glu Ser Lys Tyr Gly Pro Pro Cys Pro Pro Cys
            245                 250                 255
Pro Met Phe Trp Val Leu Val Val Val Gly Val Leu Ala Cys Tyr
            260                 265                 270
Ser Leu Leu Val Thr Val Ala Phe Ile Ile Phe Trp Val Lys Arg Gly
        275                 280                 285
Arg Lys Lys Leu Leu Tyr Ile Phe Lys Gln Pro Phe Met Arg Pro Val
    290                 295                 300
Gln Thr Thr Gln Glu Glu Asp Gly Cys Ser Cys Arg Phe Glu Glu Glu
305                 310                 315                 320
Glu Gly Gly Cys Glu Leu Arg Val Lys Phe Ser Arg Ser Ala Asp Ala
            325                 330                 335
Pro Ala Tyr Gln Gln Gly Gln Asn Gln Leu Tyr Asn Glu Leu Asn Leu
            340                 345                 350
Gly Arg Arg Glu Glu Tyr Asp Val Leu Asp Lys Arg Arg Gly Arg Asp
        355                 360                 365
Pro Glu Met Gly Gly Lys Pro Arg Arg Lys Asn Pro Gln Glu Gly Leu
    370                 375                 380
Tyr Asn Glu Leu Gln Lys Asp Lys Met Ala Glu Ala Tyr Ser Glu Ile
385                 390                 395                 400
Gly Met Lys Gly Glu Arg Arg Arg Gly Lys Gly His Asp Gly Leu Tyr
            405                 410                 415
Gln Gly Leu Ser Thr Ala Thr Lys Asp Thr Tyr Asp Ala Leu His Met
            420                 425                 430
Gln Ala Leu Pro Pro Arg Leu Glu Gly Gly Gly Glu Gly Arg Gly Ser
        435                 440                 445
Leu Leu Thr Cys Gly Asp Val Glu Glu Asn Pro Gly Pro Arg Met Leu
    450                 455                 460
Leu Leu Val Thr Ser Leu Leu Leu Cys Glu Leu Pro His Pro Ala Phe
465                 470                 475                 480
Leu Leu Ile Pro Arg Lys Val Cys Asn Gly Ile Gly Ile Gly Glu Phe
            485                 490                 495
Lys Asp Ser Leu Ser Ile Asn Ala Thr Asn Ile Lys His Phe Lys Asn
            500                 505                 510
Cys Thr Ser Ile Ser Gly Asp Leu His Ile Leu Pro Val Ala Phe Arg
        515                 520                 525
Gly Asp Ser Phe Thr His Thr Pro Pro Leu Asp Pro Gln Glu Leu Asp
    530                 535                 540
Ile Leu Lys Thr Val Lys Glu Ile Thr Gly Phe Leu Leu Ile Gln Ala
545                 550                 555                 560
Trp Pro Glu Asn Arg Thr Asp Leu His Ala Phe Glu Asn Leu Glu Ile
            565                 570                 575
```

```
Ile Arg Gly Arg Thr Lys Gln His Gly Gln Phe Ser Leu Ala Val Val
            580                 585                 590

Ser Leu Asn Ile Thr Ser Leu Gly Leu Arg Ser Leu Lys Glu Ile Ser
        595                 600                 605

Asp Gly Asp Val Ile Ile Ser Gly Asn Lys Asn Leu Cys Tyr Ala Asn
    610                 615                 620

Thr Ile Asn Trp Lys Lys Leu Phe Gly Thr Ser Gly Gln Lys Thr Lys
625                 630                 635                 640

Ile Ile Ser Asn Arg Gly Glu Asn Ser Cys Lys Ala Thr Gly Gln Val
                645                 650                 655

Cys His Ala Leu Cys Ser Pro Glu Gly Cys Trp Gly Pro Glu Pro Arg
            660                 665                 670

Asp Cys Val Ser Cys Arg Asn Val Ser Arg Gly Arg Glu Cys Val Asp
        675                 680                 685

Lys Cys Asn Leu Leu Glu Gly Glu Pro Arg Glu Phe Val Glu Asn Ser
    690                 695                 700

Glu Cys Ile Gln Cys His Pro Glu Cys Leu Pro Gln Ala Met Asn Ile
705                 710                 715                 720

Thr Cys Thr Gly Arg Gly Pro Asp Asn Cys Ile Gln Cys Ala His Tyr
                725                 730                 735

Ile Asp Gly Pro His Cys Val Lys Thr Cys Pro Ala Gly Val Met Gly
            740                 745                 750

Glu Asn Asn Thr Leu Val Trp Lys Tyr Ala Asp Ala Gly His Val Cys
        755                 760                 765

His Leu Cys His Pro Asn Cys Thr Tyr Gly Cys Thr Gly Pro Gly Leu
    770                 775                 780

Glu Gly Cys Pro Thr Asn Gly Pro Lys Ile Pro Ser Ile Ala Thr Gly
785                 790                 795                 800

Met Val Gly Ala Leu Leu Leu Leu Val Ala Leu Gly Ile Gly
                805                 810                 815

Leu Phe Met

<210> SEQ ID NO 89
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110
```

```
Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
        130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
            245

<210> SEQ ID NO 90
<211> LENGTH: 467
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
        130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205
```

```
Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Ala Ala Ile Glu Val Met Tyr Pro Pro Pro
                245                 250                 255

Tyr Leu Asp Asn Glu Lys Ser Asn Gly Thr Ile Ile His Val Lys Gly
                260                 265                 270

Lys His Leu Cys Pro Ser Pro Leu Phe Pro Gly Pro Ser Lys Pro Phe
                275                 280                 285

Trp Val Leu Val Val Val Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
                340                 345                 350

Tyr Arg Ser Arg Val Lys Phe Ser Arg Ser Ala Asp Ala Pro Ala Tyr
                355                 360                 365

Gln Gln Gly Gln Asn Gln Leu Tyr Asn Glu Leu Asn Leu Gly Arg Arg
                370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
                420                 425                 430

Gly Glu Arg Arg Arg Gly Lys Gly His Asp Gly Leu Tyr Gln Gly Leu
                435                 440                 445

Ser Thr Ala Thr Lys Asp Thr Tyr Asp Ala Leu His Met Gln Ala Leu
                450                 455                 460

Pro Pro Arg
465

<210> SEQ ID NO 91
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Arg Gly Asp Ser
1

<210> SEQ ID NO 92
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Asp Val Pro Asp Tyr Ala Ser Leu Gly Gly Pro Ser Ser Pro Lys Lys
```

```
                1               5                  10                 15
            Lys Arg Lys Val Ser Arg Gly Val Gln Val Glu Thr Ile Ser Pro Gly
                           20                  25                 30

Asp Gly Arg Thr Phe Pro Lys Arg Gly Gln Thr Cys Val Val His Tyr
                           35                  40                 45

Thr Gly Met Leu Glu Asp Gly Lys Lys Phe Asp Ser Ser Arg Asp Arg
                           50                  55                 60

Asn Lys Pro Phe Lys Phe Met Leu Gly Lys Gln Glu Val Ile Arg Gly
             65                  70                  75                 80

Trp Glu Glu Gly Val Ala Gln Met Ser Val Gly Gln Arg Ala Lys Leu
                           85                  90                 95

Thr Ile Ser Pro Asp Tyr Ala Tyr Gly Ala Thr Gly His Pro Gly Ile
                           100                 105                110

Ile Pro Pro His Ala Thr Leu Val Phe Asp Val Glu Leu Leu Lys Leu
                           115                 120                125

Glu Thr Ser Tyr
                           130

<210> SEQ ID NO 93
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Val Gln Val Glu Thr Ile Ser Pro Gly Asp Gly Arg Thr Phe Pro Lys
 1               5                  10                 15

Arg Gly Gln Thr Cys Val Val His Tyr Thr Gly Met Leu Glu Asp Gly
                20                  25                 30

Lys Lys Phe Asp Ser Ser Arg Asp Arg Asn Lys Pro Phe Lys Phe Met
            35                  40                  45

Leu Gly Lys Gln Glu Val Ile Arg Gly Trp Glu Glu Gly Val Ala Gln
 50                  55                  60

Met Ser Val Gly Gln Arg Ala Lys Leu Thr Ile Ser Pro Asp Tyr Ala
 65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
                100                 105

<210> SEQ ID NO 94
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Ile Leu Trp His Glu Met Trp His Glu Gly Leu Glu Glu Ala Ser Arg
 1               5                  10                 15

Leu Tyr Phe Gly Glu Arg Asn Val Lys Gly Met Phe Glu Val Leu Glu
                20                  25                 30

Pro Leu His Ala Met Met Glu Arg Gly Pro Gln Thr Leu Lys Glu Thr
            35                  40                  45
```

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90

<210> SEQ ID NO 95
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 96
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 97
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

```
Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95
```

<210> SEQ ID NO 98
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 98

```
Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95
```

<210> SEQ ID NO 99
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

```
Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45
```

Ser Phe Asn Gln Ala Tyr Gly Arg Asp Leu Met Glu Ala Gln Glu Trp
            50                  55                  60

Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
                85                  90                  95

<210> SEQ ID NO 100
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Ile Leu Trp His Glu Met Trp His Glu Gly Leu Leu Glu Ala Ser Arg
 1               5                  10                  15

Leu Tyr Phe Gly Glu Arg Asn Val Lys Gly Met Phe Glu Val Leu Glu
                20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
            50                  55                  60

Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
                85                  90                  95

<210> SEQ ID NO 101
<211> LENGTH: 450
<212> TYPE: DNA
<213> ORGANISM: Homo sapiens

<400> SEQUENCE: 101
cccggatggt ttctggactc tccggatcgc ccgtggaatc ccccaacctt ctcaccggca     60
ctcttggttg tgactgaggg cgataatgcg accttcacgt gctcgttctc caacacctcc    120
gaatcattcg tgctgaactg gtaccgcatg agcccgtcaa accagaccga caagctcgcc    180
gcgtttccgg aagatcggtc gcaaccggga caggattgtc ggttccgcgt gactcaactg    240
ccgaatggca gagacttcca catgagcgtg gtccgcgcta ggcgaaacga ctccgggacc    300
tacctgtgcg gagccatctc gctggcgcct aaggcccaaa tcaaagagag cttgagggcc    360
gaactgagag tgaccgagcg cagagctgag gtgccaactg cacatccatc cccatcgcct    420
cggcctgcgg ggcagtttca gaccctggtc                                    450

<210> SEQ ID NO 102
<211> LENGTH: 785
<212> TYPE: DNA
<213> ORGANISM: Homo sapiens

<400> SEQUENCE: 102
actataaaga cagtgaaaag atcagtggtt atctttgcag acgccaccat cgctgtgagc     60
cctgtactat cagccatggt caactccgtc gtcttttttg aaatcaccag ggatggcaag    120
cccttgggcc gcatctccat caaactgttt gcagacaaga ttccaaagac agcagaaaac    180
tttcgtgctc tgagcactgg agagaaagga tttcgttata gggttcctg ctttcacaga    240

```
attattccag ggtttatgtg tcagggtggt gacttcacac gccctaatgg caccggtgac      300
aagtccatct atgggagaa atttgatgat gagaacctca tccgaaagca tacaggttct       360
ggcatcttgt ccatggcaaa tgctggaccc aacacaaatg gttcccagtt tttcatctgc      420
gctgccaaga ctgagtggtt ggatggcaag catgtggcgt ttggcaaggt gaaagaacgt      480
gtgaatattg tggaagccac ggagcacttt gggtacagga atagcaagac cagcaagaag      540
atcaccattg ctgactgtgg acaattctaa tgagtttgac ttgtgtttta ttttcaccac      600
cagacccatt ccttctgtag ctcaggagag caccctcca ccacatttgc ttgcaatatc       660
ctagaatctt tgtgctcttg ctgcagttcc ctttgggttc catgttttcc ttgttcctt      720 ccatgcctag ctggattgca gagttgagtt aagtttatga ttatgaaata aaaactaagt      780
aacaa                                                                 785

<210> SEQ ID NO 103
<211> LENGTH: 123
<212> TYPE: DNA
<213> ORGANISM: Homo sapiens

<400> SEQUENCE: 103
tatggccata ccaccctgaa tgcacccaat cttgtctgat cttagaagct aagcagggtt      60
aggcctgtta gtacttggat gggagaaaaa tgatatttgc aggaaaactg gtaaagatca     120
gat                                                                   123
```